United States Patent
Just et al.

(10) Patent No.: US 10,766,939 B2
(45) Date of Patent: Sep. 8, 2020

(54) AMYLIN ANALOGUES

(71) Applicant: Zealand Pharma A/S, Glostrup (DK)

(72) Inventors: Rasmus Just, Copenhagen (DK); Oliver Demmer, Glostrup (DK); Lise Giehm, Frederiksberg (DK); Jesper Sloth Villadsen, Glostrup (DK); Henrik Munch, Glostrup (DK); Jesper Mosolff Mathiesen, Glostrup (DK); Jolanta Skarbaliene, Glostrup (DK); Maria Deryabina, Glostrup (DK); Dieter Wolfgang Hamprecht, Pozzolengo (IT)

(73) Assignee: Zealand Pharma A/S, Søborg (DK)

( * ) Notice: Subject to any disclaimer, the term of this patent is extended or adjusted under 35 U.S.C. 154(b) by 734 days.

(21) Appl. No.: 15/074,526

(22) Filed: Mar. 18, 2016

(65) Prior Publication Data

US 2016/0272693 A1 Sep. 22, 2016

(30) Foreign Application Priority Data

Mar. 18, 2015 (EP) .................................. 15159737

(51) Int. Cl.
*C07K 14/575* (2006.01)
*C07K 14/47* (2006.01)
*A61K 38/00* (2006.01)

(52) U.S. Cl.
CPC ............ *C07K 14/575* (2013.01); *C07K 14/47* (2013.01); *A61K 38/00* (2013.01)

(58) Field of Classification Search
CPC ....... C07K 14/575; C07K 14/47; A61K 38/00
See application file for complete search history.

(56) References Cited

U.S. PATENT DOCUMENTS

| 7,407,934 | B2 | 8/2008 | Kolterman et al. |
| 8,575,090 | B2 | 11/2013 | Schaeffer et al. |
| 8,575,091 | B1 | 11/2013 | Dahl et al. |
| 8,722,849 | B2 | 5/2014 | Schaeffer et al. |
| 8,741,836 | B2 | 6/2014 | Schaeffer et al. |
| 8,895,504 | B2 | 11/2014 | Schaffer et al. |
| 9,023,789 | B2 | 5/2015 | Dahl et al. |
| 10,071,140 | B2 * | 9/2018 | Mathiesen ............ C07K 14/575 |
| 2010/0221240 | A1 | 9/2010 | Kapurniotu et al. |
| 2013/0005646 | A1 | 1/2013 | Schaeffer et al. |
| 2013/0059770 | A1 * | 3/2013 | Schaeffer ............ C07K 14/575 514/1.9 |
| 2014/0018286 | A1 | 1/2014 | Schaeffer et al. |
| 2014/0087995 | A1 | 3/2014 | Dahl et al. |
| 2016/0272693 | A1 | 9/2016 | Just et al. |
| 2018/0071366 | A1 | 3/2018 | Mathiesen et al. |

FOREIGN PATENT DOCUMENTS

| WO | WO-91/07978 A1 | 6/1991 |
| WO | WO-92/11862 A1 | 7/1992 |
| WO | WO-93/10146 A1 | 5/1993 |
| WO | WO-98/26796 A1 | 6/1998 |
| WO | WO-98/50059 A1 | 11/1998 |
| WO | WO-98/55144 A1 | 12/1998 |
| WO | WO-99/34764 A2 | 7/1999 |
| WO | WO-2005/000222 A2 | 1/2005 |
| WO | WO-2005/077072 A2 | 8/2005 |
| WO | WO-2006/042745 A2 | 4/2006 |
| WO | WO-2006/083254 A1 | 8/2006 |
| WO | WO-2007/022123 A2 | 2/2007 |
| WO | WO-2007/104789 A2 | 9/2007 |
| WO | WO-2009/034118 A1 | 3/2009 |
| WO | WO-2009/034119 A1 | 3/2009 |
| WO | WO-2010/046357 A1 | 4/2010 |
| WO | WO-2010/107874 A2 | 9/2010 |
| WO | WO-2011/064282 A1 | 6/2011 |
| WO | WO-2012/168430 A2 | 12/2012 |
| WO | WO-2012/168431 A2 | 12/2012 |
| WO | WO-2012/168432 A1 | 12/2012 |
| WO | WO-2013/156594 A1 | 10/2013 |
| WO | WO-2015/040182 A2 | 3/2015 |
| WO | WO-2015040182 A2 * | 3/2015 | ........... A61K 47/542 |
| WO | WO-2015/168488 A2 | 11/2015 |
| WO | WO-2016/034604 A1 | 3/2016 |

OTHER PUBLICATIONS

Baisley et al., "Amylin receptor signaling in the nucleus accumbens negatively modulates μ-opioid-driven feeding," Neuropsychopharmacology 39(13):3009-17 (2014) (9 pages).
Database Geneseq [Online] Jun. 14, 2007, "Hybrid polypeptide amylin analog parent molecule SEQ ID No. 78.", XP002739549, retrieved from EBI accession No. GSP:AFC32081 Database accession No. AFC32081.
International Preliminary Report on Patentability for International Application No. PCT/EP2016/055793, dated Jun. 9, 2017 (37 pages).
International Search Report and Written Opinion for International Application No. PCT/EP2016/055793, dated Jun. 24, 2016 (16 pages).
Kajava et al., "A model for Ure2p prion filaments and other amyloids: the parallel superpleated beta-structure," Proc Natl Acad Sci U.S.A. 101(21):7885-90 (2004) (8 pages).
Li et al., "Suppression of polyglutamine toxicity by the yeast Sup35 prion domain in Drosophila," J Biol Chem. 282(52):37694-701 (2007).
Moriarty et al., "Effects of sequential proline substitutions on amyloid formation by human amylin20-29," Biochemistry 38(6):1811-8 (1999).
Muthusamy et al., "Design and study of peptide-based inhibitors of amylin cytotoxicity," Bioorg Med Chem Lett. 20(4):1360-2 (2010).
Rijkers et al., "Inhibition of amyloid fibril formation of human amylin by N-alkylated amino acid and alpha-hydroxy acid residue containing peptides," Chemistry 8(18):4285-91 (2002).

(Continued)

*Primary Examiner* — Karlheinz R. Skowronek
*Assistant Examiner* — Joseph Fischer
(74) *Attorney, Agent, or Firm* — Clark & Elbing LLP

(57) ABSTRACT

The present invention relates to amylin analogs and to their use in the treatment or prevention of a variety of diseases, conditions or disorders, including obesity, excess food intake and associated metabolic diseases such as diabetes. The analogs have good physical and chemical stability, good solubility, and a long duration of action, and are well suited for use in the form of a liquid formulation.

32 Claims, No Drawings

Specification includes a Sequence Listing.

(56) References Cited

OTHER PUBLICATIONS

Tenidis et al., "Identification of a penta- and hexapeptide of islet amyloid polypeptide (IAPP) with amyloidogenic and cytotoxic properties," J Mol Biol. 295(4):1055-71 (2000).

Tsai et al., "Energy landscape of amyloidogenic peptide oligomerization by parallel-tempering molecular dynamics simulation: significant role of Asn ladder," Proc Natl Acad Sci U.S.A. 102(23):8174-9 (2005) (9 pages).

Westermark et al., "Islet amyloid polypeptide: pinpointing amino acid residues linked to amyloid fibril formation," Proc Natl Acad Sci U.S.A. 87(13):5036-40 (1990).

Yan et al., "Design of a mimic of nonamyloidogenic and bioactive human islet amyloid polypeptide (IAPP) as nanomolar affinity inhibitor of IAPP cytotoxic fibrillogenesis," Proc Natl Acad Sci U.S.A. 103(7):2046-51 (2006).

Yan et al., "Selectively N-methylated soluble IAPP mimics as potent IAPP receptor agonists and nanomolar inhibitors of cytotoxic self-assembly of both IAPP and Aβ40," Angew Chem Int Ed Engl. 52(39):10378-83 (2013).

International Search Report and Written Opinion for International Application No. PCT/EP2017/072718, dated Jan. 3, 2018 (13 pages).

Bogdanowich-Knipp et al., "Solution stability of linear vs. cyclic RGD peptides," J Pept Res. 53(5):530-41 (1999).

Chai et al., "Characterization of binding sites for amylin, calcitonin, and CGRP in primate kidney," Am J Physiol. 274(1 Pt 2):F51-62 (1998).

He et al., "Synthesis and chemical stability of a disulfide bond in a model cyclic pentapeptide: Cyclo(1,4)-Cys-Gly-Phe-Cys-Gly-OH," J Pharm Sci. 95(10):2222-34 (2006).

Reidelberger et al., "Effects of amylin-related peptides on food intake, meal patterns, and gastric emptying in rats," Am J Physiol Regul Integr Comp Physiol. 282(5):R1395-404 (2002).

Trivedi et al., "The role of thiols and disulfides on protein stability," Curr Protein Pept Sci. 10(6):614-25 (2009).

Wineman-Fisher et al., "The removal of disulfide bonds in amylin oligomers leads to the conformational change of the 'native' amylin oligomers," Phys Chem Chem Phys. 18(18):12438-42 (2016).

Fortin et al., "Wildlife sequences of islet amyloid polypeptide (IAPP) indentify critical species variants for fibrillization," Amyloid. 22(3):194-202 (2015) (9 pages). doi: 10.3109/13506129.2015.1070824.

Koo et al., "Amide inequivalence in the fibrillar assembly of islet amyloid polypeptide," Protein Eng Des Sel. 21(3):147-54 (2008).

\* cited by examiner

AMYLIN ANALOGUES

The present invention relates to amylin analogues that are amylin receptor agonists, and to their medical use in the treatment and/or prevention of a variety of diseases, conditions or disorders, including treatment and/or prevention of excess food intake, obesity and excess body weight, metabolic diseases, and other conditions and disorders described herein. In particular, the present invention relates to stable amylin analogues that have a long duration of action and are well suited for use in the form of a liquid formulation.

BACKGROUND OF THE INVENTION

Amylin is one of a family of peptide hormones that includes amylin, calcitonin, calcitonin gene-related peptide, adrenomedullin and intermedin (intermedin also being known as AFP-6), and has been implicated in various metabolic diseases and disorders. Human amylin was first isolated, purified and characterized as the major component of amyloid deposits in the islets of pancreases from type 2 diabetes patients.

Native human amylin is a 37-amino acid peptide having the formula (SEQ ID NO: 1)
H-KC( )NTATC( )ATQRLANFLVHSSNNFGAILSSTNVGSNTY-NH$_2$ wherein H- at the N-terminus designates a hydrogen atom, corresponding to the presence of a free amino group on the N-terminal amino acid residue [i.e. the lysine (K) residue at sequence position number 1 in the sequence shown above]; wherein —NH$_2$ at the C-terminus indicates that the C-terminal carboxyl group is in the amide form; and wherein the parentheses ( ) associated with the two cysteine (C, Cys) residues at sequence positions 2 and 7 indicate the presence of an intramolecular disulfide bridge between the two Cys residues in question.

Amylin may be beneficial in treating metabolic disorders such as diabetes and/or obesity. Amylin is believed to regulate gastric emptying, and to suppress glucagon secretion and food intake, thereby regulating the rate of glucose release to the circulation. Amylin appears to complement the actions of insulin. Compared to healthy adults, type 1 diabetes patients have no circulating amylin, and type 2 diabetes patients exhibit reduced postprandial amylin concentrations. In human trials an amylin analogue known as pramlintide, described in WO 93/10146 and having the sequence Lys-Cys-Asn-Thr-Ala-Thr-Cys-Ala-Thr-Gln-Arg-Leu-Ala-Asn-Phe-Leu-Val-His-Ser-Ser-Asn-Asn-Phe-Gly-Pro-Ile-Leu-Pro-Pro-Thr-Asn-Val-Gly-Ser-Asn-Thr-Tyr (SEQ ID NO: 2), which also possesses a disulphide bridge between the Cys residues at positions 2 and 7, has been shown to reduce body weight or reduce weight gain. An alternative amylin analogue incorporating N-methylated residues and having a reduced tendency to fibrillation, designated IAPP-GI, has been described by Yan et al. (PNAS, 103(7), 2046-2051, 2006). IAPP-GI appears to have lower activity than native amylin, however. Further analogues of amylin or pramlintide are described in WO2013/156594, WO2012/168430, WO2012/168431 and WO2012/168432, as well as WO2006/042745.

Obesity is believed to be a major causal factor in development of type 2 diabetes, which constitutes a growing worldwide major health problem. Diseases or disorders that may develop as a consequence of untreated diabetes include cardiovascular and peripheral artery disease, micro- and macrovascular complications, stroke, and certain forms of cancer, particularly hematopoietic cancers.

There is a need in the art for further amylin analogues. For example, amylin analogues that show a reduced tendency for fibrillation and/or high chemical stability at or around pH 7 might allow for a formulation at or near physiological pH. Amylin analogues having high levels of agonist activity at the amylin receptor and/or appropriately long plasma elimination half lives, may also enable longer intervals between dosing than is currently possible (e.g. once weekly, or even less frequently) and hence improve patient compliance.

SUMMARY OF THE INVENTION

The present invention relates to compounds which are analogues of human amylin.

In a first aspect, the invention provides an amylin analogue which is a compound having the formula:

$$R^1\text{—}Z\text{—}R^2$$

wherein
$R^1$ is hydrogen, $C_{1-4}$ acyl, benzoyl or $C_{1-4}$ alkyl, or a half-life extending moiety M, wherein M is optionally linked to Z via a linker moiety L;
$R^2$ is OH or $NHR^3$, wherein $R^3$ is hydrogen or $C_{1-3}$-alkyl; and
Z is an amino acid sequence of formula I:

Arg-Cys-X3-Thr-Ala-Thr-Cys-Ala-Thr-X10-Arg-Leu-
Ala-X14-Phe-Leu-X17-Arg-X19-X20-Phe-Gly
(Me)-Ala-Ile(Me)-Leu-Ser-Ser-Thr-X31-Val-
Gly-Ser-X35-Thr-X37 (SEQ ID NO: 3)   (I);

wherein
X3 is selected from the group consisting of Asn, Gly, Pro and Gln;
X10 is selected from the group consisting of Gln, Asp and Glu;
X14 is selected from the group consisting of Asp, His, Asn and Aad;
X17 is selected from the group consisting of His, Asn, Gln, Glu, Thr, Val, Lys and Aad;
X19-X20 is selected from the group consisting of Ser-Ser, Val-Val, Ser-Val and Val-Ser, or is absent;
X31 is selected from the group consisting of Asp, Glu and Asn;
X35 is selected from the group consisting of Asp, Glu, Asn, Ser, Phe, Orn, Aad, Gly and Thr; and
X37 is selected from the group consisting of Pro, Apr and Hyp;
and wherein the compound has at least one residue selected from:
X3 is Gln;
X14 is His, Asn or Aad;
X17 is Asn, Gln, Glu, Thr or Aad;
X19-X20 is Val-Ser or Ser-Val; and
X35 is Ser, Phe, Orn, Aad, Gly or Thr;
or a pharmaceutically acceptable salt or solvate thereof.

Throughout this specification, amino acid positions of the amylin analogues are numbered according to the corresponding position in human amylin having the sequence shown above. The sequence of Formula I (and other formulae herein) contains a two amino acid deletion corresponding to the two residues Asn21 and Asn22 of human amylin. Thus, for ease of comparison with the amylin sequence, the Phe residue immediately C-terminal (downstream) of position X20 is designated as position 23, since it aligns with Phe23 of human amylin. Thus, the numbering of any given residue in Formula I above, and in other formulae elsewhere in this specification, reflects the corresponding residue in human amylin when optimally aligned therewith and does not necessarily reflect its linear position in the particular sequence.

(It will be apparent that any of the relevant formulae presented in this specification could be written to include residues X21-X22 at the appropriate positions, wherein X21 and X22 are absent.)

It has surprisingly been found that simultaneous deletion of the residues at positions X21 and X22 (and even additionally at positions X19 and X20) leads to active and stable amylin analogues. Further, without wishing to be bound by any particular theory, it is believed that the deletion of these residues may enhance the chemical stability of the molecules, especially at neutral and/or alkaline pH. Fibrillation and precipitation of the compounds may also be reduced. Thus the compounds may have superior properties for formulation as compared to existing amylin analogues.

Furthermore, the compounds described here show similar or even increased activity compared to wild type amylin (e.g. agonist activity at the hAMYR3 and/or hAMYR1 and/or hCTR2 receptors), despite being methylated at the same positions as IAPP-GI (which has lower activity than wild type amylin).

In some embodiments of formula I it may be desirable that:
X31 is Glu;
X19-X20 is Ser-Ser or is absent; and/or
X37 is Hyp or Pro.

It may be desirable that the amylin analogue contains at least one of His14, Asn14, Aad14, Gln17 and Thr17.

If X14 is Asp, then it may be desirable that X17 is Asn, Gln, Glu, Thr or Aad.

X17 is Gln may be particularly preferred.

In some circumstances, it may be desirable that X35 is not a hydrophobic residue, e.g. Phe. Such residues may increase tendency towards fibrillation in some formulations.

Z may be an amino acid sequence of formula II:

(II)
                                                  (SEQ ID NO: 4)
Arg-Cys-X3-Thr-Ala-Thr-Cys-Ala-Thr-X10-Arg-Leu-

Ala-X14-Phe-Leu-X17-Arg-X19-X20-Phe-Gly(Me)-Ala-

Ile(Me)-Leu-Ser-Ser-Thr-Glu-Val-Gly-Ser-X35-Thr-

X37;

wherein
X3 is selected from the group consisting of Asn, Gly and Gln;
X10 is selected from the group consisting of Gln, Asp and Glu;
X14 is selected from the group consisting of Asp, His and Aad;
X17 is selected from the group consisting of His, Asn, Gln, Glu, Lys and Aad;
X19-X20 is Ser-Ser or is absent;
X35 is selected from the group consisting of Asp, Glu, Asn, Ser, Orn, Aad, Gly and Thr; and
X37 is selected from the group consisting of Pro and Hyp; and wherein the compound has at least one residue selected from:
X3 is Gln;
X14 is His or Aad;
X17 is Asn, Gln, Glu or Aad; and
X35 is Ser, Phe, Orn, Aad, Gly or Thr.

In some embodiments of formula II, X17 may be selected from His and Gln.

Z may be an amino acid sequence of formula III:

(III)
                                                  (SEQ ID NO: 4)
Arg-Cys-X3-Thr-Ala-Thr-Cys-Ala-Thr-X10-Arg-Leu-

Ala-X14-Phe-Leu-X17-Arg-X19-X20-Phe-Gly(Me)-Ala-

Ile(Me)-Leu-Ser-Ser-Thr-Glu-Val-Gly-Ser-X35-Thr-

X37;

wherein
X3 is selected from the group consisting of Asn, Gly and Gln;
X10 is selected from the group consisting of Gln, Asp and Glu;
X14 is selected from the group consisting of Asp, His and Aad;
X17 is selected from the group consisting of His and Gln;
X19-X20 is Ser-Ser or is absent;
X35 is selected from the group consisting of Asp, Glu, Asn, Aad and Gly; and
X37 is selected from the group consisting of Pro and Hyp; and wherein the compound has at least one residue selected from:
X3 is Gln;
X14 is His or Aad;
X17 is Gln; and
X35 is Aad.

In any of the formulae described above, it may be desirable that:
X10 is selected from Gln and Glu;
and/or
X35 is selected from Asp, Glu, Asn and Aad, e.g. X35 is selected from Asp and Asn.

Additionally or alternatively, it may be that X3 is selected from Asn and Gly and/or X17 is Gln. The presence of Gln at position X17 is believed to correlate with good levels of chemical and physical stability.

Additionally or alternatively, X35 is Asn and/or X37 is Hyp.

In some embodiments of the formulae described above:
X3 is Gln;
X10 is selected from Glu and Asp;
X14 is selected from His and Aad;
X35 is selected from Gly and Asn; and
X37 is selected from Pro and Hyp.

In other embodiments of the formulae described above:
X3 is Gly;
X10 is selected from Glu and Asp;
X14 is selected from His and Aad;
X35 is selected from Gly and Asn; and
X37 is selected from Pro and Hyp.

Combinations of specific residues which may be present in any of the amylin analogues described include:
Gly3+Glu10;
Asn3+Glu10;
Gln3+Glu10;
Asn3+Gln10; or
Gln3+Asp10.

In some embodiments, X14 is selected from His and Aad, and/or X17 is Gln.

For example, the combination of Aad14 and Gln17 appears to provide good activity.

Additionally or alternatively, X17 may be Gln, X31 may be Glu and X37 may be Hyp, i.e. the analogue may contain the combination Gln17+Glu31+Hyp37.

In some embodiments, X19-X20 is Ser-Ser. In other embodiments X19-X20 is absent.

Certain residue combinations which may be favourable for chemical stability include:
X3 is Gly, X10 is Glu and X14 is His;
X3 is selected from Asn and Gln, X10 is Glu and X14 is His;
X3 is Gly, X10 is Glu and X14 is selected from Aad and Asp;
X10 is Asp and X14 is Aad;
X14 is selected from Aad and His, X31 is Glu and X37 is selected from Pro and Hyp; and
X14 is Aad, X31 is Glu and X37 is Hyp.

Of these combinations, the following may additionally (or alternatively) have a favourable effect on activity:
X3 is Gly, X10 is Glu and X14 is selected from Aad and Asp;
X14 is selected from Aad and His, X31 is Glu and X37 is selected from Pro and Hyp;
X14 is Aad, X31 is Glu and X37 is Hyp.

For example, the compound may comprise the residues:
Gly3+Glu10+His14
Asn3+Glu10+His14;
Gln3+Glu10+His14;
Gly3+Glu10+Aad14;
Gly3+Glu10+Asp14;
Asp10+Aad14;
His14+Glu31+Pro37
His14+Glu31+Hyp37
Aad14+Glu31+Pro37; and
Aad14+Glu31+Hyp37.

Yet further combinations of desirable residues include:
Gly3+Glu31;
Gly3+Ser19+Ser20+Glu31
Gly3+Glu10+Glu31+Asn35+Hyp37; and
Gly3+Glu10+Ser19+Ser20+Glu31+Asn35+Hyp37.

Any of the above-described residues and combinations of residues may be combined except where inconsistent with one another.

The invention also provides an amylin analogue which is a compound having the formula:

$R^1$—Z—$R^2$ wherein
$R^1$ is hydrogen, $C_{1-4}$ acyl, benzoyl or $C_{1-4}$ alkyl, or a half-life extending moiety M, wherein M is optionally linked to Z via a linker moiety L;
$R^2$ is OH or $NHR^3$, wherein $R^3$ is hydrogen or $C_{1-3}$-alkyl; and
Z is an amino acid sequence selected from the group consisting of:

```
RCNTATCATQRLADFLHRSSF-Gly(Me)-A-Ile(Me)-
LSSTEVGSETP (SEQ ID NO: 99);

RCNTATCATQRLADFLHRSSNNF-Gly(Me)-A-Ile(Me)-
LSSTNVGSNT-Apr (SEQ ID NO: 100); and

RCNTATCATQRLAHFLHRSSNNF-Gly(Me)-A-Ile(Me)-
LSSTNVGSNT-Apr (SEQ ID NO: 101);
``` or a pharmaceutically acceptable salt or solvate thereof.

Thus, the amylin analogue may have the formula:

$R^1$—Z—$R^2$ wherein
$R^1$ is hydrogen, $C_{1-4}$ acyl, benzoyl or $C_{1-4}$ alkyl, or a half-life extending moiety M, wherein M is optionally linked to Z via a linker moiety L;
$R^2$ is OH or $NHR^3$, wherein $R^3$ is hydrogen or $C_{1-3}$-alkyl; and
Z is an amino acid sequence selected from the group consisting of:

```
                                             (SEQ ID NO: 6)
RCNTATCATQRLAHFLHRSSF-Gly(Me)-A-Ile(Me)-LSSTEVGSETP (SEQ ID NO: 7)
RCNTATCATQRLANFLHRSSF-Gly(Me)-A-Ile(Me)-LSSTEVGSETP (SEQ ID NO: 8)
RCGTATCATERLAHFLNRSSF-Gly(Me)-A-Ile(Me)-LSSTEVGSNT-Hyp (SEQ ID NO: 9)
RCGTATCATERLAHFLQRSSF-Gly(Me)-A-Ile(Me)-LSSTEVGSNT-Hyp (SEQ ID NO: 10)
RCGTATCATERLAHFLERSSF-Gly(Me)-A-Ile(Me)-LSSTEVGSNT-Hyp (SEQ ID NO: 11)
RCGTATCATERLAHFLTRSSF-Gly(Me)-A-Ile(Me)-LSSTEVGSST-Hyp (SEQ ID NO: 12)
RCGTATCATERLAHFLTRSSF-Gly(Me)-A-Ile(Me)-LSSTEVGSFT-Hyp (SEQ ID NO: 13)
RCGTATCATERLAHFLTRSSF-Gly(Me)-A-Ile(Me)-LSSTEVGS-Orn-T-Hyp (SEQ ID NO: 14)
RCGTATCATERLAHFLTRSSF-Gly(Me)-A-Ile(Me)-LSSTEVGS-Aad-T-Hyp (SEQ ID NO: 15)
RCGTATCATERLAHFLTRSSF-Gly(Me)-A-Ile(Me)-LSSTEVGSGT-Hyp (SEQ ID NO: 16)
RCNTATCATQRLAHFLHRF-Gly(Me)-A-Ile(Me)-LSSTEVGSETP (SEQ ID NO: 17)
RCGTATCATERLAHFLHRSSF-Gly(Me)-A-Ile(Me)-LSSTEVGSNTP
```

-continued

RCNTATCATQRLAHFLHRSSF-Gly(Me)-A-Ile(Me)-LSSTEVGSNTP (SEQ ID NO: 18)

RCGTATCATERLANFLVRSSF-Gly(Me)-A-Ile(Me)-LSSTEVGSNT-Hyp (SEQ ID NO: 19)

RCGTATCATERLAHFLTRSSF-Gly(Me)-A-Ile(Me)-LSSTEVGSNT-Hyp (SEQ ID NO: 20)

RCGTATCATERLAHFLKRSSF-Gly(Me)-A-Ile(Me)-LSSTEVGSNT-Hyp (SEQ ID NO: 21)

RCNTATCATQRLAHFLHRSVF-Gly(Me)-A-Ile(Me)-LSSTEVGSETP (SEQ ID NO: 22)

RCNTATCATQRLAHFLHRVSF-Gly(Me)-A-Ile(Me)-LSSTEVGSETP (SEQ ID NO: 23)

RCGTATCATERLAHFLVRSSF-Gly(Me)-A-Ile(Me)-LSSTEVGSETP (SEQ ID NO: 24)

RCPTATCATDRLAHFLVRSSF-Gly(Me)-A-Ile(Me)-LSSTDVGSDTP (SEQ ID NO: 25)

RCNTATCATQRLAHFLVRSSF-Gly(Me)-A-Ile(Me)-LSSTEVGSETP (SEQ ID NO: 26)

RCPTATCATDRLAHFLHRSSF-Gly(Me)-A-Ile(Me)-LSSTDVGSNTP (SEQ ID NO: 27)

RCGTATCATERLAHFLHRSSF-Gly(Me)-A-Ile(Me)-LSSTEVGSETP (SEQ ID NO: 28)

RCPTATCATDRLAHFLHRSSF-Gly(Me)-A-Ile(Me)-LSSTDVGSDTP (SEQ ID NO: 29)

RCGTATCATERLAHFLQRSSF-Gly(Me)-A-Ile(Me)-LSSTEVGSST-Hyp (SEQ ID NO: 30)

RCGTATCATERLAHFLNRSSF-Gly(Me)-A-Ile(Me)-LSSTEVGSST-Hyp (SEQ ID NO: 31)

RCGTATCATERLAHFLHRSSF-Gly(Me)-A-Ile(Me)-LSSTEVGSST-Hyp (SEQ ID NO: 32)

RCGTATCATERLAHFLVRSSF-Gly(Me)-A-Ile(Me)-LSSTEVGSST-Hyp (SEQ ID NO: 33)

RCGTATCATERLAHFLQRSSF-Gly(Me)-A-Ile(Me)-LSSTEVGSFT-Hyp (SEQ ID NO: 34)

RCGTATCATERLAHFLNRSSF-Gly(Me)-A-Ile(Me)-LSSTEVGSFT-Hyp (SEQ ID NO: 35)

RCGTATCATERLAHFLQRSSF-Gly(Me)-A-Ile(Me)-LSSTEVGSSTP (SEQ ID NO: 36)

RCGTATCATERLAHFLNRSSF-Gly(Me)-A-Ile(Me)-LSSTEVGSSTP (SEQ ID NO: 37)

RCGTATCATERLAHFLERSSF-Gly(Me)-A-Ile(Me)-LSSTEVGSSTP (SEQ ID NO: 38)

RCGTATCATERLAHFLHRSSF-Gly(Me)-A-Ile(Me)-LSSTEVGSSTP (SEQ ID NO: 39)

RCGTATCATERLAHFLVRSSF-Gly(Me)-A-Ile(Me)-LSSTEVGSSTP (SEQ ID NO: 40)

RCGTATCATERLAHFLQRSSF-Gly(Me)-A-Ile(Me)-LSSTEVGSFTP (SEQ ID NO: 41)

RCGTATCATERLAHFLNRSSF-Gly(Me)-A-Ile(Me)-LSSTEVGSFTP (SEQ ID NO: 42)

RCGTATCATERLADFLTRSSF-Gly(Me)-A-Ile(Me)-LSSTEVGSST-Hyp (SEQ ID NO: 43)

RCGTATCATERLADFLTRSSF-Gly(Me)-A-Ile(Me)-LSSTEVGSFT-Hyp (SEQ ID NO: 44)

-continued (SEQ ID NO: 45)
RCGTATCATERLA-Aad-FLTRSSF-Gly(Me)-A-Ile(Me)-LSSTEVGSST-Hyp (SEQ ID NO: 46)
RCGTATCATERLA-Aad-FLTRSSF-Gly(Me)-A-Ile(Me)-LSSTEVGS-Orn-T-Hyp (SEQ ID NO: 47)
RCGTATCATERLAHFLTRSSF-Gly(Me)-A-Ile(Me)-LSSTEVGSST-Apr (SEQ ID NO: 48)
RCGTATCATERLAHFLTRSSF-Gly(Me)-A-Ile(Me)-LSSTEVGSSTP (SEQ ID NO: 49)
RCGTATCATERLAHFLTRSSF-Gly(Me)-A-Ile(Me)-LSSTEVGS-Orn-TP (SEQ ID NO: 50)
RCGTATCATERLAHFLTRSSF-Gly(Me)-A-Ile(Me)-LSSTEVGSTT-Hyp (SEQ ID NO: 51)
RCNTATCATORLADFLQRSSF-Gly(Me)-A-Ile(Me)-LSSTEVGSNT-Hyp (SEQ ID NO: 52)
RCNTATCATQRLAHFL-Aad-RSSF-Gly(Me)-A-Ile(Me)-LSSTEVGSNT-Hyp (SEQ ID NO: 53)
RCGTATCATERLAHFLQRSSF-Gly(Me)-A-Ile(Me)-LSSTEVGS-Orn-T-Hyp (SEQ ID NO: 54)
RCGTATCATERLAHFLQRSSF-Gly(Me)-A-Ile(Me)-LSSTEVGSGT-Hyp (SEQ ID NO: 55)
RCGTATCATERLAHFLQRSSF-Gly(Me)-A-Ile(Me)-LSSTEVGS-Aad-T-Hyp (SEQ ID NO: 56)
RCGTATCATERLADFLQRSSF-Gly(Me)-A-Ile(Me)-LSSTEVGSNT-Hyp (SEQ ID NO: 57)
RCGTATCATERLA-Aad-FLQRSSF-Gly(Me)-A-Ile(Me)-LSSTEVGSNT-Hyp (SEQ ID NO: 58)
RCNTATCATERLAHFLQRSSF-Gly(Me)-A-Ile(Me)-LSSTEVGSNT-Hyp (SEQ ID NO: 59)
RCQTATCATERLAHFLQRSSF-Gly(Me)-A-Ile(Me)-LSSTEVGSNT-Hyp (SEQ ID NO: 60)
RCNTATCATQRLAHFLQRSSF-Gly(Me)-A-Ile(Me)-LSSTEVGSNT-Hyp (SEQ ID NO: 61)
RCPTATCATDRLAHFLQRSSF-Gly(Me)-A-Ile(Me)-LSSTDVGSNT-Hyp (SEQ ID NO: 62)
RCNTATCATERLAHFLQRSSF-Gly(Me)-A-Ile(Me)-LSSTEVGSDT-Hyp (SEQ ID NO: 63)
RCNTATCATQRLAHFLQRSSF-Gly(Me)-A-Ile(Me)-LSSTEVGSNTP (SEQ ID NO: 64)
RCNTATCATERLAHFLQRSSF-Gly(Me)-A-Ile(Me)-LSSTEVGSNTP (SEQ ID NO: 65)
RCPTATCATERLAHFLQRSSF-Gly(Me)-A-Ile(Me)-LSSTEVGSNT-Hyp (SEQ ID NO: 66)
RCPTATCATQRLAHFLQRSSF-Gly(Me)-A-Ile(Me)-LSSTEVGSNT-Hyp (SEQ ID NO: 67)
RCNTATCATQRLADFLQRSSF-Gly(Me)-A-Ile(Me)-LSSTEVGSNTP (SEQ ID NO: 68)
RCNTATCATERLADFLQRSSF-Gly(Me)-A-Ile(Me)-LSSTEVGSNTP (SEQ ID NO: 69)
RCPTATCATERLADFLQRSSF-Gly(Me)-A-Ile(Me)-LSSTEVGSNTP (SEQ ID NO: 70)
RCNTATCATERLADFLQRSSF-Gly(Me)-A-Ile(Me)-LSSTEVGSNT-Hyp

```
                                                    (SEQ ID NO: 71)
RCNTATCATQRLAHFLQRSSF-Gly(Me)-A-Ile(Me)-LSSTEVGSST-Hyp (SEQ ID NO: 72)
RCPTATCATERLAHFLQRSSF-Gly(Me)-A-Ile(Me)-LSSTEVGSST-Hyp (SEQ ID NO: 73)
RCNTATCATQRLAHFLQRSSF-Gly(Me)-A-Ile(Me)-LSSTEVGSGT-Hyp (SEQ ID NO: 74)
RCPTATCATERLAHFLQRSSF-Gly(Me)-A-Ile(Me)-LSSTEVGSGT-Hyp (SEQ ID NO: 75)
RCNTATCATQRLAHFLQRSSF-Gly(Me)-A-Ile(Me)-LSSTEVGSTT-Hyp (SEQ ID NO: 76)
RCPTATCATERLAHFLQRSSF-Gly(Me)-A-Ile(Me)-LSSTEVGSTT-Hyp (SEQ ID NO: 77)
RCNTATCATQRLAHFLQRSSF-Gly(Me)-A-Ile(Me)-LSSTEVGS-Aad-T-Hyp (SEQ ID NO: 78)
RCPTATCATERLAHFLQRSSF-Gly(Me)-A-Ile(Me)-LSSTEVGS-Aad-T-Hyp (SEQ ID NO: 79)
RCGTATCATERLAHFLQRF-Gly(Me)-A-Ile(Me)-LSSTEVGSNT-Hyp (SEQ ID NO: 80)
RCGTATCATERLAHFLQRSSF-Gly(Me)-A-Ile(Me)-LSSTEVGSNTP (SEQ ID NO: 81)
RCNTATCATQRLAHFLQRF-Gly(Me)-A-Ile(Me)-LSSTEVGSGT-Hyp (SEQ ID NO: 82)
RCNTATCATQRLADFLQRSSF-Gly(Me)-A-Ile(Me)-LSSTEVGSGTP (SEQ ID NO: 83)
RCNTATCATQRLADFLQRSSF-Gly(Me)-A-Ile(Me)-LSSTEVGSGT-Hyp (SEQ ID NO: 84)
RCNTATCATQRLADFLQRSSF-Gly(Me)-A-Ile(Me)-LSSTEVGSTTP (SEQ ID NO: 85)
RCNTATCATQRLADFLQRSSF-Gly(Me)-A-Ile(Me)-LSSTEVGSTT-Hyp (SEQ ID NO: 86)
RCNTATCATQRLAHFLERSSF-Gly(Me)-A-Ile(Me)-LSSTEVGSSTP (SEQ ID NO: 87)
RCNTATCATQRLAHFLQRSSF-Gly(Me)-A-Ile(Me)-LSSTEVGSSTP (SEQ ID NO: 88)
RCNTATCATQRLA-Aad-FLQRSSF-Gly(Me)-A-Ile(Me)-LSSTEVGSNT-Hyp (SEQ ID NO: 89)
RCNTATCATQRLA-Aad-FLQRSSF-Gly(Me)-A-Ile(Me)-LSSTEVGSST-Hyp (SEQ ID NO: 90)
RCQTATCATDRLAHFLQRSSF-Gly(Me)-A-Ile(Me)-LSSTEVGSNT-Hyp (SEQ ID NO: 91)
RCQTATCATDRLA-Aad-FLQRSSF-Gly(Me)-A-Ile(Me)-LSSTEVGSNT-Hyp (SEQ ID NO: 92)
RCQTATCATERLAHFLQRSSF-Gly(Me)-A-Ile(Me)-LSSTEVGSGT-Hyp (SEQ ID NO: 93)
RCQTATCATDRLAHFLQRSSF-Gly(Me)-A-Ile(Me)-LSSTEVGSGT-Hyp (SEQ ID NO: 94)
RCQTATCATDRLAHFLQRSSF-Gly(Me)-A-Ile(Me)-LSSTEVGSNTP (SEQ ID NO: 95)
RCQTATCATERLA-Aad-FLQRSSF-Gly(Me)-A-Ile(Me)-LSSTEVGSNTP (SEQ ID NO: 96)
RCQTATCATERLA-Aad-FLQRSSF-Gly(Me)-A-Ile(Me)-LSSTEVGSGTP
```

(SEQ ID NO: 97)
RCQTATCATDRLA-Aad-FLQRF-Gly(Me)-A-Ile(Me)-LSSTEVGSNT-Hyp (SEQ ID NO: 98)
RCQTATCATERLAHFLQRF-Gly(Me)-A-Ile(Me)-LSSTEVGSNTP or a pharmaceutically acceptable salt or solvate thereof.

In some embodiments, $R^1$ is M or M-L-, and/or $R^2$ is $NH_2$.

Specific amylin analogues of the invention include:

(SEQ ID NO: 102)
[19CD]-isoGlu-RCNTATCATQRLADFLHRSSF-Gly(Me)-A-Ile(Me)-LSSTEVGSETP-$NH_2$ (SEQ ID NO: 103)
[19CD]-isoGlu-RCNTATCATQRLAHFLHRSSF-Gly(Me)-A-Ile(Me)-LSSTEVGSETP-$NH_2$ (SEQ ID NO: 104)
[19CD]-isoGlu-RCNTATCATQRLANFLHRSSF-Gly(Me)-A-Ile(Me)-LSSTEVGSETP-$NH_2$ (SEQ ID NO: 105)
[19CD]-isoGlu-RCNTATCATQRLADFLFIRSSNNF-Gly(Me)-A-Ile(Me)-LSSTNVGSNT-Apr-$NH_2$ (SEQ ID NO: 106)
[19CD]-isoGlu-RCNTATCATQRLAHFLHRSSNNF-Gly(Me)-A-Ile(Me)-LSSTNVGSNT-Apr-$NH_2$ (SEQ ID NO: 107)
[19CD]-isoGlu-RCGTATCATERLAHFLNRSSF-Gly(Me)-A-Ile(Me)-LSSTEVGSNT-Hyp-$NH_2$ (SEQ ID NO: 108)
[19CD]-isoGlu-RCGTATCATERLAHFLQRSSF-Gly(Me)-A-Ile(Me)-LSSTEVGSNT-Hyp-$NH_2$ (SEQ ID NO: 109)
[19CD]-isoGlu-RCGTATCATERLAHFLERSSF-Gly(Me)-A-Ile(Me)-LSSTEVGSNT-Hyp-$NH_2$ (SEQ ID NO: 110)
[19CD]-isoGlu-RCGTATCATERLAHFLTRSSF-Gly(Me)-A-Ile(Me)-LSSTEVGSST-Hyp-$NH_2$ (SEQ ID NO: 111)
[19CD]-isoGlu-RCGTATCATERLAHFLTRSSF-Gly(Me)-A-Ile(Me)-LSSTEVGSFT-Hyp-$NH_2$ (SEQ ID NO: 112)
[19CD]-isoGlu-RCGTATCATERLAHFLTRSSF-Gly(Me)-A-Ile(Me)-LSSTEVGS-Orn-T-Hyp-$NH_2$ (SEQ ID NO: 113)
[19CD]-isoGlu-RCGTATCATERLAHFLTRSSF-Gly(Me)-A-Ile(Me)-LSSTEVGS-Aad-T-Hyp-$NH_2$ (SEQ ID NO: 114)
[19CD]-isoGlu-RCGTATCATERLAHFLTRSSF-Gly(Me)-A-Ile(Me)-LSSTEVGSGT-Hyp-$NH_2$ (SEQ ID NO: 115)
[19CD]-isoGlu-RCNTATCATQRLAHFLHRF-Gly(Me)-A-Ile(Me)-LSSTEVGSETP-$NH_2$ (SEQ ID NO: 116)
[19CD]-isoGlu-RCGTATCATERLAHFLHRSSF-Gly(Me)-A-Ile(Me)-LSSTEVGSNTP-$NH_2$ (SEQ ID NO: 117)
[19CD]-isoGlu-RCNTATCATQRLAHFLHRSSF-Gly(Me)-A-Ile(Me)-LSSTEVGSNTP-$NH_2$ (SEQ ID NO: 118)
[19CD]-isoGlu-RCGTATCATERLANFLVRSSF-Gly(Me)-A-Ile(Me)-LSSTEVGSNT-Hyp-$NH_2$ (SEQ ID NO: 119)
[19CD]-isoGlu-RCGTATCATERLAHFLTRSSF-Gly(Me)-A-Ile(Me)-LSSTEVGSNT-Hyp-$NH_2$ (SEQ ID NO: 120)
[19CD]-isoGlu-RCGTATCATERLAHFLKRSSF-Gly(Me)-A-Ile(Me)-LSSTEVGSNT-Hyp-$NH_2$ (SEQ ID NO: 121)
[19CD]-isoGlu-RCNTATCATQRLAHFLHRSVF-Gly(Me)-A-Ile(Me)-LSSTEVGSETP-$NH_2$ (SEQ ID NO: 122)
[19CD]-isoGlu-RCNTATCATQRLAHFLHRVSF-Gly(Me)-A-Ile(Me)-LSSTEVGSETP-$NH_2$ (SEQ ID NO: 123)
[19CD]-isoGlu-RCGTATCATERLAHFLVRSSF-Gly(Me)-A-Ile(Me)-LSSTEVGSETP-$NH_2$

```
                                                        (SEQ ID NO: 124)
[19CD]-isoGlu-RCPTATCATDRLAHFLVRSSF-Gly(Me)-A-Ile(Me)-LSSTDVGSDTP-NH2

(SEQ ID NO: 125)
[19CD]-isoGlu-RCNTATCATQRLAHFLVRSSF-Gly(Me)-A-Ile(Me)-LSSTEVGSETP-NH2

(SEQ ID NO: 126)
[19CD]-isoGlu-RCPTATCATDRLAHFLHRSSF-Gly(Me)-A-Ile(Me)-LSSTDVGSNTP-NH2

(SEQ ID NO: 127)
[19CD]-isoGlu-RCGTATCATERLAHFLHRSSF-Gly(Me)-A-Ile(Me)-LSSTEVGSETP-NH2

(SEQ ID NO: 128)
[19CD]-isoGlu-RCPTATCATDRLAHFLHRSSF-Gly(Me)-A-Ile(Me)-LSSTDVGSDTP-NH2

(SEQ ID NO: 129)
[19CD]-isoGlu-RCGTATCATERLAHFLQRSSF-Gly(Me)-A-Ile(Me)-LSSTEVGSST-Hyp-NH2

(SEQ ID NO: 130)
[19CD]-isoGlu-RCGTATCATERLAHFLNRSSF-Gly(Me)-A-Ile(Me)-LSSTEVGSST-Hyp-NH2

(SEQ ID NO: 131)
[19CD]-isoGlu-RCGTATCATERLAHFLHRSSF-Gly(Me)-A-Ile(Me)-LSSTEVGSST-Hyp-NH2

(SEQ ID NO: 132)
[19CD]-isoGlu-RCGTATCATERLAHFLVRSSF-Gly(Me)-A-Ile(Me)-LSSTEVGSST-Hyp-NH2

(SEQ ID NO: 133)
[19CD]-isoGlu-RCGTATCATERLAHFLQRSSF-Gly(Me)-A-Ile(Me)-LSSTEVGSFT-Hyp-NH2

(SEQ ID NO: 134)
[19CD]-isoGlu-RCGTATCATERLAHFLNRSSF-Gly(Me)-A-Ile(Me)-LSSTEVGSFT-Hyp-NH2

(SEQ ID NO: 135)
[19CD]-isoGlu-RCGTATCATERLAHFLQRSSF-Gly(Me)-A-Ile(Me)-LSSTEVGSSTP-NH2

(SEQ ID NO: 136)
[19CD]-isoGlu-RCGTATCATERLAHFLNRSSF-Gly(Me)-A-Ile(Me)-LSSTEVGSSTP-NH2

(SEQ ID NO: 137)
[19CD]-isoGlu-RCGTATCATERLAHFLERSSF-Gly(Me)-A-Ile(Me)-LSSTEVGSSTP-NH2

(SEQ ID NO: 138)
[19CD]-isoGlu-RCGTATCATERLAFIFLHRSSF-Gly(Me)-A-Ile(Me)-LSSTEVGSSTP-NH2

(SEQ ID NO: 139)
[19CD]-isoGlu-RCGTATCATERLAHFLVRSSF-Gly(Me)-A-Ile(Me)-LSSTEVGSSTP-NH2

(SEQ ID NO: 140)
[19CD]-isoGlu-RCGTATCATERLAHFLQRSSF-Gly(Me)-A-Ile(Me)-LSSTEVGSFTP-NH2

(SEQ ID NO: 141)
[19CD]-isoGlu-RCGTATCATERLAHFLNRSSF-Gly(Me)-A-Ile(Me)-LSSTEVGSFTP-NH2

(SEQ ID NO: 142)
[19CD]-isoGlu-RCGTATCATERLADFLTRSSF-Gly(Me)-A-Ile(Me)-LSSTEVGSST-Hyp-NH2

(SEQ ID NO: 143)
[19CD]-isoGlu-RCGTATCATERLADFLTRSSF-Gly(Me)-A-Ile(Me)-LSSTEVGSFT-Hyp-NH2

(SEQ ID NO: 144)
[19CD]-isoGlu-RCGTATCATERLA-Aad-FLTRSSF-Gly(Me)-A-Ile(Me)-LSSTEVGSST-Hyp-NH2

(SEQ ID NO: 145)
[19CD]-isoGlu-RCGTATCATERLA-Aad-FLTRSSF-Gly(Me)-A-Ile(Me)-LSSTEVGS-Orn-T-Hyp-
NH2

(SEQ ID NO: 146)
[19CD]-isoGlu-RCGTATCATERLAFIFLTRSSF-Gly(Me)-A-Ile(Me)-LSSTEVGSST-Apr-NH2

(SEQ ID NO: 147)
[19CD]-isoGlu-RCGTATCATERLAHFLTRSSF-Gly(Me)-A-Ile(Me)-LSSTEVGSSTP-NH2

(SEQ ID NO: 148)
[19CD]-isoGlu-RCGTATCATERLAHFLTRSSF-Gly(Me)-A-Ile(Me)-LSSTEVGS-Orn-TP-NH2

(SEQ ID NO: 149)
[19CD]-isoGlu-RCGTATCATERLAHFLTRSSF-Gly(Me)-A-Ile(Me)-LSSTEVGSTT-Hyp-NH2

(SEQ ID NO: 150)
[19CD]-isoGlu-RCNTATCATQRLADFLQRSSF-Gly(Me)-A-Ile(Me)-LSSTEVGSNT-Hyp-NH2
```

-continued (SEQ ID NO: 151)
[19CD]-isoGlu-RCNTATCATQRLAHFL-Aad-RSSF-Gly(Me)-A-Ile(Me)-LSSTEVGSNT-Hyp-NH$_2$ (SEQ ID NO: 152)
[19CD]-isoGlu-RCGTATCATERLAHFLQRSSF-Gly(Me)-A-Ile(Me)-LSSTEVGS-Orn-T-Hyp-NH$_2$ (SEQ ID NO: 153)
[19CD]-isoGlu-RCGTATCATERLAHFLQRSSF-Gly(Me)-A-Ile(Me)-LSSTEVGSGT-Hyp-NH$_2$ (SEQ ID NO: 154)
[19CD]-isoGlu-RCGTATCATERLAHFLQRSSF-Gly(Me)-A-Ile(Me)-LSSTEVGS-Aad-T-Hyp-NH$_2$ (SEQ ID NO: 155)
[19CD]-isoGlu-RCGTATCATERLADFLQRSSF-Gly(Me)-A-Ile(Me)-LSSTEVGSNT-Hyp-NH$_2$ (SEQ ID NO: 156)
[19CD]-isoGlu-RCGTATCATERLA-Aad-FLQRSSF-Gly(Me)-A-Ile(Me)-LSSTEVGSNT-Hyp-NH$_2$ (SEQ ID NO: 157)
[19CD]-isoGlu-RCNTATCATERLAHFLQRSSF-Gly(Me)-A-Ile(Me)-LSSTEVGSNT-Hyp-NH$_2$ (SEQ ID NO: 158)
[19CD]-isoGlu-RCQTATCATERLAHFLQRSSF-Gly(Me)-A-Ile(Me)-LSSTEVGSNT-Hyp-NH$_2$ (SEQ ID NO: 159)
[19CD]-isoGlu-RCNTATCATQRLAHFLQRSSF-Gly(Me)-A-Ile(Me)-LSSTEVGSNT-Hyp-NH$_2$ (SEQ ID NO: 160)
[19CD]-isoGlu-RCPTATCATDRLAHFLQRSSF-Gly(Me)-A-Ile(Me)-LSSTDVGSNT-Hyp-NH$_2$ (SEQ ID NO: 161)
[19CD]-isoGlu-RCNTATCATQRLAHFLQRSSF-Gly(Me)-A-Ile(Me)-LSSTEVGSDT-Hyp-NH$_2$ (SEQ ID NO: 162)
[19CD]-isoGlu-RCNTATCATQRLAHFLQRSSF-Gly(Me)-A-Ile(Me)-LSSTEVGSNTP-NH$_2$ (SEQ ID NO: 163)
[19CD]-isoGlu-RCNTATCATQRLAHFLQRSSF-Gly(Me)-A-Ile(Me)-LSSTEVGSNTP-NH$_2$ (SEQ ID NO: 164)
[19CD]-isoGlu-RCPTATCATERLAHFLQRSSF-Gly(Me)-A-Ile(Me)-LSSTEVGSNT-Hyp-NH$_2$ (SEQ ID NO: 165)
[19CD]-isoGlu-RCPTATCATQRLAHFLQRSSF-Gly(Me)-A-Ile(Me)-LSSTEVGSNT-Hyp-NH$_2$ (SEQ ID NO: 166)
[19CD]-isoGlu-RCNTATCATQRLADFLQRSSF-Gly(Me)-A-Ile(Me)-LSSTEVGSNTP-NH$_2$ (SEQ ID NO: 167)
[19CD]-isoGlu-RCNTATCATERLADFLQRSSF-Gly(Me)-A-Ile(Me)-LSSTEVGSNTP-NH$_2$ (SEQ ID NO: 168)
[19CD]-isoGlu-RCPTATCATERLADFLQRSSF-Gly(Me)-A-Ile(Me)-LSSTEVGSNTP-NH$_2$ (SEQ ID NO: 169)
[19CD]-isoGlu-RCNTATCATERLADFLQRSSF-Gly(Me)-A-Ile(Me)-LSSTEVGSNT-Hyp-NH$_2$ (SEQ ID NO: 170)
[19CD]-isoGlu-RCNTATCATQRLAHFLQRSSF-Gly(Me)-A-Ile(Me)-LSSTEVGSST-Hyp-NH$_2$ (SEQ ID NO: 171)
[19CD]-isoGlu-RCPTATCATERLAHFLQRSSF-Gly(Me)-A-Ile(Me)-LSSTEVGSST-Hyp-NH$_2$ (SEQ ID NO: 172)
[19CD]-isoGlu-RCNTATCATQRLAHFLQRSSF-Gly(Me)-A-Ile(Me)-LSSTEVGSGT-Hyp-NH$_2$ (SEQ ID NO: 173)
[19CD]-isoGlu-RCPTATCATERLAHFLQRSSF-Gly(Me)-A-Ile(Me)-LSSTEVGSGT-Hyp-NH$_2$ (SEQ ID NO: 174)
[19CD]-isoGlu-RCNTATCATQRLAHFLQRSSF-Gly(Me)-A-Ile(Me)-LSSTEVGSTT-Hyp-NH$_2$ (SEQ ID NO: 175)
[19CD]-isoGlu-RCPTATCATERLAHFLQRSSF-Gly(Me)-A-Ile(Me)-LSSTEVGSTT-Hyp-NH$_2$ (SEQ ID NO: 176)
[19CD]-isoGlu-RCNTATCATQRLAHFLQRSSF-Gly(Me)-A-Ile(Me)-LSSTEVGS-Aad-T-Hyp-NH$_2$ (SEQ ID NO: 177)
[19CD]-isoGlu-RCPTATCATERLAHFLQRSSF-Gly(Me)-A-Ile(Me)-LSSTEVGS-Aad-T-Hyp-NH$_2$

```
                                                                (SEQ ID NO: 178)
[19CD]-isoGlu-RCGTATCATERLAHFLQRF-Gly(Me)-A-Ile(Me)-LSSTEVGSNT-Hyp-NH2

(SEQ ID NO: 179)
[19CD]-isoGlu-RCGTATCATERLAHFLQRSSF-Gly(Me)-A-Ile(Me)-LSSTEVGSNTP-NH2

(SEQ ID NO: 180)
[19CD]-isoGlu-RCNTATCATQRLAHFLQRF-Gly(Me)-A-Ile(Me)-LSSTEVGSGT-Hyp-NH2

(SEQ ID NO: 181)
[19CD]-isoGlu-RCNTATCATQRLADFLQRSSF-Gly(Me)-A-Ile(Me)-LSSTEVGSGTP-NH2

(SEQ ID NO: 182)
[19CD]-isoGlu-RCNTATCATQRLADFLQRSSF-Gly(Me)-A-Ile(Me)-LSSTEVGSGT-Hyp-NH2

(SEQ ID NO: 183)
[19CD]-isoGlu-RCNTATCATQRLADFLQRSSF-Gly(Me)-A-Ile(Me)-LSSTEVGSTTP-NH2

(SEQ ID NO: 184)
[19CD]-isoGlu-RCNTATCATQRLADFLQRSSF-Gly(Me)-A-Ile(Me)-LSSTEVGSTT-Hyp-NH2

(SEQ ID NO: 185)
[19CD]-isoGlu-RCNTATCATQRLAHFLERSSF-Gly(Me)-A-Ile(Me)-LSSTEVGSSTP-NH2

(SEQ ID NO: 186)
[19CD]-isoGlu-RCNTATCATQRLAHFLQRSSF-Gly(Me)-A-Ile(Me)-LSSTEVGSSTP-NH2

(SEQ ID NO: 187)
[19CD]-isoGlu-RCNTATCATQRLA-Aad-FLQRSSF-Gly(Me)-A-Ile(Me)-LSSTEVGSNT-Hyp-NH2

(SEQ ID NO: 188)
[19CD]-isoGlu-RCNTATCATQRLA-Aad-FLQRSSF-Gly(Me)-A-Ile(Me)-LSSTEVGSST-Hyp-NH2

(SEQ ID NO: 189)
[19CD]-isoGlu-RCQTATCATDRLAHFLQRSSF-Gly(Me)-A-Ile(Me)-LSSTEVGSNT-Hyp-NH2

(SEQ ID NO: 190)
[19CD]-isoGlu-RCQTATCATDRLA-Aad-FLQRSSF-Gly(Me)-A-Ile(Me)-LSSTEVGSNT-Hyp-NH2

(SEQ ID NO: 191)
[19CD]-isoGlu-RCQTATCATERLAHFLQRSSF-Gly(Me)-A-Ile(Me)-LSSTEVGSGT-Hyp-NH2

(SEQ ID NO: 192)
[19CD]-isoGlu-RCQTATCATDRLAHFLQRSSF-Gly(Me)-A-Ile(Me)-LSSTEVGSGT-Hyp-NH2

(SEQ ID NO: 193)
[19CD]-isoGlu-RCQTATCATDRLAHFLQRSSF-Gly(Me)-A-Ile(Me)-LSSTEVGSNTP-NH2

(SEQ ID NO: 194)
[19CD]-isoGlu-RCQTATCATERLA-Aad-FLQRSSF-Gly(Me)-A-Ile(Me)-LSSTEVGSNTP-NH2

(SEQ ID NO: 195)
[19CD]-isoGlu-RCQTATCATERLA-Aad-FLQRSSF-Gly(Me)-A-Ile(Me)-LSSTEVGSGTP-NH2

(SEQ ID NO: 196)
[19CD]-isoGlu-RCQTATCATDRLA-Aad-FLQRF-Gly(Me)-A-Ile(Me)-LSSTEVGSNT-Hyp-NH2

(SEQ ID NO: 197)
[19CD]-isoGlu-RCQTATCATERLAHFLQRF-Gly(Me)-A-Ile(Me)-LSSTEVGSNTP-NH2
``` wherein [19CD] represents [19-carboxynonadecanoyl];
and pharmaceutically acceptable salts and solvates thereof.

Any of the sequences or compounds described above may possess an intramolecular disulphide bridge formed between the cysteine residues present at positions 2 and 7 of the amino acid sequence (numbered from N- to C-terminus, and corresponding to the cysteine residues present at positions 2 and 7 of human amylin). In general, it may be desirable that compounds possess such a disulphide bridge at the time of administration to a subject, but it will be understood that the invention extends to compounds having the specified amino acid sequences before formation of the disulphide. The presence of the disulphide may be indicated by parentheses ( ) following each relevant cysteine residue in the sequence. All of the generic and specific formulae provided above should be construed accordingly to include this possibility. Thus, for example, Formulae I, II and III may be shown as follows:

(I)
```
                                                    (SEQ ID NO: 3)
Arg-Cys( )-X3-Thr-Ala-Thr-Cys( )-Ala-Thr-X10-Arg-

Leu-Ala-X14-Phe-Leu-X17-Arg-X19-X20-Phe-Gly(Me)-

Ala-Ile(Me)-Leu-Ser-Ser-Thr-X31-Val-Gly-Ser-X35-

Thr-X37;
```

(II)

(SEQ ID NO: 4)
Arg-Cys( )-X3-Thr-Ala-Thr-Cys( )-Ala-Thr-X10-Arg-Leu-Ala-X14-Phe-Leu-X17-Arg-X19-X20-Phe-Gly(Me)-Ala-Ile(Me)-Leu-Ser-Ser-Thr-Glu-Val-Gly-Ser-X35-Thr-X37;
and (III)

(SEQ ID NO: 5)
Arg-Cys( )-X3-Thr-Ala-Thr-Cys( )-Ala-Thr-X10-Arg-Leu-Ala-X14-Phe-Leu-X17-Arg-X19-X20-Phe-Gly(Me)-Ala-Ile(Me)-Leu-Ser-Ser-Thr-Glu-Val-Gly-Ser-X35-Thr-X37;

while the specific compounds listed above may be designated as follows:

[19CD]-isoGlu-R-C( )-NTAT-C( )-ATQRLADFLHRSSF-Gly(Me)-A-Ile(Me)-LSSTEVGSETP-NH$_2$
(Compd. 1) (SEQ ID NO: 102)

[19CD]-isoGlu-R-C( )-NTAT-C( )-ATQRLAHFLHRSSF-Gly(Me)-A-Ile(Me)-LSSTEVGSETP-NH$_2$
(Compd. 2) (SEQ ID NO: 103)

[19CD]-isoGlu-R-C( )-NTAT-C( )-ATQRLANFLHRSSF-Gly(Me)-A-Ile(Me)-LSSTEVGSETP-NH$_2$
(Compd. 3) (SEQ ID NO: 104)

[19CD]-isoGlu-R-C( )-NTAT-C( )-ATQRLADFLHRSSNNF-Gly(Me)-A-Ile(Me)-LSSTNVGSNT-Apr-NH$_2$
(Compd. 4) (SEQ ID NO: 105)

[19CD]-isoGlu-R-C( )-NTAT-C( )-ATQRLAHFLHRSSNNF-Gly(Me)-A-Ile(Me)-LSSTNVGSNT-Apr-NH$_2$
(Compd. 5) (SEQ ID NO: 106)

[19CD]-isoGlu-R-C( )-GTAT-C( )-ATERLAHFLNRSSF-Gly(Me)-A-Ile(Me)-LSSTEVGSNT-Hyp-NH$_2$
(Compd. 6) (SEQ ID NO: 107)

[19CD]-isoGlu-R-C( )-GTAT-C( )-ATERLAHFLQRSSF-Gly(Me)-A-Ile(Me)-LSSTEVGSNT-Hyp-NH$_2$
(Compd. 7) (SEQ ID NO: 108)

[19CD]-isoGlu-R-C( )-GTAT-C( )-ATERLAHFLERSSF-Gly(Me)-A-Ile(Me)-LSSTEVGSNT-Hyp-NH$_2$
(Compd. 8) (SEQ ID NO: 109)

[19CD]-isoGlu-R-C( )-GTAT-C( )-ATERLAHFLTRSSF-Gly(Me)-A-Ile(Me)-LSSTEVGSST-Hyp-NH$_2$
(Compd. 9) (SEQ ID NO: 110)

[19CD]-isoGlu-R-C( )-GTAT-C( )-ATERLAHFLTRSSF-Gly(Me)-A-Ile(Me)-LSSTEVGSFT-Hyp-NH$_2$
(Compd. 10) (SEQ ID NO: 111)

[19CD]-isoGlu-R-C( )-GTAT-C( )-ATERLAHFLTRSSF-Gly(Me)-A-Ile(Me)-LSSTEVGS-Orn-T-Hyp-NH$_2$
(Compd. 11) (SEQ ID NO: 112)

[19CD]-isoGlu-R-C( )-GTAT-C( )-ATERLAHFLTRSSF-Gly(Me)-A-Ile(Me)-LSSTEVGS-Aad-T-Hyp-NH$_2$
(Compd. 12) (SEQ ID NO: 113)

[19CD]-isoGlu-R-C( )-GTAT-C( )-ATERLAHFLTRSSF-Gly(Me)-A-Ile(Me)-LSSTEVGSGT-Hyp-NH$_2$
(Compd. 13) (SEQ ID NO: 114)

[19CD]-isoGlu-R-C( )-NTAT-C( )-ATQRLAHFLHRF-Gly(Me)-A-Ile(Me)-LSSTEVGSETP-NH$_2$
(Compd. 14) (SEQ ID NO: 115)

[19CD]-isoGlu-R-C( )-GTAT-C( )-ATERLAHFLHRSSF-Gly(Me)-A-Ile(Me)-LSSTEVGSNTP-NH$_2$
(Compd. 15) (SEQ ID NO: 116)

[19CD]-isoGlu-R-C( )-NTAT-C( )-ATQRLAHFLHRSSF-Gly(Me)-A-Ile(Me)-LSSTEVGSNTP-NH$_2$
(Compd. 16) (SEQ ID NO: 117)

[19CD]-isoGlu-R-C( )-GTAT-C( )-ATERLANFLVRSSF-Gly(Me)-A-Ile(Me)-LSSTEVGSNT-Hyp-NH$_2$
(Compd. 17) (SEQ ID NO: 118)

[19CD]-isoGlu-R-C( )-GTAT-C( )-ATERLAHFLTRSSF-Gly(Me)-A-Ile(Me)-LSSTEVGSNT-Hyp-NH$_2$
(Compd. 18) (SEQ ID NO: 119)

[19CD]-isoGlu-R-C( )-GTAT-C( )-ATERLAHFLKRSSF-Gly(Me)-A-Ile(Me)-LSSTEVGSNT-Hyp-NH$_2$
(Compd. 19) (SEQ ID NO: 120)

[19CD]-isoGlu-R-C( )-NTAT-C( )-ATQRLAHFLHRSVF-Gly(Me)-A-Ile(Me)-LSSTEVGSETP-NH$_2$
(Compd. 20) (SEQ ID NO: 121)

[19CD]-isoGlu-R-C( )-NTAT-C( )-ATQRLAHFLHRVSF-Gly(Me)-A-Ile(Me)-LSSTEVGSETP-NH$_2$
(Compd. 21) (SEQ ID NO: 122)

[19CD]-isoGlu-R-C( )-GTAT-C( )-ATERLAHFLVRSSF-Gly(Me)-A-Ile(Me)-LSSTEVGSETP-NH$_2$
(Compd. 22) (SEQ ID NO: 123)

-continued

[19CD]-isoGlu-R-C( )-PTAT-C( )-ATDRLAHFLVRSSF-Gly(Me)-A-Ile(Me)-LSSTDVGSDTP-NH<sub>2</sub>
(Compd. 23) (SEQ ID NO: 124)

[19CD]-isoGlu-R-C( )-NTAT-C( )-ATQRLAHFLVRSSF-Gly(Me)-A-Ile(Me)-LSSTEVGSETP-NH<sub>2</sub>
(Compd. 24) (SEQ ID NO: 125)

[19CD]-isoGlu-R-C( )-PTAT-C( )-ATDRLAHFLHRSSF-Gly(Me)-A-Ile(Me)-LSSTDVGSNTP-NH<sub>2</sub>
(Compd. 25) (SEQ ID NO: 126)

[19CD]-isoGlu-R-C( )-GTAT-C( )-ATERLAHFLHRSSF-Gly(Me)-A-Ile(Me)-LSSTEVGSETP-NH<sub>2</sub>
(Compd. 26) (SEQ ID NO: 127)

[19CD]-isoGlu-R-C( )-PTAT-C( )-ATDRLANFLHRSSF-Gly(Me)-A-Ile(Me)-LSSTDVGSDTP-NH<sub>2</sub>
(Compd. 27) (SEQ ID NO: 128)

[19CD]-isoGlu-R-C( )-GTAT-C( )-ATERLAHFLQRSSF-Gly(Me)-A-Ile(Me)-LSSTEVGSST-Hyp-NH<sub>2</sub>
(Compd. 28) (SEQ ID NO: 129)

[19CD]-isoGlu-R-C( )-GTAT-C( )-ATERLAHFLNRSSF-Gly(Me)-A-Ile(Me)-LSSTEVGSST-Hyp-NH<sub>2</sub>
(Compd. 29) (SEQ ID NO: 130)

[19CD]-isoGlu-R-C( )-GTAT-C( )-ATERLAHFLHRSSF-Gly(Me)-A-Ile(Me)-LSSTEVGSST-Hyp-NH<sub>2</sub>
(Compd. 30) (SEQ ID NO: 131)

[19CD]-isoGlu-R-C( )-GTAT-C( )-ATERLAHFLVRSSF-Gly(Me)-A-Ile(Me)-LSSTEVGSST-Hyp-NH<sub>2</sub>
(Compd. 31) (SEQ ID NO: 132)

[19CD]-isoGlu-R-C( )-GTAT-C( )-ATERLAHFLQRSSF-Gly(Me)-A-Ile(Me)-LSSTEVGSFT-Hyp-NH<sub>2</sub>
(Compd. 32) (SEQ ID NO: 133)

[19CD]-isoGlu-R-C( )-GTAT-C( )-ATERLAHFLNRSSF-Gly(Me)-A-Ile(Me)-LSSTEVGSFT-Hyp-NH<sub>2</sub>
(Compd. 33)(SEQ ID NO: 134)

[19CD]-isoGlu-R-C( )-GTAT-C( )-ATERLAHFLQRSSF-Gly(Me)-A-Ile(Me)-LSSTEVGSSTP-NH<sub>2</sub>
(Compd. 34) (SEQ ID NO: 135)

[19CD]-isoGlu-R-C( )-GTAT-C( )-ATERLAHFLNRSSF-Gly(Me)-A-Ile(Me)-LSSTEVGSSTP-NH<sub>2</sub>
(Compd. 35) (SEQ ID NO: 136)

[19CD]-isoGlu-R-C( )-GTAT-C( )-ATERLAHFLERSSF-Gly(Me)-A-Ile(Me)-LSSTEVGSSTP-NH<sub>2</sub>
(Compd. 36) (SEQ ID NO: 137)

[19CD]-isoGlu-R-C( )-GTAT-C( )-ATERLAHFLHRSSF-Gly(Me)-A-Ile(Me)-LSSTEVGSSTP-NH<sub>2</sub>
(Compd. 37) (SEQ ID NO: 138)

[19CD]-isoGlu-R-C( )-GTAT-C( )-ATERLAHFLVRSSF-Gly(Me)-A-Ile(Me)-LSSTEVGSSTP-NH<sub>2</sub>
(Compd. 38) (SEQ ID NO: 139)

[19CD]-isoGlu-R-C( )-GTAT-C( )-ATERLAHFLQRSSF-Gly(Me)-A-Ile(Me)-LSSTEVGSFTP-NH<sub>2</sub>
(Compd. 39) (SEQ ID NO: 140)

[19CD]-isoGlu-R-C( )-GTAT-C( )-ATERLAHFLNRSSF-Gly(Me)-A-Ile(Me)-LSSTEVGSFTP-NH<sub>2</sub>
(Compd. 40) (SEQ ID NO: 141)

[19CD]-isoGlu-R-C( )-GTAT-C( )-ATERLADFLTRSSF-Gly(Me)-A-Ile(Me)-LSSTEVGSST-Hyp-NH<sub>2</sub>
(Compd. 41) (SEQ ID NO: 142)

[19CD]-isoGlu-R-C( )-GTAT-C( )-ATERLADFLTRSSF-Gly(Me)-A-Ile(Me)-LSSTEVGSFT-Hyp-NH<sub>2</sub>
(Compd. 42) (SEQ ID NO: 143)

[19CD]-isoGlu-R-C( )-GTAT-C( )-ATERLA-Aad-FLTRSSF-Gly(Me)-A-Ile(Me)-LSSTEVGSST-Hyp-NH<sub>2</sub>
(Compd. 43) (SEQ ID NO: 144)

[19CD]-isoGlu-R-C( )-GTAT-C( )-ATERLA-Aad-FLTRSSF-Gly(Me)-A-Ile(Me)-LSSTEVGS-Orn-T-Hyp-NH<sub>2</sub>
(Compd. 44) (SEQ ID NO: 145)

[19CD]-isoGlu-R-C( )-GTAT-C( )-ATERLAHFLTRSSF-Gly(Me)-A-Ile(Me)-LSSTEVGSST-Apr-NH<sub>2</sub>
(Compd. 45) (SEQ ID NO: 146)

[19CD]-isoGlu-R-C( )-GTAT-C( )-ATERLAHFLTRSSF-Gly(Me)-A-Ile(Me)-LSSTEVGSSTP-NH<sub>2</sub>
(Compd. 46) (SEQ ID NO: 147)

[19CD]-isoGlu-R-C( )-GTAT-C( )-ATERLAHFLTRSSF-Gly(Me)-A-Ile(Me)-LSSTEVGS-Orn-TP-NH<sub>2</sub>
(Compd. 47) (SEQ ID NO: 148)

[19CD]-isoGlu-R-C( )-GTAT-C( )-ATERLAHFLTRSSF-Gly(Me)-A-Ile(Me)-LSSTEVGSTT-Hyp-NH<sub>2</sub>
(Compd. 48) (SEQ ID NO: 149)

[19CD]-isoGlu-R-C( )-NTAT-C( )-ATQRLADFLQRSSF-Gly(Me)-A-Ile(Me)-LSSTEVGSNT-Hyp-NH<sub>2</sub>
(Compd. 49) (SEQ ID NO: 150)

-continued

[19CD]-isoGlu-R-C( )-NTAT-C( )-ATQRLAHFL-Aad-RSSF-Gly(Me)-A-Ile(Me)-LSSTEVGSNT-Hyp-NH$_2$
(Compd. 50) (SEQ ID NO: 151)

[19CD]-isoGlu-R-C( )-GTAT-C( )-ATERLAHFLQRSSF-Gly(Me)-A-Ile(Me)-LSSTEVGS-Orn-T-Hyp-NH$_2$
(Compd. 51) (SEQ ID NO: 152)

[19CD]-isoGlu-R-C( )-GTAT-C( )-ATERLAHFLQRSSF-Gly(Me)-A-Ile(Me)-LSSTEVGSGT-Hyp-NH$_2$
(Compd. 52) (SEQ ID NO: 153)

[19CD]-isoGlu-R-C( )-GTAT-C( )-ATERLAHFLQRSSF-Gly(Me)-A-Ile(Me)-LSSTEVGS-Aad-T-Hyp-NH$_2$
(Compd. 53) (SEQ ID NO: 154)

[19CD]-isoGlu-R-C( )-GTAT-C( )-ATERLADFLQRSSF-Gly(Me)-A-Ile(Me)-LSSTEVGSNT-Hyp-NH$_2$
(Compd. 54) (SEQ ID NO: 155)

[19CD]-isoGlu-R-C( )-GTAT-C( )-ATERLA-Aad-FLQRSSF-Gly(Me)-A-Ile(Me)-LSSTEVGSNT-Hyp-NH$_2$
(Compd. 55) (SEQ ID NO: 156)

[19CD]-isoGlu-R-C( )-NTAT-C( )-ATERLAHFLQRSSF-Gly(Me)-A-Ile(Me)-LSSTEVGSNT-Hyp-NH$_2$
(Compd. 56) (SEQ ID NO: 157)

[19CD]-isoGlu-R-C( )-QTAT-C( )-ATERLAHFLQRSSF-Gly(Me)-A-Ile(Me)-LSSTEVGSNT-Hyp-NH$_2$
(Compd. 57) (SEQ ID NO: 158)

[19CD]-isoGlu-R-C( )-NTAT-C( )-ATQRLAHFLQRSSF-Gly(Me)-A-Ile(Me)-LSSTEVGSNT-Hyp-NH$_2$
(Compd. 58) (SEQ ID NO: 159)

[19CD]-isoGlu-R-C( )-PTAT-C( )-ATDRLAHFLQRSSF-Gly(Me)-A-Ile(Me)-LSSTDVGSNT-Hyp-NH$_2$
(Compd. 59) (SEQ ID NO: 160)

[19CD]-isoGlu-R-C( )-NTAT-C( )-ATERLAHFLQRSSF-Gly(Me)-A-Ile(Me)-LSSTEVGSDT-Hyp-NH$_2$
(Compd. 60) (SEQ ID NO: 161)

[19CD]-isoGlu-R-C( )-NTAT-C( )-ATQRLAHFLQRSSF-Gly(Me)-A-Ile(Me)-LSSTEVGSNTP-NH$_2$
(Compd. 61) (SEQ ID NO: 162)

[19CD]-isoGlu-R-C( )-NTAT-C( )-ATERLAHFLQRSSF-Gly(Me)-A-Ile(Me)-LSSTEVGSNTP-NH$_2$
(Compd. 62) (SEQ ID NO: 163)

[19CD]-isoGlu-R-C( )-PTAT-C( )-ATERLAHFLQRSSF-Gly(Me)-A-Ile(Me)-LSSTEVGSNT-Hyp-NH$_2$
(Compd. 63) (SEQ ID NO: 164)

[19CD]-isoGlu-R-C( )-PTAT-C( )-ATQRLAHFLQRSSF-Gly(Me)-A-Ile(Me)-LSSTEVGSNT-Hyp-NH$_2$
(Compd. 64) (SEQ ID NO: 165)

[19CD]-isoGlu-R-C( )-NTAT-C( )-ATQRLADFLQRSSF-Gly(Me)-A-Ile(Me)-LSSTEVGSNTP-NH$_2$
(Compd. 65) (SEQ ID NO: 166)

[19CD]-isoGlu-R-C( )-NTAT-C( )-ATERLADFLQRSSF-Gly(Me)-A-Ile(Me)-LSSTEVGSNTP-NH$_2$
(Compd. 66) (SEQ ID NO: 167)

[19CD]-isoGlu-R-C( )-PTAT-C( )-ATERLADFLQRSSF-Gly(Me)-A-Ile(Me)-LSSTEVGSNTP-NH$_2$
(Compd. 67) (SEQ ID NO: 168)

[19CD]-isoGlu-R-C( )-NTAT-C( )-ATERLADFLQRSSF-Gly(Me)-A-Ile(Me)-LSSTEVGSNT-Hyp-NH$_2$
(Compd. 68) (SEQ ID NO: 169)

[19CD]-isoGlu-R-C( )-NTAT-C( )-ATQRLAHFLQRSSF-Gly(Me)-A-Ile(Me)-LSSTEVGSST-Hyp-NH$_2$
(Compd. 69) (SEQ ID NO: 170)

[19CD]-isoGlu-R-C( )-PTAT-C( )-ATERLAHFLQRSSF-Gly(Me)-A-Ile(Me)-LSSTEVGSST-Hyp-NH$_2$
(Compd. 70) (SEQ ID NO: 171)

[19CD]-isoGlu-R-C( )-NTAT-C( )-ATQRLAHFLQRSSF-Gly(Me)-A-Ile(Me)-LSSTEVGSGT-Hyp-NH$_2$
(Compd. 71) (SEQ ID NO: 172)

[19CD]-isoGlu-R-C( )-PTAT-C( )-ATERLAHFLQRSSF-Gly(Me)-A-Ile(Me)-LSSTEVGSGT-Hyp-NH$_2$
(Compd. 72) (SEQ ID NO: 173)

[19CD]-isoGlu-R-C( )-NTAT-C( )-ATQRLAHFLQRSSF-Gly(Me)-A-Ile(Me)-LSSTEVGSTT-Hyp-NH$_2$
(Compd. 73) (SEQ ID NO: 174)

[19CD]-isoGlu-R-C( )-PTAT-C( )-ATERLAHFLQRSSF-Gly(Me)-A-Ile(Me)-LSSTEVGSTT-Hyp-NH$_2$
(Compd. 74) (SEQ ID NO: 175)

[19CD]-isoGlu-R-C( )-NTAT-C( )-ATQRLAFIFLQRSSF-Gly(Me)-A-Ile(Me)-LSSTEVGS-Aad-T-Hyp-NH$_2$
(Compd. 75) (SEQ ID NO: 176)

[19CD]-isoGlu-R-C( )-PTAT-C( )-ATERLAHFLQRSSF-Gly(Me)-A-Ile(Me)-LSSTEVGS-Aad-T-Hyp-NH$_2$
(Compd. 76) (SEQ ID NO: 177)

[19CD]-isoGlu-R-C( ),GTAT-C( )-ATERLAHFLQRF-Gly(Me)-A-Ile(Me)-LSSTEVGSNT-Hyp-NH$_2$
(Compd. 77) (SEQ ID NO: 178)

[19CD]-isoGlu-R-C( )-GTAT-C( )-ATERLAHFLQRSSF-Gly(Me)-A-Ile(Me)-LSSTEVGSNTP-NH$_2$
(Compd. 78) (SEQ ID NO: 179)

[19CD]-isoGlu-R-C( )-NTAT-C( )-ATQRLAHFLQRF-Gly(Me)-A-Ile(Me)-LSSTEVGSGT-Hyp-NH$_2$
(Compd. 79) (SEQ ID NO: 180)

[19CD]-isoGlu-R-C( )-NTAT-C( )-ATQRLADFLQRSSF-Gly(Me)-A-Ile(Me)-LSSTEVGSGTP-NH$_2$
(Compd. 80) (SEQ ID NO: 181)

[19CD]-isoGlu-R-C( )-NTAT-C( )-ATQRLADFLQRSSF-Gly(Me)-A-Ile(Me)-LSSTEVGSGT-Hyp-NH$_2$
(Compd. 81) (SEQ ID NO: 182)

[19CD]-isoGlu-R-C( )-NTAT-C( )-ATQRLADFLQRSSF-Gly(Me)-A-Ile(Me)-LSSTEVGSTTP-NH$_2$
(Compd. 82) (SEQ ID NO: 183)

[19CD]-isoGlu-R-C( )-NTAT-C( )-ATQRLADFLQRSSF-Gly(Me)-A-Ile(Me)-LSSTEVGSTT-Hyp-NH$_2$
(Compd. 83) (SEQ ID NO: 184)

[19CD]-isoGlu-R-C( )-NTAT-C( )-ATQRLAHFLERSSF-Gly(Me)-A-Ile(Me)-LSSTEVGSSTP-NH$_2$
(Compd. 84) (SEQ ID NO: 185)

[19CD]-isoGlu-R-C( )-NTAT-C( )-ATQRLAHFLQRSSF-Gly(Me)-A-Ile(Me)-LSSTEVGSSTP-NH$_2$
(Compd. 85) (SEQ ID NO: 186)

[19CD]-isoGlu-R-C( )-NTAT-C( )-ATQRLA-Aad-FLQRSSF-Gly(Me)-A-Ile(Me)-LSSTEVGSNT-Hyp-NH$_2$
(Compd. 86) (SEQ ID NO: 187)

[19CD]-isoGlu-R-C( )-NTAT-C( )-ATQRLA-Aad-FLQRSSF-Gly(Me)-A-Ile(Me)-LSSTEVGSST-Hyp-NH$_2$
(Compd. 87) (SEQ ID NO: 188)

[19CD]-isoGlu-R-C( )-QTAT-C( )-ATDRLAHFLQRSSF-Gly(Me)-A-Ile(Me)-LSSTEVGSNT-Hyp-NH$_2$
(Compd. 88) (SEQ ID NO: 189)

[19CD]-isoGlu-R-C( )-QTAT-C( )-ATDRLA-Aad-FLQRSSF-Gly(Me)-A-Ile(Me)-LSSTEVGSNT-Hyp-NH$_2$
(Compd. 89) (SEQ ID NO: 190)

[19CD]-isoGlu-R-C( )-QTAT-C( )-ATERLAHFLQRSSF-Gly(Me)-A-Ile(Me)-LSSTEVGSGT-Hyp-NH$_2$
(Compd. 90) (SEQ ID NO: 191)

[19CD]-isoGlu-R-C( )-QTAT-C( )-ATDRLAHFLQRSSF-Gly(Me)-A-Ile(Me)-LSSTEVGSGT-Hyp-NH$_2$
(Compd. 91) (SEQ ID NO: 192)

[19CD]-isoGlu-R-C( )-QTAT-C( )-ATDRLAHFLQRSSF-Gly(Me)-A-Ile(Me)-LSSTEVGSNTP-NH$_2$
(Compd. 92) (SEQ ID NO: 193)

[19CD]-isoGlu-R-C( )-QTAT-C( )-ATERLA-Aad-FLQRSSF-Gly(Me)-A-Ile(Me)-LSSTEVGSNTP-NH$_2$
(Compd. 93) (SEQ ID NO: 194)

[19CD]-isoGlu-R-C( )-QTAT-C( )-ATERLA-Aad-FLQRSSF-Gly(Me)-A-Ile(Me)-LSSTEVGSGTP-NH$_2$
(Compd. 94) (SEQ ID NO: 195)

[19CD]-isoGlu-R-C( )-QTAT-C( )-ATDRLA-Aad-FLQRF-Gly(Me)-A-Ile(Me)-LSSTEVGSNT-Hyp-NH$_2$
(Compd. 95) (SEQ ID NO: 196)

[19CD]-isoGlu-R-C( )-QTAT-C( )-ATERLAHFLQRF-Gly(Me)-A-Ile(Me)-LSSTEVGSNTP-NH$_2$
(Compd. 96) (SEQ ID NO: 197)

wherein [19CD] represents [19-carboxynonadecanoyl];
and pharmaceutically acceptable salts and solvates thereof. wherein [19CD] represents [19-carboxynonadecanoyl]; and pharmaceutically acceptable salts and solvates thereof.

In certain embodiments, the amylin analogue of the invention is not a compound having the formula:

$$R^1-Z-R^2$$

wherein
$R^1$ is hydrogen, $C_{1-4}$ acyl, benzoyl or $C_{1-4}$ alkyl, or a half-life extending moiety M, wherein M is optionally linked to Z via a linker moiety L;
$R^2$ is OH or $NHR^3$, wherein $R^3$ is hydrogen or $C_{1-3}$-alkyl; and
Z is an amino acid sequence selected from the group consisting of:

RCNTATCATQRLADFLHRSSF-Gly(Me)-A-Ile(Me)-LSSTEVGSETP (SEQ ID NO: 99)

RCNTATCATQRLAHFLHRSSF-Gly(Me)-A-IIe(Me)-LSSTEVGSETP (SEQ ID NO: 6)

RCNTATCATORLANFLHRSSF-Gly(Me)-A-Ile(Me)-LSSTEVGSETP (SEQ ID NO: 7)

RCNTATCATQRLADFLHRSSNNF-Gly(Me)-A-Ile(Me)-LSSTNVGSNT-Apr (SEQ ID NO: 100)

RCNTATCATQRLAHFLHRSSNNF-Gly(Me)-A-Ile(Me)-LSSTNVGSNT-Apr (SEQ ID NO: 101)

RCGTATCATERLAHFLNRSSF-Gly(Me)-A-Ile(Me)-LSSTEVGSNT-Hyp (SEQ ID NO: 8)

```
RCGTATCATERLAHFLQRSSF-Gly(Me)-A-Ile(Me)-
LSSTEVGSNT-Hyp (SEQ ID NO: 9)

RCGTATCATERLAHFLERSSF-Gly(Me)-A-Ile(Me)-
LSSTEVGSNT-Hyp (SEQ ID NO: 10)

RCGTATCATERLAHFLTRSSF-Gly(Me)-A-Ile(Me)-
LSSTEVGSST-Hyp (SEQ ID NO: 11)

RCGTATCATERLAHFLTRSSF-Gly(Me)-A-Ile(Me)-
LSSTEVGSFT-Hyp (SEQ ID NO: 12)

RCGTATCATERLAHFLTRSSF-Gly(Me)-A-Ile(Me)-
LSSTEVGS-Orn-T-Hyp (SEQ ID NO: 13)

RCGTATCATERLAHFLTRSSF-Gly(Me)-A-Ile(Me)-
LSSTEVGS-Aad-T-Hyp (SEQ ID NO: 14)

RCGTATCATERLAHFLTRSSF-Gly(Me)-A-Ile(Me)-
LSSTEVGSGT-Hyp (SEQ ID NO: 15)

RCNTATCATQRLAHFLHRF-Gly(Me)-A-Ile(Me)-
LSSTEVGSETP (SEQ ID NO: 16)

RCGTATCATERLAHFLHRSSF-Gly(Me)-A-Ile(Me)-
LSSTEVGSNTP (SEQ ID NO: 17)

and

RCNTATCATORLAHFLHRSSF-Gly(Me)-A-Ile(Me)-
LSSTEVGSNTP (SEQ ID NO: 18)
``` or a pharmaceutically acceptable salt or solvate thereof.

For example, in such embodiments, the compound is not:

```
[19CD]-isoGlu-RCNTATCATQRLADFLHRSSF-Gly(Me)-
A-Ile(Me)-LSSTEVGSETP-NH2 (SEQ ID NO: 102)

[19CD]-isoGlu-RCNTATCATQRLAHFLHRSSF-Gly(Me)-
A-Ile(Me)-LSSTEVGSETP-NH2 (SEQ ID NO: 103)

[19CD]-isoGlu-RCNTATCATQRLANFLHRSSF-Gly(Me)-
A-Ile(Me)-LSSTEVGSETP-NH2 (SEQ ID NO: 104)

[19CD]-isoGlu-RCNTATCATQRLADFLHRSSNNF-Gly(Me)-
A-Ile(Me)-LSSTNVGSNT-Apr-NH2 (SEQ ID NO: 105)

[19CD]-isoGlu-RCNTATCATQRLAHFLHRSSNNF-Gly(Me)-
A-Ile(Me)-LSSTNVGSNT-Apr-NH2 (SEQ ID NO: 106)

[19CD]-isoGlu-RCGTATCATERLAHFLNRSSF-Gly(Me)-
A-Ile(Me)-LSSTEVGSNT-Hyp-NH2 (SEQ ID NO: 107)

[19CD]-isoGlu-RCGTATCATERLAHFLQRSSF-Gly(Me)-
A-Ile(Me)-LSSTEVGSNT-Hyp-NH2 (SEQ ID NO: 108)

[19CD]-isoGlu-RCGTATCATERLAHFLERSSF-Gly(Me)-
A-Ile(Me)-LSSTEVGSNT-Hyp-NH2 (SEQ ID NO: 109)

[19CD]-soGlu-RCGTATCATERLAHFLTRSSF-Gly(Me)-
A-Ile(Me)-LSSTEVGSST-Hyp-NH2 (SEQ ID NO: 110)

[19CD]-isoGlu-RCGTATCATERLAHFLTRSSF-Gly(Me)-
A-Ile(Me)-LSSTEVGSFT-Hyp-NH2 (SEQ ID NO: 111)

[19CD]-isoGlu-RCGTATCATERLAHFLTRSSF-Gly(Me)-
A-Ile(Me)-LSSTEVGS-Orn-T-Hyp-NH2 (SEQ ID
NO: 112)

[19CD]-isoGlu-RCGTATCATERLAHFLTRSSF-Gly(Me)-
A-Ile(Me)-LSSTEVGS-Aad-T-Hyp-NH2 (SEQ ID
NO: 113)

[19CD]-isoGlu-RCGTATCATERLAHFLTRSSF-Gly(Me)-
A-Ile(Me)-LSSTEVGSGT-Hyp-NH2 (SEQ ID NO: 114)

[19CD]-isoGlu-RCNTATCATQRLAHFLHRF-Gly(Me)-
A-Ile(Me)-LSSTEVGSETP-NH2 (SEQ ID NO: 115)

[19CD]-isoGlu-RCGTATCATERLAHFLHRSSF-Gly(Me)-
A-Ile(Me)-LSSTEVGSNTP-NH2 (SEQ ID NO: 116)
``` or

```
[19CD]-isoGlu-RCNTATCATQRLAHFLHRSSF-Gly(Me)-
A-Ile(Me)-LSSTEVGSNTP-NH2; (SEQ ID NO: 117)
```

(wherein [19CD] represents [19-carboxynonadecanoyl]) and pharmaceutically acceptable salts and solvates thereof; or any such compounds comprising an intramolecular disulphide bridge formed between the cysteine residues present at positions 2 and 7 of the amino acid sequence.

The invention further provides a composition comprising an amylin analogue as described above. The composition may be a pharmaceutical composition, and may comprise a pharmaceutically acceptable carrier, excipient or vehicle.

The invention further provides a method for the synthesis of an amylin analogue as described above. The method may comprise the steps of synthesising the peptide by solid-phase or liquid-phase methodology, and optionally isolating and/or purifying the final product. The method may further comprise the step of forming a disulphide bond between the thiol groups of the cysteine side chains at positions 2 and 7.

The present invention further provides an amylin analogue of the invention for use in a method of medical treatment.

The amylin analogues are useful, inter alia, in the reduction of food intake, promotion of weight loss, and inhibition or reduction of weight gain. As a result, they may be used for treatment of a variety of conditions, diseases, or disorders in a subject, including, but not limited to, obesity and various obesity-related conditions, diseases, or disorders, such as diabetes (e.g. type 2 diabetes), hypertension, dyslipidemia, sleep apnea and cardiovascular disease. The subject may be affected by obesity accompanied by at least one weight-related co-morbid condition, such as diabetes (e.g. type 2 diabetes), hypertension, dyslipidemia, sleep apnea and cardiovascular disease. It will be understood that the amylin analogues may thus be administered to subjects affected by conditions characterised by inadequate control of appetite or otherwise over-feeding, such as binge-eating disorder and Prader-Willi syndrome. It will be clear that the analogues can be used for treatment of combinations of the conditions described.

Thus, the invention provides an amylin analogue of the invention for use in a method of treating, inhibiting or reducing weight gain, promoting weight loss and/or reducing excess body weight. Treatment may be achieved, for example, by control of appetite, feeding, food intake, calorie intake and/or energy expenditure.

The invention also provides an amylin analogue of the invention for use in a method of treating obesity as well as associated diseases, disorders and health conditions, including, but not limited to, morbid obesity, obesity prior to surgery, obesity-linked inflammation, obesity-linked gallbladder disease and obesity-induced sleep apnea and respiratory problems, degeneration of cartilage, osteoarthritis, and reproductive health complications of obesity or overweight such as infertility. The subject may be affected by obesity accompanied by at least one weight-related co-morbid condition, such as diabetes (e.g. type 2 diabetes), hypertension, dyslipidemia, sleep apnea and cardiovascular disease.

The invention also provides an amylin analogue of the invention for use in a method of prevention or treatment of Alzheimer's disease, diabetes, type 1 diabetes, type 2 diabetes, pre-diabetes, insulin resistance syndrome, impaired glucose tolerance (IGT), disease states associated with elevated blood glucose levels, metabolic disease including metabolic syndrome, hyperglycemia, hypertension, atherogenic dyslipidemia, hepatic steatosis ("fatty liver"; including non-alcoholic fatty liver disease (NAFLD), which itself includes non-alcoholic steatohepatitis (NASH)), kidney failure, arteriosclerosis (e.g. atherosclerosis), macrovascular disease, microvascular disease, diabetic heart (including diabetic cardiomyopathy and heart failure as a diabetic complication) coronary heart disease, peripheral artery disease or stroke, and combinations thereof.

The invention also provides an amylin analogue of the invention for use in a method of lowering circulating LDL levels and/or increasing HDL/LDL ratio.

Effects of amylin analogues on these conditions may be mediated in whole or in part via an effect on body weight, or may be independent thereof.

The invention further provides use of an amylin analogue of the invention in the manufacture of a medicament for treating, inhibiting or reducing weight gain, promoting weight loss and/or reducing excess body weight.

The invention also provides use of an amylin analogue of the invention in the manufacture of a medicament for treating obesity as well as associated diseases, disorders and health conditions, including, but not limited to, morbid obesity, obesity prior to surgery, obesity-linked inflammation, obesity-linked gallbladder disease and obesity-induced sleep apnea and respiratory problems, degeneration of cartilage, osteoarthritis, and reproductive health complications of obesity or overweight such as infertility. The subject may be affected by obesity accompanied by at least one weight-related co-morbid condition, such as diabetes (e.g. type 2 diabetes), hypertension, dyslipidemia, sleep apnea and cardiovascular disease.

The invention also provides use of an amylin analogue of the invention in the manufacture of a medicament for the prevention or treatment of Alzheimer's disease, diabetes, type 1 diabetes, type 2 diabetes, pre-diabetes, insulin resistance syndrome, impaired glucose tolerance (IGT), disease states associated with elevated blood glucose levels, metabolic disease including metabolic syndrome, hyperglycemia, hypertension, atherogenic dyslipidemia, hepatic steatosis ("fatty liver"; including non-alcoholic fatty liver disease (NAFLD), which itself includes non-alcoholic steatohepatitis (NASH)), kidney failure, arteriosclerosis (e.g. atherosclerosis), macrovascular disease, microvascular disease, diabetic heart (including diabetic cardiomyopathy and heart failure as a diabetic complication) coronary heart disease, peripheral artery disease or stroke, and combinations thereof.

The invention also provides use of an amylin analogue of the invention in the manufacture of a medicament for lowering circulating LDL levels and/or increasing HDL/LDL ratio.

The invention further provides a method of treating, inhibiting or reducing weight gain, promoting weight loss and/or reducing excess body weight in a subject, comprising administering a therapeutically effective amount of an amylin analogue of the invention to the subject.

The invention also provides a method of treating obesity as well as associated diseases, disorders and health conditions, including, but not limited to, morbid obesity, obesity prior to surgery, obesity-linked inflammation, obesity-linked gallbladder disease and obesity-induced sleep apnea and respiratory problems, degeneration of cartilage, osteoarthritis, and reproductive health complications of obesity or overweight such as infertility in a subject, comprising administering a therapeutically effective amount of an amylin analogue of the invention to the subject. The subject may be affected by obesity accompanied by at least one weight-related co-morbid condition, such as diabetes (e.g. type 2 diabetes), hypertension, dyslipidemia, sleep apnea and cardiovascular disease.

The invention also provides a method of prevention or treatment of Alzheimer's disease, diabetes, type 1 diabetes, type 2 diabetes, pre-diabetes, insulin resistance syndrome, impaired glucose tolerance (IGT), disease states associated with elevated blood glucose levels, metabolic disease including metabolic syndrome, hyperglycemia, hypertension, atherogenic dyslipidemia, hepatic steatosis ("fatty liver"; including non-alcoholic fatty liver disease (NAFLD), which itself includes non-alcoholic steatohepatitis (NASH)), kidney failure, arteriosclerosis (e.g. atherosclerosis), macrovascular disease, microvascular disease, diabetic heart (including diabetic cardiomyopathy and heart failure as a diabetic complication) coronary heart disease, peripheral artery disease or stroke, and combinations thereof, in a subject, comprising administering a therapeutically effective amount of an amylin analogue of the invention to the subject.

The invention further provides a method of lowering circulating LDL levels and/or increasing HDL/LDL ratio in a subject, comprising administering a therapeutically effective amount of an amylin analogue of the invention to the subject.

The invention further provides the use of an amylin analogue as described above in a method of cosmetic (i.e. non-therapeutic) weight loss. It will be understood that references to therapeutic uses of amylin analogues and methods comprising administration of amylin analogues may equally be taken to encompass uses and administration of such compositions.

Further aspects and embodiments of the present invention will become apparent from the disclosure below.

DETAILED DESCRIPTION OF THE INVENTION

Unless otherwise defined herein, scientific and technical terms used herein shall have the meanings that are commonly understood by those of ordinary skill in the art. Generally, nomenclature employed herein in connection with techniques of chemistry, molecular biology, cell and cancer biology, immunology, microbiology, pharmacology, and protein and nucleic acid chemistry, described herein, is that well known and commonly used in the art.

All publications, patents and published patent applications referred to in this application are specifically incorporated by reference herein. In case of conflict, the present specification, including its specific definitions, will control.

Throughout this specification, the word "comprise" or variations such as "comprises" or "comprising" will be understood to imply the inclusion of a stated integer or component, or of a stated group of integers or components, but not the exclusion of any other integer or component or group of integers or components.

The singular forms "a," "an," and "the" include the plurals unless the context clearly dictates otherwise.

The term "including" is used to mean "including but not limited to." "Including" and "including but not limited to" are used interchangeably.

The terms "patient", "subject," and "individual" may be used interchangeably and may refer to either a human or a non-human animal. Subjects are typically mammals, including humans, non-human primates (including great apes, Old World monkeys and New World monkeys), livestock animals (e.g., bovines, porcines), companion animals (e.g., canines, felines) and rodents (e.g., mice and rats).

As used herein, the term "pharmaceutically acceptable salt" is intended to indicate a salt which is not harmful to a patient or subject to which the salt in question is administered. It may suitably be a salt chosen, e.g., among acid addition salts and basic salts. Examples of acid addition salts include chloride salts, citrate salts and acetate salts. Examples of basic salts include salts where the cation is selected among alkali metal cations, such as sodium or potassium ions, alkaline earth metal cations, such as calcium or magnesium ions, as well as substituted ammonium ions, such as ions of the type $N(R^1)(R^2)(R^3)(R^4)^+$, where $R^1$, $R^2$, $R^3$ and $R^4$ independently will typically designate hydrogen, optionally substituted $C_{1-6}$-alkyl or optionally substituted $C_{2-6}$-alkenyl. Examples of relevant $C_{1-6}$-alkyl groups include methyl, ethyl, 1-propyl and 2-propyl groups. Examples of $C_{2-6}$-alkenyl groups of possible relevance include ethenyl, 1-propenyl and 2-propenyl. Other examples of pharmaceutically acceptable salts are described in "Remington's Pharmaceutical Sciences", 17th edition, Alfonso R. Gennaro (Ed.), Mark Publishing Company, Easton, Pa., USA, 1985 (and more recent editions thereof), in the "Encyclopaedia of Pharmaceutical Technology", $3^{rd}$ edition, James Swarbrick (Ed.), Informa Healthcare USA (Inc.), NY, USA, 2007, and in *J. Pharm. Sci.* 66: 2 (1977).

The term "solvate" in the context of the present invention refers to a complex of defined stoichiometry formed between a solute (in casu, a peptide or pharmaceutically acceptable salt thereof according to the invention) and a solvent. The solvent in this connection may, for example, be water, ethanol or another pharmaceutically acceptable—typically small-molecular—organic species, such as, but not limited to, acetic acid or lactic acid. When the solvent in question is water, such a solvate is normally referred to as a hydrate.

The term "agonist" as employed in the context of the invention refers to a substance that activates the receptor type in question, typically by binding to it (i.e. as a ligand).

Each embodiment of the invention described herein may be taken alone or in combination with one or more other embodiments of the invention.

Throughout the present specification, unless naturally occurring amino acids are referred to by their full name (e.g. alanine, arginine, etc.), they are designated by their conventional three-letter or single-letter abbreviations (e.g. Ala or A for alanine, Arg or R for arginine, etc.). In the case of certain less common or non-naturally occurring amino acids (i.e. amino acids other than the 20 encoded by the standard mammalian genetic code), unless they are referred to by their full name (e.g. sarcosine, ornithine, etc.), frequently employed three- or four-character codes are employed for residues thereof, including Orn (ornithine, i.e. 2,5-diaminopentanoic acid), Aib (α-aminoisobutyric acid), Dab (2,4-diaminobutanoic acid), Dap (2,3-diaminopropanoic acid), Har (homoarginine), γ-Glu (γ-glutamic acid), Gaba (γ-aminobutanoic acid), β-Ala (i.e. 3-aminopropanoic acid), 8Ado (8-amino-3,6-dioxaoctanoic acid).

Unless otherwise indicated, reference is made to the L-isomeric forms of the amino acids in question.

Additional abbreviations include the following:
Gly(Me): N-methylglycine [also known as sarcosine (Sar)]
Ile(Me): N-methylisoleucine
Aad: 2-aminoadipic acid, e.g. (2S)-2-aminoadipic acid [also (2S)-2-aminohexanedioic acid], also known as homoglutamic acid
Apr: 4-aminoproline, e.g. (2S,4R)-4-aminoproline [also denoted (4R)-4-amino-L-proline]
Hyp: 4-hydroxyproline, e.g. (2S,4R)-4-hydroxyproline [also denoted (4R)-4-hydroxy-L-proline]

The term "therapeutically effective amount" as used herein in the context of the above-described methods of treatment or other therapeutic interventions according to the invention refers to an amount that is sufficient to cure, ameliorate, alleviate or partially arrest the clinical manifestations of the particular disease, disorder or condition that is the object of the treatment or other therapeutic intervention in question e.g. as measured by established clinical endpoints or other biomarkers (established or experimental). A therapeutically relevant amount may be determined empirically by one skilled in the art based on the indication being treated or prevented and the subject to whom the therapeutically relevant amount is being administered. For example, the skilled worker may measure one or more of the clinically relevant indicators of bioactivity described herein, e.g. plasma lipid levels, blood glucose levels or insulin release. The skilled worker may determine a clinically relevant amount through in vitro or in vivo measurements. Other exemplary measures include weight gain, weight loss, and change in blood pressure.

An amount adequate to accomplish any or all of these effects is defined as a therapeutically effective amount. The administered amount and the method of administration can be tailored to achieve optimal efficacy. An amount effective for a given purpose will depend, inter alia, on the severity of the disease, disorder or condition that is the object of the particular treatment or other therapeutic intervention, on the body weight and general condition of the subject in question, on diet, on possible concurrent medication, and on other factors well known to those skilled in the medical arts. Determination of an appropriate dosage size and dosing regimen most appropriate for administration of a peptide or pharmaceutically acceptable salt or solvate thereof according to the invention to a human may be guided by the results obtained by the present invention, and may be confirmed in properly designed clinical trials. An effective dosage and treatment protocol may be determined by conventional means, starting with a low dose in laboratory animals and then increasing the dosage while monitoring the effects, and systematically varying the dosage regimen as well. Numerous factors may be taken into consideration by a clinician when determining an optimal dosage for a given subject. Such considerations are well known to the skilled person.

The terms "treatment" and grammatical variants thereof (e.g. "treated", "treating", "treat") as employed in the present context refer to an approach for obtaining beneficial or desired clinical results. For the purposes of this invention, beneficial or desired clinical results include, but are not limited to, alleviation of symptoms, diminishment of extent of disease, stabilization (i.e. not worsening) of state of disease, delay or slowing of disease progression, amelioration or palliation of the disease state, and remission (whether partial or total), whether detectable or undetectable. "Treatment" can also mean prolonging survival relative to expected survival time if not receiving treatment. A subject (e.g. a human) in need of treatment may thus be a subject already afflicted with the disease or disorder in question. The term "treatment" includes inhibition or reduction of an increase in severity of a pathological state or symptoms (e.g. weight gain or hyperglycemia) relative to the absence of treatment, and is not necessarily meant to imply complete cessation of the relevant disease, disorder or condition.

The terms "prevention" and grammatical variants thereof (e.g., "prevented", "preventing", "prevent") as employed in the present context refer to an approach for hindering or preventing the development of, or altering the pathology of, a condition, disease or disorder. Accordingly, "prevention" may refer to prophylactic or preventive measures. For the purposes of this invention, beneficial or desired clinical results include, but are not limited to, prevention or slowing of symptoms, progression or development of a disease, whether detectable or undetectable. A subject (e.g. a human) in need of "prevention" may thus be a subject not yet afflicted with the disease or disorder in question. The term "prevention" thus includes inhibiting or slowing the onset of disease relative to the absence of treatment, and is not necessarily meant to imply permanent prevention of the relevant disease, disorder or condition.

Synthesis of Amylin Analogues

The invention further provides a method of synthesis of an amylin analogue of the invention. The amylin analogues (which may also be referred to as compounds or peptides) may suitably be manufactured by standard synthetic methods. Thus, the peptides may be synthesized by, e.g., methods comprising synthesizing the peptide by standard solid-phase or liquid-phase methodology, either stepwise or by fragment assembly, and optionally isolating and purifying the final peptide product. In this context, reference may be made to WO 98/11125 or, inter alia, Fields, G. B. et al., "Principles and Practice of Solid-Phase Peptide Synthesis"; in: *Synthetic Peptides*, Gregory A. Grant (ed.), Oxford University Press ($2^{nd}$ edition, 2002) and the synthesis examples herein. The method may further comprise the step of forming a disulfide bond between the thiol groups of the cysteine side chains at positions 2 and 7, e.g. by oxidative cyclisation. In the case of solid phase synthesis, cyclisation may be performed in situ on the solid phase (e.g. resin), i.e. before removal of the peptide from the solid phase.

$C_{1-4}$ Acyl Groups $C_{1-4}$ acyl groups that may be present as a group $R^1$ in the context of compounds of the present invention include formyl (i.e. methanoyl), acetyl (i.e. ethanoyl), propanoyl, 1-butanoyl and 2-methylpropanoyl groups.

$C_{1-4}$ Alkyl Groups $C_{1-4}$ alkyl groups that may be present as a group $R^1$ in the context of compounds of the present invention include, but are not limited to, $C_{1-3}$ alkyl groups, such as methyl, ethyl, 1-propyl or 2-propyl.

$C_{1-3}$ Alkyl Groups $C_{1-3}$ alkyl groups that may be present as a group $R^3$ in the context of compounds of the present invention include methyl, ethyl, 1-propyl and 2-propyl.

Half-Life Extending Moieties M

As described herein, the N-terminal moiety $R^1$ in a compound of the invention may be a half-life extending moiety (sometimes referred to in the literature as, inter alia, a duration enhancing moiety or albumin binding moiety), optionally linked (covalently attached) to the peptide moiety Z via a linker moiety L. Among suitable half-life extending moieties are certain types of lipophilic substituents. Without wishing to be bound by any particular theory, it is thought that such lipophilic substituents (and other classes of half-life extending moieties) bind albumin in the blood stream, thereby shielding the compound of the invention from renal filtration as well as enzymatic degradation and thus possibly enhancing the half-life of the compound in vivo. The lipophilic substituent may also modulate the potency of the compound as an agonist to the amylin (calcitonin) receptor.

The lipophilic substituent may be attached to the N-terminal amino acid residue or to the linker L via an ester, a sulfonyl ester, a thioester, an amide, an amine or a sulfonamide. Accordingly it will be understood that preferably the lipophilic substituent includes an acyl group, a sulfonyl group, an N atom, an O atom or an S atom which forms part of the ester, sulfonyl ester, thioester, amide, amine or sulfonamide. Preferably, an acyl group in the lipophilic substituent forms part of an amide or ester with the amino acid residue or the linker.

The lipophilic substituent may comprise a hydrocarbon chain having from 10 to 24 C atoms, e.g. from 14 to 22 C atoms, e.g. from 16 to 20 C atoms. Preferably it has at least 14 C atoms, and preferably has 20 C atoms or fewer. For example, the hydrocarbon chain may contain 14, 15, 16, 17, 18, 19 or 20 carbon atoms. The hydrocarbon chain may be linear or branched, and may be saturated or unsaturated. Furthermore, it can include a functional group at the end of the lipophilic chain, e.g. a carboxylic acid group which may or may not be protected during synthesis. From the discussion above it will be understood that the hydrocarbon chain is preferably substituted with a moiety which forms part of the attachment to the N-terminal amino acid residue of the peptide moiety Z or to the linker L, for example an acyl group, a sulfonyl group, an N atom, an O atom or an S atom.

Most preferably, the hydrocarbon chain is substituted with an acyl group, and accordingly the hydrocarbon chain may be part of an alkanoyl group, for example a dodecanoyl, 2-butyloctanoyl, tetradecanoyl, hexadecanoyl, heptadecanoyl, octadecanoyl, nonadecanoyl or eicosanoyl group. Examples of functionalized hydrocarbon chains are 15-carboxy-pentadecanoyl, 17-carboxy-heptadecanoyl and 19-carboxy-nonadecanoyl.

As mentioned above, a lipophilic substituent M may be linked to the N-terminal amino acid residue of Z via a linker L. In embodiments, the linker moiety L may itself comprise one, two, three or more linked sub-moieties $L^1$, $L^2$, $L^3$, ... etc. When the linker L comprises only one such moiety, it is attached to the lipophilic substituent and to the N-terminal amino acid residue of Z. The linker may then be attached to the lipophilic substituent and to the N-terminal amino acid residue of Z independently by means of an ester, a sulfonyl ester, a thioester, an amide, an amine or a sulfonamide bond. Accordingly, it may include two moieties independently selected from acyl, sulfonyl, an N atom, an O atom and an S atom. The linker may consist of a linear or branched $C_{1-10}$ hydrocarbon chain or more preferably a linear $C_{1-5}$ hydrocarbon chain. Furthermore the linker can be substituted with one or more substituents selected from $C_{1-6}$ alkyl, amino $C_{1-6}$ alkyl, hydroxy $C_{1-6}$ alkyl and carboxy $C_{1-6}$ alkyl.

In some embodiments the linker may be, for example, a residue of any naturally occurring or non-naturally occurring amino acid. For example, the linker may be a residue of Gly, Pro, Ala, Val, Leu, Ile, Met, Cys, Phe, Tyr, Trp, His, Lys, Arg, Gln, Asn, α-Glu, γ-Glu, ε-Lys, Asp, β-Asp, Ser, Thr, Gaba, Aib, β-Ala (i.e. 3-aminopropanoyl), 4-aminobutanoyl, 5-aminopentanoyl, 6-aminohexanoyl, 7-aminoheptanoyl, 8-aminooctanoyl, 9-aminononanoyl, 10-aminodecanoyl or 8Ado (i.e. 8-amino-3,6-dioxaoctanoyl).

References to γ-Glu, ε-Lys, and β-Asp indicate residues of amino acids which participate in bonds via their side chain carboxyl or amine functional groups. Thus γ-Glu, and β-Asp participate in bonds via their amino and side chain carboxyl groups, while ε-Lys participates via its carboxyl and side chain amino groups.

In certain embodiments, the linker is a residue of Glu, γ-Glu, εLys, β-Ala, 4-aminobutanoyl, 8-aminooctanoyl or 8Ado. In the context of the present invention, γ-Glu and isoGlu are used interchangeably.

An example of a lipophilic substituent comprising a lipophilic moiety M and linker L is shown in the formula below:

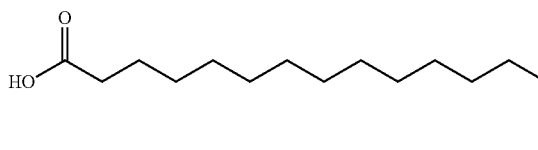

Here, the backbone nitrogen of an Arg residue is covalently attached to a γ-Glu linker (L) via an amide linkage. A 19-carboxy-nonadecanoyl group is covalently attached to the γ-Glu linker via an amide linkage. This combination of lipophilic moiety and linker, attached to an Arg residue, may be referred to by the shorthand notation [19CD]-isoGlu-R, e.g. when shown in formulae of specific compounds.

The skilled person will be well aware of suitable techniques for preparing the compounds employed in the context of the invention. For examples of suitable chemistry, see, e.g., WO98/08871, WO00/55184, WO00/55119, Madsen et al (*J. Med. Chem.* 2007, 50, 6126-32), and Knudsen et al. 2000 (*J. Med Chem.* 43, 1664-1669).

The hydrocarbon chain in a lipophilic substituent may be further substituted. For example, it may be further substituted with up to three substituents selected from $NH_2$, OH and COOH. If the hydrocarbon chain is further substituted, it is preferably further substituted with only one substituent. Alternatively or additionally, the hydrocarbon chain may include a cycloalkane or heterocycloalkane moiety, for example as shown below:

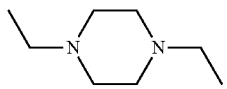

In some embodiments, the cycloalkane or heterocycloalkane moiety is a six-membered ring, e.g. a piperidine ring.

In alternative embodiments of the present invention, the N-terminal amino acid of Z in a compound of the invention may be linked (covalently attached) to a biotinylic substituent, optionally via a linker moiety L. Without wishing to be bound by any particular theory, it is likewise believed that such biotinylic substituents bind to albumin in the blood stream, thereby shielding the compound of the invention from enzymatic degradation and thus possibly enhancing the half-life of the compound in vivo. A linker, when present, may provide spacing between the peptide moiety Z and the biotinylic substituent.

The biotinylic substituent may be attached to the N-terminal amino acid residue or to the linker via an maleimide ester bond, a sulfonyl ester bond, a thioester bond, an amide bond, an amine bond or a sulfonamide bond. Accordingly it will be understood that the biotinylic substituent preferably comprises an maleimido group, an acyl group, a sulfonyl group, an N atom, an O atom or an S atom which forms part of the ester, sulfonyl ester, thioester, amide, amine or sulfonamide bond in question.

Examples of biotinylic substituents may include

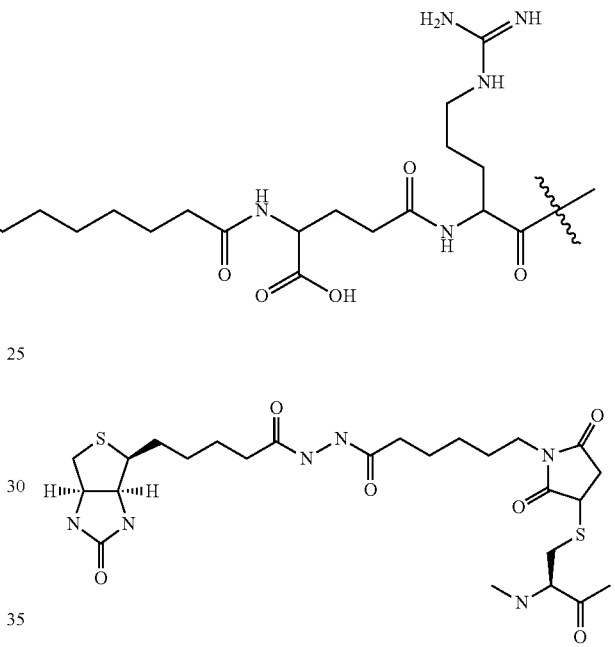

Biotin is known as Vitamin H or Coenzyme R, and is a water-soluble B-complex vitamin (vitamin B7). It has been shown to increase oral uptake of certain drugs.

Efficacy of Compounds

The compounds of the invention are amylin receptor agonists, i.e. they are capable of binding to, and inducing signalling by, one or more receptors or receptor complexes regarded as physiological receptors for human amylin. These include the human calcitonin receptor hCTR2, as well as complexes comprising the human calcitonin receptor hCTR2 and at least one of the human receptor activity modifying proteins designated hRAMP1, hRAMP2 and hRAMP3. Complexes between hCTR2 and hRAMP1, hRAMP2 and hRAMP3 are designated hAMYR1, hAMYR2 and hAMYR3 (i.e. human amylin receptors 1, 2 and 3) respectively.

Without wishing to be bound by theory, a compound may be considered an amylin receptor agonist if it has agonist activity at one or more of hAMYR1, hAMYR2 and hAMYR3, e.g. against hAMYR1 and/or hAMYR3, e.g. at hAMYR3.

Typically an amylin receptor agonist will also have agonist activity at hCTR2 when expressed in the absence of hRAMP1, hRAMP2 and hRAMP3. Typically, the agonist will have activity at hCTR2 (when expressed in the absence of hRAMP1, hRAMP2 and hRAMP3) which is less than 10-fold higher than its activity at any one of hAMYR1, hAMYR2 and hAMYR3 (i.e. its activity at all of these receptors) in a comparable assay. Agonist activity at hCTR2 may be less than 5-fold higher than agonist activity at hAMYR1, hAMYR2 and hAMYR3, substantially equal to (e.g. +/−10%) agonist activity at hAMYR1, hAMYR2 and hAMYR3, or less than agonist activity at hAMYR1, hAMYR2 and hAMYR3. In this regard, it may be sufficient just to compare activity between hCTR2 and hAMYR3.

The ability to induce cAMP formation (i.e. to induce adenylate cyclase activity) as a result of binding to the relevant receptor or receptor complex is typically regarded as indicative of agonist activity. Other intracellular signaling pathways or events may also be used as read-outs for amylin receptor agonist activity. These may include calcium release, β-arrestin recruitment, receptor internalization, kinase activation or inactivation, lipase activation, inositol phosphate release, diacylglycerol release or nuclear transcription factor translocation.

A suitable comparable assay format would utilize cells which express hCTR2 and which differ only in their expression of hRAMP1, 2 and 3. For example, a "base" cell line which does not express any of hCTR2, hRAMP1, hRAMP2 and hRAMP3 may be engineered to generate cells which express (i) hCTR2, and (ii) one of hAMYR1, hAMYR2 and hAMYR3 (i.e. hCTR2 plus one of hRAMP1, hRAMP2 and hRAMP3), e.g. hAMYR3. The base cells will typically be mammalian cells and may be primate cells. They may be non-human primate cells. Preferably the base cell does not express any of CTR2, RAMP1, RAMP2 or RAMP3 (whether human, or native to the base cell if the base cell is non-human). The base cells may be fibroblast cells. Suitable non-human fibroblast base cells include COS7 cells, from African green monkey, which do not express native CTR2 or RAMPs.

Comparative activity may be measured by any suitable means, such as via determination of $EC_{50}$ values as described below. It will be apparent that the same biological read-out must be for both receptor types.

Compounds of the present invention may exhibit a number of advantageous properties in relation to human amylin and existing analogues thereof, such as pramlintide, IAPP-GI, and analogues described in WO2012/168430, WO2012/168431 and WO2012/168432. As compared to human amylin or any of those analogues, compounds of the invention may, for example, exhibit improved efficacy (e.g., in the form of improved in vitro activity or potency at one or more of the receptors hCTR2, hAMRY1, hAMRy2 or hAMYR3. Additionally or alternatively, compounds of the invention may exhibit improved solubility in aqueous media, especially at pH values in the range from 4 to 7.5, or at a range of pH values across that range. Moreover, compounds of the present invention may additionally or alternatively exhibit reduced tendency to undergo fibrillation in pharmaceutically relevant aqueous media, especially at pH values in the range from 4 to 7, or at a range of pH values across that range. Furthermore, compounds of the present invention may additionally or alternatively exhibit improved chemical stability (i.e. reduced tendency to undergo chemical degradation) in aqueous media, especially at pH values in the range from 4 to 9, or at a range of pH values across that range.

Compounds of the invention may thus be well suited for formulation in acidic media (e.g. pH 4) and in neutral or near-neutral media (e.g. pH 7 or 7.4). In contrast to pramlintide, for example, which generally exhibits poor chemical stability and rapid fibrillation in pharmaceutically relevant aqueous media at neutral pH, compounds of the invention may be thus well suited for co-formulation with, for example, insulin, various insulin analogues and/or other therapeutic (e.g. anti-diabetic or anti-obesity) agents that require a neutral or near-neutral formulation pH.

In general it is preferred to use a biological assay which measures intracellular signalling caused by binding of the compound to the relevant receptor, as discussed above. Activation of the calcitonin/amylin receptor by compounds of the invention (which behave as agonists of the receptor) induces cAMP formation and activation of other intracellular signaling pathways and events. Thus, production of cAMP or any other suitable parameter in suitable cells expressing the receptor can be used to monitor agonist activity towards the receptor.

The skilled person will be aware of suitable assay formats, and examples are provided below. For example, the assays may make use of the human calcitonin receptor (hCTR2) having primary accession number GI: 4502547 (NP_001733.1) or the hAMYR3 receptor (see Example 2, below). Where sequences of precursor proteins are referred to, it should be understood that assays may make use of the mature protein, lacking the signal sequence.

$EC_{50}$ values may be used as a numerical measure of agonist potency at a given receptor. An $EC_{50}$ value is a measure of the concentration of a compound required to achieve half of that compound's maximal activity in a particular assay. Thus, for example, a compound having $EC_{50}$ [hCTR2] lower than the $EC_{50}$ [hCTR2] of native amylin, or lower than that of pramlintide, in a particular assay may be considered to have higher potency or activity at the receptor than amylin, or higher than that of pramlintide, respectively.

In some embodiments of compounds of the present invention, the $EC_{50}$ towards hCTR2 is below 1.4 nM.

In some embodiments of compounds of the present invention, the $EC_{50}$ towards hCTR2 is below 0.8 nM.

In some embodiments of compounds of the present invention, the $EC_{50}$ towards hCTR2 is below 0.4 nM.

In some embodiments of compounds of the present invention, the $EC_{50}$ towards hCTR2 is below 0.2 nM.

In some embodiments of compounds of the present invention, the $EC_{50}$ towards hCTR2 is below 0.1 nM.

An $EC_{50}$ towards hCTR2 of approximately 0.2 (+/−10%) or below may be desirable. The $EC_{50}$ at hCTR2 may be an indication of the effect of a compound on food intake, weight gain and/or weight loss. Compounds with lower $EC_{50}$ values at hCTR2 may have a greater effect on these parameters.

In some embodiments of compounds of the present invention, the $EC_{50}$ towards hAMYR3 is below 1 nM.

In some embodiments of compounds of the present invention, the $EC_{50}$ towards hAMYR3 is below 0.5 nM.

In some embodiments of compounds of the present invention, the $EC_{50}$ towards hAMYR3 is below 0.4 nM.

In some embodiments of compounds of the present invention, the $EC_{50}$ towards hAMYR3 is below 0.3 nM.

In some embodiments of compounds of the present invention, the $EC_{50}$ towards hAMYR3 is below 0.2 nM.

For example, the $EC_{50}$ at hCTR2 (when expressed in the absence of hRAMP1, hRAMP2 and hRAMP3) may be less than 10-fold lower than the $EC_{50}$ at any or all of hAMYR1, hAMYR2 and hAMYR3, e.g. at hAMYR3.

The $EC_{50}$ at hCTR2 (when expressed in the absence of hRAMP1, hRAMP2 and hRAMP3) may be less than 5-fold lower than the $EC_{50}$ at any or all of hAMYR1, hAMYR2 and hAMYR3, e.g. at hAMYR3.

The $EC_{50}$ at hCTR2 (when expressed in the absence of hRAMP1, hRAMP2 and hRAMP3) may be substantially equal to (e.g. +/−50%) the $EC_{50}$ at any or all of hAMYR1, hAMYR2 and hAMYR3, e.g. at hAMYR3.

The $EC_{50}$ at hCTR2 (when expressed in the absence of hRAMP1, hRAMP2 and hRAMP3) may be higher than the $EC_{50}$ at any or all of hAMYR1, hAMYR2 and hAMYR3, e.g. at hAMYR3.

Such assays may be performed under the conditions described in Examples 2 and 3.

Additionally or alternatively, compounds of the invention may show excellent solubility. For example, they may show solubility of greater than or equal to 1 mg/ml at pH 4, pH 5, pH 6, pH 7 and/or pH 7.5, e.g. at 25° C., e.g. under the conditions described in Example 4.

Additionally or alternatively, compounds of the invention may show excellent resistance to fibrillation. For example, they may show no detectable fibrillation after 96 hours at pH 4.0 and/or pH 7.0, e.g. at 40° C., e.g. under the conditions described in Example 5.

Additionally or alternatively, compounds of the invention may show excellent chemical stability, i.e. resistance to degradation in solution. For example, they may retain at least 70% purity, at least 75% purity, at least 80% purity, at least 85% purity, at least 90% purity, or at least 95% purity after incubation at pH 4, pH 7.5, and/or pH 9 at 40° C. for 7 days, e.g. under the conditions described in Example 6.

Therapeutic Uses

The compounds of the invention are useful, inter alia, in the reduction of food intake, promotion of weight loss, and inhibition or reduction of weight gain. They may therefore provide an attractive treatment option for, inter alia, obesity and metabolic diseases caused, characterised by, or associated with, excess body weight.

Thus, the compounds may be used in a method of treating, inhibiting or reducing weight gain, promoting weight loss, reducing food intake, and/or reducing excess body weight. Treatment may be achieved, for example, by control of appetite, feeding, food intake, calorie intake and/or energy expenditure.

The compounds may be used in a method of treating obesity as well as associated diseases, disorders and health conditions, including, but not limited to, morbid obesity, obesity prior to surgery, obesity-linked inflammation, obesity-linked gallbladder disease and obesity-induced sleep apnea and respiratory problems, degeneration of cartilage, osteoarthritis, and reproductive health complications of obesity or overweight such as infertility.

The compounds may also be used in a method of prevention or treatment of Alzheimer's disease, diabetes, type 1 diabetes, type 2 diabetes, pre-diabetes, insulin resistance syndrome, impaired glucose tolerance (IGT), disease states associated with elevated blood glucose levels, metabolic disease including metabolic syndrome, hyperglycemia, hypertension, atherogenic dyslipidemia, hepatic steatosis ("fatty liver"; including non-alcoholic fatty liver disease (NAFLD), which itself includes non-alcoholic steatohepatitis (NASH)), kidney failure, arteriosclerosis (e.g. atherosclerosis), macrovascular disease, microvascular disease, diabetic heart (including diabetic cardiomyopathy and heart failure as a diabetic complication) coronary heart disease, peripheral artery disease or stroke.

The compounds may also be useful in lowering circulating LDL levels and/or increasing HDL/LDL ratio.

The effects of the compounds described above may be mediated in whole or in part via an effect on body weight, or may be independent thereof.

Metabolic syndrome is characterized by a group of metabolic risk factors in one person. They include abdominal obesity (excessive fat tissue around the abdominal internal organs), atherogenic dyslipidemia (blood fat disorders including high triglycerides, low HDL cholesterol and/or high LDL cholesterol, which foster plaque buildup in artery walls), elevated blood pressure (hypertension), insulin resistance and glucose intolerance, prothrombotic state (e.g. high fibrinogen or plasminogen activator inhibitor-1 in the blood), and proinflammatory state (e.g., elevated C-reactive protein in the blood).

Individuals with metabolic syndrome are at increased risk of coronary heart disease and other diseases related to other manifestations of arteriosclerosis (e.g. stroke and peripheral vascular disease). The dominant underlying risk factor for this syndrome appears to be abdominal obesity.

Pharmaceutical Compositions

The invention also extends to compositions, such as pharmaceutical compositions, comprising amylin analogues. As with all aspects of the invention, it is to be understood that reference to an amylin analogue encompasses reference to pharmaceutically acceptable salts and solvates.

The amylin analogues of the present invention may be formulated as pharmaceutical compositions which are suited for administration with or without storage, and which typically comprise a therapeutically effective amount of at least one peptide of the invention, together with a pharmaceutically acceptable carrier, excipient or vehicle.

The term "pharmaceutically acceptable carrier" includes any of the standard pharmaceutical carriers. Pharmaceutically acceptable carriers for therapeutic use are well known in the pharmaceutical art and are described, for example, in "Remington's Pharmaceutical Sciences", 17th edition, Alfonso R. Gennaro (Ed.), Mark Publishing Company, Easton, Pa., USA, 1985. For example, sterile saline and phosphate-buffered saline at slightly acidic or physiological pH may be used. Suitable pH-buffering agents may, e.g., be phosphate, citrate, acetate, tris(hydroxymethyl)aminomethane (TRIS), N-tris(hydroxymethyl)methyl-3-aminopropanesulfonic acid (TAPS), ammonium bicarbonate, diethanolamine, histidine, arginine, lysine or acetate (e.g. as sodium acetate), or mixtures thereof. The term further encompasses any carrier agents listed in the US Pharmacopeia for use in animals, including humans.

A pharmaceutical composition of the invention may be in unit dosage form. In such form, the composition is divided into unit doses containing appropriate quantities of the active component or components. The unit dosage form may be presented as a packaged preparation, the package containing discrete quantities of the preparation, for example, packaged tablets, capsules or powders in vials or ampoules. The unit dosage form may also be, e.g., a capsule, cachet or tablet in itself, or it may be an appropriate number of any of these packaged forms. A unit dosage form may also be provided in single-dose injectable form, for example in the form of a pen device containing a liquid-phase (typically aqueous) composition. Compositions may be formulated for any suitable route and means of administration. Pharmaceutically acceptable carriers or diluents include those used in formulations suitable for e.g. oral, intravitreal, rectal, vaginal, nasal, topical, enteral or parenteral (including subcutaneous (sc), intramuscular (im), intravenous (iv), intradermal and transdermal) administration or administration by inhalation. The formulations may conveniently be presented in unit dosage form and may be prepared by any of the methods well known in the art of pharmaceutical formulation.

Subcutaneous or transdermal modes of administration may in some cases be suitable for peptides of the invention.

Further embodiments relate to devices, dosage forms and packages used to deliver the pharmaceutical formulations of the present invention. Thus, at least one peptide in a stable or preserved formulation or solution described herein can be administered to a patient in accordance with the present invention via a variety of delivery methods, including by sc or im injection, or by transdermal, pulmonary or transmucosal administration, or by implant, or by use of an osmotic pump, cartridge, micro-pump or other means recognized by a person of skill in the art.

Still further embodiments relate to oral formulations and oral administration. Formulations for oral administration may rely on the co-administration of adjuvants (e.g. resorcinols and/or nonionic surfactants such as polyoxyethylene oleyl ether and n-hexadecylpolyethylene ether) to artificially increase the permeability of the intestinal walls, and/or the co-administration of enzymatic inhibitors (e.g. pancreatic trypsin inhibitors, diisopropylfluorophosphate (DFF) or trasylol) to inhibit enzymatic degradation. The active constituent compound of a solid-type dosage form for oral administration can be mixed with at least one additive, such as sucrose, lactose, cellulose, mannitol, trehalose, raffinose, maltitol, dextran, starches, agar, alginates, chitins, chitosans, pectins, gum tragacanth, gum arabic, gelatin, collagen, casein, albumin, synthetic or semisynthetic polymer, or glyceride. These dosage forms can also contain other type(s) of additives, e.g. an inactive diluting agent, a lubricant (such as magnesium stearate), a paraben, a preserving agent (such as sorbic acid, ascorbic acid or alpha-tocopherol), an antioxidant (such as cysteine), a disintegrant, binder, thickener, buffering agent, pH-adjusting agent, sweetening agent, flavoring agent or perfuming agent.

Dosages

A typical dosage of an amylin analogue as employed in the context of the present invention may be in the range from about 0.0001 to about 100 mg/kg body weight per day, such as from about 0.0005 to about 50 mg/kg body weight per day, such as from about 0.001 to about 10 mg/kg body weight per day, e.g. from about 0.01 to about 1 mg/kg body weight per day, administered in one or more doses, such as from one to three doses. The exact dosage employed will depend, inter alia, on: the nature and severity of the disease or disorder to be treated, on the sex, age, body weight and general condition of the subject to be treated, on possible other, concomitant, disease or disorder that is undergoing or is to undergo treatment, as well as on other factors that will be known to a medical practitioner of skill in the art.

An amylin analogue of the invention may be administered continuously (e.g. by intravenous administration or another continuous drug administration method), or may be administered to a subject at intervals, typically at regular time intervals, depending on the desired dosage and the pharmaceutical composition selected by the skilled practitioner for the particular subject. Regular administration dosing intervals include, e.g., once daily, twice daily, once every two, three, four, five or six days, once or twice weekly, once or twice monthly, and the like. Such regular peptide administration regimens may, in certain circumstances such as, e.g., during chronic long-term administration, be advantageously interrupted for a period of time so that the medicated subject reduces the level of, or stops taking, the medication, often referred to as taking a "drug holiday." Drug holidays are useful for, e.g., maintaining or regaining sensitivity to a drug especially during long-term chronic treatment, or to reduce unwanted side-effects of long-term chronic treatment of the subject with the drug. The timing of a drug holiday depends on the timing of the regular dosing regimen and the purpose for taking the drug holiday (e.g., to regain drug sensitivity and/or to reduce unwanted side effects of continuous, long-term administration). In some embodiments, the drug holiday may be a reduction in the dosage of the drug (e.g. to below the therapeutically effective amount for a certain interval of time). In other embodiments, administration of the drug is stopped for a certain interval of time before administration is started again using the same or a different dosing regimen (e.g. at a lower or higher dose and/or frequency of administration). A drug holiday of the invention may thus be selected from a wide range of time-periods and dosage regimens. An exemplary drug holiday is two or more days, one or more weeks, or one or more months, up to about 24 months of drug holiday. So, for example, a regular daily dosing regimen with a peptide of the invention may, for example, be interrupted by a drug holiday of a week, or two weeks, or four weeks, after which time the preceding, regular dosage regimen (e.g. a daily or a weekly dosing regimen) is resumed. A variety of other drug holiday regimens are envisioned to be useful for administering peptides of the invention.

Thus, the peptide may be delivered via an administration regime which comprises two or more administration phases separated by respective drug holiday phases.

During each administration phase, the peptide is administered to the recipient subject in a therapeutically effective amount according to a pre-determined administration pattern. The administration pattern may comprise continuous administration of the drug to the recipient subject over the duration of the administration phase. Alternatively, the administration pattern may comprise administration of a plurality of doses of the peptide to the recipient subject, wherein said doses are spaced by dosing intervals.

A dosing pattern may comprise at least two doses per administration phase, at least five doses per administration phase, at least 10 doses per administration phase, at least 20 doses per administration phase, at least 30 doses per administration phase, or more.

Said dosing intervals may be regular dosing intervals, which may be as set out above, including once daily, twice daily, once every two, three, four, five or six days, once or twice weekly, once or twice monthly, or a regular and even less frequent dosing interval, depending on the particular dosage formulation, bioavailability, and pharmacokinetic profile of the peptide.

An administration phase may have a duration of at least two days, at least a week, at least 2 weeks, at least 4 weeks, at least a month, at least 2 months, at least 3 months, at least 6 months, or more.

Where an administration pattern comprises a plurality of doses, the duration of a possible following drug holiday phase is longer than the dosing interval used in that administration pattern. Where the dosing interval is irregular, the duration of a drug holiday phase may be greater than the mean interval between doses over the course of the administration phase. Alternatively the duration of the drug holiday may be longer than the longest interval between consecutive doses during the administration phase.

The duration of a possible drug holiday phase may be at least twice that of the relevant dosing interval (or mean thereof), at least 3 times, at least 4 times, at least 5 times, at least 10 times, or at least 20 times that of the relevant dosing interval or mean thereof.

Within these constraints, a drug holiday phase may have a duration of at least two days, at least a week, at least 2 weeks, at least 4 weeks, at least a month, at least 2 months, at least 3 months, at least 6 months, or more, depending on the administration pattern during the previous administration phase.

An administration regime entailing the use of drug holiday comprises at least 2 administration phases. Consecutive administration phases are separated by respective drug holiday phases. Thus the administration regime may comprise at least 3, at least 4, at least 5, at least 10, at least 15, at least 20, at least 25, or at least 30 administration phases, or more, each separated by respective drug holiday phases.

Consecutive administration phases may utilise the same administration pattern, although this may not always be desirable or necessary. However, if other drugs or active agents are administered in combination with a peptide of the invention, then typically the same combination of drugs or active agents is given in consecutive administration phases. In certain embodiments, the recipient subject is a human.

Combination Therapy

An amylin analogue of the invention may be administered as part of a combination therapy together with another active agent for the treatment of the disease or disorder in question, e.g. an anti-diabetic agent, an anti-obesity agent, an agent for treatment of metabolic syndrome, an anti-dyslipidemia agent, an anti-hypertensive agent, a proton pump inhibitor, or an anti-inflammatory agent. In such cases, the two active agents may be given together or separately, e.g. as constituents in the same pharmaceutical composition or formulation, or as separate formulations.

Thus a peptide of the invention may have some benefit if administered in combination with an anti-diabetic agent of known type, including, but not limited to, metformin, a sulfonylurea, a glinide, a DPP-IV inhibitor, a glitazone, a GLP-1 receptor agonist (including GLP-1 or a GLP-1 analogue, an exendin-4 or an exendin-4 analogue, any other GLP-1 receptor agonist including liraglutide (Saxenda™, Victoza™), Dulaglutide or Albiglutide or a glucagon-GLP-1 dual agonist, e.g. as described in WO2008/101017, WO2008/152403, WO2010/070252, WO2010/070253, WO2010/070255, WO2010/070251, WO2011/006497, WO2011/160630, WO2011/160633, WO2013/092703, WO2014/041195), an SGLT2 inhibitor (i.e. an inhibitor of sodium-glucose transport, e.g. a gliflozin such as empagliflozin, canagliflozin, dapagliflozin or ipragliflozin), a GPR40 agonist (FFAR1/FFA1 agonist, e.g. fasiglifam), or an insulin or an insulin analogue. Examples of appropriate insulin analogues include, but are not limited to, Lantus™, Novorapid™, Humalog™, Novomix™, Actraphane™ HM, Levemir™ Degludec™ and Apidra™. Other relevant anti-diabetic agents in this connection include GLP-1 receptor agonists, such as exenatide (Byetta™ and Bydureon™ exendin-4) and Byetta LAR™, lixisenatide (Lyxumia™) and liraglutide (Victoza™).

Moreover, a peptide of the invention may be used in combination with an anti-obesity agent of known type, including, but not limited to, peptide YY or an analogue thereof, neuropeptide Y (NPY) or an analogue thereof, a cannabinoid receptor 1 antagonist, a lipase inhibitor, Human prolslet Peptide (HIP), a melanocortin receptor 4 agonist, a GLP-1 receptor agonist (including GLP-1 or a GLP-1 analogue, an exendin-4 or an exendin-4 analogue, any other GLP-1 receptor agonist including liraglutide (Saxenda™, Victoza™), Dulaglutide or Albiglutide or a glucagon-GLP-1 dual agonist, e.g. as described in WO2008/101017, WO2008/152403, WO2010/070252, WO2010/070253, WO2010/070255, WO2010/070251, WO2011/006497, WO2011/160630, WO2011/160633, WO2013/092703, WO2014/041195), Orlistat™, Sibutramine™, phentermine, a melanin concentrating hormone receptor 1 antagonist, CCK, amylin, pramlintide and leptin, as well as analogues thereof.

A peptide of the invention may further be used in combination with an anti-hypertension agent of a known type, including, but not limited to, an angiotensin-converting enzyme inhibitor, an angiotensin II receptor blocker, a diuretic, a beta-blocker and a calcium channel blocker.

A peptide of the invention may still further be used in combination with an anti-dyslipidemia agent of known type, including, but not limited to, a statin, a fibrate, a niacin, a PSCK9 (Proprotein convertase subtilisin/kexin type 9) inhibitor, and a cholesterol absorption inhibitor.

A peptide of the invention may also be used in combination with a proton pump inhibitor (i.e. a pharmaceutical agent possessing pharmacological activity as an inhibitor of $H^+/K^+$-ATPase) of known type, including, but not limited to, an agent of the benzimidazole derivative type or of the imidazopyridine derivative type, such as Omeprazole™, Lansoprazole™, Dexlansoprazole™, Esomeprazole™ Pantoprazole™, Rabeprazole™, Zolpidem™, Alpidem™, Saripidem™ or Necopidem™.

In addition, with regard to anti-inflammatory treatment, a peptide of the invention may be beneficial if administered in combination with an anti-inflammatory agent of known type, including, but not limited to:

steroids and corticosteroids, such as beclomethasone, methylprednisolone, betamethasone, prednisone, dexamethasone, and hydrocortisone;

non-steroidal anti-inflammatory agents (NSAIDs), such as propionic acid derivatives (e.g. alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid and tioxaprofen); acetic acid derivatives (e.g. indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin and zomepirac); fenamic acid derivatives (e.g. flufenamic acid, meclofenamic acid, mefenamic acid, niflumic acid and tolfenamic acid); biphenylcarboxylic acid derivatives (e.g. diflunisal and flufenisal); oxicams (e.g. isoxicam, piroxicam, sudoxicam and tenoxicam); salicylates (e.g. acetylsalicylic acid and sulfasalazine); and pyrazolones (e.g. apazone, bezpiperylon, feprazone, mofebutazone, oxyphenbutazone and phenylbutazone);

COX II inhibitors, such as rofecoxib and celecoxib; preparations of interferon beta (e.g. interferon beta-1a or interferon beta-1 b);

and certain other compounds, such as 5-aminosalicylic acid and prodrugs and pharmaceutically acceptable salts thereof.

Metformin has also been demonstrated to have anti-inflammatory properties (see, e.g., Haffner et al., *Diabetes* 54: 1566-1572 (2005)) and as such may also be useful in combination with compounds (peptides) of the invention.

Devices and Kits

In some embodiments, the invention relates to a device comprising an amylin analogue or pharmaceutical composition of the invention, for delivery of the analogue to a subject. Via such devices, amylin analogues can be administered to a patient via a variety of delivery methods, including: intravenous, subcutaneous, intramuscular or intraperitoneal injection; oral administration; transdermal administration; pulmonary or transmucosal administration; administration by implant, osmotic pump, cartridge or micro pump; or by other means recognized by a person of skill in the art.

In some embodiments, the invention relates to a kit comprising an amylin analogue of the invention or a pharmaceutical composition of the invention. In certain embodiments, the kit further comprises packaging and/or instructions for use.

The device or kit may be useful for combination therapy as described above. Thus the device or kit may further comprise a further active agent, e.g. an anti-diabetic agent, an anti-obesity agent, an agent for treatment of metabolic syndrome, an anti-dyslipidemia agent, an anti-hypertensive agent, a proton pump inhibitor, or an anti-inflammatory agent as described above, or a pharmaceutical composition comprising such an active agent.

EXAMPLES

The following examples demonstrate certain specific embodiments of the present invention. The following examples were carried out using standard techniques that are well known and routine to those of skill in the art, except where otherwise described in detail. It is to be understood that these examples are for illustrative purposes only and do not purport to be wholly definitive as to conditions or scope of the invention. As such, they should not be construed as limiting the scope of the present invention in any way.

Abbreviations employed in the examples include:
Acm: acetaminomethyl
COMU™: (1-cyano-2-ethoxy-2-oxoethylidenaminooxy)dimethylamino-morpholino-carbenium hexafluorophosphate
DCM: dichloromethane
DMF: N,N-dimethylformamide
HATU: 2-(7-aza-1H-benzotriazole-1-yl)-1,1,3,3-tetramethyluronium hexafluorophosphate
DIPEA: diisopropylethylamine
DODT: 3,6-dioxa-1,8-octanedithiol
EtOH: ethanol
Et₂O: diethyl ether
TFA: trifluoroacetic acid
TIS: triisopropylsilane
MeCN: acetonitrile
HPLC: high performance liquid chromatography
RP-HPLC: reverse phase high performance liquid chromatography
MS: mass spectrometry
ESI-MS: electron spray ionization mass spectrometry
IBMX: 3-isobutyl-1-methylxanthine
BSA: bovine serum albumin
cAMP: cyclic adenosine monophosphate
DMEM: Dulbecco's Modified Eagle Medium
FCS: fetal calf serum
HEPES: N-2-hydroxyethylpiperazine-N'-2-ethanesulfonic acid
p-ERK: phosphorylated extracellular regulated kinase
PBS: phosphate-buffered saline
Boc: tert-butoxycarbonyl
Fmoc: 9-fluorenylmethoxycarbonyl
Trt: trityl (i.e. triphenylmethyl)
NEP: N-ethylpyrrolidone
NMP N-methylpyrrolidone
v/v: volume/volume
w/v: weight/volume The following examples are provided to illustrate certain embodiments of the invention and are not intended to limit the scope of the invention.

Measurement of Physiological Parameters

Unless otherwise specified, whole-blood glucose levels were determined on tail-vein blood samples by the Biosen (EKF Diagnostic, Germany) enzyme-based electrode method. Blood samples were analyzed for glycated hemoglobin (HbA1c) using a Cobas c111 analyzer (Roche Diagnostics, Mannheim, Germany). Plasma insulin levels were measured using a Meso Scale Discovery (MSD) system (Rockville, Md., USA). Liver fat content was determined by magnetic resonance (MR) scanning using an Echo systems MR scanner. Fat depots were measured by weighing of excised fat.

Example 1: Synthesis of Compounds

The following compounds were synthesised:

```
[19CD]-isoGlu-R-C( )-NTAT-C( )-ATQRLADFLHRSSF-Gly(Me)-A-Ile(Me)-LSSTEVGSETP-NH₂
(Compd. 1) (SEQ ID NO: 102)

[19CD]-isoGlu-R-C( )-NTAT-C( )-ATQRLAHFLHRSSF-Gly(Me)-A-Ile(Me)-LSSTEVGSETP-NH₂
(Compd.2) (SEQ ID NO: 103)

[19CD]-isoGlu-R-C( )-NTAT-C( )-ATQRLANFLHRSSF-Gly(Me)-A-Ile(Me)-LSSTEVGSETP-NH₂
(Compd. 3) (SEQ ID NO: 104)

[19CD]-isoGlu-R-C( )-NTAT-C( )-ATQRLADFLHRSSNNF-Gly(Me)-A-Ile(Me)-LSSINVGSNT-Apr-NH₂
(Compd. 4) (SEQ ID NO: 105)

[19CD]-soGlu-R-CQ-NTAT-C( )-ATQRLAHFLHRSSNNF-Gly(Me)-A-Ile(Me)-LSSTNVGSNT-Apr-NH₂
(Compd. 5) (SEQ ID NO: 106)

[19CD]-isoGlu-R-C( )-GTAT-C( )-ATERLAHFLNRSSF-Gly(Me)-A-Ile(Me)-LSSTEVGSNT-Hyp-NH₂
(Compd. 6)(SEQ ID NO: 107)

[19CD]-isoGlu-R-C( )-GTAT-C( )-ATERLAHFLQRSSF-Gly(Me)-A-Ile(Me)-LSSTEVGSNT-Hyp-NH₂
(Compd. 7)(SEQ ID NO: 108)

[19CD]-isoGlu-R-C( )-GTAT-C( )-ATERLAHFLERSSF-Gly(Me)-A-Ile(Me)-LSSTEVGSNT-Hyp-NH₂
(Compd. 8)(SEQ ID NO: 109)

[19CD]-isoGlu-R-C( )-GTAT-C( )-ATERLAHFLTRSSF-Gly(Me)-A-Ile(Me)-LSSTEVGSST-Hyp-NH₂
(Compd. 9)(SEQ ID NO: 110)

[19CD]-isoGlu-R-C( )-GTAT-C( )-ATERLAHFLTRSSF-Gly(Me)-A-Ile(Me)-LSSTEVGSFT-Hyp-NH₂
(Compd. 10) (SEQ ID NO: 111)
```

-continued

[19CD]-isoGlu-R-C( )-GTAT-C( )-ATERLAHFLTRSSF-Gly(Me)-A-Ile(Me)-LSSTEVGS-Orn-T-Hyp-NH$_2$
(Compd. 11) (SEQ ID NO: 112)

[19CD]-isoGlu-R-C( )-GTAT-C( )-ATERLAHFLTRSSF-Gly(Me)-A-Ile(Me)-LSSTEVGS-Aad-T-Hyp-NH$_2$
(Compd. 12) (SEQ ID NO: 113)

[19CD]-isoGlu-R-C( )-GTAT-C( )-ATERLAHFLTRSSF-Gly(Me)-A-Ile(Me)-LSSTEVGSGT-Hyp-NH$_2$
(Compd. 13) (SEQ ID NO: 114)

[19CD]-isoGlu-R-C( )-NTAT-C( )-ATQRLAHFLHRF-Gly(Me)-A-Ile(Me)-LSSTEVGSETP-NH$_2$
(Compd. 14) (SEQ ID NO: 115)

[19CD]-isoGlu-R-C( )-GTAT-C( )-ATERLAHFLHRSSF-Gly(Me)-A-Ile(Me)-LSSTEVGSNTP-NH$_2$
(Compd. 15) (SEQ ID NO: 116)

[19CD]-isoGlu-R-C( )-NTAT-C( )-ATQRLAHFLHRSSF-Gly(Me)-A-Ile(Me)-LSSTEVGSNTP-NH$_2$
(Compd. 16) (SEQ ID NO: 117)

[19CD]-isoGlu-R-C( )-GTAT-C( )-ATERLANFLVRSSF-Gly(Me)-A-Ile(Me)-LSSTEVGSNT-Hyp-NH$_2$
(Compd. 17) (SEQ ID NO: 118)

[19CD]-isoGlu-R-C( )-GTAT-C( )-ATERLAHFLTRSSF-Gly(Me)-A-Ile(Me)-LSSTEVGSNT-Hyp-NH$_2$
(Compd. 18) (SEQ ID NO: 119)

[19CD]-isoGlu-R-C( )-GTAT-C( )-ATERLAHFLKRSSF-Gly(Me)-A-Ile(Me)-LSSTEVGSNT-Hyp-NH$_2$
(Compd. 19) (SEQ ID NO: 120)

[19CD]-isoGlu-R-C( )-NTAT-C( )-ATQRLAHFLHRSVF-Gly(Me)-A-Ile(Me)-LSSTEVGSETP-NH$_2$
(Compd. 20) (SEQ ID NO: 121)

[19CD]-isoGlu-R-C( )-NTAT-C( )-ATQRLAHFLHRVSF-Gly(Me)-A-Ile(Me)-LSSTEVGSETP-NH$_2$
(Compd. 21) (SEQ. ID NO: 122)

[19CD]-isoGlu-R-C( )-GTAT-C( )-ATERLAHFLVRSSF-Gly(Me)-A-Ile(Me)-LSSTEVGSETP-NH$_2$
(Compd. 22) (SEQ ID NO: 123)

[19CD]-isoGlu-R-C( )-PTAT-C( )-ATDRLAHFLVRSSF-Gly(Me)-A-Ile(Me)-LSSTDVGSDTP-NH$_2$
(Compd. 23) (SEQ ID NO: 124)

[19CD]-isoGlu-R-C( )-NTAT-C( )-ATQRLAHFLVRSSF-Gly(Me)-A-Ile(Me)-LSSTEVGSETP-NH$_2$
(Compd. 24) (SEQ ID NO: 125)

[19CD]-isoGlu-R-C( )-PTAT-C( )-ATDRLANFLHRSSF-Gly(Me)-A-Ile(Me)-LSSTDVGSNTP-NH$_2$
(Compd. 25) (SEQ ID NO: 126)

[19CD]-isoGlu-R-C( )-GTAT-C( )-ATERLAHFLI-IRSSF-Gly(Me)-A-Ile(Me)-LSSTEVGSETP-NH$_2$
(Compd. 26) (SEQ ID NO: 127)

[19CD]-isoGlu-R-C( )-PTAT-C( )-ATDRLAHFLHRSSF-Gly(Me)-A-Ile(Me)-LSSTDVGSDTP-NH$_2$
(Compd. 27) (SEQ ID NO: 128)

[19CD]-isoGlu-R-C( )-GTAT-C( )-ATERLAHFLQRSSF-Gly(Me)-A-Ile(Me)-LSSTEVGSST-Hyp-NH$_2$
(Compd. 28) (SEQ ID NO: 129)

[19CD]-isoGlu-R-C( )-GTAT-C( )-ATERLAHFLNRSSF-Gly(Me)-A-Ile(Me)-LSSTEVGSST-Hyp-NH$_2$
(Compd. 29) (SEQ ID NO: 130)

[19CD]-isoGlu-R-C( )-GTAT-C( )-ATERLAHFLHRSSF-Gly(Me)-A-Ile(Me)-LSSTEVGSST-Hyp-NH$_2$
(Compd. 30) (SEQ ID NO: 131)

[19CD]-isoGlu-R-C( )-GTAT-C( )-ATERLAHFLVRSSF-Gly(Me)-A-Ile(Me)-LSSTEVGSST-Hyp-NH$_2$
(Compd. 31) (SEQ ID NO: 132)

[19CD]-isoGlu-R-C( )-GTAT-C( )-ATERLAHFLQRSSF-Gly(Me)-A-Ile(Me)-LSSTEVGSFT-Hyp-NH$_2$
(Compd. 32) (SEQ ID NO: 133)

[19CD]-isoGlu-R-C( )-GTAT-C( )-ATERLAHFLNRSSF-Gly(Me)-A-Ile(Me)-LSSTEVGSFT-Hyp-NH$_2$
(Compd. 33) (SEQ ID NO: 134)

[19CD]-isoGlu-R-C( )-GTAT-C( )-ATERLAHFLQRSSF-Gly(Me)-A-Ile(Me)-LSSTEVGSSTP-NH$_2$
(Compd. 34) (SEQ ID NO: 135)

[19CD]-isoGlu-R-C( )-GTAT-C( )-ATERLAHFLNRSSF-Gly(Me)-A-Ile(Me)-LSSTEVGSSTP-NH$_2$
(Compd. 35) (SEQ ID NO: 136)

[19CD]-isoGlu-R-C( )-GTAT-C( )-ATERLAHFLERSSF-Gly(Me)-A-Ile(Me)-LSSTEVGSSTP-NH$_2$
(Compd. 36) (SEQ ID NO: 137)

[19CD]-isoGlu-R-C( )-GTAT-C( )-ATERLAHFLHRSSF-Gly(Me)-A-Ile(Me)-LSSTEVGSSTP-NH$_2$
(Compd. 37) (SEQ ID NO: 138)

-continued

[19CD]-isoGlu-R-C( )-GTAT-C( )-ATERLAHFLVRSSF-Gly(Me)-A-Ile(Me)-LSSTEVGSSTP-NH$_2$
(Compd. 38) (SEQ ID NO: 139)

[19CD]-isoGlu-R-C( )-GTAT-C( )-ATERLAHFLQRSSF-Gly(Me)-A-Ile(Me)-LSSTEVGSFTP-NH$_2$
(Compd. 39) (SEQ ID NO: 140)

[19CD]-isoGlu-R-C( )-GTAT-C( )-ATERLAHFLNRSSF-Gly(Me)-A-Ile(Me)-LSSTEVGSFTP-NH$_2$
(Compd. 40) (SEQ ID NO: 141)

[19CD]-isoGlu-R-C( )-GTAT-C( )-ATERLADFLTRSSF-Gly(Me)-A-Ile(Me)-LSSTEVGSST-Hyp-NH$_2$
(Compd. 41) (SEQ ID NO: 142)

[19CD]-isoGlu-R-C( )-GTAT-C( )-ATERLADFLTRSSF-Gly(Me)-A-Ile(Me)-LSSTEVGSFT-Hyp-NH$_2$
(Compd. 42) (SEQ ID NO: 143)

[19CD]-isoGlu-R-C( )-GTAT-C( )-ATERLA-Aad-FLTRSSF-Gly(Me)-A-Ile(Me)-LSSTEVGSST-Hyp-NH$_2$
(Compd. 43) (SEQ ID NO: 144)

[19CD]-isoGlu-R-C( )-GTAT-C( )-ATERLA-Aad-FLTRSSF-Gly(Me)-A-Ile(Me)-LSSTEVGS-Orn-T-Hyp-NH$_2$ (Compd. 44) (SEQ ID NO: 145)

[19CD]-isoGlu-R-C( )-GTAT-C( )-ATERLAHFLTRSSF-Gly(Me)-A-Ile(Me)-LSSTEVGSST-Apr-NH$_2$
(Compd. 45) (SEQ ID NO: 146)

[19CD]-isoGlu-R-C( )-GTAT-C( )-ATERLAHFLTRSSF-Gly(Me)-A-Ile(Me)-LSSTEVGSSTP-NH$_2$
(Compd. 46) (SEQ ID NO: 147)

[19CD]-isoGlu-R-C( )-GTAT-C( )-ATERLAHFLTRSSF-Gly(Me)-A-Ile(Me)-LSSTEVGS-Orn-TP-NH$_2$
(Compd. 47) (SEQ ID NO: 148)

[19CD]-isoGlu-R-C( )-GTAT-C( )-ATERLAHFLTRSSF-Gly(Me)-A-Ile(Me)-LSSTEVGSTT-Hyp-NH$_2$
(Compd. 48) (SEQ ID NO: 149)

[19CD]-isoGlu-R-C( )-NTAT-C( )-ATQRLADFLQRSSF-Gly(Me)-A-Ile(Me)-LSSTEVGSNT-Hyp-NH$_2$
(Compd. 49) (SEQ ID NO: 150)

[19CD]-isoGlu-R-C( )-NTAT-C( )-ATQRLAHFL-Aad-RSSF-Gly(Me)-A-Ile(Me)-LSSTEVGSNT-Hyp-NH$_2$
(Compd. 50) (SEQ ID NO: 151)

[19CD]-isoGlu-R-C( )-GTAT-C( )-ATERLAHFLQRSSF-Gly(Me)-A-Ile(Me)-LSSTEVGS-Orn-T-Hyp-NH$_2$
(Compd. 51) (SEQ ID NO: 152)

[19CD]-isoGlu-R-C( )-GTAT-C( )-ATERLAHFLQRSSF-Gly(Me)-A-Ile(Me)-LSSTEVGSGT-Hyp-NH$_2$
(Compd. 52) (SEQ ID NO: 153)

[19CD]-isoGlu-R-C( )-GTAT-C( )-ATERLAHFLQRSSF-Gly(Me)-A-Ile(Me)-LSSTEVGS-Aad-T-Hyp-NH$_2$
(Compd. 53) (SEQ ID NO: 154)

[19CD]-isoGlu-R-C( )-GTAT-C( )-ATERLADFLQRSSF-Gly(Me)-A-Ile(Me)-LSSTEVGSNT-Hyp-NH$_2$
(Compd. 54) (SEQ ID NO: 155)

[19CD]-isoGlu-R-C( )-GTAT-C( )-ATERLA-Aad-FLQRSSF-Gly(Me)-A-Ile(Me)-LSSTEVGSNT-Hyp-NH$_2$
(Compd. 55) (SEQ ID NO:156 )

[19CD]-isoGlu-R-C( )-NTAT-C( )-ATERLAHFLQRSSF-Gly(Me)-A-Ile(Me)-LSSTEVGSNT-Hyp-NH$_2$
(Compd. 56) (SEQ ID NO: 157)

[19CD]-isoGlu-R-C( )-QTAT-C( )-ATERLAHFLQRSSF-Gly(Me)-A-Ile(Me)-LSSTEVGSNT-Hyp-NH$_2$
(Compd. 57) (SEQ ID NO: 158)

[19CD]-isoGlu-R-C( )-NTAT-C( )-ATQRLAHFLQRSSF-Gly(Me)-A-Ile(Me)-LSSTEVGSNT-Hyp-NH$_2$
(Compd. 58) (SEQ ID NO: 159)

[19CD]-isoGlu-R-C( )-PTAT-C( )-ATDRLAHFLQRSSF-Gly(Me)-A-Ile(Me)-LSSTDVGSNT-Hyp-NH$_2$
(Compd. 59) (SEQ ID NO: 160)

[19CD]-isoGlu-R-C( )-NTAT-C( )-ATQRLAHFLQRSSF-Gly(Me)-A-Ile(Me)-LSSTEVGSDT-Hyp-NH$_2$
(Compd. 60) (SEQ ID NO: 161)

[19CD]-isoGlu-R-C( )-NTAT-C( )-ATQRLAHFLQRSSF-Gly(Me)-A-Ile(Me)-LSSTEVGSNTP-NH$_2$
(Compd. 61) (SEQ ID NO: 162)

[19CD]-isoGlu-R-C( )-NTAT-C( )-ATERLAHFLQRSSF-Gly(Me)-A-Ile(Me)-LSSTEVGSNTP-NH$_2$
(Compd. 62) (SEQ ID NO: 163)

[19CD]-isoGlu-R-C( )-PTAT-C( )-ATERLAHFLQRSSF-Gly(Me)-A-Ile(Me)-LSSTEVGSNT-Hyp-NH$_2$
(Compd. 63) (SEQ ID NO: 164)

[19CD]-isoGlu-R-C( )-PTAT-C( )-ATQRLAHFLQRSSF-Gly(Me)-A-Ile(Me)-LSSTEVGSNT-Hyp-NH$_2$
(Compd. 64) (SEQ ID NO: 165)

-continued

[19CD]-isoGlu-R-C( )-NTAT-C( )-ATQRLADFLQRSSF-Gly(Me)-A-Ile(Me)-LSSTEVGSNTP-NH$_2$
(Compd. 65) (SEQ ID NO: 166)

[19CD]-isoGlu-R-C( )-NTAT-C( )-ATERLADFLQRSSF-Gly(Me)-A-Ile(Me)-LSSTEVGSNTP-NH$_2$
(Compd. 66) (SEQ ID NO: 167)

[19CD]-isoGlu-R-C( )-PTAT-C( )-ATERLADFLQRSSF-Gly(Me)-A-Ile(Me)-LSSTEVGSNTP-NH$_2$
(Compd. 67) (SEQ ID NO: 168)

[19CD]-isoGlu-R-C( )-NTAT-C( )-ATERLADFLQRSSF-Gly(Me)-A-Ile(Me)-LSSTEVGSNT-Hyp-NH$_2$
(Compd. 68) (SEQ ID NO: 169)

[19CD]-isoGlu-R-C( )-NTAT-C( )-ATQRLAHFLQRSSF-Gly(Me)-A-Ile(Me)-LSSTEVGSST-Hyp-NH$_2$
(Compd. 69) (SEQ ID NO: 170)

[19CD]-isoGlu-R-C( )-PTAT-C( )-ATERLAHFLQRSSF-Gly(Me)-A-Ile(Me)-LSSTEVGSST-Hyp-NH$_2$
(Compd. 70) (SEQ ID NO: 171)

[19CD]-isoGlu-R-C( )-NTAT-C( )-ATQRLAHFLQRSSF-Gly(Me)-A-Ile(Me)-LSSTEVGSGT-Hyp-NH$_2$
(Compd. 71) (SEQ ID NO: 172)

[19CD]-isoGlu-R-C( )-PTAT-C( )-ATERLAHFLQRSSF-Gly(Me)-A-Ile(Me)-LSSTEVGSGT-Hyp-NH$_2$
(Compd. 72) (SEQ ID NO: 173)

[19CD]-isoGlu-R-C( )-NTAT-C( )-ATQRLAHFLQRSSF-Gly(Me)-A-Ile(Me)-LSSTEVGSTT-Hyp-NH$_2$
(Compd. 73) (SEQ ID NO: 174)

[19CD]-isoGlu-R-C( )-PTAT-C( )-ATERLAHFLQRSSF-Gly(Me)-A-Ile(Me)-LSSTEVGSTT-Hyp-NH$_2$
(Compd. 74) (SEQ ID NO: 175)

[19CD]-isoGlu-R-C( )-NTAT-C( )-ATQRLAHFLQRSSF-Gly(Me)-A-Ile(Me)-LSSTEVGS-Aad-T-Hyp-NH$_2$
(Compd. 75) (SEQ ID NO: 176)

[19CD]-isoGlu-R-C( )-PTAT-C( )-ATERLANFLQRSSF-Gly(Me)-A-Ile(Me)-LSSTEVGS-Aad-T-Hyp-NH$_2$
(Compd. 76) (SEQ ID NO: 177)

[19CD]-isoGlu-R-C( )-GTAT-C( )-ATERLAHFLQRF-Gly(Me)-A-Ile(Me)-LSSTEVGSNT-Hyp-NH$_2$
(Compd. 77) (SEQ ID NO: 178)

[19CD]-isoGlu-R-C( )-GTAT-C( )-ATERLAHFLQRSSF-Gly(Me)-A-Ile(Me)-LSSTEVGSNTP-NH$_2$
(Compd. 78) (SEQ ID NO: 179)

[19CD]-isoGlu-R-C( )-NTAT-C( )-ATQRLAHFLQRF-Gly(Me)-A-Ile(Me)-LSSTEVGSGT-Hyp-NH$_2$
(Compd. 79) (SEQ ID NO: 180)

[19CD]-isoGlu-R-C( )-NTAT-C( )-ATQRLADFLQRSSF-Gly(Me)-A-Ile(Me)-LSSTEVGSGTP-NH$_2$
(Compd. 80) (SEQ ID NO: 181)

[19CD]-isoGlu-R-C( )-NTAT-C( )-ATQRLADFLQRSSF-Gly(Me)-A-Ile(Me)-LSSTEVGSGT-Hyp-NH$_2$
(Compd. 81) (SEQ ID NO: 182)

[19CD]-isoGlu-R-C( )-NTAT-C( )-ATQRLADFLQRSSF-Gly(Me)-A-Ile(Me)-LSSTEVGSTTP-NH$_2$
(Compd. 82) (SEQ ID NO: 183)

[19CD]-isoGlu-R-C( )-NTAT-COATQRLADFLQRSSF-Gly(Me)-A-Ile(Me)-LSSTEVGSTT-Hyp-NH$_2$
(Compd. 83) (SEQ ID NO: 184)

[19CD]-isoGlu-R-C( )-NTAT-C( )-ATQRLAHFLERSSF-Gly(Me)-A-Ile(Me)-LSSTEVGSSTP-NH$_2$
(Compd. 84) (SEQ ID NO: 185)

[19CD]-isoGlu-R-C( )-NTAT-C( )-ATQRLAHFLQRSSF-Gly(Me)-A-Ile(Me)-LSSTEVGSSTP-NH$_2$
(Compd. 85) (SEQ ID NO: 186)

[19CD]-isoGlu-R-C( )-NTAT-C( )-ATQRLA-Aad-FLQRSSF-Gly(Me)-A-Ile(Me)-LSSTEVGSNT-Hyp-NH$_2$
(Compd. 86) (SEQ ID NO: 187)

[19CD]-isoGlu-R-C( )-NTAT-C( )-ATQRLA-Aad-FLQRSSF-Gly(Me)-A-Ile(Me)-LSSTEVGSST-Hyp-NH$_2$
(Compd. 87) (SEQ ID NO: 188)

[19CD]-isoGlu-R-C( )-QTAT-C( )-ATDRLAHFLQRSSF-Gly(Me)-A-Ile(Me)-LSSTEVGSNT-Hyp-NH$_2$
(Compd. 88) (SEQ ID NO: 189)

[19CD]-isoGlu-R-C( )-QTAT-C( )-ATDRLA-Aad-FLQRSSF-Gly(Me)-A-Ile(Me)-LSSTEVGSNT-Hyp-NH$_2$
(Compd. 89) (SEQ ID NO: 190)

[19CD]-isoGlu-R-C( )-QTAT-C( )-ATERLAHFLQRSSF-Gly(Me)-A-Ile(Me)-LSSTEVGSGT-Hyp-NH$_2$
(Compd. 90) (SEQ ID NO: 191)

[19CD]-isoGlu-R-C( )-QTAT-C( )-ATDRLAHFLQRSSF-Gly(Me)-A-Ile(Me)-LSSTEVGSGT-Hyp-NH$_2$
(Compd. 91) (SEQ ID NO: 192)

-continued

```
[19CD]-isoGlu-R-C( )-QTAT-C( )-ATDRLAHFLQRSSF-Gly(Me)-A-Ile(Me)-LSSTEVGSNTP-NH2
(Compd. 92) (SEQ ID NO: 193)

[19CD]-isoGlu-R-C( )-QTAT-C( )-ATERLA-Aad-FLQRSSF-Gly(Me)-A-Ile(Me)-LSSTEVGSNTP-NH2
(Compd. 93) (SEQ ID NO: 194)

[19CD]-isoGlu-R-C( )-QTAT-C( )-ATERLA-Aad-FLQRSSF-Gly(Me)-A-Ile(Me)-LSSTEVGSGTP-NH2
(Compd. 94) (SEQ ID NO: 195)

[19CD]-isoGlu-R-C( )-QTAT-C( )-ATDRLA-Aad-FLQRF-Gly(Me)-A-Ile(Me)-LSSTEVGSNT-Hyp-NH2
(Compd. 95) (SEQ ID NO: 196)

[19CD]-isoGlu-R-C( )-QTAT-C( )-ATERLAHFLQRF-Gly(Me)-A-Ile(Me)-LSSTEVGSNTP-NH2
(Compd. 96) (SEQ ID NO: 197)
```

([19CD]-isoGlu represents a [19-carboxynonadecanoyl] group linked to the free alpha-amino group of the N-arginine residue via an iso-glutamic acid linker.)

Also synthesized, for use as controls, were:

```
Pramlintide:
H-KC( )NTATC( )ATQRLANFLVHSSNNFGPILPPTNVGSNTY-NH2 (SEQ ID NO: 198)
```

NN96: N-α-[(S)-4-carboxy-4-(19-carboxynonadecanoy-lamino)butyryl]-[Arg1,Glu14,His17,Pro37]-pramlintide-NH2
(NN96 is disclosed in WO 2012/168430 and has the amino acid sequence:

```
RC( )NTATC( )ATQRLAEFLHHSSNNFGPILPPTNVGSNTP)
(SEQ ID NO: 199)

[19CD]-isoGlu-R-C( )-NTAT-C( )-
ATQRLAEFLHHSSFGPILPPTNVGSNTP-NH2 (Compd. 97)
(SEQ ID NO: 200)

[19CD]-isoGlu-R-C( )-GTAT-C( )-ATERLA-Aad-
FLQRSSNNF-Gly(Me)-A-Ile(Me)-LSSTEVGSNT-Hyp-NH2
(Compd. 98) (SEQ ID NO: 201)

[19CD]-isoGlu-R-C( )-QTAT-C( )-ATERLAHFLQRSSNNF-
Gly(Me)-A-Ile(Me)-LSSTEVGSNT-Hyp-NH2
(Compd. 99) (SEQ ID NO: 202)

[19CD]-isoGlu-R-C( )-QTAT-C( )-ATDRLA-Aad-
FLQRSSNNF-Gly(Me)-A-Ile(Me)-LSSTEVGSNT-Hyp-NH2
(Compd. 100) (SEQ ID NO: 203)
```

Compound 97 has the same sequence as NN96 except for a deletion of the Asn residues at positions 21 and 22.

Compounds 98, 99 and 100 have the same sequences as compound 55, compound 57 and compound 89 respectively, except for Asn residues inserted at positions 21 and 22.

Parentheses "( )" indicate intramolecular disulphide bridges between the side chains of cysteine residues at positions 2 and 7 of the relevant amino acid sequences.

Unless otherwise specified, reagents and solvents employed in the following were available commercially in standard laboratory reagent or analytical grade, and were used without further purification.

Suitable general procedures for synthesis include the following:

General Procedures for Solid-Phase Synthesis of Peptides

A CEM Liberty Peptide Synthesizer was employed, using standard Fmoc chemistry. TentaGel™ S Ram resin (1 g; 0.25 mmol/g) was swelled in DMF (10 ml) prior to use and transferred between tube and reaction vessel using DCM and DMF. Pseudoprolines [i.e. dipeptides employed to minimize aggregation during peptide synthesis, such as Fmoc-Phe-Thr(ψ-Me,Me-Pro)-OH and Fmoc-Asp-Ser(ψ-Me,Me-Pro)-OH and Fmoc-Ser-Ser(ψ-Me,Me-Pro)-OH] were used where appropriate, and non-naturally occurring amino acids and other suitable building blocks were employed without any changes to the general procedure.

The following optical isomers of particular amino acids (including non-naturally occurring amino acids) were employed in the synthesis of the compounds:

Apr: (2S,4R)-4-aminoproline [also denoted (4R)-4-amino-L-proline];

Hyp: (2S,4R)-4-hydroxyproline [also denoted (4R)-4-hydroxy-L-proline].

Aad: (2S)-2-aminoadipic acid

Coupling:

An Fmoc-amino acid in DMF/DCM (2:1; 0.2 M; 5 ml) was added to the resin in a CEM Discover microwave unit together with COMU/DMF (0.5 M; 2 ml) and DIPEA/DMF (2.0 M; 1 ml). The coupling mixture was heated to 75° C. for 5 min. while nitrogen was bubbled through the mixture. The resin was then washed with DMF (4×10 ml). Alternatively the coupling was done without heating and the reaction time extended to 60 min in this case.

In the case of difficult couplings (e.g. coupling of a residue immediately after an N-methylated amino acid residue or other sterically hindered amino acid residue as recognized by a person of skill in the art) the coupling was repeated one or more times.

Deprotection:

Piperidine/DMF (1:4, i.e. 1 part piperidine to 4 parts DMF by volume; 10 ml) was added to the resin for initial deprotection, and the mixture was microwave-heated (40° C.; 30 sec.). The reaction vessel was drained and a second portion of piperidine/DMF (1:4; 10 ml) was added and heated (75° C.; 3 min) again. The resin was then washed with DMF (6×10 ml).

Oxidative Cyclisation

Intramolecular ring formation (disulfide bridge formation) between the Cys residues in positions 2 and 7 (initially coupled in the form of Acm-protected cysteines) was performed with the peptide still attached to the resin, using 163 mg thallium(III) trifluoroacetate [Tl(TFA)$_3$] in 5 mL NMP in a simultaneous Acm-deprotection and disulfide-formation step.

Cleavage:

The resin was washed with EtOH (3×10 ml) and Et$_2$O (3×10 ml) and dried to constant weight at room temperature (r.t.). The crude peptide was cleaved from the resin by treatment with TFA/TIS/H$_2$O (90:5:5; 40 ml; 2 h; room temp.) or alternatively with TFA/DODT (95:5; 40 ml; 2 h; room temp.). Most of the TFA was removed under reduced pressure, and the crude peptide was precipitated and washed three times with Et$_2$O and dried to constant weight at room temperature.

Purification and Characterisation:

The crude peptide was purified by preparative reverse phase HPLC using a PerSeptive Biosystems VISION Workstation or a Gilson system (Pumps: "Pump 305", "331 Pump", "332 Pump", "402 Syringe Pump"; column changer "Valvemate® II" UV detector "UV/Vis-155"; and the fraction collector "GX 281" equipped with a suitable column and a fraction collector, and run with a gradient of buffer A (0.1% aqueous TFA) and buffer B (0.1% TFA, 90% MeCN, water). Fractions were analysed by analytical HPLC and MS, and relevant fractions were pooled and lyophilised. The final product was characterized by HPLC and MS.

One of skill in the art will appreciate that standard methods of peptide synthesis may be used to generate the compounds of the invention.

Example 2: Generation of Cell Lines Expressing (i) Human Calcitonin Receptor (hCTR2), and (ii) Human Amylin Receptor 3 (hAMYR3) Consisting of hCTR2 Co-Expressed with Human Receptor Activity Modifying Protein 3 (hRAMP3)

The cell line COS7, originating from African Green Monkey kidney fibroblast cells, was used for establishment of the stable cell lines described below. The COS7 cellular background was used due to it being RAMP nave, and as such it provides the best available system for testing of the monomeric hCTR and different heterodimeric amylin receptor subtypes functionally generated by introduction of the individual RAMPs.

Calcitonin Receptor Cell Line:

A cell line expressing the human calcitonin receptor (hCTR2) was generated in the COS7 cellular background as stable clones. In brief, hCTR2 (GI: 4502547) was amplified by PCR using primers encoding terminal restriction sites for subcloning. The 5'-end primers additionally encoded a near Kozak consensus sequence to ensure efficient translation. The fidelity of the DNA encoding the receptor was confirmed by DNA sequencing. The PCR products encoding the receptor were subcloned into a mammalian expression vector containing a neomycin (G418) resistance marker. The mammalian expression vector encoding the receptor was transfected into COS7 cells by a standard liposome transfection method. 48 hours post-transfection, cells were seeded for limited dilution cloning and selected with 1 mg/ml G418 in the culture medium. After 3 weeks, surviving colonies of hCTR2-expressing cells were picked, propagated and tested in the amylin efficacy assay as described in Example 3 below. One hCTR2-expressing clone was chosen for compound profiling.

Amylin Receptor Cell Line:

A cell line expressing the human amylin receptor 3 (hAMYR3) was generated in the COS7 cellular background as stable clones. In brief, hCTR2 (GI:4502547) and hRAMP3 (GI:118572586) were amplified by PCR using primers encoding terminal restriction sites for subcloning. The 5'-end primers additionally encoded a near Kozak consensus sequence to ensure efficient translation. The fidelity of the DNA encoding the receptor was confirmed by DNA sequencing. The PCR products encoding the receptor were subcloned into a proprietary tri-cistronic mammalian expression vector with RAMP3, hCTR2 and neomycin (G418) resistance marker. The mammalian expression vector encoding the receptor was transfected into COS7 cells by a standard liposome transfection method. 48 hours post-transfection, cells were seeded for limited dilution cloning and selected with 1 mg/ml G418 in the culture medium. After 3 weeks, surviving colonies of hAMY3R-expressing cells were picked, propagated and tested in the amylin efficacy assay as described in Example 3 below. The functional generation of the amylin receptor phenotype was verified in the efficacy assay by a left-shifted efficacy response to amylin relative to monomeric calcitonin receptor, and one hAMYR3-expressing clone was chosen for compound profiling.

Example 3: hCTR2 and hAMYR3 Assays

In vitro activity of test peptides at the hCTR2 and hAMYR3 receptors was assessed by measuring the induction of cAMP following stimulation of the receptor using the AlphaScreen® cAMP Assay kit from Perkin-Elmer.

Briefly, COS7 cells expressing hCTR2 (see Example 2, above) were seeded at 30-40,000 cells per well in 96-well microtiter plates coated with 0.01% poly-L-lysine, and grown for 1 day in culture in 100 µl growth medium [DMEM, 10% FCS, Penicillin (100 IU/ml), Streptomycin (100 µg/ml)]. On the day of analysis, growth medium was removed and the cells were washed once with 200 µl Tyrode buffer [Tyrode's Salts (9.6 g/l), 10 mM HEPES, pH 7.4]. Cells were incubated in 100 µl Tyrode buffer containing increasing concentrations of test peptides, 100 µM IBMX and 0.1% casein for 15 min at 37° C. The reaction was stopped by carefully decanting off the compound/buffer medium and replacing it with lysis/detection buffer (80 µl 0.1% w/v BSA, 5 mM HEPES, 0.3% v/v Tween-20 in deionized water). After incubation at room temperature for 10 min., the cAMP content of the resulting cell lysate was estimated according to the AlphaScreen® cAMP Assay manufacturer's instructions. EC$_{50}$ values were estimated by computer-aided curve fitting using the 4-parameter logistic (4PL) non-linear model.

The in vitro activity results (expressed as EC$_{50}$ values) are summarized in Table 1, below.

Example 4: Assessment of Solubility

A stock solution of the test peptide (2 mg/ml; determined from the weighed amount of peptide) in demineralized water adjusted to pH 2.5 with HCl was prepared, and aliquots were diluted 1:1 in 100 mM acetate buffer (pH 4.0 and pH 5.0), 100 mM histidine buffer (pH 6.0 and pH 7.0) and 100 mM phosphate buffer (pH 6.0, pH 7.0 and pH7.5), respectively, and loaded in a standard flat-bottom, non-sterile 96-well UV Microplate. The absorbance of samples (single samples, n=1) at 280 and 325 nm was measured in an absorbance-based plate reader, which was preheated to ambient temperature (typically 25° C.). The turbidity absorbance criterion for a peptide solubility of ≥1 mg/ml was an absorbance at 325 nm of ≤0.02 absorbance units (which is 5 to 6 times the standard deviation of 8 buffer samples in a plate).

Measurements were made on Compounds 1-17, 19, 27-38, 49-69 and 71-87. With the exception of Compound 10 at pH 6.0. Compound 31 at pH 7.0 and 7.5, and Compound 38 at pH 6.0 and 7.5, all of the tested compounds exhibited solubility ≥1 mg/ml in all the test buffers.

Example 5: Assessment of Physical Stability

Aggregation in the form of fibril formation was detected using the amyloid-specific dye Thioflavin T (ThT), which is frequently employed to demonstrate the presence of fibrils in solution (see, e.g., Groenning, M., *J. Chem. Biol.* 3(1) (2010), pp. 1-18; Groenning et al., *J. Struct. Biol.* 158 (2007) pp. 358-369; and Levine, H., III, *Protein Sci.* 2 (1993) pp. 404-410) Test peptides (2 mg/ml) were dissolved in demineralized water adjusted to pH 2.5 with HCl, at ambient temperature (typically 25° C.). Solutions containing (i) 1 mg/ml of test peptide, 40 µM ThT and 50 mM phosphate (Ph) buffer (pH 7.0), (ii) 1 mg/ml of test peptide, 40 µM ThT and 50 mM histidine (His) buffer (pH 7.0), and (iii) 1 mg/ml of test peptide, 40 µM ThT and 50 mM acetate (Ac) buffer (pH 4.0), were loaded in a 96-well black fluorescence plate (clear bottom) in triplicate. Data were collected at fixed intervals of 10 min, each preceded by 300 s of automixing (agitation), over a period of 96 hours at 40° C. Physical stability, expressed as lag-time of fibril formation (in hours), was defined as the intersection between two linear regressions representing the initial stable phase and the growth phase. Data are summarized in Table 1 below.

Example 6: Assessment of Chemical Stability

Samples of each test peptide were dissolved in MilliQ™ water, and the pH of the solution was adjusted to pH 4, pH 6, pH 7.5 or pH 9, respectively, using either HCl or NaOH. The final peptide concentration was 0.2 mg/ml. Samples were placed in glass vials and incubated at 40° C. The samples were analyzed by RP-HPLC on a C8 column with gradient elution using an ammonium formate/water eluent system, or on a C18 column with gradient elution using a trifluoroacetic acid/water eluent system. The area-percentage (area-%) of the main peak after incubation time T=t (relative to time T=0) was determined by UV spectroscopy at 220 nm.

The purity was first determined as follows:

Purity (area-%)=(area of main peak/total area of all peaks)×100.

The purity was then normalized between time points by setting purity at time 0 (T=0) to 100 for each pH value for a given peptide, as follows:

Normalised area-% at time $t(T=t)$=[area-% $(T=t)$/area-% $(T=0)$]×100.

The chemical stability assessment results (in the form of normalized purity values) are summarized in Table 1 (below). The normalized purity values in Table 1 were determined after 7 days of incubation.

TABLE 1

EC$_{50}$, chemical stability and fibrillation data

| Cmpd. No. | hCTR2 EC$_{50}$ (nM) | hAMYR3 EC$_{50}$ (nM) | Normalized purity after 7 days, 40° C.** | | | | Fibrillation$^{\S\S}$ | | |
|---|---|---|---|---|---|---|---|---|---|
| | | | pH 4 | pH 6 | pH 7.5 | pH 9 | pH 4.0 (Ac) | pH 7.0 (His) | pH 7.0 (Phos.) |
| 1 | 0.079 | 0.230 | | | | | FND | FND | FND |
| 2 | 0.076 | 0.120 | A | | A | B | FND | FD | FND |
| 3 | 0.160 | 0.200 | A | | B | B | FD | FD | FD |
| 4 | 0.210 | 0.220 | B | | C | C | FND | FND | FND |
| 5 | 0.200 | 0.180 | B | | C | C | FND | FND | FND |
| 6 | 0.077 | 0.220 | A | B | | B | FND | FND | FND |
| 7 | 0.087 | 0.340 | A | A | A | A | FND | FND | FND |
| 8 | 0.180 | 0.360 | A | B | A | A | FND | FND | FND |
| 9 | 0.099 | 0.290 | A | B | B | B | FND | FD | FD |
| 10 | 0.160 | 0.350 | A | A | B | B | FND | FD | FD |
| 11 | 0.130 | 0.200 | A | B | A | B | FND | FD | FD |
| 12 | 0.120 | 0.250 | A | A | B | B | FND | FD | FD |
| 13 | 0.120 | 0.380 | A | A | A | A | FND | FD | FD |
| 14 | 0.150 | 0.260 | A | A | A | A | FND | FD | FND |
| 15 | 0.044 | 0.079 | A | B | B | B | FND | FD | FND |
| 16 | 0.073 | 0.110 | A | A | A | B | FD | FD | FND |
| 17 | 0.13 | 0.61 | | | | | | | |
| 18 | 0.12 | 0.41 | | | | | FND | FD | FD |
| 19 | 0.16 | 0.28 | A | A | A | C | FND | FND | FND |
| 20 | 0.19 | 0.33 | | | | | FND | FD | FND |
| 21 | 0.12 | 0.23 | | | | | FND | FD | FD |
| 22 | 0.078 | 0.59 | | | | | FND | FD | FND |
| 23 | 0.094 | 0.13 | | | | | | | |
| 24 | 0.085 | 0.19 | | | | | | | |
| 25 | 0.046 | 0.094 | | | | | | | |
| 26 | 0.057 | 0.12 | | | | | | | |
| 27 | 0.063 | 0.16 | | | | | FD | FD | FD |
| 28 | 0.11 | 0.13 | A | B | B | B | FND | FND | FND |
| 29 | 0.09 | 0.12 | A | | B | B | | | |
| 30 | 0.07 | 0.12 | | | | | FND | FD | FD |
| 31 | 0.09 | 0.29 | | | | | | | |
| 32 | 0.17 | 0.23 | | | | | FND | FD | FD |
| 33 | 0.11 | 0.15 | | | | | | | |
| 34 | 0.09 | 0.12 | A | B | B | B | FND | FND | FND |
| 35 | 0.05 | 0.11 | A | A | B | B | FND | FND | FND |
| 36 | 0.21 | 0.36 | A | A | B | B | FND | FND | FD |
| 37 | 0.04 | 0.07 | | | | | | | |
| 38 | 0.06 | 0.12 | | | | | | | |
| 39 | 0.16 | 0.22 | | | | | | | |
| 40 | 0.12 | 0.19 | | | | | | | |
| 41 | 0.15 | 0.34 | B | A | A | A | | | |

TABLE 1-continued

EC$_{50}$, chemical stability and fibrillation data

| Cmpd. No. | hCTR2 EC$_{50}$ (nM) | hAMYR3 EC$_{50}$ (nM) | Normalized purity after 7 days, 40° C.** | | | | Fibrillation$^{§§}$ | | |
|---|---|---|---|---|---|---|---|---|---|
| | | | pH 4 | pH 6 | pH 7.5 | pH 9 | pH 4.0 (Ac) | pH 7.0 (His) | pH 7.0 (Phos.) |
| 42 | 0.12 | 0.34 | | | | | | | |
| 43 | 0.22 | 0.35 | A | A | A | A | | | |
| 44 | 0.2 | 0.3 | | | | | | | |
| 45 | 0.16 | 0.31 | | | | | | | |
| 46 | 0.1 | 0.14 | | | | | | | |
| 47 | 0.1 | 0.19 | | | | | | | |
| 48 | 0.12 | 0.26 | A | A | A | A | FND | FND | FND |
| 49 | 0.06 | 0.15 | A | A | A | B | FD | FND | FND |
| 50 | 0.12 | 0.19 | | | | | | | |
| 51 | 0.08 | 0.11 | A | B | B | B | FND | FND | FND |
| 52 | 0.07 | 0.09 | A | B | B | B | FND | FND | FND |
| 53 | 0.14 | 0.13 | A | A | B | B | FND | FND | FND |
| 54 | 0.08 | 0.14 | A | A | B | B | FND | FND | FND |
| 55 | 0.11 | 0.08 | A | A | A | B | FND | FND | FND |
| 56 | 0.06 | 0.08 | A | A | A | B | FND | FND | FND |
| 57 | 0.08 | 0.11 | A | A | A | A | FND | FND | FND |
| 58 | 0.05 | 0.1 | A | A | B | B | FND | FD | FND |
| 59 | 0.03 | 0.11 | A | B | C | B | FND | FD | FD |
| 60 | 0.08 | 0.09 | A | A | A | B | FND | FND | FND |
| 61 | 0.12 | 0.17 | | | | | | | |
| 62 | 0.18 | 0.22 | | | | | | | |
| 63 | 0.35 | 0.37 | | | | | | | |
| 64 | 0.11 | 0.15 | | | | | | | |
| 65 | 0.14 | 0.26 | A | A | A | A | | | |
| 66 | 0.19 | 0.30 | | | | | | | |
| 67 | 0.27 | 0.65 | | | | | | | |
| 68 | 0.32 | 0.29 | | | | | | | |
| 69 | 0.12 | 0.17 | A | A | B | B | | | |
| 70 | 0.35 | 0.36 | | | | | | | |
| 71 | 0.11 | 0.18 | A | A | A | B | FND | FD | FD |
| 72 | 0.35 | 0.27 | | | | | | | |
| 73 | 0.12 | 0.24 | | | | | | | |
| 74 | 0.58 | 0.39 | | | | | | | |
| 75 | 0.36 | 0.26 | | | | | | | |
| 76 | 0.44 | 0.49 | | | | | | | |
| 77 | 0.16 | 0.42 | A | A | B | B | FND | FND | FND |
| 78 | 0.15 | 0.24 | | | | | | | |
| 79 | 0.12 | 0.23 | A | A | B | B | FND | FD | FD |
| 80 | 0.13 | 0.28 | A | A | A | A | | | |
| 81 | 0.10 | 0.23 | A | A | A | A | | | |
| 82 | 0.21 | 0.53 | | | | | | | |
| 83 | 0.13 | 0.32 | | | | | | | |
| 84 | 0.15 | 0.54 | | | | | | | |
| 85 | 0.1 | 0.14 | | | | | | | |
| 86 | 0.1 | 0.15 | A | A | A | A | | | |
| 87 | 0.2 | 0.13 | | | | | | | |
| 88 | 0.06 | | A | A | A | A | FND | FND | FND |
| 89 | 0.16 | 0.20 | A | A | A | B | FND | FND | FND |
| 90 | 0.20 | 0.24 | A | A | A | A | FND | FND | FND |
| 91 | 0.08 | 0.17 | A | A | A | A | FND | FND | FND |
| 92 | 0.10 | 0.22 | A | A | A | A | | | |
| 93 | | 0.43 | | | | | | | |
| 95 | 0.18 | 0.20 | A | A | A | A | | | |
| 96 | 0.33 | 0.28 | A | A | A | A | FND | FND | FND |
| Pramlintide | 1.40 | 0.230 | | | | | FD | | FD |
| NN96 | 0.089 | 0.150 | A | A | B | B | FND | FD | FD |

**A = >90%; B = 70-90%; C = <70%; Blank = not determined.
$^{§§}$FND = fibrillation not detected; FD = fibrillation detected.

Example 7: Pharmacokinetic (PK) Profiling in Rats

Compounds 6, 7, 9, 11, 13, 15, 28, 34, 36, 49, 55, 57 and 71 were tested for their pharmacokinetic properties in rats.

Sprague Dawley male rats were given a single subcutaneous (sc) bolus of each peptide to be tested, as specified below.

30 nmol/kg doses of compound were administered. Blood samples were drawn from the tail vein prior to dosing and at 24, 48, 72, 96 and 168 hours after dosing. Blood samples were taken from two rats at each time point, and only 2 blood samples were drawn from each rat, i.e. 10 rats were used for each compound. The rats were euthanized immediately after the last blood sampling by concussion and cervical dislocation.

The dosing vehicle used for each test peptide was a mannitol-containing histidine buffer (pH 7.0). Plasma samples were analyzed after precipitation with ethanol by liquid chromatography mass spectrometry (LC-MS/MS). Mean plasma concentrations were used for calculation of the pharmacokinetic parameters using the non-compartmental approach in Phoenix WinNonlin 6.3.

Plasma terminal elimination half-life ($t_{1/2}$) was determined as $\ln(2)/\lambda z$, where $\lambda z$ is the magnitude of the slope of the log linear regression of the log concentration versus time profile during the terminal phase. Apparent clearance (CL/F) was determined as dose/$AUC_{inf}$ (sc), where $AUC_{inf}$ is the area under the plasma concentration vs. time curve extrapolated to infinity ($AUC_{inf}=AUC_{last}+C_{last}/\lambda z$, where $C_{last}$ is the last observed plasma concentration).

Results

As shown in Table 2, below, the plasma terminal elimination half-lives for all tested peptides were determined to be in the range of 14.1 hours to 36.7 hours, while the apparent clearance values for all tested peptides were in the range of 0.00406 to 0.0146 liter/hour/kg.

TABLE 2

Plasma terminal elimination half-lives ($t_{1/2}$) and apparent clearance values (Cl/F; l/h/kg)

| Compound No. | Cl/F | $t_{1/2}$ (hours) |
|---|---|---|
| 6 | 0.0069 | 24.2 |
| 7 | 0.0087 | 25.4 |
| 9 | 0.0096 | 17.9 |
| 11 | 0.0118 | 14.1 |
| 13 | 0.0106 | 15.0 |
| 15 | 0.0116 | 18.9 |
| 28 | 0.0128 | 17.1 |
| 34 | 0.0148 | 17.2 |
| 36 | 0.0117 | 25.7 |
| 49 | 0.00406 | 36.7 |
| 55 | 0.0045 | 26.2 |
| 57 | 0.0078 | 17.9 |
| 71 | 0.0146 | 14.7 |

Example 8: Effect on Acute Food Intake and Body Weight in Normal Sprague Dawley Rats Compounds 6, 7, 9, 11, 13, 15, 28, 34, 36, 49, 55, 57, 59, 71 and 79 were tested for their effect on food intake and body weight in rats.

Sprague Dawley (SD) rats were obtained from Taconic A/S, Denmark. The animals arrived at least 7 days before the study start to allow acclimatization to experimental conditions. From arrival and throughout the study, the rats were housed in groups of 2 (n=2) in a light-, temperature- and humidity-controlled room (reversed 12/12 h light/dark cycle: lights turned off during day-time and on during night-time; temperature 20-22° C.; relative humidity 50-80%). Animals had access ad libitum to food (Altromin™ 1324, Brogaarden A/S, Gentofte, Denmark) and water (domestic quality tap water with citric acid added to pH ~3.6) during the entire study. Stratification of rats was based on body weight (BW) on a cage-by-cage basis; mean BWs per cage were used as the basis for pairing four cages together in a group (n=8 per group). A vehicle group and positive control group were included in each set of tests. Rats were dosed subcutaneously (sc) once in the morning immediately before turning off the lights, using a body weight-corrected dose (30 nmol/kg) of test peptide. Dosing volume was 5 ml/kg. Food intake was recorded manually at t=−24 and 0 hours (pre-dose) and at t=24, 48, 72 and 96 hours after dosing. Body weight was measured daily.

Statistical analyses were performed using GraphPad™ Prism version 5. The measured parameters were compared using one-way ANOVA followed by Dunnett's multiple comparison tests. Differences were considered statistically significant at $p<0.05$.

Results

As shown in Table 3, below, 48 hours after dosing, each of the tested compounds had given rise to a clear, statistically significant inhibition of food intake (vehicle-corrected, in %). This reduction in food intake was reflected by a decrease in body weight (vehicle-corrected, in %) observed on day 4 post-dosing (after 96 h) in the treated rats. (Not shown.) Normal feeding behavior was subsequently resumed.

TABLE 3

Acute food intake data

| Compound No. | FI inhibition after 48 h (vehicle corrected) (%) |
|---|---|
| 6 | 97 ± 0.2 |
| 7 | 94 ± 1.4 |
| 9 | 91 ± 2.5 |
| 11 | 88 ± 3.4 |
| 13 | 88 ± 2.4 |
| 15 | 93 ± 1.6 |
| 28 | 74 ± 5.4 |
| 34 | 70 ± 6.6 |
| 36 | 20 ± 3.4 |
| 49 | 98 ± 0.2 |
| 55 | 90 ± 2.4 |
| 57 | 77 ± 8.7 |
| 59 | 99 ± 0.1 |
| 71 | 84 ± 5.7 |
| 79 | 71 ± 5.6 |

Example 9: Oral Glucose Tolerance Test (OGTT) in Rats

Male Sprague Dawley rats [Crl:CD(SD), weight range 260-280 g upon arrival] were housed in groups of 2 (n=2) or 3 (n=3). The animals were maintained on a 12 h/12 h light/dark cycle. Animals had access ad libitum to a standard chow diet and tap water (domestic quality tap water) during the initial one week acclimatization period.

Fasted rats (fasted for 7 hours) were employed in the test. Rats had previously been randomized into two groups, designated test group and control group, respectively. The total number of animals per group was 10 (n=10).

A single subcutaneous injection of either vehicle (control group; vehicle: 50 mM histidine buffer, pH 7, with 200 mM mannitol) or Compound 7 in vehicle [test group; dose 30 nmol/kg body weight (2 ml/kg)] was subsequently administered to each animal. All rats then received an oral glucose bolus (2 g/kg) 16 hours after vehicle or compound administration. Blood glucose levels in tail blood samples taken 20 min. before glucose administration (time zero, baseline) and then 15 min., 30 min., 60 min., 90 min., 120 min. and 180 min after glucose administration were determined using a glucometer (GlucoSmart Swing™; MSP Bodmann GmbH, Germany).

Baseline glucose levels were essentially the same in the test and control groups, but the elevation of glucose levels over the course of the 180 minute measurement time period was significantly lowered in the test group compared to the control group. Table 4 (below) summarizes the blood glucose AUC (area under curve) determined over the period from t=15 min. to t=180 min. from a plot of measured glucose levels as a function of time. The data are presented as mean±S.E.M. The two-sided unpaired Student t-test was used for statistical comparison of the test group and the control group.

TABLE 4

|  | Control group | Test group (Compound 7) | p-value |
|---|---|---|---|
| Glucose AUC, t = 15-180 min. (mmol/L); mean ± S.E.M. | 270 ± 38 | 122 ± 29 | p < 0.0062 |

It is clear from the results that the tested compound significantly improves glucose tolerance in the test group compared to the control group.

Example 10: Effect of Deletion at Positions 21 and 22

The chemical stability assessment described in Example 6 was repeated for four pairs of compounds, each differing only by the presence or absence of an Asn-Asn (N-N) doublet at positions 21 and 22.

TABLE 5

| Compound | Positions 21-22 | pH 4 | pH 6 | pH 7.5 | pH 9 |
|---|---|---|---|---|---|
| NN96 | N-N | A | A | B | B |
| 97 | Δ | A | A | A | A |
| 55 | Δ | A | A | A | B |

TABLE 5-continued

| Compound | Positions 21-22 | pH 4 | pH 6 | pH 7.5 | pH 9 |
|---|---|---|---|---|---|
| 98 | N-N | A | A | B | B |
| 57 | Δ | A | A | A | B |
| 99 | N-N | A | A | B | B |
| 89 | Δ | A | A | A | A |
| 100 | N-N | A | A | A | B |

[Designations "A", "B" and "C" are the same as in Table 1. "Δ" signifies a deletion at positions 21 and 22.]

It can be seen that deletion of the Asn-Asn doublet at positions 21 and 22 tends to increase chemical stability in the neutral to alkaline pH range.

Activity at the human calcitonin (hCTR2) and amylin (hAMYR3) was also determined, as described in Example 3. As shown in Table 6, the deletion tends to increase the activity at both receptors, especially in compounds containing methylated amino acid residues.

TABLE 6

| Compound | hCTR2 EC$_{50}$ (nM) | hAMYR3 EC$_{50}$ (nM) |
|---|---|---|
| NN96 | 0.089 | 0.150 |
| 97 | 0.10 | 0.13 |
| 55 | 0.11 | 0.08 |
| 98 | 7.2 | 0.38 |
| 57 | 0.08 | 0.11 |
| 99 | 3.8 | 0.59 |
| 89 | 0.16 | 0.20 |
| 100 | 2.2 | 0.53 |

SEQUENCE LISTING

```
<160> NUMBER OF SEQ ID NOS: 203

<210> SEQ ID NO 1
<211> LENGTH: 37
<212> TYPE: PRT
<213> ORGANISM: Homo sapiens
<220> FEATURE:
<221> NAME/KEY: DISULFID
<222> LOCATION: (2)..(7)

<400> SEQUENCE: 1

Lys Cys Asn Thr Ala Thr Cys Ala Thr Gln Arg Leu Ala Asn Phe Leu
1               5                   10                  15

Val His Ser Ser Asn Asn Phe Gly Ala Ile Leu Ser Ser Thr Asn Val
            20                  25                  30

Gly Ser Asn Thr Tyr
        35

<210> SEQ ID NO 2
<211> LENGTH: 37
<212> TYPE: PRT
<213> ORGANISM: Artificial sequence
<220> FEATURE:
<223> OTHER INFORMATION: Synthetic Amylin analogue
<220> FEATURE:
<221> NAME/KEY: DISULFID
<222> LOCATION: (2)..(7)

<400> SEQUENCE: 2

Lys Cys Asn Thr Ala Thr Cys Ala Thr Gln Arg Leu Ala Asn Phe Leu
1               5                   10                  15
```

```
Val His Ser Ser Asn Asn Phe Gly Pro Ile Leu Pro Pro Thr Asn Val
            20                  25                  30

Gly Ser Asn Thr Tyr
        35

<210> SEQ ID NO 3
<211> LENGTH: 37
<212> TYPE: PRT
<213> ORGANISM: Artificial sequence
<220> FEATURE:
<223> OTHER INFORMATION: Amino acid sequence Z of Formula I in synthetic
      amylin analogue which is a compound having the formula R1-Z-R2 in
      PCT/EP2016/055793
<220> FEATURE:
<221> NAME/KEY: VARIANT
<222> LOCATION: (1)..(37)
<223> OTHER INFORMATION: The compound has at least one residue selected
      from: Xaa3 is Gln; Xaa14 is His, Asn or Aad; Xaa17 is Asn, Gln,
      Glu, Thr or Aad; Xaa19-Xaa20 is Val-Ser or Ser-Val; & Xaa35 is
      Ser, Phe, Orn, Aad, Gly or Thr
<220> FEATURE:
<221> NAME/KEY: DISULFID
<222> LOCATION: (2)..(7)
<223> OTHER INFORMATION: Sequence may possess an intramolecular
      disulphide bridge formed between the cysteine residues present at
      positions 2 and 7
<220> FEATURE:
<221> NAME/KEY: VARIANT
<222> LOCATION: (3)..(3)
<223> OTHER INFORMATION: Xaa is selected from the group consisting of
      Asn, Gly, Pro and Gln
<220> FEATURE:
<221> NAME/KEY: VARIANT
<222> LOCATION: (10)..(10)
<223> OTHER INFORMATION: Xaa is selected from the group consisting of
      Gln, Asp and Glu
<220> FEATURE:
<221> NAME/KEY: VARIANT
<222> LOCATION: (14)..(14)
<223> OTHER INFORMATION: Xaa is selected from the group consisting of
      Asp, His, Asn and Aad
<220> FEATURE:
<221> NAME/KEY: VARIANT
<222> LOCATION: (17)..(17)
<223> OTHER INFORMATION: Xaa is selected from the group consisting of
      His, Asn, Gln, Glu, Thr, Val, Lys and Aad
<220> FEATURE:
<221> NAME/KEY: VARIANT
<222> LOCATION: (19)..(20)
<223> OTHER INFORMATION: Xaa-Xaa is selected from the group consisting
      of Ser-Ser, Val-Val, Ser-Val and Val-Ser, or is absent
<220> FEATURE:
<221> NAME/KEY: SITE
<222> LOCATION: (21)..(22)
<223> OTHER INFORMATION: Xaa21-Xaa22 are absent
<220> FEATURE:
<221> NAME/KEY: MOD_RES
<222> LOCATION: (24)..(24)
<223> OTHER INFORMATION: MeGly
<220> FEATURE:
<221> NAME/KEY: MOD_RES
<222> LOCATION: (26)..(26)
<223> OTHER INFORMATION: MeIle
<220> FEATURE:
<221> NAME/KEY: VARIANT
<222> LOCATION: (31)..(31)
<223> OTHER INFORMATION: Xaa is selected from the group consisting of
      Asp, Glu and Asn
<220> FEATURE:
<221> NAME/KEY: VARIANT
<222> LOCATION: (35)..(35)
<223> OTHER INFORMATION: Xaa is selected from the group consisting of
      Asp, Glu, Asn, Ser, Phe, Orn, Aad, Gly and Thr
<220> FEATURE:
<221> NAME/KEY: VARIANT
<222> LOCATION: (37)..(37)
```

<223> OTHER INFORMATION: Xaa is selected from the group consisting of
      Pro, Apr and Hyp

<400> SEQUENCE: 3

Arg Cys Xaa Thr Ala Thr Cys Ala Thr Xaa Arg Leu Ala Xaa Phe Leu
1               5                   10                  15

Xaa Arg Xaa Xaa Xaa Xaa Phe Gly Ala Ile Leu Ser Ser Thr Xaa Val
            20                  25                  30

Gly Ser Xaa Thr Xaa
        35

<210> SEQ ID NO 4
<211> LENGTH: 37
<212> TYPE: PRT
<213> ORGANISM: Artificial sequence
<220> FEATURE:
<223> OTHER INFORMATION: Amino acid sequence Z of Formula II in
      synthetic amylin analogue which is a compound having the formula
      R1-Z-R2 in PCT/EP2016/055793
<220> FEATURE:
<221> NAME/KEY: VARIANT
<222> LOCATION: (1)..(37)
<223> OTHER INFORMATION: The compound has at least one residue selected
      from: Xaa3 is Gln; Xaa14 is His or Aad; Xaa17 is Asn, Gln, Glu or
      Aad; and Xaa35 is Ser, Orn, Aad, Gly or Thr
<220> FEATURE:
<221> NAME/KEY: DISULFID
<222> LOCATION: (2)..(7)
<223> OTHER INFORMATION: Sequence may possess an intramolecular
      disulphide bridge formed between the cysteine residues present at
      positions 2 and 7
<220> FEATURE:
<221> NAME/KEY: VARIANT
<222> LOCATION: (3)..(3)
<223> OTHER INFORMATION: Xaa is selected from the group consisting of
      Asn, Gly and Gln
<220> FEATURE:
<221> NAME/KEY: VARIANT
<222> LOCATION: (10)..(10)
<223> OTHER INFORMATION: Xaa is selected from the group consisting of
      Gln, Asp and Glu
<220> FEATURE:
<221> NAME/KEY: VARIANT
<222> LOCATION: (14)..(14)
<223> OTHER INFORMATION: Xaa is selected from the group consisting of
      Asp, His and Aad
<220> FEATURE:
<221> NAME/KEY: VARIANT
<222> LOCATION: (17)..(17)
<223> OTHER INFORMATION: Xaa is selected from the group consisting of
      His, Asn, Gln, Glu, Lys and Aad
<220> FEATURE:
<221> NAME/KEY: VARIANT
<222> LOCATION: (19)..(20)
<223> OTHER INFORMATION: Xaa-Xaa is Ser-Ser or is absent
<220> FEATURE:
<221> NAME/KEY: SITE
<222> LOCATION: (21)..(22)
<223> OTHER INFORMATION: Xaa21-Xaa22 are absent
<220> FEATURE:
<221> NAME/KEY: MOD_RES
<222> LOCATION: (24)..(24)
<223> OTHER INFORMATION: MeGly
<220> FEATURE:
<221> NAME/KEY: MOD_RES
<222> LOCATION: (26)..(26)
<223> OTHER INFORMATION: MeIle
<220> FEATURE:
<221> NAME/KEY: VARIANT
<222> LOCATION: (35)..(35)
<223> OTHER INFORMATION: Xaa is selected from the group consisting of
      Asp, Glu, Asn, Ser, Orn, Aad, Gly and Thr
<220> FEATURE:
<221> NAME/KEY: VARIANT
<222> LOCATION: (37)..(37)

```
<223> OTHER INFORMATION: Xaa is selected from the group consisting of
      Pro and Hyp

<400> SEQUENCE: 4

Arg Cys Xaa Thr Ala Thr Cys Ala Thr Xaa Arg Leu Ala Xaa Phe Leu
1               5                  10                  15

Xaa Arg Xaa Xaa Xaa Xaa Phe Gly Ala Ile Leu Ser Ser Thr Glu Val
            20                  25                  30

Gly Ser Xaa Thr Xaa
        35

<210> SEQ ID NO 5
<211> LENGTH: 37
<212> TYPE: PRT
<213> ORGANISM: Artificial sequence
<220> FEATURE:
<223> OTHER INFORMATION: Amino acid sequence Z of Formula III in
      synthetic amylin analogue which is a compound having the formula
      R1-Z-R2 in PCT/EP2016/055793
<220> FEATURE:
<221> NAME/KEY: VARIANT
<222> LOCATION: (1)..(37)
<223> OTHER INFORMATION: The compound has at least one residue selected
      from: Xaa3 is Gln; Xaa14 is His or Aad; Xaa17 is Gln; and Xaa35 is
      Aad.
<220> FEATURE:
<221> NAME/KEY: DISULFID
<222> LOCATION: (2)..(7)
<223> OTHER INFORMATION: Sequence may possess an intramolecular
      disulphide bridge formed between the cysteine residues present at
      positions 2 and 7
<220> FEATURE:
<221> NAME/KEY: VARIANT
<222> LOCATION: (3)..(3)
<223> OTHER INFORMATION: Xaa is selected from the group consisting of
      Asn, Gly and Gln
<220> FEATURE:
<221> NAME/KEY: VARIANT
<222> LOCATION: (10)..(10)
<223> OTHER INFORMATION: Xaa is selected from the group consisting of
      Gln, Asp and Glu
<220> FEATURE:
<221> NAME/KEY: VARIANT
<222> LOCATION: (14)..(14)
<223> OTHER INFORMATION: Xaa is selected from the group consisting of
      Asp, His and Aad
<220> FEATURE:
<221> NAME/KEY: VARIANT
<222> LOCATION: (17)..(17)
<223> OTHER INFORMATION: Xaa is selected from the group consisting of
      His and Gln
<220> FEATURE:
<221> NAME/KEY: VARIANT
<222> LOCATION: (19)..(20)
<223> OTHER INFORMATION: Xaa-Xaa is Ser-Ser or is absent
<220> FEATURE:
<221> NAME/KEY: SITE
<222> LOCATION: (21)..(22)
<223> OTHER INFORMATION: Xaa21-Xaa22 are absent
<220> FEATURE:
<221> NAME/KEY: MOD_RES
<222> LOCATION: (24)..(24)
<223> OTHER INFORMATION: MeGly
<220> FEATURE:
<221> NAME/KEY: MOD_RES
<222> LOCATION: (26)..(26)
<223> OTHER INFORMATION: MeIle
<220> FEATURE:
<221> NAME/KEY: VARIANT
<222> LOCATION: (35)..(35)
<223> OTHER INFORMATION: Xaa is selected from the group consisting of
      Asp, Glu, Asn, Aad and Gly
<220> FEATURE:
<221> NAME/KEY: VARIANT
<222> LOCATION: (37)..(37)
```

```
<223> OTHER INFORMATION: Xaa is selected from the group consisting of
      Pro and Hyp

<400> SEQUENCE: 5

Arg Cys Xaa Thr Ala Thr Cys Ala Thr Xaa Arg Leu Ala Xaa Phe Leu
1               5                   10                  15

Xaa Arg Xaa Xaa Xaa Xaa Phe Gly Ala Ile Leu Ser Ser Thr Glu Val
            20                  25                  30

Gly Ser Xaa Thr Xaa
        35

<210> SEQ ID NO 6
<211> LENGTH: 35
<212> TYPE: PRT
<213> ORGANISM: Artificial sequence
<220> FEATURE:
<223> OTHER INFORMATION: Amino acid sequence Z in synthetic amylin
      analogue which is a compound having the formula R1-Z-R2 in
      PCT/EP2016/055793
<220> FEATURE:
<221> NAME/KEY: DISULFID
<222> LOCATION: (2)..(7)
<223> OTHER INFORMATION: Sequence may possess an intramolecular
      disulphide bridge formed between the cysteine residues present at
      positions 2 and 7
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle

<400> SEQUENCE: 6

Arg Cys Asn Thr Ala Thr Cys Ala Thr Gln Arg Leu Ala His Phe Leu
1               5                   10                  15

His Arg Ser Ser Phe Gly Ala Ile Leu Ser Ser Thr Glu Val Gly Ser
            20                  25                  30

Glu Thr Pro
        35

<210> SEQ ID NO 7
<211> LENGTH: 35
<212> TYPE: PRT
<213> ORGANISM: Artificial sequence
<220> FEATURE:
<223> OTHER INFORMATION: Amino acid sequence Z in synthetic amylin
      analogue which is a compound having the formula R1-Z-R2 in
      PCT/EP2016/055793
<220> FEATURE:
<221> NAME/KEY: DISULFID
<222> LOCATION: (2)..(7)
<223> OTHER INFORMATION: Sequence may possess an intramolecular
      disulphide bridge formed between the cysteine residues present at
      positions 2 and 7
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle

<400> SEQUENCE: 7

Arg Cys Asn Thr Ala Thr Cys Ala Thr Gln Arg Leu Ala Asn Phe Leu
1               5                   10                  15

His Arg Ser Ser Phe Gly Ala Ile Leu Ser Ser Thr Glu Val Gly Ser
```

Glu Thr Pro
        35

<210> SEQ ID NO 8
<211> LENGTH: 35
<212> TYPE: PRT
<213> ORGANISM: Artificial sequence
<220> FEATURE:
<223> OTHER INFORMATION: Amino acid sequence Z in synthetic amylin
      analogue which is a compound having the formula R1-Z-R2 in
      PCT/EP2016/055793
<220> FEATURE:
<221> NAME/KEY: DISULFID
<222> LOCATION: (2)..(7)
<223> OTHER INFORMATION: Sequence may possess an intramolecular
      disulphide bridge formed between the cysteine residues present at
      positions 2 and 7
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle
<220> FEATURE:
<221> NAME/KEY: MOD_RES
<222> LOCATION: (35)..(35)
<223> OTHER INFORMATION: 4Hyp

<400> SEQUENCE: 8

Arg Cys Gly Thr Ala Thr Cys Ala Thr Glu Arg Leu Ala His Phe Leu
1               5                   10                  15

Asn Arg Ser Ser Phe Gly Ala Ile Leu Ser Ser Thr Glu Val Gly Ser
            20                  25                  30

Asn Thr Pro
        35

<210> SEQ ID NO 9
<211> LENGTH: 35
<212> TYPE: PRT
<213> ORGANISM: Artificial sequence
<220> FEATURE:
<223> OTHER INFORMATION: Amino acid sequence Z in synthetic amylin
      analogue which is a compound having the formula R1-Z-R2 in
      PCT/EP2016/055793
<220> FEATURE:
<221> NAME/KEY: DISULFID
<222> LOCATION: (2)..(7)
<223> OTHER INFORMATION: Sequence may possess an intramolecular
      disulphide bridge formed between the cysteine residues present at
      positions 2 and 7
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle
<220> FEATURE:
<221> NAME/KEY: MOD_RES
<222> LOCATION: (35)..(35)
<223> OTHER INFORMATION: 4Hyp

<400> SEQUENCE: 9

Arg Cys Gly Thr Ala Thr Cys Ala Thr Glu Arg Leu Ala His Phe Leu
1               5                   10                  15

Gln Arg Ser Ser Phe Gly Ala Ile Leu Ser Ser Thr Glu Val Gly Ser
            20                  25                  30

Asn Thr Pro
        35

<210> SEQ ID NO 10
<211> LENGTH: 35
<212> TYPE: PRT
<213> ORGANISM: Artificial sequence
<220> FEATURE:
<223> OTHER INFORMATION: Amino acid sequence Z in synthetic amylin
      analogue which is a compound having the formula R1-Z-R2 in
      PCT/EP2016/055793
<220> FEATURE:
<221> NAME/KEY: DISULFID
<222> LOCATION: (2)..(7)
<223> OTHER INFORMATION: Sequence may possess an intramolecular
      disulphide bridge formed between the cysteine residues present at
      positions 2 and 7
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle
<220> FEATURE:
<221> NAME/KEY: MOD_RES
<222> LOCATION: (35)..(35)
<223> OTHER INFORMATION: 4Hyp

<400> SEQUENCE: 10

Arg Cys Gly Thr Ala Thr Cys Ala Thr Glu Arg Leu Ala His Phe Leu
1               5                   10                  15

Glu Arg Ser Ser Phe Gly Ala Ile Leu Ser Ser Thr Glu Val Gly Ser
            20                  25                  30

Asn Thr Pro
        35

<210> SEQ ID NO 11
<211> LENGTH: 35
<212> TYPE: PRT
<213> ORGANISM: Artificial sequence
<220> FEATURE:
<223> OTHER INFORMATION: Amino acid sequence Z in synthetic amylin
      analogue which is a compound having the formula R1-Z-R2 in
      PCT/EP2016/055793
<220> FEATURE:
<221> NAME/KEY: DISULFID
<222> LOCATION: (2)..(7)
<223> OTHER INFORMATION: Sequence may possess an intramolecular
      disulphide bridge formed between the cysteine residues present at
      positions 2 and 7
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle
<220> FEATURE:
<221> NAME/KEY: MOD_RES
<222> LOCATION: (35)..(35)
<223> OTHER INFORMATION: 4Hyp

<400> SEQUENCE: 11

Arg Cys Gly Thr Ala Thr Cys Ala Thr Glu Arg Leu Ala His Phe Leu
1               5                   10                  15

Thr Arg Ser Ser Phe Gly Ala Ile Leu Ser Ser Thr Glu Val Gly Ser
            20                  25                  30

Ser Thr Pro
        35

<210> SEQ ID NO 12
<211> LENGTH: 35
<212> TYPE: PRT
<213> ORGANISM: Artificial sequence
<220> FEATURE:
<223> OTHER INFORMATION: Amino acid sequence Z in synthetic amylin
      analogue which is a compound having the formula R1-Z-R2 in
      PCT/EP2016/055793
<220> FEATURE:
<221> NAME/KEY: DISULFID
<222> LOCATION: (2)..(7)
<223> OTHER INFORMATION: Sequence may possess an intramolecular
      disulphide bridge formed between the cysteine residues present at
      positions 2 and 7
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle
<220> FEATURE:
<221> NAME/KEY: MOD_RES
<222> LOCATION: (35)..(35)
<223> OTHER INFORMATION: 4Hyp

<400> SEQUENCE: 12

Arg Cys Gly Thr Ala Thr Cys Ala Thr Glu Arg Leu Ala His Phe Leu
1               5                   10                  15

Thr Arg Ser Ser Phe Gly Ala Ile Leu Ser Ser Thr Glu Val Gly Ser
            20                  25                  30

Phe Thr Pro
        35

<210> SEQ ID NO 13
<211> LENGTH: 35
<212> TYPE: PRT
<213> ORGANISM: Artificial sequence
<220> FEATURE:
<223> OTHER INFORMATION: Amino acid sequence Z in synthetic amylin
      analogue which is a compound having the formula R1-Z-R2 in
      PCT/EP2016/055793
<220> FEATURE:
<221> NAME/KEY: DISULFID
<222> LOCATION: (2)..(7)
<223> OTHER INFORMATION: Sequence may possess an intramolecular
      disulphide bridge formed between the cysteine residues present at
      positions 2 and 7
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle
<220> FEATURE:
<221> NAME/KEY: MOD_RES
<222> LOCATION: (33)..(33)
<223> OTHER INFORMATION: Orn
<220> FEATURE:
<221> NAME/KEY: MOD_RES
<222> LOCATION: (35)..(35)
<223> OTHER INFORMATION: 4Hyp

<400> SEQUENCE: 13

Arg Cys Gly Thr Ala Thr Cys Ala Thr Glu Arg Leu Ala His Phe Leu
1               5                   10                  15

Thr Arg Ser Ser Phe Gly Ala Ile Leu Ser Ser Thr Glu Val Gly Ser
            20                  25                  30

Arg Thr Pro
        35

<210> SEQ ID NO 14
<211> LENGTH: 35
<212> TYPE: PRT
<213> ORGANISM: Artificial sequence
<220> FEATURE:
<223> OTHER INFORMATION: Amino acid sequence Z in synthetic amylin
      analogue which is a compound having the formula R1-Z-R2 in
      PCT/EP2016/055793
<220> FEATURE:
<221> NAME/KEY: DISULFID
<222> LOCATION: (2)..(7)
<223> OTHER INFORMATION: Sequence may possess an intramolecular
      disulphide bridge formed between the cysteine residues present at
      positions 2 and 7
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle
<220> FEATURE:
<221> NAME/KEY: MOD_RES
<222> LOCATION: (33)..(33)
<223> OTHER INFORMATION: Aad
<220> FEATURE:
<221> NAME/KEY: MOD_RES
<222> LOCATION: (35)..(35)
<223> OTHER INFORMATION: 4Hyp

<400> SEQUENCE: 14

Arg Cys Gly Thr Ala Thr Cys Ala Thr Glu Arg Leu Ala His Phe Leu
1               5                   10                  15

Thr Arg Ser Ser Phe Gly Ala Ile Leu Ser Ser Thr Glu Val Gly Ser
            20                  25                  30

Glu Thr Pro
        35

<210> SEQ ID NO 15
<211> LENGTH: 35
<212> TYPE: PRT
<213> ORGANISM: Artificial sequence
<220> FEATURE:
<223> OTHER INFORMATION: Amino acid sequence Z in synthetic amylin
      analogue which is a compound having the formula R1-Z-R2 in
      PCT/EP2016/055793
<220> FEATURE:
<221> NAME/KEY: DISULFID
<222> LOCATION: (2)..(7)
<223> OTHER INFORMATION: Sequence may possess an intramolecular
      disulphide bridge formed between the cysteine residues present at
      positions 2 and 7
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle
<220> FEATURE:
<221> NAME/KEY: MOD_RES
<222> LOCATION: (35)..(35)
<223> OTHER INFORMATION: 4Hyp

<400> SEQUENCE: 15

```
Arg Cys Gly Thr Ala Thr Cys Ala Thr Glu Arg Leu Ala His Phe Leu
1               5                   10                  15

Thr Arg Ser Ser Phe Gly Ala Ile Leu Ser Ser Thr Glu Val Gly Ser
            20                  25                  30

Gly Thr Pro
        35

<210> SEQ ID NO 16
<211> LENGTH: 33
<212> TYPE: PRT
<213> ORGANISM: Artificial sequence
<220> FEATURE:
<223> OTHER INFORMATION: Amino acid sequence Z in synthetic amylin
      analogue which is a compound having the formula R1-Z-R2 in
      PCT/EP2016/055793
<220> FEATURE:
<221> NAME/KEY: DISULFID
<222> LOCATION: (2)..(7)
<223> OTHER INFORMATION: Sequence may possess an intramolecular
      disulphide bridge formed between the cysteine residues present at
      positions 2 and 7
<220> FEATURE:
<221> NAME/KEY: MOD_RES
<222> LOCATION: (20)..(20)
<223> OTHER INFORMATION: MeGly
<220> FEATURE:
<221> NAME/KEY: MOD_RES
<222> LOCATION: (22)..(22)
<223> OTHER INFORMATION: MeIle

<400> SEQUENCE: 16

Arg Cys Asn Thr Ala Thr Cys Ala Thr Gln Arg Leu Ala His Phe Leu
1               5                   10                  15

His Arg Phe Gly Ala Ile Leu Ser Ser Thr Glu Val Gly Ser Glu Thr
            20                  25                  30

Pro

<210> SEQ ID NO 17
<211> LENGTH: 35
<212> TYPE: PRT
<213> ORGANISM: Artificial sequence
<220> FEATURE:
<223> OTHER INFORMATION: Amino acid sequence Z in synthetic amylin
      analogue which is a compound having the formula R1-Z-R2 in
      PCT/EP2016/055793
<220> FEATURE:
<221> NAME/KEY: DISULFID
<222> LOCATION: (2)..(7)
<223> OTHER INFORMATION: Sequence may possess an intramolecular
      disulphide bridge formed between the cysteine residues present at
      positions 2 and 7
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle

<400> SEQUENCE: 17

Arg Cys Gly Thr Ala Thr Cys Ala Thr Glu Arg Leu Ala His Phe Leu
1               5                   10                  15

His Arg Ser Ser Phe Gly Ala Ile Leu Ser Ser Thr Glu Val Gly Ser
            20                  25                  30

Asn Thr Pro
        35
```

```
<210> SEQ ID NO 18
<211> LENGTH: 35
<212> TYPE: PRT
<213> ORGANISM: Artificial sequence
<220> FEATURE:
<223> OTHER INFORMATION: Amino acid sequence Z in synthetic amylin
      analogue which is a compound having the formula R1-Z-R2 in
      PCT/EP2016/055793
<220> FEATURE:
<221> NAME/KEY: DISULFID
<222> LOCATION: (2)..(7)
<223> OTHER INFORMATION: Sequence may possess an intramolecular
      disulphide bridge formed between the cysteine residues present at
      positions 2 and 7
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle

<400> SEQUENCE: 18

Arg Cys Asn Thr Ala Thr Cys Ala Thr Gln Arg Leu Ala His Phe Leu
1               5                   10                  15

His Arg Ser Ser Phe Gly Ala Ile Leu Ser Ser Thr Glu Val Gly Ser
            20                  25                  30

Asn Thr Pro
        35

<210> SEQ ID NO 19
<211> LENGTH: 35
<212> TYPE: PRT
<213> ORGANISM: Artificial sequence
<220> FEATURE:
<223> OTHER INFORMATION: Amino acid sequence Z in synthetic amylin
      analogue which is a compound having the formula R1-Z-R2 in
      PCT/EP2016/055793
<220> FEATURE:
<221> NAME/KEY: DISULFID
<222> LOCATION: (2)..(7)
<223> OTHER INFORMATION: Sequence may possess an intramolecular
      disulphide bridge formed between the cysteine residues present at
      positions 2 and 7
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle
<220> FEATURE:
<221> NAME/KEY: MOD_RES
<222> LOCATION: (35)..(35)
<223> OTHER INFORMATION: 4Hyp

<400> SEQUENCE: 19

Arg Cys Gly Thr Ala Thr Cys Ala Thr Glu Arg Leu Ala Asn Phe Leu
1               5                   10                  15

Val Arg Ser Ser Phe Gly Ala Ile Leu Ser Ser Thr Glu Val Gly Ser
            20                  25                  30

Asn Thr Pro
        35

<210> SEQ ID NO 20
<211> LENGTH: 35
<212> TYPE: PRT
<213> ORGANISM: Artificial sequence
<220> FEATURE:
```

```
<223> OTHER INFORMATION: Amino acid sequence Z in synthetic amylin
      analogue which is a compound having the formula R1-Z-R2 in
      PCT/EP2016/055793
<220> FEATURE:
<221> NAME/KEY: DISULFID
<222> LOCATION: (2)..(7)
<223> OTHER INFORMATION: Sequence may possess an intramolecular
      disulphide bridge formed between the cysteine residues present at
      positions 2 and 7
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle
<220> FEATURE:
<221> NAME/KEY: MOD_RES
<222> LOCATION: (35)..(35)
<223> OTHER INFORMATION: 4Hyp

<400> SEQUENCE: 20

Arg Cys Gly Thr Ala Thr Cys Ala Thr Glu Arg Leu Ala His Phe Leu
1               5                   10                  15

Thr Arg Ser Ser Phe Gly Ala Ile Leu Ser Ser Thr Glu Val Gly Ser
            20                  25                  30

Asn Thr Pro
        35

<210> SEQ ID NO 21
<211> LENGTH: 35
<212> TYPE: PRT
<213> ORGANISM: Artificial sequence
<220> FEATURE:
<223> OTHER INFORMATION: Amino acid sequence Z in synthetic amylin
      analogue which is a compound having the formula R1-Z-R2 in
      PCT/EP2016/055793
<220> FEATURE:
<221> NAME/KEY: DISULFID
<222> LOCATION: (2)..(7)
<223> OTHER INFORMATION: Sequence may possess an intramolecular
      disulphide bridge formed between the cysteine residues present at
      positions 2 and 7
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle
<220> FEATURE:
<221> NAME/KEY: MOD_RES
<222> LOCATION: (35)..(35)
<223> OTHER INFORMATION: 4Hyp

<400> SEQUENCE: 21

Arg Cys Gly Thr Ala Thr Cys Ala Thr Glu Arg Leu Ala His Phe Leu
1               5                   10                  15

Lys Arg Ser Ser Phe Gly Ala Ile Leu Ser Ser Thr Glu Val Gly Ser
            20                  25                  30

Asn Thr Pro
        35

<210> SEQ ID NO 22
<211> LENGTH: 35
<212> TYPE: PRT
<213> ORGANISM: Artificial sequence
<220> FEATURE:
<223> OTHER INFORMATION: Amino acid sequence Z in synthetic amylin
```

-continued analogue which is a compound having the formula R1-Z-R2 in
PCT/EP2016/055793
<220> FEATURE:
<221> NAME/KEY: DISULFID
<222> LOCATION: (2)..(7)
<223> OTHER INFORMATION: Sequence may possess an intramolecular
disulphide bridge formed between the cysteine residues present at
positions 2 and 7
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle

<400> SEQUENCE: 22

Arg Cys Asn Thr Ala Thr Cys Ala Thr Gln Arg Leu Ala His Phe Leu
1               5                   10                  15

His Arg Ser Val Phe Gly Ala Ile Leu Ser Ser Thr Glu Val Gly Ser
            20                  25                  30

Glu Thr Pro
        35

<210> SEQ ID NO 23
<211> LENGTH: 35
<212> TYPE: PRT
<213> ORGANISM: Artificial sequence
<220> FEATURE:
<223> OTHER INFORMATION: Amino acid sequence Z in synthetic amylin
analogue which is a compound having the formula R1-Z-R2 in
PCT/EP2016/055793
<220> FEATURE:
<221> NAME/KEY: DISULFID
<222> LOCATION: (2)..(7)
<223> OTHER INFORMATION: Sequence may possess an intramolecular
disulphide bridge formed between the cysteine residues present at
positions 2 and 7
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle

<400> SEQUENCE: 23

Arg Cys Asn Thr Ala Thr Cys Ala Thr Gln Arg Leu Ala His Phe Leu
1               5                   10                  15

His Arg Val Ser Phe Gly Ala Ile Leu Ser Ser Thr Glu Val Gly Ser
            20                  25                  30

Glu Thr Pro
        35

<210> SEQ ID NO 24
<211> LENGTH: 35
<212> TYPE: PRT
<213> ORGANISM: Artificial sequence
<220> FEATURE:
<223> OTHER INFORMATION: Amino acid sequence Z in synthetic amylin
analogue which is a compound having the formula R1-Z-R2 in
PCT/EP2016/055793
<220> FEATURE:
<221> NAME/KEY: DISULFID
<222> LOCATION: (2)..(7)
<223> OTHER INFORMATION: Sequence may possess an intramolecular
disulphide bridge formed between the cysteine residues present at
positions 2 and 7
<220> FEATURE:

```
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle

<400> SEQUENCE: 24

Arg Cys Gly Thr Ala Thr Cys Ala Thr Glu Arg Leu Ala His Phe Leu
1               5                   10                  15

Val Arg Ser Ser Phe Gly Ala Ile Leu Ser Ser Thr Glu Val Gly Ser
            20                  25                  30

Glu Thr Pro
        35

<210> SEQ ID NO 25
<211> LENGTH: 35
<212> TYPE: PRT
<213> ORGANISM: Artificial sequence
<220> FEATURE:
<223> OTHER INFORMATION: Amino acid sequence Z in synthetic amylin
      analogue which is a compound having the formula R1-Z-R2 in
      PCT/EP2016/055793
<220> FEATURE:
<221> NAME/KEY: DISULFID
<222> LOCATION: (2)..(7)
<223> OTHER INFORMATION: Sequence may possess an intramolecular
      disulphide bridge formed between the cysteine residues present at
      positions 2 and 7
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle

<400> SEQUENCE: 25

Arg Cys Pro Thr Ala Thr Cys Ala Thr Asp Arg Leu Ala His Phe Leu
1               5                   10                  15

Val Arg Ser Ser Phe Gly Ala Ile Leu Ser Ser Thr Asp Val Gly Ser
            20                  25                  30

Asp Thr Pro
        35

<210> SEQ ID NO 26
<211> LENGTH: 35
<212> TYPE: PRT
<213> ORGANISM: Artificial sequence
<220> FEATURE:
<223> OTHER INFORMATION: Amino acid sequence Z in synthetic amylin
      analogue which is a compound having the formula R1-Z-R2 in
      PCT/EP2016/055793
<220> FEATURE:
<221> NAME/KEY: DISULFID
<222> LOCATION: (2)..(7)
<223> OTHER INFORMATION: Sequence may possess an intramolecular
      disulphide bridge formed between the cysteine residues present at
      positions 2 and 7
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle

<400> SEQUENCE: 26
```

Arg Cys Asn Thr Ala Thr Cys Ala Thr Gln Arg Leu Ala His Phe Leu
1               5                   10                  15

Val Arg Ser Ser Phe Gly Ala Ile Leu Ser Ser Thr Glu Val Gly Ser
            20                  25                  30

Glu Thr Pro
        35

<210> SEQ ID NO 27
<211> LENGTH: 35
<212> TYPE: PRT
<213> ORGANISM: Artificial sequence
<220> FEATURE:
<223> OTHER INFORMATION: Amino acid sequence Z in synthetic amylin
      analogue which is a compound having the formula R1-Z-R2 in
      PCT/EP2016/055793
<220> FEATURE:
<221> NAME/KEY: DISULFID
<222> LOCATION: (2)..(7)
<223> OTHER INFORMATION: Sequence may possess an intramolecular
      disulphide bridge formed between the cysteine residues present at
      positions 2 and 7
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle

<400> SEQUENCE: 27

Arg Cys Pro Thr Ala Thr Cys Ala Thr Asp Arg Leu Ala His Phe Leu
1               5                   10                  15

His Arg Ser Ser Phe Gly Ala Ile Leu Ser Ser Thr Asp Val Gly Ser
            20                  25                  30

Asn Thr Pro
        35

<210> SEQ ID NO 28
<211> LENGTH: 35
<212> TYPE: PRT
<213> ORGANISM: Artificial sequence
<220> FEATURE:
<223> OTHER INFORMATION: Amino acid sequence Z in synthetic amylin
      analogue which is a compound having the formula R1-Z-R2 in
      PCT/EP2016/055793
<220> FEATURE:
<221> NAME/KEY: DISULFID
<222> LOCATION: (2)..(7)
<223> OTHER INFORMATION: Sequence may possess an intramolecular
      disulphide bridge formed between the cysteine residues present at
      positions 2 and 7
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle

<400> SEQUENCE: 28

Arg Cys Gly Thr Ala Thr Cys Ala Thr Glu Arg Leu Ala His Phe Leu
1               5                   10                  15

His Arg Ser Ser Phe Gly Ala Ile Leu Ser Ser Thr Glu Val Gly Ser
            20                  25                  30

Glu Thr Pro
        35

```
<210> SEQ ID NO 29
<211> LENGTH: 35
<212> TYPE: PRT
<213> ORGANISM: Artificial sequence
<220> FEATURE:
<223> OTHER INFORMATION: Amino acid sequence Z in synthetic amylin
      analogue which is a compound having the formula R1-Z-R2 in
      PCT/EP2016/055793
<220> FEATURE:
<221> NAME/KEY: DISULFID
<222> LOCATION: (2)..(7)
<223> OTHER INFORMATION: Sequence may possess an intramolecular
      disulphide bridge formed between the cysteine residues present at
      positions 2 and 7
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle

<400> SEQUENCE: 29

Arg Cys Pro Thr Ala Thr Cys Ala Thr Asp Arg Leu Ala His Phe Leu
1               5                   10                  15

His Arg Ser Ser Phe Gly Ala Ile Leu Ser Ser Thr Asp Val Gly Ser
            20                  25                  30

Asp Thr Pro
        35

<210> SEQ ID NO 30
<211> LENGTH: 35
<212> TYPE: PRT
<213> ORGANISM: Artificial sequence
<220> FEATURE:
<223> OTHER INFORMATION: Amino acid sequence Z in synthetic amylin
      analogue which is a compound having the formula R1-Z-R2 in
      PCT/EP2016/055793
<220> FEATURE:
<221> NAME/KEY: DISULFID
<222> LOCATION: (2)..(7)
<223> OTHER INFORMATION: Sequence may possess an intramolecular
      disulphide bridge formed between the cysteine residues present at
      positions 2 and 7
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle
<220> FEATURE:
<221> NAME/KEY: MOD_RES
<222> LOCATION: (35)..(35)
<223> OTHER INFORMATION: 4Hyp

<400> SEQUENCE: 30

Arg Cys Gly Thr Ala Thr Cys Ala Thr Glu Arg Leu Ala His Phe Leu
1               5                   10                  15

Gln Arg Ser Ser Phe Gly Ala Ile Leu Ser Ser Thr Glu Val Gly Ser
            20                  25                  30

Ser Thr Pro
        35

<210> SEQ ID NO 31
<211> LENGTH: 35
<212> TYPE: PRT
```

```
<213> ORGANISM: Artificial sequence
<220> FEATURE:
<223> OTHER INFORMATION: Amino acid sequence Z in synthetic amylin
      analogue which is a compound having the formula R1-Z-R2 in
      PCT/EP2016/055793
<220> FEATURE:
<221> NAME/KEY: DISULFID
<222> LOCATION: (2)..(7)
<223> OTHER INFORMATION: Sequence may possess an intramolecular
      disulphide bridge formed between the cysteine residues present at
      positions 2 and 7
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle
<220> FEATURE:
<221> NAME/KEY: MOD_RES
<222> LOCATION: (35)..(35)
<223> OTHER INFORMATION: 4Hyp

<400> SEQUENCE: 31

Arg Cys Gly Thr Ala Thr Cys Ala Thr Glu Arg Leu Ala His Phe Leu
1               5                   10                  15

Asn Arg Ser Ser Phe Gly Ala Ile Leu Ser Ser Thr Glu Val Gly Ser
            20                  25                  30

Ser Thr Pro
        35

<210> SEQ ID NO 32
<211> LENGTH: 35
<212> TYPE: PRT
<213> ORGANISM: Artificial sequence
<220> FEATURE:
<223> OTHER INFORMATION: Amino acid sequence Z in synthetic amylin
      analogue which is a compound having the formula R1-Z-R2 in
      PCT/EP2016/055793
<220> FEATURE:
<221> NAME/KEY: DISULFID
<222> LOCATION: (2)..(7)
<223> OTHER INFORMATION: Sequence may possess an intramolecular
      disulphide bridge formed between the cysteine residues present at
      positions 2 and 7
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle
<220> FEATURE:
<221> NAME/KEY: MOD_RES
<222> LOCATION: (35)..(35)
<223> OTHER INFORMATION: 4Hyp

<400> SEQUENCE: 32

Arg Cys Gly Thr Ala Thr Cys Ala Thr Glu Arg Leu Ala His Phe Leu
1               5                   10                  15

His Arg Ser Ser Phe Gly Ala Ile Leu Ser Ser Thr Glu Val Gly Ser
            20                  25                  30

Ser Thr Pro
        35

<210> SEQ ID NO 33
<211> LENGTH: 35
<212> TYPE: PRT
<213> ORGANISM: Artificial sequence
```

-continued

```
<220> FEATURE:
<223> OTHER INFORMATION: Amino acid sequence Z in synthetic amylin
      analogue which is a compound having the formula R1-Z-R2 in
      PCT/EP2016/055793
<220> FEATURE:
<221> NAME/KEY: DISULFID
<222> LOCATION: (2)..(7)
<223> OTHER INFORMATION: Sequence may possess an intramolecular
      disulphide bridge formed between the cysteine residues present at
      positions 2 and 7
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle
<220> FEATURE:
<221> NAME/KEY: MOD_RES
<222> LOCATION: (35)..(35)
<223> OTHER INFORMATION: 4Hyp

<400> SEQUENCE: 33

Arg Cys Gly Thr Ala Thr Cys Ala Thr Glu Arg Leu Ala His Phe Leu
1               5                   10                  15

Val Arg Ser Ser Phe Gly Ala Ile Leu Ser Ser Thr Glu Val Gly Ser
            20                  25                  30

Ser Thr Pro
        35

<210> SEQ ID NO 34
<211> LENGTH: 35
<212> TYPE: PRT
<213> ORGANISM: Artificial sequence
<220> FEATURE:
<223> OTHER INFORMATION: Amino acid sequence Z in synthetic amylin
      analogue which is a compound having the formula R1-Z-R2 in
      PCT/EP2016/055793
<220> FEATURE:
<221> NAME/KEY: DISULFID
<222> LOCATION: (2)..(7)
<223> OTHER INFORMATION: Sequence may possess an intramolecular
      disulphide bridge formed between the cysteine residues present at
      positions 2 and 7
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle
<220> FEATURE:
<221> NAME/KEY: MOD_RES
<222> LOCATION: (35)..(35)
<223> OTHER INFORMATION: 4Hyp

<400> SEQUENCE: 34

Arg Cys Gly Thr Ala Thr Cys Ala Thr Glu Arg Leu Ala His Phe Leu
1               5                   10                  15

Gln Arg Ser Ser Phe Gly Ala Ile Leu Ser Ser Thr Glu Val Gly Ser
            20                  25                  30

Phe Thr Pro
        35

<210> SEQ ID NO 35
<211> LENGTH: 35
<212> TYPE: PRT
<213> ORGANISM: Artificial sequence
<220> FEATURE:
```

```
<223> OTHER INFORMATION: Amino acid sequence Z in synthetic amylin
      analogue which is a compound having the formula R1-Z-R2 in
      PCT/EP2016/055793
<220> FEATURE:
<221> NAME/KEY: DISULFID
<222> LOCATION: (2)..(7)
<223> OTHER INFORMATION: Sequence may possess an intramolecular
      disulphide bridge formed between the cysteine residues present at
      positions 2 and 7
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle
<220> FEATURE:
<221> NAME/KEY: MOD_RES
<222> LOCATION: (35)..(35)
<223> OTHER INFORMATION: 4Hyp

<400> SEQUENCE: 35

Arg Cys Gly Thr Ala Thr Cys Ala Thr Glu Arg Leu Ala His Phe Leu
1               5                   10                  15

Asn Arg Ser Ser Phe Gly Ala Ile Leu Ser Ser Thr Glu Val Gly Ser
            20                  25                  30

Phe Thr Pro
        35

<210> SEQ ID NO 36
<211> LENGTH: 35
<212> TYPE: PRT
<213> ORGANISM: Artificial sequence
<220> FEATURE:
<223> OTHER INFORMATION: Amino acid sequence Z in synthetic amylin
      analogue which is a compound having the formula R1-Z-R2 in
      PCT/EP2016/055793
<220> FEATURE:
<221> NAME/KEY: DISULFID
<222> LOCATION: (2)..(7)
<223> OTHER INFORMATION: Sequence may possess an intramolecular
      disulphide bridge formed between the cysteine residues present at
      positions 2 and 7
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle

<400> SEQUENCE: 36

Arg Cys Gly Thr Ala Thr Cys Ala Thr Glu Arg Leu Ala His Phe Leu
1               5                   10                  15

Gln Arg Ser Ser Phe Gly Ala Ile Leu Ser Ser Thr Glu Val Gly Ser
            20                  25                  30

Ser Thr Pro
        35

<210> SEQ ID NO 37
<211> LENGTH: 35
<212> TYPE: PRT
<213> ORGANISM: Artificial sequence
<220> FEATURE:
<223> OTHER INFORMATION: Amino acid sequence Z in synthetic amylin
      analogue which is a compound having the formula R1-Z-R2 in
      PCT/EP2016/055793
<220> FEATURE:
<221> NAME/KEY: DISULFID
```

```
<222> LOCATION: (2)..(7)
<223> OTHER INFORMATION: Sequence may possess an intramolecular
      disulphide bridge formed between the cysteine residues present at
      positions 2 and 7
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle

<400> SEQUENCE: 37

Arg Cys Gly Thr Ala Thr Cys Ala Thr Glu Arg Leu Ala His Phe Leu
 1               5                  10                  15

Asn Arg Ser Ser Phe Gly Ala Ile Leu Ser Ser Thr Glu Val Gly Ser
            20                  25                  30

Ser Thr Pro
        35

<210> SEQ ID NO 38
<211> LENGTH: 35
<212> TYPE: PRT
<213> ORGANISM: Artificial sequence
<220> FEATURE:
<223> OTHER INFORMATION: Amino acid sequence Z in synthetic amylin
      analogue which is a compound having the formula R1-Z-R2 in
      PCT/EP2016/055793
<220> FEATURE:
<221> NAME/KEY: DISULFID
<222> LOCATION: (2)..(7)
<223> OTHER INFORMATION: Sequence may possess an intramolecular
      disulphide bridge formed between the cysteine residues present at
      positions 2 and 7
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle

<400> SEQUENCE: 38

Arg Cys Gly Thr Ala Thr Cys Ala Thr Glu Arg Leu Ala His Phe Leu
 1               5                  10                  15

Glu Arg Ser Ser Phe Gly Ala Ile Leu Ser Ser Thr Glu Val Gly Ser
            20                  25                  30

Ser Thr Pro
        35

<210> SEQ ID NO 39
<211> LENGTH: 35
<212> TYPE: PRT
<213> ORGANISM: Artificial sequence
<220> FEATURE:
<223> OTHER INFORMATION: Amino acid sequence Z in synthetic amylin
      analogue which is a compound having the formula R1-Z-R2 in
      PCT/EP2016/055793
<220> FEATURE:
<221> NAME/KEY: DISULFID
<222> LOCATION: (2)..(7)
<223> OTHER INFORMATION: Sequence may possess an intramolecular
      disulphide bridge formed between the cysteine residues present at
      positions 2 and 7
<220> FEATURE:
<221> NAME/KEY: MOD_RES
<222> LOCATION: (22)..(22)
<223> OTHER INFORMATION: MeGly
<220> FEATURE:
```

```
<221> NAME/KEY: MOD_RES
<222> LOCATION: (24)..(24)
<223> OTHER INFORMATION: MeIle

<400> SEQUENCE: 39

Arg Cys Gly Thr Ala Thr Cys Ala Thr Glu Arg Leu Ala His Phe Leu
1               5                   10                  15

His Arg Ser Ser Phe Gly Ala Ile Leu Ser Ser Thr Glu Val Gly Ser
            20                  25                  30

Ser Thr Pro
        35

<210> SEQ ID NO 40
<211> LENGTH: 35
<212> TYPE: PRT
<213> ORGANISM: Artificial sequence
<220> FEATURE:
<223> OTHER INFORMATION: Amino acid sequence Z in synthetic amylin
      analogue which is a compound having the formula R1-Z-R2 in
      PCT/EP2016/055793
<220> FEATURE:
<221> NAME/KEY: DISULFID
<222> LOCATION: (2)..(7)
<223> OTHER INFORMATION: Sequence may possess an intramolecular
      disulphide bridge formed between the cysteine residues present at
      positions 2 and 7
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle

<400> SEQUENCE: 40

Arg Cys Gly Thr Ala Thr Cys Ala Thr Glu Arg Leu Ala His Phe Leu
1               5                   10                  15

Val Arg Ser Ser Phe Gly Ala Ile Leu Ser Ser Thr Glu Val Gly Ser
            20                  25                  30

Ser Thr Pro
        35

<210> SEQ ID NO 41
<211> LENGTH: 35
<212> TYPE: PRT
<213> ORGANISM: Artificial sequence
<220> FEATURE:
<223> OTHER INFORMATION: Amino acid sequence Z in synthetic amylin
      analogue which is a compound having the formula R1-Z-R2 in
      PCT/EP2016/055793
<220> FEATURE:
<221> NAME/KEY: DISULFID
<222> LOCATION: (2)..(7)
<223> OTHER INFORMATION: Sequence may possess an intramolecular
      disulphide bridge formed between the cysteine residues present at
      positions 2 and 7
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle

<400> SEQUENCE: 41

Arg Cys Gly Thr Ala Thr Cys Ala Thr Glu Arg Leu Ala His Phe Leu
1               5                   10                  15
```

-continued

```
Gln Arg Ser Ser Phe Gly Ala Ile Leu Ser Ser Thr Glu Val Gly Ser
            20                  25                  30

Phe Thr Pro
        35

<210> SEQ ID NO 42
<211> LENGTH: 35
<212> TYPE: PRT
<213> ORGANISM: Artificial sequence
<220> FEATURE:
<223> OTHER INFORMATION: Amino acid sequence Z in synthetic amylin
      analogue which is a compound having the formula R1-Z-R2 in
      PCT/EP2016/055793
<220> FEATURE:
<221> NAME/KEY: DISULFID
<222> LOCATION: (2)..(7)
<223> OTHER INFORMATION: Sequence may possess an intramolecular
      disulphide bridge formed between the cysteine residues present at
      positions 2 and 7
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle

<400> SEQUENCE: 42

Arg Cys Gly Thr Ala Thr Cys Ala Thr Glu Arg Leu Ala His Phe Leu
1               5                   10                  15

Asn Arg Ser Ser Phe Gly Ala Ile Leu Ser Ser Thr Glu Val Gly Ser
            20                  25                  30

Phe Thr Pro
        35

<210> SEQ ID NO 43
<211> LENGTH: 35
<212> TYPE: PRT
<213> ORGANISM: Artificial sequence
<220> FEATURE:
<223> OTHER INFORMATION: Amino acid sequence Z in synthetic amylin
      analogue which is a compound having the formula R1-Z-R2 in
      PCT/EP2016/055793
<220> FEATURE:
<221> NAME/KEY: DISULFID
<222> LOCATION: (2)..(7)
<223> OTHER INFORMATION: Sequence may possess an intramolecular
      disulphide bridge formed between the cysteine residues present at
      positions 2 and 7
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle
<220> FEATURE:
<221> NAME/KEY: MOD_RES
<222> LOCATION: (35)..(35)
<223> OTHER INFORMATION: 4Hyp

<400> SEQUENCE: 43

Arg Cys Gly Thr Ala Thr Cys Ala Thr Glu Arg Leu Ala Asp Phe Leu
1               5                   10                  15

Thr Arg Ser Ser Phe Gly Ala Ile Leu Ser Ser Thr Glu Val Gly Ser
            20                  25                  30

Ser Thr Pro
        35
```

```
<210> SEQ ID NO 44
<211> LENGTH: 35
<212> TYPE: PRT
<213> ORGANISM: Artificial sequence
<220> FEATURE:
<223> OTHER INFORMATION: Amino acid sequence Z in synthetic amylin
      analogue which is a compound having the formula R1-Z-R2 in
      PCT/EP2016/055793
<220> FEATURE:
<221> NAME/KEY: DISULFID
<222> LOCATION: (2)..(7)
<223> OTHER INFORMATION: Sequence may possess an intramolecular
      disulphide bridge formed between the cysteine residues present at
      positions 2 and 7
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle
<220> FEATURE:
<221> NAME/KEY: MOD_RES
<222> LOCATION: (35)..(35)
<223> OTHER INFORMATION: 4Hyp

<400> SEQUENCE: 44

Arg Cys Gly Thr Ala Thr Cys Ala Thr Glu Arg Leu Ala Asp Phe Leu
1               5                   10                  15

Thr Arg Ser Ser Phe Gly Ala Ile Leu Ser Ser Thr Glu Val Gly Ser
            20                  25                  30

Phe Thr Pro
        35

<210> SEQ ID NO 45
<211> LENGTH: 35
<212> TYPE: PRT
<213> ORGANISM: Artificial sequence
<220> FEATURE:
<223> OTHER INFORMATION: Amino acid sequence Z in synthetic amylin
      analogue which is a compound having the formula R1-Z-R2 in
      PCT/EP2016/055793
<220> FEATURE:
<221> NAME/KEY: DISULFID
<222> LOCATION: (2)..(7)
<223> OTHER INFORMATION: Sequence may possess an intramolecular
      disulphide bridge formed between the cysteine residues present at
      positions 2 and 7
<220> FEATURE:
<221> NAME/KEY: MOD_RES
<222> LOCATION: (14)..(14)
<223> OTHER INFORMATION: Aad
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle
<220> FEATURE:
<221> NAME/KEY: MOD_RES
<222> LOCATION: (35)..(35)
<223> OTHER INFORMATION: 4Hyp

<400> SEQUENCE: 45

Arg Cys Gly Thr Ala Thr Cys Ala Thr Glu Arg Leu Ala Glu Phe Leu
1               5                   10                  15

Thr Arg Ser Ser Phe Gly Ala Ile Leu Ser Ser Thr Glu Val Gly Ser
            20                  25                  30
```

Ser Thr Pro
        35

<210> SEQ ID NO 46
<211> LENGTH: 35
<212> TYPE: PRT
<213> ORGANISM: Artificial sequence
<220> FEATURE:
<223> OTHER INFORMATION: Amino acid sequence Z in synthetic amylin
      analogue which is a compound having the formula R1-Z-R2 in
      PCT/EP2016/055793
<220> FEATURE:
<221> NAME/KEY: DISULFID
<222> LOCATION: (2)..(7)
<223> OTHER INFORMATION: Sequence may possess an intramolecular
      disulphide bridge formed between the cysteine residues present at
      positions 2 and 7
<220> FEATURE:
<221> NAME/KEY: MOD_RES
<222> LOCATION: (14)..(14)
<223> OTHER INFORMATION: Aad
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle
<220> FEATURE:
<221> NAME/KEY: MOD_RES
<222> LOCATION: (33)..(33)
<223> OTHER INFORMATION: Orn
<220> FEATURE:
<221> NAME/KEY: MOD_RES
<222> LOCATION: (35)..(35)
<223> OTHER INFORMATION: 4Hyp

<400> SEQUENCE: 46

Arg Cys Gly Thr Ala Thr Cys Ala Thr Glu Arg Leu Ala Glu Phe Leu
1               5                  10                  15

Thr Arg Ser Ser Phe Gly Ala Ile Leu Ser Ser Thr Glu Val Gly Ser
            20                  25                  30

Arg Thr Pro
        35

<210> SEQ ID NO 47
<211> LENGTH: 35
<212> TYPE: PRT
<213> ORGANISM: Artificial sequence
<220> FEATURE:
<223> OTHER INFORMATION: Amino acid sequence Z in synthetic amylin
      analogue which is a compound having the formula R1-Z-R2 in
      PCT/EP2016/055793
<220> FEATURE:
<221> NAME/KEY: DISULFID
<222> LOCATION: (2)..(7)
<223> OTHER INFORMATION: Sequence may possess an intramolecular
      disulphide bridge formed between the cysteine residues present at
      positions 2 and 7
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle
<220> FEATURE:
<221> NAME/KEY: SITE
<222> LOCATION: (35)..(35)
<223> OTHER INFORMATION: Xaa is Apr, 4-aminoproline -continued

```
<400> SEQUENCE: 47

Arg Cys Gly Thr Ala Thr Cys Ala Thr Glu Arg Leu Ala His Phe Leu
1               5                   10                  15

Thr Arg Ser Ser Phe Gly Ala Ile Leu Ser Ser Thr Glu Val Gly Ser
            20                  25                  30

Ser Thr Xaa
        35

<210> SEQ ID NO 48
<211> LENGTH: 35
<212> TYPE: PRT
<213> ORGANISM: Artificial sequence
<220> FEATURE:
<223> OTHER INFORMATION: Amino acid sequence Z in synthetic amylin
      analogue which is a compound having the formula R1-Z-R2 in
      PCT/EP2016/055793
<220> FEATURE:
<221> NAME/KEY: DISULFID
<222> LOCATION: (2)..(7)
<223> OTHER INFORMATION: Sequence may possess an intramolecular
      disulphide bridge formed between the cysteine residues present at
      positions 2 and 7
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle

<400> SEQUENCE: 48

Arg Cys Gly Thr Ala Thr Cys Ala Thr Glu Arg Leu Ala His Phe Leu
1               5                   10                  15

Thr Arg Ser Ser Phe Gly Ala Ile Leu Ser Ser Thr Glu Val Gly Ser
            20                  25                  30

Ser Thr Pro
        35

<210> SEQ ID NO 49
<211> LENGTH: 35
<212> TYPE: PRT
<213> ORGANISM: Artificial sequence
<220> FEATURE:
<223> OTHER INFORMATION: Amino acid sequence Z in synthetic amylin
      analogue which is a compound having the formula R1-Z-R2 in
      PCT/EP2016/055793
<220> FEATURE:
<221> NAME/KEY: DISULFID
<222> LOCATION: (2)..(7)
<223> OTHER INFORMATION: Sequence may possess an intramolecular
      disulphide bridge formed between the cysteine residues present at
      positions 2 and 7
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle
<220> FEATURE:
<221> NAME/KEY: MOD_RES
<222> LOCATION: (33)..(33)
<223> OTHER INFORMATION: Orn

<400> SEQUENCE: 49

Arg Cys Gly Thr Ala Thr Cys Ala Thr Glu Arg Leu Ala His Phe Leu
1               5                   10                  15
```

Thr Arg Ser Ser Phe Gly Ala Ile Leu Ser Ser Thr Glu Val Gly Ser
            20                  25                  30

Arg Thr Pro
        35

<210> SEQ ID NO 50
<211> LENGTH: 35
<212> TYPE: PRT
<213> ORGANISM: Artificial sequence
<220> FEATURE:
<223> OTHER INFORMATION: Amino acid sequence Z in synthetic amylin
      analogue which is a compound having the formula R1-Z-R2 in
      PCT/EP2016/055793
<220> FEATURE:
<221> NAME/KEY: DISULFID
<222> LOCATION: (2)..(7)
<223> OTHER INFORMATION: Sequence may possess an intramolecular
      disulphide bridge formed between the cysteine residues present at
      positions 2 and 7
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle
<220> FEATURE:
<221> NAME/KEY: MOD_RES
<222> LOCATION: (35)..(35)
<223> OTHER INFORMATION: 4Hyp

<400> SEQUENCE: 50

Arg Cys Gly Thr Ala Thr Cys Ala Thr Glu Arg Leu Ala His Phe Leu
1               5                   10                  15

Thr Arg Ser Ser Phe Gly Ala Ile Leu Ser Ser Thr Glu Val Gly Ser
            20                  25                  30

Thr Thr Pro
        35

<210> SEQ ID NO 51
<211> LENGTH: 35
<212> TYPE: PRT
<213> ORGANISM: Artificial sequence
<220> FEATURE:
<223> OTHER INFORMATION: Amino acid sequence Z in synthetic amylin
      analogue which is a compound having the formula R1-Z-R2 in
      PCT/EP2016/055793
<220> FEATURE:
<221> NAME/KEY: DISULFID
<222> LOCATION: (2)..(7)
<223> OTHER INFORMATION: Sequence may possess an intramolecular
      disulphide bridge formed between the cysteine residues present at
      positions 2 and 7
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle
<220> FEATURE:
<221> NAME/KEY: MOD_RES
<222> LOCATION: (35)..(35)
<223> OTHER INFORMATION: 4Hyp

<400> SEQUENCE: 51

Arg Cys Asn Thr Ala Thr Cys Ala Thr Gln Arg Leu Ala Asp Phe Leu
1               5                   10                  15

Gln Arg Ser Ser Phe Gly Ala Ile Leu Ser Ser Thr Glu Val Gly Ser

Asn Thr Pro
    35

<210> SEQ ID NO 52
<211> LENGTH: 35
<212> TYPE: PRT
<213> ORGANISM: Artificial sequence
<220> FEATURE:
<223> OTHER INFORMATION: Amino acid sequence Z in synthetic amylin
      analogue which is a compound having the formula R1-Z-R2 in
      PCT/EP2016/055793
<220> FEATURE:
<221> NAME/KEY: DISULFID
<222> LOCATION: (2)..(7)
<223> OTHER INFORMATION: Sequence may possess an intramolecular
      disulphide bridge formed between the cysteine residues present at
      positions 2 and 7
<220> FEATURE:
<221> NAME/KEY: MOD_RES
<222> LOCATION: (17)..(17)
<223> OTHER INFORMATION: Aad
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle
<220> FEATURE:
<221> NAME/KEY: MOD_RES
<222> LOCATION: (35)..(35)
<223> OTHER INFORMATION: 4Hyp

<400> SEQUENCE: 52

Arg Cys Asn Thr Ala Thr Cys Ala Thr Gln Arg Leu Ala His Phe Leu
1               5                   10                  15

Glu Arg Ser Ser Phe Gly Ala Ile Leu Ser Ser Thr Glu Val Gly Ser
            20                  25                  30

Asn Thr Pro
    35

<210> SEQ ID NO 53
<211> LENGTH: 35
<212> TYPE: PRT
<213> ORGANISM: Artificial sequence
<220> FEATURE:
<223> OTHER INFORMATION: Amino acid sequence Z in synthetic amylin
      analogue which is a compound having the formula R1-Z-R2 in
      PCT/EP2016/055793
<220> FEATURE:
<221> NAME/KEY: DISULFID
<222> LOCATION: (2)..(7)
<223> OTHER INFORMATION: Sequence may possess an intramolecular
      disulphide bridge formed between the cysteine residues present at
      positions 2 and 7
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle
<220> FEATURE:
<221> NAME/KEY: MOD_RES
<222> LOCATION: (33)..(33)
<223> OTHER INFORMATION: Orn
<220> FEATURE:
<221> NAME/KEY: MOD_RES
<222> LOCATION: (35)..(35)
<223> OTHER INFORMATION: 4Hyp

<400> SEQUENCE: 53

Arg Cys Gly Thr Ala Thr Cys Ala Thr Glu Arg Leu Ala His Phe Leu
1               5                   10                  15

Gln Arg Ser Ser Phe Gly Ala Ile Leu Ser Ser Thr Glu Val Gly Ser
            20                  25                  30

Arg Thr Pro
        35

<210> SEQ ID NO 54
<211> LENGTH: 35
<212> TYPE: PRT
<213> ORGANISM: Artificial sequence
<220> FEATURE:
<223> OTHER INFORMATION: Amino acid sequence Z in synthetic amylin
      analogue which is a compound having the formula R1-Z-R2 in
      PCT/EP2016/055793
<220> FEATURE:
<221> NAME/KEY: DISULFID
<222> LOCATION: (2)..(7)
<223> OTHER INFORMATION: Sequence may possess an intramolecular
      disulphide bridge formed between the cysteine residues present at
      positions 2 and 7
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle
<220> FEATURE:
<221> NAME/KEY: MOD_RES
<222> LOCATION: (35)..(35)
<223> OTHER INFORMATION: 4Hyp

<400> SEQUENCE: 54

Arg Cys Gly Thr Ala Thr Cys Ala Thr Glu Arg Leu Ala His Phe Leu
1               5                   10                  15

Gln Arg Ser Ser Phe Gly Ala Ile Leu Ser Ser Thr Glu Val Gly Ser
            20                  25                  30

Gly Thr Pro
        35

<210> SEQ ID NO 55
<211> LENGTH: 35
<212> TYPE: PRT
<213> ORGANISM: Artificial sequence
<220> FEATURE:
<223> OTHER INFORMATION: Amino acid sequence Z in synthetic amylin
      analogue which is a compound having the formula R1-Z-R2 in
      PCT/EP2016/055793
<220> FEATURE:
<221> NAME/KEY: DISULFID
<222> LOCATION: (2)..(7)
<223> OTHER INFORMATION: Sequence may possess an intramolecular
      disulphide bridge formed between the cysteine residues present at
      positions 2 and 7
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle
<220> FEATURE:
<221> NAME/KEY: MOD_RES
<222> LOCATION: (33)..(33)
<223> OTHER INFORMATION: Aad
<220> FEATURE:

```
<221> NAME/KEY: MOD_RES
<222> LOCATION: (35)..(35)
<223> OTHER INFORMATION: 4Hyp

<400> SEQUENCE: 55

Arg Cys Gly Thr Ala Thr Cys Ala Thr Glu Arg Leu Ala His Phe Leu
1               5                   10                  15

Gln Arg Ser Ser Phe Gly Ala Ile Leu Ser Ser Thr Glu Val Gly Ser
            20                  25                  30

Glu Thr Pro
        35

<210> SEQ ID NO 56
<211> LENGTH: 35
<212> TYPE: PRT
<213> ORGANISM: Artificial sequence
<220> FEATURE:
<223> OTHER INFORMATION: Amino acid sequence Z in synthetic amylin
      analogue which is a compound having the formula R1-Z-R2 in
      PCT/EP2016/055793
<220> FEATURE:
<221> NAME/KEY: DISULFID
<222> LOCATION: (2)..(7)
<223> OTHER INFORMATION: Sequence may possess an intramolecular
      disulphide bridge formed between the cysteine residues present at
      positions 2 and 7
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle
<220> FEATURE:
<221> NAME/KEY: MOD_RES
<222> LOCATION: (35)..(35)
<223> OTHER INFORMATION: 4Hyp

<400> SEQUENCE: 56

Arg Cys Gly Thr Ala Thr Cys Ala Thr Glu Arg Leu Ala Asp Phe Leu
1               5                   10                  15

Gln Arg Ser Ser Phe Gly Ala Ile Leu Ser Ser Thr Glu Val Gly Ser
            20                  25                  30

Asn Thr Pro
        35

<210> SEQ ID NO 57
<211> LENGTH: 35
<212> TYPE: PRT
<213> ORGANISM: Artificial sequence
<220> FEATURE:
<223> OTHER INFORMATION: Amino acid sequence Z in synthetic amylin
      analogue which is a compound having the formula R1-Z-R2 in
      PCT/EP2016/055793
<220> FEATURE:
<221> NAME/KEY: DISULFID
<222> LOCATION: (2)..(7)
<223> OTHER INFORMATION: Sequence may possess an intramolecular
      disulphide bridge formed between the cysteine residues present at
      positions 2 and 7
<220> FEATURE:
<221> NAME/KEY: MOD_RES
<222> LOCATION: (14)..(14)
<223> OTHER INFORMATION: Aad
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
```

```
<222> LOCATION: (24)..(24)
<223> OTHER INFORMATION: MeIle
<220> FEATURE:
<221> NAME/KEY: MOD_RES
<222> LOCATION: (35)..(35)
<223> OTHER INFORMATION: 4Hyp

<400> SEQUENCE: 57

Arg Cys Gly Thr Ala Thr Cys Ala Thr Glu Arg Leu Ala Glu Phe Leu
1               5                   10                  15

Gln Arg Ser Ser Phe Gly Ala Ile Leu Ser Ser Thr Glu Val Gly Ser
            20                  25                  30

Asn Thr Pro
        35

<210> SEQ ID NO 58
<211> LENGTH: 35
<212> TYPE: PRT
<213> ORGANISM: Artificial sequence
<220> FEATURE:
<223> OTHER INFORMATION: Amino acid sequence Z in synthetic amylin
      analogue which is a compound having the formula R1-Z-R2 in
      PCT/EP2016/055793
<220> FEATURE:
<221> NAME/KEY: DISULFID
<222> LOCATION: (2)..(7)
<223> OTHER INFORMATION: Sequence may possess an intramolecular
      disulphide bridge formed between the cysteine residues present at
      positions 2 and 7
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle
<220> FEATURE:
<221> NAME/KEY: MOD_RES
<222> LOCATION: (35)..(35)
<223> OTHER INFORMATION: 4Hyp

<400> SEQUENCE: 58

Arg Cys Asn Thr Ala Thr Cys Ala Thr Glu Arg Leu Ala His Phe Leu
1               5                   10                  15

Gln Arg Ser Ser Phe Gly Ala Ile Leu Ser Ser Thr Glu Val Gly Ser
            20                  25                  30

Asn Thr Pro
        35

<210> SEQ ID NO 59
<211> LENGTH: 35
<212> TYPE: PRT
<213> ORGANISM: Artificial sequence
<220> FEATURE:
<223> OTHER INFORMATION: Amino acid sequence Z in synthetic amylin
      analogue which is a compound having the formula R1-Z-R2 in
      PCT/EP2016/055793
<220> FEATURE:
<221> NAME/KEY: DISULFID
<222> LOCATION: (2)..(7)
<223> OTHER INFORMATION: Sequence may possess an intramolecular
      disulphide bridge formed between the cysteine residues present at
      positions 2 and 7
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
```

<223> OTHER INFORMATION: MeIle
<220> FEATURE:
<221> NAME/KEY: MOD_RES
<222> LOCATION: (35)..(35)
<223> OTHER INFORMATION: 4Hyp

<400> SEQUENCE: 59

Arg Cys Gln Thr Ala Thr Cys Ala Thr Glu Arg Leu Ala His Phe Leu
1               5                   10                  15

Gln Arg Ser Ser Phe Gly Ala Ile Leu Ser Ser Thr Glu Val Gly Ser
            20                  25                  30

Asn Thr Pro
        35

<210> SEQ ID NO 60
<211> LENGTH: 35
<212> TYPE: PRT
<213> ORGANISM: Artificial sequence
<220> FEATURE:
<223> OTHER INFORMATION: Amino acid sequence Z in synthetic amylin
      analogue which is a compound having the formula R1-Z-R2 in
      PCT/EP2016/055793
<220> FEATURE:
<221> NAME/KEY: DISULFID
<222> LOCATION: (2)..(7)
<223> OTHER INFORMATION: Sequence may possess an intramolecular
      disulphide bridge formed between the cysteine residues present at
      positions 2 and 7
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle
<220> FEATURE:
<221> NAME/KEY: MOD_RES
<222> LOCATION: (35)..(35)
<223> OTHER INFORMATION: 4Hyp

<400> SEQUENCE: 60

Arg Cys Asn Thr Ala Thr Cys Ala Thr Gln Arg Leu Ala His Phe Leu
1               5                   10                  15

Gln Arg Ser Ser Phe Gly Ala Ile Leu Ser Ser Thr Glu Val Gly Ser
            20                  25                  30

Asn Thr Pro
        35

<210> SEQ ID NO 61
<211> LENGTH: 35
<212> TYPE: PRT
<213> ORGANISM: Artificial sequence
<220> FEATURE:
<223> OTHER INFORMATION: Amino acid sequence Z in synthetic amylin
      analogue which is a compound having the formula R1-Z-R2 in
      PCT/EP2016/055793
<220> FEATURE:
<221> NAME/KEY: DISULFID
<222> LOCATION: (2)..(7)
<223> OTHER INFORMATION: Sequence may possess an intramolecular
      disulphide bridge formed between the cysteine residues present at
      positions 2 and 7
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle

```
<220> FEATURE:
<221> NAME/KEY: MOD_RES
<222> LOCATION: (35)..(35)
<223> OTHER INFORMATION: 4Hyp

<400> SEQUENCE: 61

Arg Cys Pro Thr Ala Thr Cys Ala Thr Asp Arg Leu Ala His Phe Leu
1               5                   10                  15

Gln Arg Ser Ser Phe Gly Ala Ile Leu Ser Ser Thr Asp Val Gly Ser
            20                  25                  30

Asn Thr Pro
        35

<210> SEQ ID NO 62
<211> LENGTH: 35
<212> TYPE: PRT
<213> ORGANISM: Artificial sequence
<220> FEATURE:
<223> OTHER INFORMATION: Amino acid sequence Z in synthetic amylin
      analogue which is a compound having the formula R1-Z-R2 in
      PCT/EP2016/055793
<220> FEATURE:
<221> NAME/KEY: DISULFID
<222> LOCATION: (2)..(7)
<223> OTHER INFORMATION: Sequence may possess an intramolecular
      disulphide bridge formed between the cysteine residues present at
      positions 2 and 7
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle
<220> FEATURE:
<221> NAME/KEY: MOD_RES
<222> LOCATION: (35)..(35)
<223> OTHER INFORMATION: 4Hyp

<400> SEQUENCE: 62

Arg Cys Asn Thr Ala Thr Cys Ala Thr Glu Arg Leu Ala His Phe Leu
1               5                   10                  15

Gln Arg Ser Ser Phe Gly Ala Ile Leu Ser Ser Thr Glu Val Gly Ser
            20                  25                  30

Asp Thr Pro
        35

<210> SEQ ID NO 63
<211> LENGTH: 35
<212> TYPE: PRT
<213> ORGANISM: Artificial sequence
<220> FEATURE:
<223> OTHER INFORMATION: Amino acid sequence Z in synthetic amylin
      analogue which is a compound having the formula R1-Z-R2 in
      PCT/EP2016/055793
<220> FEATURE:
<221> NAME/KEY: DISULFID
<222> LOCATION: (2)..(7)
<223> OTHER INFORMATION: Sequence may possess an intramolecular
      disulphide bridge formed between the cysteine residues present at
      positions 2 and 7
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle
```

-continued

```
<400> SEQUENCE: 63

Arg Cys Asn Thr Ala Thr Cys Ala Thr Gln Arg Leu Ala His Phe Leu
1               5                   10                  15

Gln Arg Ser Ser Phe Gly Ala Ile Leu Ser Ser Thr Glu Val Gly Ser
            20                  25                  30

Asn Thr Pro
        35

<210> SEQ ID NO 64
<211> LENGTH: 35
<212> TYPE: PRT
<213> ORGANISM: Artificial sequence
<220> FEATURE:
<223> OTHER INFORMATION: Amino acid sequence Z in synthetic amylin
      analogue which is a compound having the formula R1-Z-R2 in
      PCT/EP2016/055793
<220> FEATURE:
<221> NAME/KEY: DISULFID
<222> LOCATION: (2)..(7)
<223> OTHER INFORMATION: Sequence may possess an intramolecular
      disulphide bridge formed between the cysteine residues present at
      positions 2 and 7
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle

<400> SEQUENCE: 64

Arg Cys Asn Thr Ala Thr Cys Ala Thr Glu Arg Leu Ala His Phe Leu
1               5                   10                  15

Gln Arg Ser Ser Phe Gly Ala Ile Leu Ser Ser Thr Glu Val Gly Ser
            20                  25                  30

Asn Thr Pro
        35

<210> SEQ ID NO 65
<211> LENGTH: 35
<212> TYPE: PRT
<213> ORGANISM: Artificial sequence
<220> FEATURE:
<223> OTHER INFORMATION: Amino acid sequence Z in synthetic amylin
      analogue which is a compound having the formula R1-Z-R2 in
      PCT/EP2016/055793
<220> FEATURE:
<221> NAME/KEY: DISULFID
<222> LOCATION: (2)..(7)
<223> OTHER INFORMATION: Sequence may possess an intramolecular
      disulphide bridge formed between the cysteine residues present at
      positions 2 and 7
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle
<220> FEATURE:
<221> NAME/KEY: MOD_RES
<222> LOCATION: (35)..(35)
<223> OTHER INFORMATION: 4Hyp

<400> SEQUENCE: 65

Arg Cys Pro Thr Ala Thr Cys Ala Thr Glu Arg Leu Ala His Phe Leu
1               5                   10                  15
```

Gln Arg Ser Ser Phe Gly Ala Ile Leu Ser Ser Thr Glu Val Gly Ser
            20                  25                  30

Asn Thr Pro
        35

<210> SEQ ID NO 66
<211> LENGTH: 35
<212> TYPE: PRT
<213> ORGANISM: Artificial sequence
<220> FEATURE:
<223> OTHER INFORMATION: Amino acid sequence Z in synthetic amylin
      analogue which is a compound having the formula R1-Z-R2 in
      PCT/EP2016/055793
<220> FEATURE:
<221> NAME/KEY: DISULFID
<222> LOCATION: (2)..(7)
<223> OTHER INFORMATION: Sequence may possess an intramolecular
      disulphide bridge formed between the cysteine residues present at
      positions 2 and 7
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle
<220> FEATURE:
<221> NAME/KEY: MOD_RES
<222> LOCATION: (35)..(35)
<223> OTHER INFORMATION: 4Hyp

<400> SEQUENCE: 66

Arg Cys Pro Thr Ala Thr Cys Ala Thr Gln Arg Leu Ala His Phe Leu
1               5                   10                  15

Gln Arg Ser Ser Phe Gly Ala Ile Leu Ser Ser Thr Glu Val Gly Ser
            20                  25                  30

Asn Thr Pro
        35

<210> SEQ ID NO 67
<211> LENGTH: 35
<212> TYPE: PRT
<213> ORGANISM: Artificial sequence
<220> FEATURE:
<223> OTHER INFORMATION: Amino acid sequence Z in synthetic amylin
      analogue which is a compound having the formula R1-Z-R2 in
      PCT/EP2016/055793
<220> FEATURE:
<221> NAME/KEY: DISULFID
<222> LOCATION: (2)..(7)
<223> OTHER INFORMATION: Sequence may possess an intramolecular
      disulphide bridge formed between the cysteine residues present at
      positions 2 and 7
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle

<400> SEQUENCE: 67

Arg Cys Asn Thr Ala Thr Cys Ala Thr Gln Arg Leu Ala Asp Phe Leu
1               5                   10                  15

Gln Arg Ser Ser Phe Gly Ala Ile Leu Ser Ser Thr Glu Val Gly Ser
            20                  25                  30

Asn Thr Pro
        35

```
<210> SEQ ID NO 68
<211> LENGTH: 35
<212> TYPE: PRT
<213> ORGANISM: Artificial sequence
<220> FEATURE:
<223> OTHER INFORMATION: Amino acid sequence Z in synthetic amylin
      analogue which is a compound having the formula R1-Z-R2 in
      PCT/EP2016/055793
<220> FEATURE:
<221> NAME/KEY: DISULFID
<222> LOCATION: (2)..(7)
<223> OTHER INFORMATION: Sequence may possess an intramolecular
      disulphide bridge formed between the cysteine residues present at
      positions 2 and 7
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle

<400> SEQUENCE: 68

Arg Cys Asn Thr Ala Thr Cys Ala Thr Glu Arg Leu Ala Asp Phe Leu
1               5                   10                  15

Gln Arg Ser Ser Phe Gly Ala Ile Leu Ser Ser Thr Glu Val Gly Ser
            20                  25                  30

Asn Thr Pro
        35

<210> SEQ ID NO 69
<211> LENGTH: 35
<212> TYPE: PRT
<213> ORGANISM: Artificial sequence
<220> FEATURE:
<223> OTHER INFORMATION: Amino acid sequence Z in synthetic amylin
      analogue which is a compound having the formula R1-Z-R2 in
      PCT/EP2016/055793
<220> FEATURE:
<221> NAME/KEY: DISULFID
<222> LOCATION: (2)..(7)
<223> OTHER INFORMATION: Sequence may possess an intramolecular
      disulphide bridge formed between the cysteine residues present at
      positions 2 and 7
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle

<400> SEQUENCE: 69

Arg Cys Pro Thr Ala Thr Cys Ala Thr Glu Arg Leu Ala Asp Phe Leu
1               5                   10                  15

Gln Arg Ser Ser Phe Gly Ala Ile Leu Ser Ser Thr Glu Val Gly Ser
            20                  25                  30

Asn Thr Pro
        35

<210> SEQ ID NO 70
<211> LENGTH: 35
<212> TYPE: PRT
<213> ORGANISM: Artificial sequence
<220> FEATURE:
<223> OTHER INFORMATION: Amino acid sequence Z in synthetic amylin
      analogue which is a compound having the formula R1-Z-R2 in
```

```
                                   PCT/EP2016/055793
<220> FEATURE:
<221> NAME/KEY: DISULFID
<222> LOCATION: (2)..(7)
<223> OTHER INFORMATION: Sequence may possess an intramolecular
      disulphide bridge formed between the cysteine residues present at
      positions 2 and 7
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle
<220> FEATURE:
<221> NAME/KEY: MOD_RES
<222> LOCATION: (35)..(35)
<223> OTHER INFORMATION: 4Hyp

<400> SEQUENCE: 70

Arg Cys Asn Thr Ala Thr Cys Ala Thr Glu Arg Leu Ala Asp Phe Leu
1               5                   10                  15

Gln Arg Ser Ser Phe Gly Ala Ile Leu Ser Ser Thr Glu Val Gly Ser
            20                  25                  30

Asn Thr Pro
        35

<210> SEQ ID NO 71
<211> LENGTH: 35
<212> TYPE: PRT
<213> ORGANISM: Artificial sequence
<220> FEATURE:
<223> OTHER INFORMATION: Amino acid sequence Z in synthetic amylin
      analogue which is a compound having the formula R1-Z-R2 in
      PCT/EP2016/055793
<220> FEATURE:
<221> NAME/KEY: DISULFID
<222> LOCATION: (2)..(7)
<223> OTHER INFORMATION: Sequence may possess an intramolecular
      disulphide bridge formed between the cysteine residues present at
      positions 2 and 7
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle
<220> FEATURE:
<221> NAME/KEY: MOD_RES
<222> LOCATION: (35)..(35)
<223> OTHER INFORMATION: 4Hyp

<400> SEQUENCE: 71

Arg Cys Asn Thr Ala Thr Cys Ala Thr Gln Arg Leu Ala His Phe Leu
1               5                   10                  15

Gln Arg Ser Ser Phe Gly Ala Ile Leu Ser Ser Thr Glu Val Gly Ser
            20                  25                  30

Ser Thr Pro
        35

<210> SEQ ID NO 72
<211> LENGTH: 35
<212> TYPE: PRT
<213> ORGANISM: Artificial sequence
<220> FEATURE:
<223> OTHER INFORMATION: Amino acid sequence Z in synthetic amylin
      analogue which is a compound having the formula R1-Z-R2 in
      PCT/EP2016/055793
```

```
<220> FEATURE:
<221> NAME/KEY: DISULFID
<222> LOCATION: (2)..(7)
<223> OTHER INFORMATION: Sequence may possess an intramolecular
      disulphide bridge formed between the cysteine residues present at
      positions 2 and 7
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle
<220> FEATURE:
<221> NAME/KEY: MOD_RES
<222> LOCATION: (35)..(35)
<223> OTHER INFORMATION: 4Hyp

<400> SEQUENCE: 72

Arg Cys Pro Thr Ala Thr Cys Ala Thr Glu Arg Leu Ala His Phe Leu
1               5                   10                  15

Gln Arg Ser Ser Phe Gly Ala Ile Leu Ser Ser Thr Glu Val Gly Ser
            20                  25                  30

Ser Thr Pro
        35

<210> SEQ ID NO 73
<211> LENGTH: 35
<212> TYPE: PRT
<213> ORGANISM: Artificial sequence
<220> FEATURE:
<223> OTHER INFORMATION: Amino acid sequence Z in synthetic amylin
      analogue which is a compound having the formula R1-Z-R2 in
      PCT/EP2016/055793
<220> FEATURE:
<221> NAME/KEY: DISULFID
<222> LOCATION: (2)..(7)
<223> OTHER INFORMATION: Sequence may possess an intramolecular
      disulphide bridge formed between the cysteine residues present at
      positions 2 and 7
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle
<220> FEATURE:
<221> NAME/KEY: MOD_RES
<222> LOCATION: (35)..(35)
<223> OTHER INFORMATION: 4Hyp

<400> SEQUENCE: 73

Arg Cys Asn Thr Ala Thr Cys Ala Thr Gln Arg Leu Ala His Phe Leu
1               5                   10                  15

Gln Arg Ser Ser Phe Gly Ala Ile Leu Ser Ser Thr Glu Val Gly Ser
            20                  25                  30

Gly Thr Pro
        35

<210> SEQ ID NO 74
<211> LENGTH: 35
<212> TYPE: PRT
<213> ORGANISM: Artificial sequence
<220> FEATURE:
<223> OTHER INFORMATION: Amino acid sequence Z in synthetic amylin
      analogue which is a compound having the formula R1-Z-R2 in
      PCT/EP2016/055793
<220> FEATURE:
```

```
<221> NAME/KEY: DISULFID
<222> LOCATION: (2)..(7)
<223> OTHER INFORMATION: Sequence may possess an intramolecular
      disulphide bridge formed between the cysteine residues present at
      positions 2 and 7
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle
<220> FEATURE:
<221> NAME/KEY: MOD_RES
<222> LOCATION: (35)..(35)
<223> OTHER INFORMATION: 4Hyp

<400> SEQUENCE: 74

Arg Cys Pro Thr Ala Thr Cys Ala Thr Glu Arg Leu Ala His Phe Leu
1               5                   10                  15

Gln Arg Ser Ser Phe Gly Ala Ile Leu Ser Ser Thr Glu Val Gly Ser
            20                  25                  30

Gly Thr Pro
        35

<210> SEQ ID NO 75
<211> LENGTH: 35
<212> TYPE: PRT
<213> ORGANISM: Artificial sequence
<220> FEATURE:
<223> OTHER INFORMATION: Amino acid sequence Z in synthetic amylin
      analogue which is a compound having the formula R1-Z-R2 in
      PCT/EP2016/055793
<220> FEATURE:
<221> NAME/KEY: DISULFID
<222> LOCATION: (2)..(7)
<223> OTHER INFORMATION: Sequence may possess an intramolecular
      disulphide bridge formed between the cysteine residues present at
      positions 2 and 7
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle
<220> FEATURE:
<221> NAME/KEY: MOD_RES
<222> LOCATION: (35)..(35)
<223> OTHER INFORMATION: 4Hyp

<400> SEQUENCE: 75

Arg Cys Asn Thr Ala Thr Cys Ala Thr Gln Arg Leu Ala His Phe Leu
1               5                   10                  15

Gln Arg Ser Ser Phe Gly Ala Ile Leu Ser Ser Thr Glu Val Gly Ser
            20                  25                  30

Thr Thr Pro
        35

<210> SEQ ID NO 76
<211> LENGTH: 35
<212> TYPE: PRT
<213> ORGANISM: Artificial sequence
<220> FEATURE:
<223> OTHER INFORMATION: Amino acid sequence Z in synthetic amylin
      analogue which is a compound having the formula R1-Z-R2 in
      PCT/EP2016/055793
<220> FEATURE:
<221> NAME/KEY: DISULFID
```

```
<222> LOCATION: (2)..(7)
<223> OTHER INFORMATION: Sequence may possess an intramolecular
      disulphide bridge formed between the cysteine residues present at
      positions 2 and 7
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle
<220> FEATURE:
<221> NAME/KEY: MOD_RES
<222> LOCATION: (35)..(35)
<223> OTHER INFORMATION: 4Hyp

<400> SEQUENCE: 76

Arg Cys Pro Thr Ala Thr Cys Ala Thr Glu Arg Leu Ala His Phe Leu
1               5                   10                  15

Gln Arg Ser Ser Phe Gly Ala Ile Leu Ser Ser Thr Glu Val Gly Ser
            20                  25                  30

Thr Thr Pro
        35

<210> SEQ ID NO 77
<211> LENGTH: 35
<212> TYPE: PRT
<213> ORGANISM: Artificial sequence
<220> FEATURE:
<223> OTHER INFORMATION: Amino acid sequence Z in synthetic amylin
      analogue which is a compound having the formula R1-Z-R2 in
      PCT/EP2016/055793
<220> FEATURE:
<221> NAME/KEY: DISULFID
<222> LOCATION: (2)..(7)
<223> OTHER INFORMATION: Sequence may possess an intramolecular
      disulphide bridge formed between the cysteine residues present at
      positions 2 and 7
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle
<220> FEATURE:
<221> NAME/KEY: MOD_RES
<222> LOCATION: (33)..(33)
<223> OTHER INFORMATION: Aad
<220> FEATURE:
<221> NAME/KEY: MOD_RES
<222> LOCATION: (35)..(35)
<223> OTHER INFORMATION: 4Hyp

<400> SEQUENCE: 77

Arg Cys Asn Thr Ala Thr Cys Ala Thr Gln Arg Leu Ala His Phe Leu
1               5                   10                  15

Gln Arg Ser Ser Phe Gly Ala Ile Leu Ser Ser Thr Glu Val Gly Ser
            20                  25                  30

Glu Thr Pro
        35

<210> SEQ ID NO 78
<211> LENGTH: 35
<212> TYPE: PRT
<213> ORGANISM: Artificial sequence
<220> FEATURE:
<223> OTHER INFORMATION: Amino acid sequence Z in synthetic amylin
      analogue which is a compound having the formula R1-Z-R2 in
```

```
                    PCT/EP2016/055793
<220> FEATURE:
<221> NAME/KEY: DISULFID
<222> LOCATION: (2)..(7)
<223> OTHER INFORMATION: Sequence may possess an intramolecular
      disulphide bridge formed between the cysteine residues present at
      positions 2 and 7
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle
<220> FEATURE:
<221> NAME/KEY: MOD_RES
<222> LOCATION: (33)..(33)
<223> OTHER INFORMATION: Aad
<220> FEATURE:
<221> NAME/KEY: MOD_RES
<222> LOCATION: (35)..(35)
<223> OTHER INFORMATION: 4Hyp

<400> SEQUENCE: 78

Arg Cys Pro Thr Ala Thr Cys Ala Thr Glu Arg Leu Ala His Phe Leu
1               5                   10                  15

Gln Arg Ser Ser Phe Gly Ala Ile Leu Ser Ser Thr Glu Val Gly Ser
            20                  25                  30

Glu Thr Pro
        35

<210> SEQ ID NO 79
<211> LENGTH: 33
<212> TYPE: PRT
<213> ORGANISM: Artificial sequence
<220> FEATURE:
<223> OTHER INFORMATION: Amino acid sequence Z in synthetic amylin
      analogue which is a compound having the formula R1-Z-R2 in
      PCT/EP2016/055793
<220> FEATURE:
<221> NAME/KEY: DISULFID
<222> LOCATION: (2)..(7)
<223> OTHER INFORMATION: Sequence may possess an intramolecular
      disulphide bridge formed between the cysteine residues present at
      positions 2 and 7
<220> FEATURE:
<221> NAME/KEY: MOD_RES
<222> LOCATION: (20)..(20)
<223> OTHER INFORMATION: MeGly
<220> FEATURE:
<221> NAME/KEY: MOD_RES
<222> LOCATION: (22)..(22)
<223> OTHER INFORMATION: MeIle
<220> FEATURE:
<221> NAME/KEY: MOD_RES
<222> LOCATION: (33)..(33)
<223> OTHER INFORMATION: 4Hyp

<400> SEQUENCE: 79

Arg Cys Gly Thr Ala Thr Cys Ala Thr Glu Arg Leu Ala His Phe Leu
1               5                   10                  15

Gln Arg Phe Gly Ala Ile Leu Ser Ser Thr Glu Val Gly Ser Asn Thr
            20                  25                  30

Pro

<210> SEQ ID NO 80
<211> LENGTH: 35
<212> TYPE: PRT
<213> ORGANISM: Artificial sequence
<220> FEATURE:
```

```
<223> OTHER INFORMATION: Amino acid sequence Z in synthetic amylin
      analogue which is a compound having the formula R1-Z-R2 in
      PCT/EP2016/055793
<220> FEATURE:
<221> NAME/KEY: DISULFID
<222> LOCATION: (2)..(7)
<223> OTHER INFORMATION: Sequence may possess an intramolecular
      disulphide bridge formed between the cysteine residues present at
      positions 2 and 7
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle

<400> SEQUENCE: 80

Arg Cys Gly Thr Ala Thr Cys Ala Thr Glu Arg Leu Ala His Phe Leu
1               5                   10                  15

Gln Arg Ser Ser Phe Gly Ala Ile Leu Ser Ser Thr Glu Val Gly Ser
            20                  25                  30

Asn Thr Pro
        35

<210> SEQ ID NO 81
<211> LENGTH: 33
<212> TYPE: PRT
<213> ORGANISM: Artificial sequence
<220> FEATURE:
<223> OTHER INFORMATION: Amino acid sequence Z in synthetic amylin
      analogue which is a compound having the formula R1-Z-R2 in
      PCT/EP2016/055793
<220> FEATURE:
<221> NAME/KEY: DISULFID
<222> LOCATION: (2)..(7)
<223> OTHER INFORMATION: Sequence may possess an intramolecular
      disulphide bridge formed between the cysteine residues present at
      positions 2 and 7
<220> FEATURE:
<221> NAME/KEY: MOD_RES
<222> LOCATION: (20)..(20)
<223> OTHER INFORMATION: MeGly
<220> FEATURE:
<221> NAME/KEY: MOD_RES
<222> LOCATION: (22)..(22)
<223> OTHER INFORMATION: MeIle
<220> FEATURE:
<221> NAME/KEY: MOD_RES
<222> LOCATION: (33)..(33)
<223> OTHER INFORMATION: 4Hyp

<400> SEQUENCE: 81

Arg Cys Asn Thr Ala Thr Cys Ala Thr Gln Arg Leu Ala His Phe Leu
1               5                   10                  15

Gln Arg Phe Gly Ala Ile Leu Ser Ser Thr Glu Val Gly Ser Gly Thr
            20                  25                  30

Pro

<210> SEQ ID NO 82
<211> LENGTH: 35
<212> TYPE: PRT
<213> ORGANISM: Artificial sequence
<220> FEATURE:
<223> OTHER INFORMATION: Amino acid sequence Z in synthetic amylin
      analogue which is a compound having the formula R1-Z-R2 in
      PCT/EP2016/055793
<220> FEATURE:
<221> NAME/KEY: DISULFID
<222> LOCATION: (2)..(7)
```

```
<223> OTHER INFORMATION: Sequence may possess an intramolecular
      disulphide bridge formed between the cysteine residues present at
      positions 2 and 7
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle

<400> SEQUENCE: 82

Arg Cys Asn Thr Ala Thr Cys Ala Thr Gln Arg Leu Ala Asp Phe Leu
1               5                   10                  15

Gln Arg Ser Ser Phe Gly Ala Ile Leu Ser Ser Thr Glu Val Gly Ser
            20                  25                  30

Gly Thr Pro
        35

<210> SEQ ID NO 83
<211> LENGTH: 35
<212> TYPE: PRT
<213> ORGANISM: Artificial sequence
<220> FEATURE:
<223> OTHER INFORMATION: Amino acid sequence Z in synthetic amylin
      analogue which is a compound having the formula R1-Z-R2 in
      PCT/EP2016/055793
<220> FEATURE:
<221> NAME/KEY: DISULFID
<222> LOCATION: (2)..(7)
<223> OTHER INFORMATION: Sequence may possess an intramolecular
      disulphide bridge formed between the cysteine residues present at
      positions 2 and 7
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle
<220> FEATURE:
<221> NAME/KEY: MOD_RES
<222> LOCATION: (35)..(35)
<223> OTHER INFORMATION: 4Hyp

<400> SEQUENCE: 83

Arg Cys Asn Thr Ala Thr Cys Ala Thr Gln Arg Leu Ala Asp Phe Leu
1               5                   10                  15

Gln Arg Ser Ser Phe Gly Ala Ile Leu Ser Ser Thr Glu Val Gly Ser
            20                  25                  30

Gly Thr Pro
        35

<210> SEQ ID NO 84
<211> LENGTH: 35
<212> TYPE: PRT
<213> ORGANISM: Artificial sequence
<220> FEATURE:
<223> OTHER INFORMATION: Amino acid sequence Z in synthetic amylin
      analogue which is a compound having the formula R1-Z-R2 in
      PCT/EP2016/055793
<220> FEATURE:
<221> NAME/KEY: DISULFID
<222> LOCATION: (2)..(7)
<223> OTHER INFORMATION: Sequence may possess an intramolecular
      disulphide bridge formed between the cysteine residues present at
      positions 2 and 7
<220> FEATURE:
<221> NAME/KEY: MOD_RES
```

```
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle

<400> SEQUENCE: 84

Arg Cys Asn Thr Ala Thr Cys Ala Thr Gln Arg Leu Ala Asp Phe Leu
1               5                   10                  15
Gln Arg Ser Ser Phe Gly Ala Ile Leu Ser Ser Thr Glu Val Gly Ser
            20                  25                  30
Thr Thr Pro
        35

<210> SEQ ID NO 85
<211> LENGTH: 35
<212> TYPE: PRT
<213> ORGANISM: Artificial sequence
<220> FEATURE:
<223> OTHER INFORMATION: Amino acid sequence Z in synthetic amylin
      analogue which is a compound having the formula R1-Z-R2 in
      PCT/EP2016/055793
<220> FEATURE:
<221> NAME/KEY: DISULFID
<222> LOCATION: (2)..(7)
<223> OTHER INFORMATION: Sequence may possess an intramolecular
      disulphide bridge formed between the cysteine residues present at
      positions 2 and 7
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle
<220> FEATURE:
<221> NAME/KEY: MOD_RES
<222> LOCATION: (35)..(35)
<223> OTHER INFORMATION: 4Hyp

<400> SEQUENCE: 85

Arg Cys Asn Thr Ala Thr Cys Ala Thr Gln Arg Leu Ala Asp Phe Leu
1               5                   10                  15
Gln Arg Ser Ser Phe Gly Ala Ile Leu Ser Ser Thr Glu Val Gly Ser
            20                  25                  30
Thr Thr Pro
        35

<210> SEQ ID NO 86
<211> LENGTH: 35
<212> TYPE: PRT
<213> ORGANISM: Artificial sequence
<220> FEATURE:
<223> OTHER INFORMATION: Amino acid sequence Z in synthetic amylin
      analogue which is a compound having the formula R1-Z-R2 in
      PCT/EP2016/055793
<220> FEATURE:
<221> NAME/KEY: DISULFID
<222> LOCATION: (2)..(7)
<223> OTHER INFORMATION: Sequence may possess an intramolecular
      disulphide bridge formed between the cysteine residues present at
      positions 2 and 7
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
```

<223> OTHER INFORMATION: MeIle

<400> SEQUENCE: 86

Arg Cys Asn Thr Ala Thr Cys Ala Thr Gln Arg Leu Ala His Phe Leu
1               5                   10                  15

Glu Arg Ser Ser Phe Gly Ala Ile Leu Ser Ser Thr Glu Val Gly Ser
            20                  25                  30

Ser Thr Pro
        35

<210> SEQ ID NO 87
<211> LENGTH: 35
<212> TYPE: PRT
<213> ORGANISM: Artificial sequence
<220> FEATURE:
<223> OTHER INFORMATION: Amino acid sequence Z in synthetic amylin
      analogue which is a compound having the formula R1-Z-R2 in
      PCT/EP2016/055793
<220> FEATURE:
<221> NAME/KEY: DISULFID
<222> LOCATION: (2)..(7)
<223> OTHER INFORMATION: Sequence may possess an intramolecular
      disulphide bridge formed between the cysteine residues present at
      positions 2 and 7
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle

<400> SEQUENCE: 87

Arg Cys Asn Thr Ala Thr Cys Ala Thr Gln Arg Leu Ala His Phe Leu
1               5                   10                  15

Gln Arg Ser Ser Phe Gly Ala Ile Leu Ser Ser Thr Glu Val Gly Ser
            20                  25                  30

Ser Thr Pro
        35

<210> SEQ ID NO 88
<211> LENGTH: 35
<212> TYPE: PRT
<213> ORGANISM: Artificial sequence
<220> FEATURE:
<223> OTHER INFORMATION: Amino acid sequence Z in synthetic amylin
      analogue which is a compound having the formula R1-Z-R2 in
      PCT/EP2016/055793
<220> FEATURE:
<221> NAME/KEY: DISULFID
<222> LOCATION: (2)..(7)
<223> OTHER INFORMATION: Sequence may possess an intramolecular
      disulphide bridge formed between the cysteine residues present at
      positions 2 and 7
<220> FEATURE:
<221> NAME/KEY: MOD_RES
<222> LOCATION: (14)..(14)
<223> OTHER INFORMATION: Aad
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle
<220> FEATURE:
<221> NAME/KEY: MOD_RES
<222> LOCATION: (35)..(35)
<223> OTHER INFORMATION: 4Hyp

<400> SEQUENCE: 88

Arg Cys Asn Thr Ala Thr Cys Ala Thr Gln Arg Leu Ala Glu Phe Leu
1               5                   10                  15

Gln Arg Ser Ser Phe Gly Ala Ile Leu Ser Ser Thr Glu Val Gly Ser
            20                  25                  30

Asn Thr Pro
        35

<210> SEQ ID NO 89
<211> LENGTH: 35
<212> TYPE: PRT
<213> ORGANISM: Artificial sequence
<220> FEATURE:
<223> OTHER INFORMATION: Amino acid sequence Z in synthetic amylin
      analogue which is a compound having the formula R1-Z-R2 in
      PCT/EP2016/055793
<220> FEATURE:
<221> NAME/KEY: DISULFID
<222> LOCATION: (2)..(7)
<223> OTHER INFORMATION: Sequence may possess an intramolecular
      disulphide bridge formed between the cysteine residues present at
      positions 2 and 7
<220> FEATURE:
<221> NAME/KEY: MOD_RES
<222> LOCATION: (14)..(14)
<223> OTHER INFORMATION: Aad
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle
<220> FEATURE:
<221> NAME/KEY: MOD_RES
<222> LOCATION: (35)..(35)
<223> OTHER INFORMATION: 4Hyp

<400> SEQUENCE: 89

Arg Cys Asn Thr Ala Thr Cys Ala Thr Gln Arg Leu Ala Glu Phe Leu
1               5                   10                  15

Gln Arg Ser Ser Phe Gly Ala Ile Leu Ser Ser Thr Glu Val Gly Ser
            20                  25                  30

Ser Thr Pro
        35

<210> SEQ ID NO 90
<211> LENGTH: 35
<212> TYPE: PRT
<213> ORGANISM: Artificial sequence
<220> FEATURE:
<223> OTHER INFORMATION: Amino acid sequence Z in synthetic amylin
      analogue which is a compound having the formula R1-Z-R2 in
      PCT/EP2016/055793
<220> FEATURE:
<221> NAME/KEY: DISULFID
<222> LOCATION: (2)..(7)
<223> OTHER INFORMATION: Sequence may possess an intramolecular
      disulphide bridge formed between the cysteine residues present at
      positions 2 and 7
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle
<220> FEATURE:

-continued

```
<221> NAME/KEY: MOD_RES
<222> LOCATION: (35)..(35)
<223> OTHER INFORMATION: 4Hyp

<400> SEQUENCE: 90

Arg Cys Gln Thr Ala Thr Cys Ala Thr Asp Arg Leu Ala His Phe Leu
1               5                   10                  15

Gln Arg Ser Ser Phe Gly Ala Ile Leu Ser Ser Thr Glu Val Gly Ser
            20                  25                  30

Asn Thr Pro
        35

<210> SEQ ID NO 91
<211> LENGTH: 35
<212> TYPE: PRT
<213> ORGANISM: Artificial sequence
<220> FEATURE:
<223> OTHER INFORMATION: Amino acid sequence Z in synthetic amylin
      analogue which is a compound having the formula R1-Z-R2 in
      PCT/EP2016/055793
<220> FEATURE:
<221> NAME/KEY: DISULFID
<222> LOCATION: (2)..(7)
<223> OTHER INFORMATION: Sequence may possess an intramolecular
      disulphide bridge formed between the cysteine residues present at
      positions 2 and 7
<220> FEATURE:
<221> NAME/KEY: MOD_RES
<222> LOCATION: (14)..(14)
<223> OTHER INFORMATION: Aad
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle
<220> FEATURE:
<221> NAME/KEY: MOD_RES
<222> LOCATION: (35)..(35)
<223> OTHER INFORMATION: 4Hyp

<400> SEQUENCE: 91

Arg Cys Gln Thr Ala Thr Cys Ala Thr Asp Arg Leu Ala Glu Phe Leu
1               5                   10                  15

Gln Arg Ser Ser Phe Gly Ala Ile Leu Ser Ser Thr Glu Val Gly Ser
            20                  25                  30

Asn Thr Pro
        35

<210> SEQ ID NO 92
<211> LENGTH: 35
<212> TYPE: PRT
<213> ORGANISM: Artificial sequence
<220> FEATURE:
<223> OTHER INFORMATION: Amino acid sequence Z in synthetic amylin
      analogue which is a compound having the formula R1-Z-R2 in
      PCT/EP2016/055793
<220> FEATURE:
<221> NAME/KEY: DISULFID
<222> LOCATION: (2)..(7)
<223> OTHER INFORMATION: Sequence may possess an intramolecular
      disulphide bridge formed between the cysteine residues present at
      positions 2 and 7
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
```

```
<222> LOCATION: (24)..(24)
<223> OTHER INFORMATION: MeIle
<220> FEATURE:
<221> NAME/KEY: MOD_RES
<222> LOCATION: (35)..(35)
<223> OTHER INFORMATION: 4Hyp

<400> SEQUENCE: 92

Arg Cys Gln Thr Ala Thr Cys Ala Thr Glu Arg Leu Ala His Phe Leu
1               5                   10                  15
Gln Arg Ser Ser Phe Gly Ala Ile Leu Ser Ser Thr Glu Val Gly Ser
            20                  25                  30
Gly Thr Pro
        35

<210> SEQ ID NO 93
<211> LENGTH: 35
<212> TYPE: PRT
<213> ORGANISM: Artificial sequence
<220> FEATURE:
<223> OTHER INFORMATION: Amino acid sequence Z in synthetic amylin
      analogue which is a compound having the formula R1-Z-R2 in
      PCT/EP2016/055793
<220> FEATURE:
<221> NAME/KEY: DISULFID
<222> LOCATION: (2)..(7)
<223> OTHER INFORMATION: Sequence may possess an intramolecular
      disulphide bridge formed between the cysteine residues present at
      positions 2 and 7
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle
<220> FEATURE:
<221> NAME/KEY: MOD_RES
<222> LOCATION: (35)..(35)
<223> OTHER INFORMATION: 4Hyp

<400> SEQUENCE: 93

Arg Cys Gln Thr Ala Thr Cys Ala Thr Asp Arg Leu Ala His Phe Leu
1               5                   10                  15
Gln Arg Ser Ser Phe Gly Ala Ile Leu Ser Ser Thr Glu Val Gly Ser
            20                  25                  30
Gly Thr Pro
        35

<210> SEQ ID NO 94
<211> LENGTH: 35
<212> TYPE: PRT
<213> ORGANISM: Artificial sequence
<220> FEATURE:
<223> OTHER INFORMATION: Amino acid sequence Z in synthetic amylin
      analogue which is a compound having the formula R1-Z-R2 in
      PCT/EP2016/055793
<220> FEATURE:
<221> NAME/KEY: DISULFID
<222> LOCATION: (2)..(7)
<223> OTHER INFORMATION: Sequence may possess an intramolecular
      disulphide bridge formed between the cysteine residues present at
      positions 2 and 7
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
```

<223> OTHER INFORMATION: MeIle

<400> SEQUENCE: 94

Arg Cys Gln Thr Ala Thr Cys Ala Thr Asp Arg Leu Ala His Phe Leu
1               5                   10                  15

Gln Arg Ser Ser Phe Gly Ala Ile Leu Ser Ser Thr Glu Val Gly Ser
            20                  25                  30

Asn Thr Pro
        35

<210> SEQ ID NO 95
<211> LENGTH: 35
<212> TYPE: PRT
<213> ORGANISM: Artificial sequence
<220> FEATURE:
<223> OTHER INFORMATION: Amino acid sequence Z in synthetic amylin
      analogue which is a compound having the formula R1-Z-R2 in
      PCT/EP2016/055793
<220> FEATURE:
<221> NAME/KEY: DISULFID
<222> LOCATION: (2)..(7)
<223> OTHER INFORMATION: Sequence may possess an intramolecular
      disulphide bridge formed between the cysteine residues present at
      positions 2 and 7
<220> FEATURE:
<221> NAME/KEY: MOD_RES
<222> LOCATION: (14)..(14)
<223> OTHER INFORMATION: Aad
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle

<400> SEQUENCE: 95

Arg Cys Gln Thr Ala Thr Cys Ala Thr Glu Arg Leu Ala Glu Phe Leu
1               5                   10                  15

Gln Arg Ser Ser Phe Gly Ala Ile Leu Ser Ser Thr Glu Val Gly Ser
            20                  25                  30

Asn Thr Pro
        35

<210> SEQ ID NO 96
<211> LENGTH: 35
<212> TYPE: PRT
<213> ORGANISM: Artificial sequence
<220> FEATURE:
<223> OTHER INFORMATION: Amino acid sequence Z in synthetic amylin
      analogue which is a compound having the formula R1-Z-R2 in
      PCT/EP2016/055793
<220> FEATURE:
<221> NAME/KEY: DISULFID
<222> LOCATION: (2)..(7)
<223> OTHER INFORMATION: Sequence may possess an intramolecular
      disulphide bridge formed between the cysteine residues present at
      positions 2 and 7
<220> FEATURE:
<221> NAME/KEY: MOD_RES
<222> LOCATION: (14)..(14)
<223> OTHER INFORMATION: Aad
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle

<400> SEQUENCE: 96

Arg Cys Gln Thr Ala Thr Cys Ala Thr Glu Arg Leu Ala Glu Phe Leu
1               5                   10                  15

Gln Arg Ser Ser Phe Gly Ala Ile Leu Ser Ser Thr Glu Val Gly Ser
            20                  25                  30

Gly Thr Pro
        35

<210> SEQ ID NO 97
<211> LENGTH: 33
<212> TYPE: PRT
<213> ORGANISM: Artificial sequence
<220> FEATURE:
<223> OTHER INFORMATION: Amino acid sequence Z in synthetic amylin
      analogue which is a compound having the formula R1-Z-R2 in
      PCT/EP2016/055793
<220> FEATURE:
<221> NAME/KEY: DISULFID
<222> LOCATION: (2)..(7)
<223> OTHER INFORMATION: Sequence may possess an intramolecular
      disulphide bridge formed between the cysteine residues present at
      positions 2 and 7
<220> FEATURE:
<221> NAME/KEY: MOD_RES
<222> LOCATION: (14)..(14)
<223> OTHER INFORMATION: Aad
<220> FEATURE:
<221> NAME/KEY: MOD_RES
<222> LOCATION: (20)..(20)
<223> OTHER INFORMATION: MeGly
<220> FEATURE:
<221> NAME/KEY: MOD_RES
<222> LOCATION: (22)..(22)
<223> OTHER INFORMATION: MeIle
<220> FEATURE:
<221> NAME/KEY: MOD_RES
<222> LOCATION: (33)..(33)
<223> OTHER INFORMATION: 4Hyp

<400> SEQUENCE: 97

Arg Cys Gln Thr Ala Thr Cys Ala Thr Asp Arg Leu Ala Glu Phe Leu
1               5                   10                  15

Gln Arg Phe Gly Ala Ile Leu Ser Ser Thr Glu Val Gly Ser Asn Thr
            20                  25                  30

Pro

<210> SEQ ID NO 98
<211> LENGTH: 33
<212> TYPE: PRT
<213> ORGANISM: Artificial sequence
<220> FEATURE:
<223> OTHER INFORMATION: Amino acid sequence Z in synthetic amylin
      analogue which is a compound having the formula R1-Z-R2 in
      PCT/EP2016/055793
<220> FEATURE:
<221> NAME/KEY: DISULFID
<222> LOCATION: (2)..(7)
<223> OTHER INFORMATION: Sequence may possess an intramolecular
      disulphide bridge formed between the cysteine residues present at
      positions 2 and 7
<220> FEATURE:
<221> NAME/KEY: MOD_RES
<222> LOCATION: (20)..(20)
<223> OTHER INFORMATION: MeGly
<220> FEATURE:
<221> NAME/KEY: MOD_RES
<222> LOCATION: (22)..(22)
<223> OTHER INFORMATION: MeIle

<400> SEQUENCE: 98

```
Arg Cys Gln Thr Ala Thr Cys Ala Thr Glu Arg Leu Ala His Phe Leu
1               5                   10                  15

Gln Arg Phe Gly Ala Ile Leu Ser Ser Thr Glu Val Gly Ser Asn Thr
            20                  25                  30

Pro

<210> SEQ ID NO 99
<211> LENGTH: 35
<212> TYPE: PRT
<213> ORGANISM: Artificial sequence
<220> FEATURE:
<223> OTHER INFORMATION: Amino acid sequence Z in synthetic amylin
      analogue which is a compound having the formula R1-Z-R2 in
      PCT/EP2016/055793
<220> FEATURE:
<221> NAME/KEY: DISULFID
<222> LOCATION: (2)..(7)
<223> OTHER INFORMATION: Sequence may possess an intramolecular
      disulphide bridge formed between the cysteine residues present at
      positions 2 and 7
<220> FEATURE:
<221> NAME/KEY: MOD_RES
<222> LOCATION: (22)..(22)
<223> OTHER INFORMATION: MeGly
<220> FEATURE:
<221> NAME/KEY: MOD_RES
<222> LOCATION: (24)..(24)
<223> OTHER INFORMATION: MeIle

<400> SEQUENCE: 99

Arg Cys Asn Thr Ala Thr Cys Ala Thr Gln Arg Leu Ala Asp Phe Leu
1               5                   10                  15

His Arg Ser Ser Phe Gly Ala Ile Leu Ser Ser Thr Glu Val Gly Ser
            20                  25                  30

Glu Thr Pro
        35

<210> SEQ ID NO 100
<211> LENGTH: 37
<212> TYPE: PRT
<213> ORGANISM: Artificial sequence
<220> FEATURE:
<223> OTHER INFORMATION: Amino acid sequence Z in synthetic amylin
      analogue which is a compound having the formula R1-Z-R2 in
      PCT/EP2016/055793
<220> FEATURE:
<221> NAME/KEY: DISULFID
<222> LOCATION: (2)..(7)
<223> OTHER INFORMATION: Sequence may possess an intramolecular
      disulphide bridge formed between the cysteine residues present at
      positions 2 and 7
<220> FEATURE:
<221> NAME/KEY: MOD_RES
<222> LOCATION: (24)..(24)
<223> OTHER INFORMATION: MeGly
<220> FEATURE:
<221> NAME/KEY: MOD_RES
<222> LOCATION: (26)..(26)
<223> OTHER INFORMATION: MeIle
<220> FEATURE:
<221> NAME/KEY: SITE
<222> LOCATION: (37)..(37)
<223> OTHER INFORMATION: Xaa is Apr, 4-aminoproline

<400> SEQUENCE: 100

Arg Cys Asn Thr Ala Thr Cys Ala Thr Gln Arg Leu Ala Asp Phe Leu
1               5                   10                  15

His Arg Ser Ser Asn Asn Phe Gly Ala Ile Leu Ser Ser Thr Asn Val
            20                  25                  30
```

Gly Ser Asn Thr Xaa
        35

<210> SEQ ID NO 101
<211> LENGTH: 37
<212> TYPE: PRT
<213> ORGANISM: Artificial sequence
<220> FEATURE:
<223> OTHER INFORMATION: Amino acid sequence Z in synthetic amylin
      analogue which is a compound having the formula R1-Z-R2 in
      PCT/EP2016/055793
<220> FEATURE:
<221> NAME/KEY: DISULFID
<222> LOCATION: (2)..(7)
<223> OTHER INFORMATION: Sequence may possess an intramolecular
      disulphide bridge formed between the cysteine residues present at
      positions 2 and 7
<220> FEATURE:
<221> NAME/KEY: MOD_RES
<222> LOCATION: (24)..(24)
<223> OTHER INFORMATION: MeGly
<220> FEATURE:
<221> NAME/KEY: MOD_RES
<222> LOCATION: (26)..(26)
<223> OTHER INFORMATION: MeIle
<220> FEATURE:
<221> NAME/KEY: MOD_RES
<222> LOCATION: (37)..(37)
<223> OTHER INFORMATION: Xaa is Apr, 4-aminoproline

<400> SEQUENCE: 101

Arg Cys Asn Thr Ala Thr Cys Ala Thr Gln Arg Leu Ala His Phe Leu
1               5                   10                  15

His Arg Ser Ser Asn Asn Phe Gly Ala Ile Leu Ser Ser Thr Asn Val
            20                  25                  30

Gly Ser Asn Thr Xaa
        35

<210> SEQ ID NO 102
<211> LENGTH: 36
<212> TYPE: PRT
<213> ORGANISM: Artificial sequence
<220> FEATURE:
<223> OTHER INFORMATION: Synthetic amylin analogue
<220> FEATURE:
<221> NAME/KEY: SITE
<222> LOCATION: (1)..(1)
<223> OTHER INFORMATION: Xaa is isoGlu
<220> FEATURE:
<221> NAME/KEY: SITE
<222> LOCATION: (1)..(1)
<223> OTHER INFORMATION: Linked to [19-carboxynonadecanoyl]
<220> FEATURE:
<221> NAME/KEY: DISULFID
<222> LOCATION: (3)..(8)
<223> OTHER INFORMATION: Sequence may possess an intramolecular
      disulphide bridge formed between the cysteine residues present at
      positions 3 and 8, corresponding to the cysteine residues present
      at positions 2 and 7 of human amylin. Feature is present in Compd.
      1.
<220> FEATURE:
<221> NAME/KEY: MOD_RES
<222> LOCATION: (23)..(23)
<223> OTHER INFORMATION: MeGly
<220> FEATURE:
<221> NAME/KEY: MOD_RES
<222> LOCATION: (25)..(25)
<223> OTHER INFORMATION: MeIle

<400> SEQUENCE: 102

Xaa Arg Cys Asn Thr Ala Thr Cys Ala Thr Gln Arg Leu Ala Asp Phe
1               5                   10                  15

Leu His Arg Ser Ser Phe Gly Ala Ile Leu Ser Ser Thr Glu Val Gly
            20                  25                  30

Ser Glu Thr Pro
        35

<210> SEQ ID NO 103
<211> LENGTH: 36
<212> TYPE: PRT
<213> ORGANISM: Artificial sequence
<220> FEATURE:
<223> OTHER INFORMATION: Synthetic amylin analogue
<220> FEATURE:
<221> NAME/KEY: SITE
<222> LOCATION: (1)..(1)
<223> OTHER INFORMATION: Xaa is isoGlu
<220> FEATURE:
<221> NAME/KEY: SITE
<222> LOCATION: (1)..(1)
<223> OTHER INFORMATION: Linked to [19-carboxynonadecanoyl]
<220> FEATURE:
<221> NAME/KEY: DISULFID
<222> LOCATION: (3)..(8)
<223> OTHER INFORMATION: Sequence may possess an intramolecular
      disulphide bridge formed between the cysteine residues present at
      positions 3 and 8, corresponding to the cysteine residues present
      at positions 2 and 7 of human amylin. Feature is present in Compd.
      2.
<220> FEATURE:
<221> NAME/KEY: MOD_RES
<222> LOCATION: (23)..(23)
<223> OTHER INFORMATION: MeGly
<220> FEATURE:
<221> NAME/KEY: MOD_RES
<222> LOCATION: (25)..(25)
<223> OTHER INFORMATION: MeIle

<400> SEQUENCE: 103

Xaa Arg Cys Asn Thr Ala Thr Cys Ala Thr Gln Arg Leu Ala His Phe
1               5                   10                  15

Leu His Arg Ser Ser Phe Gly Ala Ile Leu Ser Ser Thr Glu Val Gly
            20                  25                  30

Ser Glu Thr Pro
        35

<210> SEQ ID NO 104
<211> LENGTH: 36
<212> TYPE: PRT
<213> ORGANISM: Artificial sequence
<220> FEATURE:
<223> OTHER INFORMATION: Synthetic amylin analogue
<220> FEATURE:
<221> NAME/KEY: SITE
<222> LOCATION: (1)..(1)
<223> OTHER INFORMATION: Xaa is isoGlu
<220> FEATURE:
<221> NAME/KEY: SITE
<222> LOCATION: (1)..(1)
<223> OTHER INFORMATION: Linked to [19-carboxynonadecanoyl]
<220> FEATURE:
<221> NAME/KEY: DISULFID
<222> LOCATION: (3)..(8)
<223> OTHER INFORMATION: Sequence may possess an intramolecular
      disulphide bridge formed between the cysteine residues present at
      positions 3 and 8, corresponding to the cysteine residues present
      at positions 2 and 7 of human amylin. Feature is present in Compd.
      3.
<220> FEATURE:
<221> NAME/KEY: MOD_RES
<222> LOCATION: (23)..(23)
<223> OTHER INFORMATION: MeGly
<220> FEATURE:
<221> NAME/KEY: MOD_RES

```
<222> LOCATION: (25)..(25)
<223> OTHER INFORMATION: MeIle

<400> SEQUENCE: 104

Xaa Arg Cys Asn Thr Ala Thr Cys Ala Thr Gln Arg Leu Ala Asn Phe
 1               5                  10                  15

Leu His Arg Ser Ser Phe Gly Ala Ile Leu Ser Ser Thr Glu Val Gly
            20                  25                  30

Ser Glu Thr Pro
            35

<210> SEQ ID NO 105
<211> LENGTH: 38
<212> TYPE: PRT
<213> ORGANISM: Artificial sequence
<220> FEATURE:
<223> OTHER INFORMATION: Synthetic amylin analogue
<220> FEATURE:
<221> NAME/KEY: SITE
<222> LOCATION: (1)..(1)
<223> OTHER INFORMATION: Xaa is isoGlu
<220> FEATURE:
<221> NAME/KEY: SITE
<222> LOCATION: (1)..(1)
<223> OTHER INFORMATION: Linked to [19-carboxynonadecanoyl]
<220> FEATURE:
<221> NAME/KEY: DISULFID
<222> LOCATION: (3)..(8)
<223> OTHER INFORMATION: Sequence may possess an intramolecular
      disulphide bridge formed between the cysteine residues present at
      positions 3 and 8, corresponding to the cysteine residues present
      at positions 2 and 7 of human amylin. Feature is present in Compd.
      4.
<220> FEATURE:
<221> NAME/KEY: MOD_RES
<222> LOCATION: (25)..(25)
<223> OTHER INFORMATION: MeGly
<220> FEATURE:
<221> NAME/KEY: MOD_RES
<222> LOCATION: (27)..(27)
<223> OTHER INFORMATION: MeIle
<220> FEATURE:
<221> NAME/KEY: SITE
<222> LOCATION: (38)..(38)
<223> OTHER INFORMATION: Xaa is Apr, 4-aminoproline

<400> SEQUENCE: 105

Xaa Arg Cys Asn Thr Ala Thr Cys Ala Thr Gln Arg Leu Ala Asp Phe
 1               5                  10                  15

Leu His Arg Ser Ser Asn Asn Phe Gly Ala Ile Leu Ser Ser Thr Asn
            20                  25                  30

Val Gly Ser Asn Thr Xaa
            35

<210> SEQ ID NO 106
<211> LENGTH: 38
<212> TYPE: PRT
<213> ORGANISM: Artificial sequence
<220> FEATURE:
<223> OTHER INFORMATION: Synthetic amylin analogue
<220> FEATURE:
<221> NAME/KEY: SITE
<222> LOCATION: (1)..(1)
<223> OTHER INFORMATION: Xaa is isoGlu
<220> FEATURE:
<221> NAME/KEY: SITE
<222> LOCATION: (1)..(1)
<223> OTHER INFORMATION: Linked to [19-carboxynonadecanoyl]
<220> FEATURE:
<221> NAME/KEY: DISULFID
<222> LOCATION: (3)..(8)
```

```
<223> OTHER INFORMATION: Sequence may possess an intramolecular
      disulphide bridge formed between the cysteine residues present at
      positions 3 and 8, corresponding to the cysteine residues present
      at positions 2 and 7 of human amylin. Feature is present in Compd.
      5.
<220> FEATURE:
<221> NAME/KEY: MOD_RES
<222> LOCATION: (25)..(25)
<223> OTHER INFORMATION: MeGly
<220> FEATURE:
<221> NAME/KEY: MOD_RES
<222> LOCATION: (27)..(27)
<223> OTHER INFORMATION: MeIle
<220> FEATURE:
<221> NAME/KEY: SITE
<222> LOCATION: (38)..(38)
<223> OTHER INFORMATION: Xaa is Apr, 4-aminoproline

<400> SEQUENCE: 106

Xaa Arg Cys Asn Thr Ala Thr Cys Ala Thr Gln Arg Leu Ala His Phe
1               5                   10                  15

Leu His Arg Ser Ser Asn Asn Phe Gly Ala Ile Leu Ser Ser Thr Asn
            20                  25                  30

Val Gly Ser Asn Thr Xaa
        35

<210> SEQ ID NO 107
<211> LENGTH: 36
<212> TYPE: PRT
<213> ORGANISM: Artificial sequence
<220> FEATURE:
<223> OTHER INFORMATION: Synthetic amylin analogue
<220> FEATURE:
<221> NAME/KEY: SITE
<222> LOCATION: (1)..(1)
<223> OTHER INFORMATION: Xaa is isoGlu
<220> FEATURE:
<221> NAME/KEY: SITE
<222> LOCATION: (1)..(1)
<223> OTHER INFORMATION: Linked to [19-carboxynonadecanoyl]
<220> FEATURE:
<221> NAME/KEY: DISULFID
<222> LOCATION: (3)..(8)
<223> OTHER INFORMATION: Sequence may possess an intramolecular
      disulphide bridge formed between the cysteine residues present at
      positions 3 and 8, corresponding to the cysteine residues present
      at positions 2 and 7 of human amylin. Feature is present in Compd.
      6.
<220> FEATURE:
<221> NAME/KEY: MOD_RES
<222> LOCATION: (23)..(23)
<223> OTHER INFORMATION: MeGly
<220> FEATURE:
<221> NAME/KEY: MOD_RES
<222> LOCATION: (25)..(25)
<223> OTHER INFORMATION: MeIle
<220> FEATURE:
<221> NAME/KEY: MOD_RES
<222> LOCATION: (36)..(36)
<223> OTHER INFORMATION: 4Hyp

<400> SEQUENCE: 107

Xaa Arg Cys Gly Thr Ala Thr Cys Ala Thr Glu Arg Leu Ala His Phe
1               5                   10                  15

Leu Asn Arg Ser Ser Phe Gly Ala Ile Leu Ser Ser Thr Glu Val Gly
            20                  25                  30

Ser Asn Thr Pro
        35

<210> SEQ ID NO 108
<211> LENGTH: 36
```

```
<212> TYPE: PRT
<213> ORGANISM: Artificial sequence
<220> FEATURE:
<223> OTHER INFORMATION: Synthetic amylin analogue
<220> FEATURE:
<221> NAME/KEY: SITE
<222> LOCATION: (1)..(1)
<223> OTHER INFORMATION: Xaa is isoGlu
<220> FEATURE:
<221> NAME/KEY: SITE
<222> LOCATION: (1)..(1)
<223> OTHER INFORMATION: Linked to [19-carboxynonadecanoyl]
<220> FEATURE:
<221> NAME/KEY: DISULFID
<222> LOCATION: (3)..(8)
<223> OTHER INFORMATION: Sequence may possess an intramolecular
      disulphide bridge formed between the cysteine residues present at
      positions 3 and 8, corresponding to the cysteine residues present
      at positions 2 and 7 of human amylin. Feature is present in Compd.
      7.
<220> FEATURE:
<221> NAME/KEY: MOD_RES
<222> LOCATION: (23)..(23)
<223> OTHER INFORMATION: MeGly
<220> FEATURE:
<221> NAME/KEY: MOD_RES
<222> LOCATION: (25)..(25)
<223> OTHER INFORMATION: MeIle
<220> FEATURE:
<221> NAME/KEY: MOD_RES
<222> LOCATION: (36)..(36)
<223> OTHER INFORMATION: 4Hyp

<400> SEQUENCE: 108

Xaa Arg Cys Gly Thr Ala Thr Cys Ala Thr Glu Arg Leu Ala His Phe
 1               5                  10                  15

Leu Gln Arg Ser Ser Phe Gly Ala Ile Leu Ser Ser Thr Glu Val Gly
                20                  25                  30

Ser Asn Thr Pro
            35

<210> SEQ ID NO 109
<211> LENGTH: 36
<212> TYPE: PRT
<213> ORGANISM: Artificial sequence
<220> FEATURE:
<223> OTHER INFORMATION: Synthetic amylin analogue
<220> FEATURE:
<221> NAME/KEY: SITE
<222> LOCATION: (1)..(1)
<223> OTHER INFORMATION: Xaa is isoGlu
<220> FEATURE:
<221> NAME/KEY: SITE
<222> LOCATION: (1)..(1)
<223> OTHER INFORMATION: Linked to [19-carboxynonadecanoyl]
<220> FEATURE:
<221> NAME/KEY: DISULFID
<222> LOCATION: (3)..(8)
<223> OTHER INFORMATION: Sequence may possess an intramolecular
      disulphide bridge formed between the cysteine residues present at
      positions 3 and 8, corresponding to the cysteine residues present
      at positions 2 and 7 of human amylin. Feature is present in Compd.
      8.
<220> FEATURE:
<221> NAME/KEY: MOD_RES
<222> LOCATION: (23)..(23)
<223> OTHER INFORMATION: MeGly
<220> FEATURE:
<221> NAME/KEY: MOD_RES
<222> LOCATION: (25)..(25)
<223> OTHER INFORMATION: MeIle
<220> FEATURE:
<221> NAME/KEY: MOD_RES
<222> LOCATION: (36)..(36)
<223> OTHER INFORMATION: 4Hyp
```

<400> SEQUENCE: 109

Xaa Arg Cys Gly Thr Ala Thr Cys Ala Thr Glu Arg Leu Ala His Phe
1               5                   10                  15

Leu Glu Arg Ser Ser Phe Gly Ala Ile Leu Ser Ser Thr Glu Val Gly
            20                  25                  30

Ser Asn Thr Pro
        35

<210> SEQ ID NO 110
<211> LENGTH: 36
<212> TYPE: PRT
<213> ORGANISM: Artificial sequence
<220> FEATURE:
<223> OTHER INFORMATION: Synthetic amylin analogue
<220> FEATURE:
<221> NAME/KEY: SITE
<222> LOCATION: (1)..(1)
<223> OTHER INFORMATION: Xaa is isoGlu
<220> FEATURE:
<221> NAME/KEY: SITE
<222> LOCATION: (1)..(1)
<223> OTHER INFORMATION: Linked to [19-carboxynonadecanoyl]
<220> FEATURE:
<221> NAME/KEY: DISULFID
<222> LOCATION: (3)..(8)
<223> OTHER INFORMATION: Sequence may possess an intramolecular
      disulphide bridge formed between the cysteine residues present at
      positions 3 and 8, corresponding to the cysteine residues present
      at positions 2 and 7 of human amylin. Feature is present in Compd.
      9.
<220> FEATURE:
<221> NAME/KEY: MOD_RES
<222> LOCATION: (23)..(23)
<223> OTHER INFORMATION: MeGly
<220> FEATURE:
<221> NAME/KEY: MOD_RES
<222> LOCATION: (25)..(25)
<223> OTHER INFORMATION: MeIle
<220> FEATURE:
<221> NAME/KEY: MOD_RES
<222> LOCATION: (36)..(36)
<223> OTHER INFORMATION: 4Hyp

<400> SEQUENCE: 110

Xaa Arg Cys Gly Thr Ala Thr Cys Ala Thr Glu Arg Leu Ala His Phe
1               5                   10                  15

Leu Thr Arg Ser Ser Phe Gly Ala Ile Leu Ser Ser Thr Glu Val Gly
            20                  25                  30

Ser Ser Thr Pro
        35

<210> SEQ ID NO 111
<211> LENGTH: 36
<212> TYPE: PRT
<213> ORGANISM: Artificial sequence
<220> FEATURE:
<223> OTHER INFORMATION: Synthetic amylin analogue
<220> FEATURE:
<221> NAME/KEY: SITE
<222> LOCATION: (1)..(1)
<223> OTHER INFORMATION: Xaa is isoGlu
<220> FEATURE:
<221> NAME/KEY: SITE
<222> LOCATION: (1)..(1)
<223> OTHER INFORMATION: Linked to [19-carboxynonadecanoyl]
<220> FEATURE:
<221> NAME/KEY: DISULFID
<222> LOCATION: (3)..(8)
<223> OTHER INFORMATION: Sequence may possess an intramolecular
      disulphide bridge formed between the cysteine residues present at

```
       positions 3 and 8, corresponding to the cysteine residues present
       at positions 2 and 7 of human amylin. Feature is present in Compd.
       10.
<220> FEATURE:
<221> NAME/KEY: MOD_RES
<222> LOCATION: (23)..(23)
<223> OTHER INFORMATION: MeGly
<220> FEATURE:
<221> NAME/KEY: MOD_RES
<222> LOCATION: (25)..(25)
<223> OTHER INFORMATION: MeIle
<220> FEATURE:
<221> NAME/KEY: MOD_RES
<222> LOCATION: (36)..(36)
<223> OTHER INFORMATION: 4Hyp

<400> SEQUENCE: 111

Xaa Arg Cys Gly Thr Ala Thr Cys Ala Thr Glu Arg Leu Ala His Phe
1               5                   10                  15

Leu Thr Arg Ser Ser Phe Gly Ala Ile Leu Ser Ser Thr Glu Val Gly
            20                  25                  30

Ser Phe Thr Pro
            35

<210> SEQ ID NO 112
<211> LENGTH: 36
<212> TYPE: PRT
<213> ORGANISM: Artificial sequence
<220> FEATURE:
<223> OTHER INFORMATION: Synthetic amylin analogue
<220> FEATURE:
<221> NAME/KEY: SITE
<222> LOCATION: (1)..(1)
<223> OTHER INFORMATION: Xaa is isoGlu
<220> FEATURE:
<221> NAME/KEY: SITE
<222> LOCATION: (1)..(1)
<223> OTHER INFORMATION: Linked to [19-carboxynonadecanoyl]
<220> FEATURE:
<221> NAME/KEY: DISULFID
<222> LOCATION: (3)..(8)
<223> OTHER INFORMATION: Sequence may possess an intramolecular
       disulphide bridge formed between the cysteine residues present at
       positions 3 and 8, corresponding to the cysteine residues present
       at positions 2 and 7 of human amylin. Feature is present in Compd.
       11.
<220> FEATURE:
<221> NAME/KEY: MOD_RES
<222> LOCATION: (23)..(23)
<223> OTHER INFORMATION: MeGly
<220> FEATURE:
<221> NAME/KEY: MOD_RES
<222> LOCATION: (25)..(25)
<223> OTHER INFORMATION: MeIle
<220> FEATURE:
<221> NAME/KEY: MOD_RES
<222> LOCATION: (34)..(34)
<223> OTHER INFORMATION: Orn
<220> FEATURE:
<221> NAME/KEY: MOD_RES
<222> LOCATION: (36)..(36)
<223> OTHER INFORMATION: 4Hyp

<400> SEQUENCE: 112

Xaa Arg Cys Gly Thr Ala Thr Cys Ala Thr Glu Arg Leu Ala His Phe
1               5                   10                  15

Leu Thr Arg Ser Ser Phe Gly Ala Ile Leu Ser Ser Thr Glu Val Gly
            20                  25                  30

Ser Arg Thr Pro
            35
```

```
<210> SEQ ID NO 113
<211> LENGTH: 36
<212> TYPE: PRT
<213> ORGANISM: Artificial sequence
<220> FEATURE:
<223> OTHER INFORMATION: Synthetic amylin analogue
<220> FEATURE:
<221> NAME/KEY: SITE
<222> LOCATION: (1)..(1)
<223> OTHER INFORMATION: Xaa is isoGlu
<220> FEATURE:
<221> NAME/KEY: SITE
<222> LOCATION: (1)..(1)
<223> OTHER INFORMATION: Linked to [19-carboxynonadecanoyl]
<220> FEATURE:
<221> NAME/KEY: DISULFID
<222> LOCATION: (3)..(8)
<223> OTHER INFORMATION: Sequence may possess an intramolecular
      disulphide bridge formed between the cysteine residues present at
      positions 3 and 8, corresponding to the cysteine residues present
      at positions 2 and 7 of human amylin. Feature is present in Compd.
      12.
<220> FEATURE:
<221> NAME/KEY: MOD_RES
<222> LOCATION: (23)..(23)
<223> OTHER INFORMATION: MeGly
<220> FEATURE:
<221> NAME/KEY: MOD_RES
<222> LOCATION: (25)..(25)
<223> OTHER INFORMATION: MeIle
<220> FEATURE:
<221> NAME/KEY: MOD_RES
<222> LOCATION: (34)..(34)
<223> OTHER INFORMATION: Aad
<220> FEATURE:
<221> NAME/KEY: MOD_RES
<222> LOCATION: (36)..(36)
<223> OTHER INFORMATION: 4Hyp

<400> SEQUENCE: 113

Xaa Arg Cys Gly Thr Ala Thr Cys Ala Thr Glu Arg Leu Ala His Phe
1               5                   10                  15

Leu Thr Arg Ser Ser Phe Gly Ala Ile Leu Ser Ser Thr Glu Val Gly
            20                  25                  30

Ser Glu Thr Pro
        35

<210> SEQ ID NO 114
<211> LENGTH: 36
<212> TYPE: PRT
<213> ORGANISM: Artificial sequence
<220> FEATURE:
<223> OTHER INFORMATION: Synthetic amylin analogue
<220> FEATURE:
<221> NAME/KEY: SITE
<222> LOCATION: (1)..(1)
<223> OTHER INFORMATION: Xaa is isoGlu
<220> FEATURE:
<221> NAME/KEY: SITE
<222> LOCATION: (1)..(1)
<223> OTHER INFORMATION: Linked to [19-carboxynonadecanoyl]
<220> FEATURE:
<221> NAME/KEY: DISULFID
<222> LOCATION: (3)..(8)
<223> OTHER INFORMATION: Sequence may possess an intramolecular
      disulphide bridge formed between the cysteine residues present at
      positions 3 and 8, corresponding to the cysteine residues present
      at positions 2 and 7 of human amylin. Feature is present in Compd.
      13.
<220> FEATURE:
<221> NAME/KEY: MOD_RES
<222> LOCATION: (23)..(23)
<223> OTHER INFORMATION: MeGly
<220> FEATURE:
<221> NAME/KEY: MOD_RES
```

```
<222> LOCATION: (25)..(25)
<223> OTHER INFORMATION: MeIle
<220> FEATURE:
<221> NAME/KEY: MOD_RES
<222> LOCATION: (36)..(36)
<223> OTHER INFORMATION: 4Hyp

<400> SEQUENCE: 114

Xaa Arg Cys Gly Thr Ala Thr Cys Ala Thr Glu Arg Leu Ala His Phe
1               5                   10                  15

Leu Thr Arg Ser Ser Phe Gly Ala Ile Leu Ser Ser Thr Glu Val Gly
            20                  25                  30

Ser Gly Thr Pro
        35

<210> SEQ ID NO 115
<211> LENGTH: 34
<212> TYPE: PRT
<213> ORGANISM: Artificial sequence
<220> FEATURE:
<223> OTHER INFORMATION: Synthetic amylin analogue
<220> FEATURE:
<221> NAME/KEY: SITE
<222> LOCATION: (1)..(1)
<223> OTHER INFORMATION: Xaa is isoGlu
<220> FEATURE:
<221> NAME/KEY: SITE
<222> LOCATION: (1)..(1)
<223> OTHER INFORMATION: Linked to [19-carboxynonadecanoyl]
<220> FEATURE:
<221> NAME/KEY: DISULFID
<222> LOCATION: (3)..(8)
<223> OTHER INFORMATION: Sequence may possess an intramolecular
      disulphide bridge formed between the cysteine residues present at
      positions 3 and 8, corresponding to the cysteine residues present
      at positions 2 and 7 of human amylin. Feature is present in Compd.
      14.
<220> FEATURE:
<221> NAME/KEY: MOD_RES
<222> LOCATION: (21)..(21)
<223> OTHER INFORMATION: MeGly
<220> FEATURE:
<221> NAME/KEY: MOD_RES
<222> LOCATION: (23)..(23)
<223> OTHER INFORMATION: MeIle

<400> SEQUENCE: 115

Xaa Arg Cys Asn Thr Ala Thr Cys Ala Thr Gln Arg Leu Ala His Phe
1               5                   10                  15

Leu His Arg Phe Gly Ala Ile Leu Ser Ser Thr Glu Val Gly Ser Glu
            20                  25                  30

Thr Pro

<210> SEQ ID NO 116
<211> LENGTH: 36
<212> TYPE: PRT
<213> ORGANISM: Artificial sequence
<220> FEATURE:
<223> OTHER INFORMATION: Synthetic amylin analogue
<220> FEATURE:
<221> NAME/KEY: SITE
<222> LOCATION: (1)..(1)
<223> OTHER INFORMATION: Xaa is isoGlu
<220> FEATURE:
<221> NAME/KEY: SITE
<222> LOCATION: (1)..(1)
<223> OTHER INFORMATION: Linked to [19-carboxynonadecanoyl]
<220> FEATURE:
<221> NAME/KEY: DISULFID
<222> LOCATION: (3)..(8)
<223> OTHER INFORMATION: Sequence may possess an intramolecular
```

```
       disulphide bridge formed between the cysteine residues present at
       positions 3 and 8, corresponding to the cysteine residues present
       at positions 2 and 7 of human amylin. Feature is present in Compd.
       15.
<220> FEATURE:
<221> NAME/KEY: MOD_RES
<222> LOCATION: (23)..(23)
<223> OTHER INFORMATION: MeGly
<220> FEATURE:
<221> NAME/KEY: MOD_RES
<222> LOCATION: (25)..(25)
<223> OTHER INFORMATION: MeIle

<400> SEQUENCE: 116

Xaa Arg Cys Gly Thr Ala Thr Cys Ala Thr Glu Arg Leu Ala His Phe
1               5                   10                  15

Leu His Arg Ser Ser Phe Gly Ala Ile Leu Ser Ser Thr Glu Val Gly
            20                  25                  30

Ser Asn Thr Pro
        35

<210> SEQ ID NO 117
<211> LENGTH: 36
<212> TYPE: PRT
<213> ORGANISM: Artificial sequence
<220> FEATURE:
<223> OTHER INFORMATION: Synthetic amylin analogue
<220> FEATURE:
<221> NAME/KEY: SITE
<222> LOCATION: (1)..(1)
<223> OTHER INFORMATION: Xaa is isoGlu
<220> FEATURE:
<221> NAME/KEY: SITE
<222> LOCATION: (1)..(1)
<223> OTHER INFORMATION: Linked to [19-carboxynonadecanoyl]
<220> FEATURE:
<221> NAME/KEY: DISULFID
<222> LOCATION: (3)..(8)
<223> OTHER INFORMATION: Sequence may possess an intramolecular
       disulphide bridge formed between the cysteine residues present at
       positions 3 and 8, corresponding to the cysteine residues present
       at positions 2 and 7 of human amylin. Feature is present in Compd.
       16.
<220> FEATURE:
<221> NAME/KEY: MOD_RES
<222> LOCATION: (23)..(23)
<223> OTHER INFORMATION: MeGly
<220> FEATURE:
<221> NAME/KEY: MOD_RES
<222> LOCATION: (25)..(25)
<223> OTHER INFORMATION: MeIle

<400> SEQUENCE: 117

Xaa Arg Cys Asn Thr Ala Thr Cys Ala Thr Gln Arg Leu Ala His Phe
1               5                   10                  15

Leu His Arg Ser Ser Phe Gly Ala Ile Leu Ser Ser Thr Glu Val Gly
            20                  25                  30

Ser Asn Thr Pro
        35

<210> SEQ ID NO 118
<211> LENGTH: 36
<212> TYPE: PRT
<213> ORGANISM: Artificial sequence
<220> FEATURE:
<223> OTHER INFORMATION: Synthetic amylin analogue
<220> FEATURE:
<221> NAME/KEY: SITE
<222> LOCATION: (1)..(1)
<223> OTHER INFORMATION: Xaa is isoGlu
<220> FEATURE:
```

```
<221> NAME/KEY: SITE
<222> LOCATION: (1)..(1)
<223> OTHER INFORMATION: Linked to [19-carboxynonadecanoyl]
<220> FEATURE:
<221> NAME/KEY: DISULFID
<222> LOCATION: (3)..(8)
<223> OTHER INFORMATION: Sequence may possess an intramolecular
      disulphide bridge formed between the cysteine residues present at
      positions 3 and 8, corresponding to the cysteine residues present
      at positions 2 and 7 of human amylin. Feature is present in Compd.
      17.
<220> FEATURE:
<221> NAME/KEY: MOD_RES
<222> LOCATION: (23)..(23)
<223> OTHER INFORMATION: MeGly
<220> FEATURE:
<221> NAME/KEY: MOD_RES
<222> LOCATION: (25)..(25)
<223> OTHER INFORMATION: MeIle
<220> FEATURE:
<221> NAME/KEY: MOD_RES
<222> LOCATION: (36)..(36)
<223> OTHER INFORMATION: 4Hyp

<400> SEQUENCE: 118

Xaa Arg Cys Gly Thr Ala Thr Cys Ala Thr Glu Arg Leu Ala Asn Phe
1               5                   10                  15

Leu Val Arg Ser Ser Phe Gly Ala Ile Leu Ser Ser Thr Glu Val Gly
            20                  25                  30

Ser Asn Thr Pro
        35

<210> SEQ ID NO 119
<211> LENGTH: 36
<212> TYPE: PRT
<213> ORGANISM: Artificial sequence
<220> FEATURE:
<223> OTHER INFORMATION: Synthetic amylin analogue
<220> FEATURE:
<221> NAME/KEY: SITE
<222> LOCATION: (1)..(1)
<223> OTHER INFORMATION: Xaa is isoGlu
<220> FEATURE:
<221> NAME/KEY: SITE
<222> LOCATION: (1)..(1)
<223> OTHER INFORMATION: Linked to [19-carboxynonadecanoyl]
<220> FEATURE:
<221> NAME/KEY: DISULFID
<222> LOCATION: (3)..(8)
<223> OTHER INFORMATION: Sequence may possess an intramolecular
      disulphide bridge formed between the cysteine residues present at
      positions 3 and 8, corresponding to the cysteine residues present
      at positions 2 and 7 of human amylin. Feature is present in Compd.
      18.
<220> FEATURE:
<221> NAME/KEY: MOD_RES
<222> LOCATION: (23)..(23)
<223> OTHER INFORMATION: MeGly
<220> FEATURE:
<221> NAME/KEY: MOD_RES
<222> LOCATION: (25)..(25)
<223> OTHER INFORMATION: MeIle
<220> FEATURE:
<221> NAME/KEY: MOD_RES
<222> LOCATION: (36)..(36)
<223> OTHER INFORMATION: 4Hyp

<400> SEQUENCE: 119

Xaa Arg Cys Gly Thr Ala Thr Cys Ala Thr Glu Arg Leu Ala His Phe
1               5                   10                  15

Leu Thr Arg Ser Ser Phe Gly Ala Ile Leu Ser Ser Thr Glu Val Gly
            20                  25                  30
```

Ser Asn Thr Pro
        35

<210> SEQ ID NO 120
<211> LENGTH: 36
<212> TYPE: PRT
<213> ORGANISM: Artificial sequence
<220> FEATURE:
<223> OTHER INFORMATION: Synthetic amylin analogue
<220> FEATURE:
<221> NAME/KEY: SITE
<222> LOCATION: (1)..(1)
<223> OTHER INFORMATION: Xaa is isoGlu
<220> FEATURE:
<221> NAME/KEY: SITE
<222> LOCATION: (1)..(1)
<223> OTHER INFORMATION: Linked to [19-carboxynonadecanoyl]
<220> FEATURE:
<221> NAME/KEY: DISULFID
<222> LOCATION: (3)..(8)
<223> OTHER INFORMATION: Sequence may possess an intramolecular
      disulphide bridge formed between the cysteine residues present at
      positions 3 and 8, corresponding to the cysteine residues present
      at positions 2 and 7 of human amylin. Feature is present in Compd.
      19.
<220> FEATURE:
<221> NAME/KEY: MOD_RES
<222> LOCATION: (23)..(23)
<223> OTHER INFORMATION: MeGly
<220> FEATURE:
<221> NAME/KEY: MOD_RES
<222> LOCATION: (25)..(25)
<223> OTHER INFORMATION: MeIle
<220> FEATURE:
<221> NAME/KEY: MOD_RES
<222> LOCATION: (36)..(36)
<223> OTHER INFORMATION: 4Hyp

<400> SEQUENCE: 120

Xaa Arg Cys Gly Thr Ala Thr Cys Ala Thr Glu Arg Leu Ala His Phe
1               5                  10                  15

Leu Lys Arg Ser Ser Phe Gly Ala Ile Leu Ser Ser Thr Glu Val Gly
            20                  25                  30

Ser Asn Thr Pro
        35

<210> SEQ ID NO 121
<211> LENGTH: 36
<212> TYPE: PRT
<213> ORGANISM: Artificial sequence
<220> FEATURE:
<223> OTHER INFORMATION: Synthetic amylin analogue
<220> FEATURE:
<221> NAME/KEY: SITE
<222> LOCATION: (1)..(1)
<223> OTHER INFORMATION: Xaa is isoGlu
<220> FEATURE:
<221> NAME/KEY: SITE
<222> LOCATION: (1)..(1)
<223> OTHER INFORMATION: Linked to [19-carboxynonadecanoyl]
<220> FEATURE:
<221> NAME/KEY: DISULFID
<222> LOCATION: (3)..(8)
<223> OTHER INFORMATION: Sequence may possess an intramolecular
      disulphide bridge formed between the cysteine residues present at
      positions 3 and 8, corresponding to the cysteine residues present
      at positions 2 and 7 of human amylin. Feature is present in Compd.
      20.
<220> FEATURE:
<221> NAME/KEY: MOD_RES
<222> LOCATION: (23)..(23)
<223> OTHER INFORMATION: MeGly
<220> FEATURE:
<221> NAME/KEY: MOD_RES

```
<222> LOCATION: (25)..(25)
<223> OTHER INFORMATION: MeIle

<400> SEQUENCE: 121

Xaa Arg Cys Asn Thr Ala Thr Cys Ala Thr Gln Arg Leu Ala His Phe
1               5                   10                  15

Leu His Arg Ser Val Phe Gly Ala Ile Leu Ser Ser Thr Glu Val Gly
            20                  25                  30

Ser Glu Thr Pro
        35

<210> SEQ ID NO 122
<211> LENGTH: 36
<212> TYPE: PRT
<213> ORGANISM: Artificial sequence
<220> FEATURE:
<223> OTHER INFORMATION: Synthetic amylin analogue
<220> FEATURE:
<221> NAME/KEY: SITE
<222> LOCATION: (1)..(1)
<223> OTHER INFORMATION: Xaa is isoGlu
<220> FEATURE:
<221> NAME/KEY: SITE
<222> LOCATION: (1)..(1)
<223> OTHER INFORMATION: Linked to [19-carboxynonadecanoyl]
<220> FEATURE:
<221> NAME/KEY: DISULFID
<222> LOCATION: (3)..(8)
<223> OTHER INFORMATION: Sequence may possess an intramolecular
      disulphide bridge formed between the cysteine residues present at
      positions 3 and 8, corresponding to the cysteine residues present
      at positions 2 and 7 of human amylin. Feature is present in Compd.
      21.
<220> FEATURE:
<221> NAME/KEY: MOD_RES
<222> LOCATION: (23)..(23)
<223> OTHER INFORMATION: MeGly
<220> FEATURE:
<221> NAME/KEY: MOD_RES
<222> LOCATION: (25)..(25)
<223> OTHER INFORMATION: MeIle

<400> SEQUENCE: 122

Xaa Arg Cys Asn Thr Ala Thr Cys Ala Thr Gln Arg Leu Ala His Phe
1               5                   10                  15

Leu His Arg Val Ser Phe Gly Ala Ile Leu Ser Ser Thr Glu Val Gly
            20                  25                  30

Ser Glu Thr Pro
        35

<210> SEQ ID NO 123
<211> LENGTH: 36
<212> TYPE: PRT
<213> ORGANISM: Artificial sequence
<220> FEATURE:
<223> OTHER INFORMATION: Synthetic amylin analogue
<220> FEATURE:
<221> NAME/KEY: SITE
<222> LOCATION: (1)..(1)
<223> OTHER INFORMATION: Xaa is isoGlu
<220> FEATURE:
<221> NAME/KEY: SITE
<222> LOCATION: (1)..(1)
<223> OTHER INFORMATION: Linked to [19-carboxynonadecanoyl]
<220> FEATURE:
<221> NAME/KEY: DISULFID
<222> LOCATION: (3)..(8)
<223> OTHER INFORMATION: Sequence may possess an intramolecular
      disulphide bridge formed between the cysteine residues present at
      positions 3 and 8, corresponding to the cysteine residues present
      at positions 2 and 7 of human amylin. Feature is present in Compd.
```

```
                                 22
<220> FEATURE:
<221> NAME/KEY: MOD_RES
<222> LOCATION: (23)..(23)
<223> OTHER INFORMATION: MeGly
<220> FEATURE:
<221> NAME/KEY: MOD_RES
<222> LOCATION: (25)..(25)
<223> OTHER INFORMATION: MeIle

<400> SEQUENCE: 123

Xaa Arg Cys Gly Thr Ala Thr Cys Ala Thr Glu Arg Leu Ala His Phe
1               5                   10                  15

Leu Val Arg Ser Ser Phe Gly Ala Ile Leu Ser Ser Thr Glu Val Gly
            20                  25                  30

Ser Glu Thr Pro
        35

<210> SEQ ID NO 124
<211> LENGTH: 36
<212> TYPE: PRT
<213> ORGANISM: Artificial sequence
<220> FEATURE:
<223> OTHER INFORMATION: Synthetic amylin analogue
<220> FEATURE:
<221> NAME/KEY: SITE
<222> LOCATION: (1)..(1)
<223> OTHER INFORMATION: Xaa is isoGlu
<220> FEATURE:
<221> NAME/KEY: SITE
<222> LOCATION: (1)..(1)
<223> OTHER INFORMATION: Linked to [19-carboxynonadecanoyl]
<220> FEATURE:
<221> NAME/KEY: DISULFID
<222> LOCATION: (3)..(8)
<223> OTHER INFORMATION: Sequence may possess an intramolecular
      disulphide bridge formed between the cysteine residues present at
      positions 3 and 8, corresponding to the cysteine residues present
      at positions 2 and 7 of human amylin. Feature is present in Compd.
      23.
<220> FEATURE:
<221> NAME/KEY: MOD_RES
<222> LOCATION: (23)..(23)
<223> OTHER INFORMATION: MeGly
<220> FEATURE:
<221> NAME/KEY: MOD_RES
<222> LOCATION: (25)..(25)
<223> OTHER INFORMATION: MeIle

<400> SEQUENCE: 124

Xaa Arg Cys Pro Thr Ala Thr Cys Ala Thr Asp Arg Leu Ala His Phe
1               5                   10                  15

Leu Val Arg Ser Ser Phe Gly Ala Ile Leu Ser Ser Thr Asp Val Gly
            20                  25                  30

Ser Asp Thr Pro
        35

<210> SEQ ID NO 125
<211> LENGTH: 36
<212> TYPE: PRT
<213> ORGANISM: Artificial sequence
<220> FEATURE:
<223> OTHER INFORMATION: Synthetic amylin analogue
<220> FEATURE:
<221> NAME/KEY: SITE
<222> LOCATION: (1)..(1)
<223> OTHER INFORMATION: Xaa is isoGlu
<220> FEATURE:
<221> NAME/KEY: SITE
<222> LOCATION: (1)..(1)
<223> OTHER INFORMATION: Linked to [19-carboxynonadecanoyl]
```

```
<220> FEATURE:
<221> NAME/KEY: DISULFID
<222> LOCATION: (3)..(8)
<223> OTHER INFORMATION: Sequence may possess an intramolecular
      disulphide bridge formed between the cysteine residues present at
      positions 3 and 8, corresponding to the cysteine residues present
      at positions 2 and 7 of human amylin. Feature is present in Compd.
      24.
<220> FEATURE:
<221> NAME/KEY: MOD_RES
<222> LOCATION: (23)..(23)
<223> OTHER INFORMATION: MeGly
<220> FEATURE:
<221> NAME/KEY: MOD_RES
<222> LOCATION: (25)..(25)
<223> OTHER INFORMATION: MeIle

<400> SEQUENCE: 125

Xaa Arg Cys Asn Thr Ala Thr Cys Ala Thr Gln Arg Leu Ala His Phe
1               5                   10                  15

Leu Val Arg Ser Ser Phe Gly Ala Ile Leu Ser Ser Thr Glu Val Gly
            20                  25                  30

Ser Glu Thr Pro
            35

<210> SEQ ID NO 126
<211> LENGTH: 36
<212> TYPE: PRT
<213> ORGANISM: Artificial sequence
<220> FEATURE:
<223> OTHER INFORMATION: Synthetic amylin analogue
<220> FEATURE:
<221> NAME/KEY: SITE
<222> LOCATION: (1)..(1)
<223> OTHER INFORMATION: Xaa is isoGlu
<220> FEATURE:
<221> NAME/KEY: SITE
<222> LOCATION: (1)..(1)
<223> OTHER INFORMATION: Linked to [19-carboxynonadecanoyl]
<220> FEATURE:
<221> NAME/KEY: DISULFID
<222> LOCATION: (3)..(8)
<223> OTHER INFORMATION: Sequence may possess an intramolecular
      disulphide bridge formed between the cysteine residues present at
      positions 3 and 8, corresponding to the cysteine residues present
      at positions 2 and 7 of human amylin. Feature is present in Compd.
      25.
<220> FEATURE:
<221> NAME/KEY: MOD_RES
<222> LOCATION: (23)..(23)
<223> OTHER INFORMATION: MeGly
<220> FEATURE:
<221> NAME/KEY: MOD_RES
<222> LOCATION: (25)..(25)
<223> OTHER INFORMATION: MeIle

<400> SEQUENCE: 126

Xaa Arg Cys Pro Thr Ala Thr Cys Ala Thr Asp Arg Leu Ala His Phe
1               5                   10                  15

Leu His Arg Ser Ser Phe Gly Ala Ile Leu Ser Ser Thr Asp Val Gly
            20                  25                  30

Ser Asn Thr Pro
            35

<210> SEQ ID NO 127
<211> LENGTH: 36
<212> TYPE: PRT
<213> ORGANISM: Artificial sequence
<220> FEATURE:
<223> OTHER INFORMATION: Synthetic amylin analogue
<220> FEATURE:
```

```
<221> NAME/KEY: SITE
<222> LOCATION: (1)..(1)
<223> OTHER INFORMATION: Xaa is isoGlu
<220> FEATURE:
<221> NAME/KEY: SITE
<222> LOCATION: (1)..(1)
<223> OTHER INFORMATION: Linked to [19-carboxynonadecanoyl]
<220> FEATURE:
<221> NAME/KEY: DISULFID
<222> LOCATION: (3)..(8)
<223> OTHER INFORMATION: Sequence may possess an intramolecular
      disulphide bridge formed between the cysteine residues present at
      positions 3 and 8, corresponding to the cysteine residues present
      at positions 2 and 7 of human amylin. Feature is present in Compd.
      26.
<220> FEATURE:
<221> NAME/KEY: MOD_RES
<222> LOCATION: (23)..(23)
<223> OTHER INFORMATION: MeGly
<220> FEATURE:
<221> NAME/KEY: MOD_RES
<222> LOCATION: (25)..(25)
<223> OTHER INFORMATION: MeIle

<400> SEQUENCE: 127

Xaa Arg Cys Gly Thr Ala Thr Cys Ala Thr Glu Arg Leu Ala His Phe
1               5                   10                  15

Leu His Arg Ser Ser Phe Gly Ala Ile Leu Ser Ser Thr Glu Val Gly
            20                  25                  30

Ser Glu Thr Pro
        35

<210> SEQ ID NO 128
<211> LENGTH: 36
<212> TYPE: PRT
<213> ORGANISM: Artificial sequence
<220> FEATURE:
<223> OTHER INFORMATION: Synthetic amylin analogue
<220> FEATURE:
<221> NAME/KEY: SITE
<222> LOCATION: (1)..(1)
<223> OTHER INFORMATION: Xaa is isoGlu
<220> FEATURE:
<221> NAME/KEY: SITE
<222> LOCATION: (1)..(1)
<223> OTHER INFORMATION: Linked to [19-carboxynonadecanoyl]
<220> FEATURE:
<221> NAME/KEY: DISULFID
<222> LOCATION: (3)..(8)
<223> OTHER INFORMATION: Sequence may possess an intramolecular
      disulphide bridge formed between the cysteine residues present at
      positions 3 and 8, corresponding to the cysteine residues present
      at positions 2 and 7 of human amylin. Feature is present in Compd.
      27.
<220> FEATURE:
<221> NAME/KEY: MOD_RES
<222> LOCATION: (23)..(23)
<223> OTHER INFORMATION: MeGly
<220> FEATURE:
<221> NAME/KEY: MOD_RES
<222> LOCATION: (25)..(25)
<223> OTHER INFORMATION: MeIle

<400> SEQUENCE: 128

Xaa Arg Cys Pro Thr Ala Thr Cys Ala Thr Asp Arg Leu Ala His Phe
1               5                   10                  15

Leu His Arg Ser Ser Phe Gly Ala Ile Leu Ser Ser Thr Asp Val Gly
            20                  25                  30

Ser Asp Thr Pro
        35
```

```
<210> SEQ ID NO 129
<211> LENGTH: 36
<212> TYPE: PRT
<213> ORGANISM: Artificial sequence
<220> FEATURE:
<223> OTHER INFORMATION: Synthetic amylin analogue
<220> FEATURE:
<221> NAME/KEY: SITE
<222> LOCATION: (1)..(1)
<223> OTHER INFORMATION: Xaa is isoGlu
<220> FEATURE:
<221> NAME/KEY: SITE
<222> LOCATION: (1)..(1)
<223> OTHER INFORMATION: Linked to [19-carboxynonadecanoyl]
<220> FEATURE:
<221> NAME/KEY: DISULFID
<222> LOCATION: (3)..(8)
<223> OTHER INFORMATION: Sequence may possess an intramolecular
      disulphide bridge formed between the cysteine residues present at
      positions 3 and 8, corresponding to the cysteine residues present
      at positions 2 and 7 of human amylin. Feature is present in Compd.
      28.
<220> FEATURE:
<221> NAME/KEY: MOD_RES
<222> LOCATION: (23)..(23)
<223> OTHER INFORMATION: MeGly
<220> FEATURE:
<221> NAME/KEY: MOD_RES
<222> LOCATION: (25)..(25)
<223> OTHER INFORMATION: MeIle
<220> FEATURE:
<221> NAME/KEY: MOD_RES
<222> LOCATION: (36)..(36)
<223> OTHER INFORMATION: 4Hyp

<400> SEQUENCE: 129

Xaa Arg Cys Gly Thr Ala Thr Cys Ala Thr Glu Arg Leu Ala His Phe
1               5                   10                  15

Leu Gln Arg Ser Ser Phe Gly Ala Ile Leu Ser Ser Thr Glu Val Gly
            20                  25                  30

Ser Ser Thr Pro
        35

<210> SEQ ID NO 130
<211> LENGTH: 36
<212> TYPE: PRT
<213> ORGANISM: Artificial sequence
<220> FEATURE:
<223> OTHER INFORMATION: Synthetic amylin analogue
<220> FEATURE:
<221> NAME/KEY: SITE
<222> LOCATION: (1)..(1)
<223> OTHER INFORMATION: Xaa is isoGlu
<220> FEATURE:
<221> NAME/KEY: SITE
<222> LOCATION: (1)..(1)
<223> OTHER INFORMATION: Linked to [19-carboxynonadecanoyl]
<220> FEATURE:
<221> NAME/KEY: DISULFID
<222> LOCATION: (3)..(8)
<223> OTHER INFORMATION: Sequence may possess an intramolecular
      disulphide bridge formed between the cysteine residues present at
      positions 3 and 8, corresponding to the cysteine residues present
      at positions 2 and 7 of human amylin. Feature is present in Compd.
      29.
<220> FEATURE:
<221> NAME/KEY: MOD_RES
<222> LOCATION: (23)..(23)
<223> OTHER INFORMATION: MeGly
<220> FEATURE:
<221> NAME/KEY: MOD_RES
<222> LOCATION: (25)..(25)
<223> OTHER INFORMATION: MeIle
<220> FEATURE:
<221> NAME/KEY: MOD_RES
```

```
<222> LOCATION: (36)..(36)
<223> OTHER INFORMATION: 4Hyp

<400> SEQUENCE: 130

Xaa Arg Cys Gly Thr Ala Thr Cys Ala Thr Glu Arg Leu Ala His Phe
1               5                   10                  15

Leu Asn Arg Ser Ser Phe Gly Ala Ile Leu Ser Ser Thr Glu Val Gly
            20                  25                  30

Ser Ser Thr Pro
        35

<210> SEQ ID NO 131
<211> LENGTH: 36
<212> TYPE: PRT
<213> ORGANISM: Artificial sequence
<220> FEATURE:
<223> OTHER INFORMATION: Synthetic amylin analogue
<220> FEATURE:
<221> NAME/KEY: SITE
<222> LOCATION: (1)..(1)
<223> OTHER INFORMATION: Xaa is isoGlu
<220> FEATURE:
<221> NAME/KEY: SITE
<222> LOCATION: (1)..(1)
<223> OTHER INFORMATION: Linked to [19-carboxynonadecanoyl]
<220> FEATURE:
<221> NAME/KEY: DISULFID
<222> LOCATION: (3)..(8)
<223> OTHER INFORMATION: Sequence may possess an intramolecular
      disulphide bridge formed between the cysteine residues present at
      positions 3 and 8, corresponding to the cysteine residues present
      at positions 2 and 7 of human amylin. Feature is present in Compd.
      30.
<220> FEATURE:
<221> NAME/KEY: MOD_RES
<222> LOCATION: (23)..(23)
<223> OTHER INFORMATION: MeGly
<220> FEATURE:
<221> NAME/KEY: MOD_RES
<222> LOCATION: (25)..(25)
<223> OTHER INFORMATION: MeIle
<220> FEATURE:
<221> NAME/KEY: MOD_RES
<222> LOCATION: (36)..(36)
<223> OTHER INFORMATION: 4Hyp

<400> SEQUENCE: 131

Xaa Arg Cys Gly Thr Ala Thr Cys Ala Thr Glu Arg Leu Ala His Phe
1               5                   10                  15

Leu His Arg Ser Ser Phe Gly Ala Ile Leu Ser Ser Thr Glu Val Gly
            20                  25                  30

Ser Ser Thr Pro
        35

<210> SEQ ID NO 132
<211> LENGTH: 36
<212> TYPE: PRT
<213> ORGANISM: Artificial sequence
<220> FEATURE:
<223> OTHER INFORMATION: Synthetic amylin analogue
<220> FEATURE:
<221> NAME/KEY: SITE
<222> LOCATION: (1)..(1)
<223> OTHER INFORMATION: Xaa is isoGlu
<220> FEATURE:
<221> NAME/KEY: SITE
<222> LOCATION: (1)..(1)
<223> OTHER INFORMATION: Linked to [19-carboxynonadecanoyl]
<220> FEATURE:
<221> NAME/KEY: DISULFID
<222> LOCATION: (3)..(8)
```

```
<223> OTHER INFORMATION: Sequence may possess an intramolecular
      disulphide bridge formed between the cysteine residues present at
      positions 3 and 8, corresponding to the cysteine residues present
      at positions 2 and 7 of human amylin. Feature is present in Compd.
      31.
<220> FEATURE:
<221> NAME/KEY: MOD_RES
<222> LOCATION: (23)..(23)
<223> OTHER INFORMATION: MeGly
<220> FEATURE:
<221> NAME/KEY: MOD_RES
<222> LOCATION: (25)..(25)
<223> OTHER INFORMATION: MeIle
<220> FEATURE:
<221> NAME/KEY: MOD_RES
<222> LOCATION: (36)..(36)
<223> OTHER INFORMATION: 4Hyp

<400> SEQUENCE: 132

Xaa Arg Cys Gly Thr Ala Thr Cys Ala Thr Glu Arg Leu Ala His Phe
1               5                   10                  15

Leu Val Arg Ser Ser Phe Gly Ala Ile Leu Ser Ser Thr Glu Val Gly
            20                  25                  30

Ser Ser Thr Pro
        35

<210> SEQ ID NO 133
<211> LENGTH: 36
<212> TYPE: PRT
<213> ORGANISM: Artificial sequence
<220> FEATURE:
<223> OTHER INFORMATION: Synthetic amylin analogue
<220> FEATURE:
<221> NAME/KEY: SITE
<222> LOCATION: (1)..(1)
<223> OTHER INFORMATION: Xaa is isoGlu
<220> FEATURE:
<221> NAME/KEY: SITE
<222> LOCATION: (1)..(1)
<223> OTHER INFORMATION: Linked to [19-carboxynonadecanoyl]
<220> FEATURE:
<221> NAME/KEY: DISULFID
<222> LOCATION: (3)..(8)
<223> OTHER INFORMATION: Sequence may possess an intramolecular
      disulphide bridge formed between the cysteine residues present at
      positions 3 and 8, corresponding to the cysteine residues present
      at positions 2 and 7 of human amylin. Feature is present in Compd.
      32.
<220> FEATURE:
<221> NAME/KEY: MOD_RES
<222> LOCATION: (23)..(23)
<223> OTHER INFORMATION: MeGly
<220> FEATURE:
<221> NAME/KEY: MOD_RES
<222> LOCATION: (25)..(25)
<223> OTHER INFORMATION: MeIle
<220> FEATURE:
<221> NAME/KEY: MOD_RES
<222> LOCATION: (36)..(36)
<223> OTHER INFORMATION: 4Hyp

<400> SEQUENCE: 133

Xaa Arg Cys Gly Thr Ala Thr Cys Ala Thr Glu Arg Leu Ala His Phe
1               5                   10                  15

Leu Gln Arg Ser Ser Phe Gly Ala Ile Leu Ser Ser Thr Glu Val Gly
            20                  25                  30

Ser Phe Thr Pro
        35

<210> SEQ ID NO 134
<211> LENGTH: 36
```

```
<212> TYPE: PRT
<213> ORGANISM: Artificial sequence
<220> FEATURE:
<223> OTHER INFORMATION: Synthetic amylin analogue
<220> FEATURE:
<221> NAME/KEY: SITE
<222> LOCATION: (1)..(1)
<223> OTHER INFORMATION: Xaa is isoGlu
<220> FEATURE:
<221> NAME/KEY: SITE
<222> LOCATION: (1)..(1)
<223> OTHER INFORMATION: Linked to [19-carboxynonadecanoyl]
<220> FEATURE:
<221> NAME/KEY: DISULFID
<222> LOCATION: (3)..(8)
<223> OTHER INFORMATION: Sequence may possess an intramolecular
      disulphide bridge formed between the cysteine residues present at
      positions 3 and 8, corresponding to the cysteine residues present
      at positions 2 and 7 of human amylin. Feature is present in Compd.
      33.
<220> FEATURE:
<221> NAME/KEY: MOD_RES
<222> LOCATION: (23)..(23)
<223> OTHER INFORMATION: MeGly
<220> FEATURE:
<221> NAME/KEY: MOD_RES
<222> LOCATION: (25)..(25)
<223> OTHER INFORMATION: MeIle
<220> FEATURE:
<221> NAME/KEY: MOD_RES
<222> LOCATION: (36)..(36)
<223> OTHER INFORMATION: 4Hyp

<400> SEQUENCE: 134

Xaa Arg Cys Gly Thr Ala Thr Cys Ala Thr Glu Arg Leu Ala His Phe
1               5                   10                  15

Leu Asn Arg Ser Ser Phe Gly Ala Ile Leu Ser Ser Thr Glu Val Gly
            20                  25                  30

Ser Phe Thr Pro
        35

<210> SEQ ID NO 135
<211> LENGTH: 36
<212> TYPE: PRT
<213> ORGANISM: Artificial sequence
<220> FEATURE:
<223> OTHER INFORMATION: Synthetic amylin analogue
<220> FEATURE:
<221> NAME/KEY: SITE
<222> LOCATION: (1)..(1)
<223> OTHER INFORMATION: Xaa is isoGlu
<220> FEATURE:
<221> NAME/KEY: SITE
<222> LOCATION: (1)..(1)
<223> OTHER INFORMATION: Linked to [19-carboxynonadecanoyl]
<220> FEATURE:
<221> NAME/KEY: DISULFID
<222> LOCATION: (3)..(8)
<223> OTHER INFORMATION: Sequence may possess an intramolecular
      disulphide bridge formed between the cysteine residues present at
      positions 3 and 8, corresponding to the cysteine residues present
      at positions 2 and 7 of human amylin. Feature is present in Compd.
      34.
<220> FEATURE:
<221> NAME/KEY: MOD_RES
<222> LOCATION: (23)..(23)
<223> OTHER INFORMATION: MeGly
<220> FEATURE:
<221> NAME/KEY: MOD_RES
<222> LOCATION: (25)..(25)
<223> OTHER INFORMATION: MeIle

<400> SEQUENCE: 135

Xaa Arg Cys Gly Thr Ala Thr Cys Ala Thr Glu Arg Leu Ala His Phe
```

```
                1               5                  10                  15
Leu Gln Arg Ser Ser Phe Gly Ala Ile Leu Ser Ser Thr Glu Val Gly
                        20                  25                  30

Ser Ser Thr Pro
        35

<210> SEQ ID NO 136
<211> LENGTH: 36
<212> TYPE: PRT
<213> ORGANISM: Artificial sequence
<220> FEATURE:
<223> OTHER INFORMATION: Synthetic amylin analogue
<220> FEATURE:
<221> NAME/KEY: SITE
<222> LOCATION: (1)..(1)
<223> OTHER INFORMATION: Xaa is isoGlu
<220> FEATURE:
<221> NAME/KEY: SITE
<222> LOCATION: (1)..(1)
<223> OTHER INFORMATION: Linked to [19-carboxynonadecanoyl]
<220> FEATURE:
<221> NAME/KEY: DISULFID
<222> LOCATION: (3)..(8)
<223> OTHER INFORMATION: Sequence may possess an intramolecular
      disulphide bridge formed between the cysteine residues present at
      positions 3 and 8, corresponding to the cysteine residues present
      at positions 2 and 7 of human amylin. Feature is present in Compd.
      35.
<220> FEATURE:
<221> NAME/KEY: MOD_RES
<222> LOCATION: (23)..(23)
<223> OTHER INFORMATION: MeGly
<220> FEATURE:
<221> NAME/KEY: MOD_RES
<222> LOCATION: (25)..(25)
<223> OTHER INFORMATION: MeIle

<400> SEQUENCE: 136

Xaa Arg Cys Gly Thr Ala Thr Cys Ala Thr Glu Arg Leu Ala His Phe
1               5                  10                  15

Leu Asn Arg Ser Ser Phe Gly Ala Ile Leu Ser Ser Thr Glu Val Gly
                        20                  25                  30

Ser Ser Thr Pro
        35

<210> SEQ ID NO 137
<211> LENGTH: 36
<212> TYPE: PRT
<213> ORGANISM: Artificial sequence
<220> FEATURE:
<223> OTHER INFORMATION: Synthetic amylin analogue
<220> FEATURE:
<221> NAME/KEY: SITE
<222> LOCATION: (1)..(1)
<223> OTHER INFORMATION: Xaa is isoGlu
<220> FEATURE:
<221> NAME/KEY: SITE
<222> LOCATION: (1)..(1)
<223> OTHER INFORMATION: Linked to [19-carboxynonadecanoyl]
<220> FEATURE:
<221> NAME/KEY: DISULFID
<222> LOCATION: (3)..(8)
<223> OTHER INFORMATION: Sequence may possess an intramolecular
      disulphide bridge formed between the cysteine residues present at
      positions 3 and 8, corresponding to the cysteine residues present
      at positions 2 and 7 of human amylin. Feature is present in Compd.
      36.
<220> FEATURE:
<221> NAME/KEY: MOD_RES
<222> LOCATION: (23)..(23)
<223> OTHER INFORMATION: MeGly
<220> FEATURE:
```

```
<221> NAME/KEY: MOD_RES
<222> LOCATION: (25)..(25)
<223> OTHER INFORMATION: MeIle

<400> SEQUENCE: 137

Xaa Arg Cys Gly Thr Ala Thr Cys Ala Thr Glu Arg Leu Ala His Phe
1               5                   10                  15

Leu Glu Arg Ser Ser Phe Gly Ala Ile Leu Ser Ser Thr Glu Val Gly
            20                  25                  30

Ser Ser Thr Pro
        35

<210> SEQ ID NO 138
<211> LENGTH: 36
<212> TYPE: PRT
<213> ORGANISM: Artificial sequence
<220> FEATURE:
<223> OTHER INFORMATION: Synthetic amylin analogue
<220> FEATURE:
<221> NAME/KEY: SITE
<222> LOCATION: (1)..(1)
<223> OTHER INFORMATION: Xaa is isoGlu
<220> FEATURE:
<221> NAME/KEY: SITE
<222> LOCATION: (1)..(1)
<223> OTHER INFORMATION: Linked to [19-carboxynonadecanoyl]
<220> FEATURE:
<221> NAME/KEY: DISULFID
<222> LOCATION: (3)..(8)
<223> OTHER INFORMATION: Sequence may possess an intramolecular
      disulphide bridge formed between the cysteine residues present at
      positions 3 and 8, corresponding to the cysteine residues present
      at positions 2 and 7 of human amylin. Feature is present in Compd.
      37.
<220> FEATURE:
<221> NAME/KEY: MOD_RES
<222> LOCATION: (23)..(23)
<223> OTHER INFORMATION: MeGly
<220> FEATURE:
<221> NAME/KEY: MOD_RES
<222> LOCATION: (25)..(25)
<223> OTHER INFORMATION: MeIle

<400> SEQUENCE: 138

Xaa Arg Cys Gly Thr Ala Thr Cys Ala Thr Glu Arg Leu Ala His Phe
1               5                   10                  15

Leu His Arg Ser Ser Phe Gly Ala Ile Leu Ser Ser Thr Glu Val Gly
            20                  25                  30

Ser Ser Thr Pro
        35

<210> SEQ ID NO 139
<211> LENGTH: 36
<212> TYPE: PRT
<213> ORGANISM: Artificial sequence
<220> FEATURE:
<223> OTHER INFORMATION: Synthetic amylin analogue
<220> FEATURE:
<221> NAME/KEY: SITE
<222> LOCATION: (1)..(1)
<223> OTHER INFORMATION: Xaa is isoGlu
<220> FEATURE:
<221> NAME/KEY: SITE
<222> LOCATION: (1)..(1)
<223> OTHER INFORMATION: Linked to [19-carboxynonadecanoyl]
<220> FEATURE:
<221> NAME/KEY: DISULFID
<222> LOCATION: (3)..(8)
<223> OTHER INFORMATION: Sequence may possess an intramolecular
      disulphide bridge formed between the cysteine residues present at
      positions 3 and 8, corresponding to the cysteine residues present
``` at positions 2 and 7 of human amylin. Feature is present in Compd.
38.
<220> FEATURE:
<221> NAME/KEY: MOD_RES
<222> LOCATION: (23)..(23)
<223> OTHER INFORMATION: MeGly
<220> FEATURE:
<221> NAME/KEY: MOD_RES
<222> LOCATION: (25)..(25)
<223> OTHER INFORMATION: MeIle

<400> SEQUENCE: 139

Xaa Arg Cys Gly Thr Ala Thr Cys Ala Thr Glu Arg Leu Ala His Phe
1               5                   10                  15

Leu Val Arg Ser Ser Phe Gly Ala Ile Leu Ser Ser Thr Glu Val Gly
            20                  25                  30

Ser Ser Thr Pro
        35

<210> SEQ ID NO 140
<211> LENGTH: 36
<212> TYPE: PRT
<213> ORGANISM: Artificial sequence
<220> FEATURE:
<223> OTHER INFORMATION: Synthetic amylin analogue
<220> FEATURE:
<221> NAME/KEY: SITE
<222> LOCATION: (1)..(1)
<223> OTHER INFORMATION: Xaa is isoGlu
<220> FEATURE:
<221> NAME/KEY: SITE
<222> LOCATION: (1)..(1)
<223> OTHER INFORMATION: Linked to [19-carboxynonadecanoyl]
<220> FEATURE:
<221> NAME/KEY: DISULFID
<222> LOCATION: (3)..(8)
<223> OTHER INFORMATION: Sequence may possess an intramolecular
    disulphide bridge formed between the cysteine residues present at
    positions 3 and 8, corresponding to the cysteine residues present
    at positions 2 and 7 of human amylin. Feature is present in Compd.
    39.
<220> FEATURE:
<221> NAME/KEY: MOD_RES
<222> LOCATION: (23)..(23)
<223> OTHER INFORMATION: MeGly
<220> FEATURE:
<221> NAME/KEY: MOD_RES
<222> LOCATION: (25)..(25)
<223> OTHER INFORMATION: MeIle

<400> SEQUENCE: 140

Xaa Arg Cys Gly Thr Ala Thr Cys Ala Thr Glu Arg Leu Ala His Phe
1               5                   10                  15

Leu Gln Arg Ser Ser Phe Gly Ala Ile Leu Ser Ser Thr Glu Val Gly
            20                  25                  30

Ser Phe Thr Pro
        35

<210> SEQ ID NO 141
<211> LENGTH: 36
<212> TYPE: PRT
<213> ORGANISM: Artificial sequence
<220> FEATURE:
<223> OTHER INFORMATION: Synthetic amylin analogue
<220> FEATURE:
<221> NAME/KEY: SITE
<222> LOCATION: (1)..(1)
<223> OTHER INFORMATION: Xaa is isoGlu
<220> FEATURE:
<221> NAME/KEY: SITE
<222> LOCATION: (1)..(1)

```
<223> OTHER INFORMATION: Linked to [19-carboxynonadecanoyl]
<220> FEATURE:
<221> NAME/KEY: DISULFID
<222> LOCATION: (3)..(8)
<223> OTHER INFORMATION: Sequence may possess an intramolecular
      disulphide bridge formed between the cysteine residues present at
      positions 3 and 8, corresponding to the cysteine residues present
      at positions 2 and 7 of human amylin. Feature is present in Compd.
      40.
<220> FEATURE:
<221> NAME/KEY: MOD_RES
<222> LOCATION: (23)..(23)
<223> OTHER INFORMATION: MeGly
<220> FEATURE:
<221> NAME/KEY: MOD_RES
<222> LOCATION: (25)..(25)
<223> OTHER INFORMATION: MeIle

<400> SEQUENCE: 141

Xaa Arg Cys Gly Thr Ala Thr Cys Ala Thr Glu Arg Leu Ala His Phe
1               5                   10                  15

Leu Asn Arg Ser Ser Phe Gly Ala Ile Leu Ser Ser Thr Glu Val Gly
            20                  25                  30

Ser Phe Thr Pro
        35

<210> SEQ ID NO 142
<211> LENGTH: 36
<212> TYPE: PRT
<213> ORGANISM: Artificial sequence
<220> FEATURE:
<223> OTHER INFORMATION: Synthetic amylin analogue
<220> FEATURE:
<221> NAME/KEY: SITE
<222> LOCATION: (1)..(1)
<223> OTHER INFORMATION: Xaa is isoGlu
<220> FEATURE:
<221> NAME/KEY: SITE
<222> LOCATION: (1)..(1)
<223> OTHER INFORMATION: Linked to [19-carboxynonadecanoyl]
<220> FEATURE:
<221> NAME/KEY: DISULFID
<222> LOCATION: (3)..(8)
<223> OTHER INFORMATION: Sequence may possess an intramolecular
      disulphide bridge formed between the cysteine residues present at
      positions 3 and 8, corresponding to the cysteine residues present
      at positions 2 and 7 of human amylin. Feature is present in Compd.
      41.
<220> FEATURE:
<221> NAME/KEY: MOD_RES
<222> LOCATION: (23)..(23)
<223> OTHER INFORMATION: MeGly
<220> FEATURE:
<221> NAME/KEY: MOD_RES
<222> LOCATION: (25)..(25)
<223> OTHER INFORMATION: MeIle
<220> FEATURE:
<221> NAME/KEY: MOD_RES
<222> LOCATION: (36)..(36)
<223> OTHER INFORMATION: 4Hyp

<400> SEQUENCE: 142

Xaa Arg Cys Gly Thr Ala Thr Cys Ala Thr Glu Arg Leu Ala Asp Phe
1               5                   10                  15

Leu Thr Arg Ser Ser Phe Gly Ala Ile Leu Ser Ser Thr Glu Val Gly
            20                  25                  30

Ser Ser Thr Pro
        35

<210> SEQ ID NO 143
<211> LENGTH: 36
```

```
<212> TYPE: PRT
<213> ORGANISM: Artificial sequence
<220> FEATURE:
<223> OTHER INFORMATION: Synthetic amylin analogue
<220> FEATURE:
<221> NAME/KEY: SITE
<222> LOCATION: (1)..(1)
<223> OTHER INFORMATION: Xaa is isoGlu
<220> FEATURE:
<221> NAME/KEY: SITE
<222> LOCATION: (1)..(1)
<223> OTHER INFORMATION: Linked to [19-carboxynonadecanoyl]
<220> FEATURE:
<221> NAME/KEY: DISULFID
<222> LOCATION: (3)..(8)
<223> OTHER INFORMATION: Sequence may possess an intramolecular
      disulphide bridge formed between the cysteine residues present at
      positions 3 and 8, corresponding to the cysteine residues present
      at positions 2 and 7 of human amylin. Feature is present in Compd.
      42.
<220> FEATURE:
<221> NAME/KEY: MOD_RES
<222> LOCATION: (23)..(23)
<223> OTHER INFORMATION: MeGly
<220> FEATURE:
<221> NAME/KEY: MOD_RES
<222> LOCATION: (25)..(25)
<223> OTHER INFORMATION: MeIle
<220> FEATURE:
<221> NAME/KEY: MOD_RES
<222> LOCATION: (36)..(36)
<223> OTHER INFORMATION: 4Hyp

<400> SEQUENCE: 143

Xaa Arg Cys Gly Thr Ala Thr Cys Ala Thr Glu Arg Leu Ala Asp Phe
1               5                   10                  15

Leu Thr Arg Ser Ser Phe Gly Ala Ile Leu Ser Ser Thr Glu Val Gly
            20                  25                  30

Ser Phe Thr Pro
            35

<210> SEQ ID NO 144
<211> LENGTH: 36
<212> TYPE: PRT
<213> ORGANISM: Artificial sequence
<220> FEATURE:
<223> OTHER INFORMATION: Synthetic amylin analogue
<220> FEATURE:
<221> NAME/KEY: SITE
<222> LOCATION: (1)..(1)
<223> OTHER INFORMATION: Xaa is isoGlu
<220> FEATURE:
<221> NAME/KEY: SITE
<222> LOCATION: (1)..(1)
<223> OTHER INFORMATION: Linked to [19-carboxynonadecanoyl]
<220> FEATURE:
<221> NAME/KEY: DISULFID
<222> LOCATION: (3)..(8)
<223> OTHER INFORMATION: Sequence may possess an intramolecular
      disulphide bridge formed between the cysteine residues present at
      positions 3 and 8, corresponding to the cysteine residues present
      at positions 2 and 7 of human amylin. Feature is present in Compd.
      43.
<220> FEATURE:
<221> NAME/KEY: MOD_RES
<222> LOCATION: (15)..(15)
<223> OTHER INFORMATION: Aad
<220> FEATURE:
<221> NAME/KEY: MOD_RES
<222> LOCATION: (23)..(23)
<223> OTHER INFORMATION: MeGly
<220> FEATURE:
<221> NAME/KEY: MOD_RES
<222> LOCATION: (25)..(25)
<223> OTHER INFORMATION: MeIle
```

-continued

```
<220> FEATURE:
<221> NAME/KEY: MOD_RES
<222> LOCATION: (36)..(36)
<223> OTHER INFORMATION: 4Hyp

<400> SEQUENCE: 144

Xaa Arg Cys Gly Thr Ala Thr Cys Ala Thr Glu Arg Leu Ala Glu Phe
1               5                   10                  15

Leu Thr Arg Ser Ser Phe Gly Ala Ile Leu Ser Ser Thr Glu Val Gly
            20                  25                  30

Ser Ser Thr Pro
        35

<210> SEQ ID NO 145
<211> LENGTH: 36
<212> TYPE: PRT
<213> ORGANISM: Artificial sequence
<220> FEATURE:
<223> OTHER INFORMATION: Synthetic amylin analogue
<220> FEATURE:
<221> NAME/KEY: SITE
<222> LOCATION: (1)..(1)
<223> OTHER INFORMATION: Xaa is isoGlu
<220> FEATURE:
<221> NAME/KEY: SITE
<222> LOCATION: (1)..(1)
<223> OTHER INFORMATION: Linked to [19-carboxynonadecanoyl]
<220> FEATURE:
<221> NAME/KEY: DISULFID
<222> LOCATION: (3)..(8)
<223> OTHER INFORMATION: Sequence may possess an intramolecular
      disulphide bridge formed between the cysteine residues present at
      positions 3 and 8, corresponding to the cysteine residues present
      at positions 2 and 7 of human amylin. Feature is present in Compd.
      44.
<220> FEATURE:
<221> NAME/KEY: MOD_RES
<222> LOCATION: (15)..(15)
<223> OTHER INFORMATION: Aad
<220> FEATURE:
<221> NAME/KEY: MOD_RES
<222> LOCATION: (23)..(23)
<223> OTHER INFORMATION: MeGly
<220> FEATURE:
<221> NAME/KEY: MOD_RES
<222> LOCATION: (25)..(25)
<223> OTHER INFORMATION: MeIle
<220> FEATURE:
<221> NAME/KEY: MOD_RES
<222> LOCATION: (34)..(34)
<223> OTHER INFORMATION: Orn
<220> FEATURE:
<221> NAME/KEY: MOD_RES
<222> LOCATION: (36)..(36)
<223> OTHER INFORMATION: 4Hyp

<400> SEQUENCE: 145

Xaa Arg Cys Gly Thr Ala Thr Cys Ala Thr Glu Arg Leu Ala Glu Phe
1               5                   10                  15

Leu Thr Arg Ser Ser Phe Gly Ala Ile Leu Ser Ser Thr Glu Val Gly
            20                  25                  30

Ser Arg Thr Pro
        35

<210> SEQ ID NO 146
<211> LENGTH: 36
<212> TYPE: PRT
<213> ORGANISM: Artificial sequence
<220> FEATURE:
<223> OTHER INFORMATION: Synthetic amylin analogue
<220> FEATURE:
```

```
<221> NAME/KEY: SITE
<222> LOCATION: (1)..(1)
<223> OTHER INFORMATION: Xaa is isoGlu
<220> FEATURE:
<221> NAME/KEY: SITE
<222> LOCATION: (1)..(1)
<223> OTHER INFORMATION: Linked to [19-carboxynonadecanoyl]
<220> FEATURE:
<221> NAME/KEY: DISULFID
<222> LOCATION: (3)..(8)
<223> OTHER INFORMATION: Sequence may possess an intramolecular
      disulphide bridge formed between the cysteine residues present at
      positions 3 and 8, corresponding to the cysteine residues present
      at positions 2 and 7 of human amylin. Feature is present in Compd.
      45.
<220> FEATURE:
<221> NAME/KEY: MOD_RES
<222> LOCATION: (23)..(23)
<223> OTHER INFORMATION: MeGly
<220> FEATURE:
<221> NAME/KEY: MOD_RES
<222> LOCATION: (25)..(25)
<223> OTHER INFORMATION: MeIle
<220> FEATURE:
<221> NAME/KEY: SITE
<222> LOCATION: (36)..(36)
<223> OTHER INFORMATION: Xaa is Apr, 4-aminoproline

<400> SEQUENCE: 146

Xaa Arg Cys Gly Thr Ala Thr Cys Ala Thr Glu Arg Leu Ala His Phe
1               5                   10                  15

Leu Thr Arg Ser Ser Phe Gly Ala Ile Leu Ser Ser Thr Glu Val Gly
            20                  25                  30

Ser Ser Thr Xaa
        35

<210> SEQ ID NO 147
<211> LENGTH: 36
<212> TYPE: PRT
<213> ORGANISM: Artificial sequence
<220> FEATURE:
<223> OTHER INFORMATION: Synthetic amylin analogue
<220> FEATURE:
<221> NAME/KEY: SITE
<222> LOCATION: (1)..(1)
<223> OTHER INFORMATION: Xaa is isoGlu
<220> FEATURE:
<221> NAME/KEY: SITE
<222> LOCATION: (1)..(1)
<223> OTHER INFORMATION: Linked to [19-carboxynonadecanoyl]
<220> FEATURE:
<221> NAME/KEY: DISULFID
<222> LOCATION: (3)..(8)
<223> OTHER INFORMATION: Sequence may possess an intramolecular
      disulphide bridge formed between the cysteine residues present at
      positions 3 and 8, corresponding to the cysteine residues present
      at positions 2 and 7 of human amylin. Feature is present in Compd.
      46.
<220> FEATURE:
<221> NAME/KEY: MOD_RES
<222> LOCATION: (23)..(23)
<223> OTHER INFORMATION: MeGly
<220> FEATURE:
<221> NAME/KEY: MOD_RES
<222> LOCATION: (25)..(25)
<223> OTHER INFORMATION: MeIle

<400> SEQUENCE: 147

Xaa Arg Cys Gly Thr Ala Thr Cys Ala Thr Glu Arg Leu Ala His Phe
1               5                   10                  15

Leu Thr Arg Ser Ser Phe Gly Ala Ile Leu Ser Ser Thr Glu Val Gly
            20                  25                  30
```

Ser Ser Thr Pro
        35

<210> SEQ ID NO 148
<211> LENGTH: 36
<212> TYPE: PRT
<213> ORGANISM: Artificial sequence
<220> FEATURE:
<223> OTHER INFORMATION: Synthetic amylin analogue
<220> FEATURE:
<221> NAME/KEY: SITE
<222> LOCATION: (1)..(1)
<223> OTHER INFORMATION: Xaa is isoGlu
<220> FEATURE:
<221> NAME/KEY: SITE
<222> LOCATION: (1)..(1)
<223> OTHER INFORMATION: Linked to [19-carboxynonadecanoyl]
<220> FEATURE:
<221> NAME/KEY: DISULFID
<222> LOCATION: (3)..(8)
<223> OTHER INFORMATION: Sequence may possess an intramolecular
      disulphide bridge formed between the cysteine residues present at
      positions 3 and 8, corresponding to the cysteine residues present
      at positions 2 and 7 of human amylin. Feature is present in Compd.
      47.
<220> FEATURE:
<221> NAME/KEY: MOD_RES
<222> LOCATION: (23)..(23)
<223> OTHER INFORMATION: MeGly
<220> FEATURE:
<221> NAME/KEY: MOD_RES
<222> LOCATION: (25)..(25)
<223> OTHER INFORMATION: MeIle
<220> FEATURE:
<221> NAME/KEY: MOD_RES
<222> LOCATION: (34)..(34)
<223> OTHER INFORMATION: Orn

<400> SEQUENCE: 148

Xaa Arg Cys Gly Thr Ala Thr Cys Ala Thr Glu Arg Leu Ala His Phe
1               5                   10                  15

Leu Thr Arg Ser Ser Phe Gly Ala Ile Leu Ser Ser Thr Glu Val Gly
            20                  25                  30

Ser Arg Thr Pro
        35

<210> SEQ ID NO 149
<211> LENGTH: 36
<212> TYPE: PRT
<213> ORGANISM: Artificial sequence
<220> FEATURE:
<223> OTHER INFORMATION: Synthetic amylin analogue
<220> FEATURE:
<221> NAME/KEY: SITE
<222> LOCATION: (1)..(1)
<223> OTHER INFORMATION: Xaa is isoGlu
<220> FEATURE:
<221> NAME/KEY: SITE
<222> LOCATION: (1)..(1)
<223> OTHER INFORMATION: Linked to [19-carboxynonadecanoyl]
<220> FEATURE:
<221> NAME/KEY: DISULFID
<222> LOCATION: (3)..(8)
<223> OTHER INFORMATION: Sequence may possess an intramolecular
      disulphide bridge formed between the cysteine residues present at
      positions 3 and 8, corresponding to the cysteine residues present
      at positions 2 and 7 of human amylin. Feature is present in Compd.
      48.
<220> FEATURE:
<221> NAME/KEY: MOD_RES
<222> LOCATION: (23)..(23)
<223> OTHER INFORMATION: MeGly
<220> FEATURE:
<221> NAME/KEY: MOD_RES

```
<222> LOCATION: (25)..(25)
<223> OTHER INFORMATION: MeIle
<220> FEATURE:
<221> NAME/KEY: MOD_RES
<222> LOCATION: (36)..(36)
<223> OTHER INFORMATION: 4Hyp

<400> SEQUENCE: 149

Xaa Arg Cys Gly Thr Ala Thr Cys Ala Thr Glu Arg Leu Ala His Phe
 1               5                  10                  15

Leu Thr Arg Ser Ser Phe Gly Ala Ile Leu Ser Ser Thr Glu Val Gly
            20                  25                  30

Ser Thr Thr Pro
        35

<210> SEQ ID NO 150
<211> LENGTH: 36
<212> TYPE: PRT
<213> ORGANISM: Artificial sequence
<220> FEATURE:
<223> OTHER INFORMATION: Synthetic amylin analogue
<220> FEATURE:
<221> NAME/KEY: SITE
<222> LOCATION: (1)..(1)
<223> OTHER INFORMATION: Xaa is isoGlu
<220> FEATURE:
<221> NAME/KEY: SITE
<222> LOCATION: (1)..(1)
<223> OTHER INFORMATION: Linked to [19-carboxynonadecanoyl]
<220> FEATURE:
<221> NAME/KEY: DISULFID
<222> LOCATION: (3)..(8)
<223> OTHER INFORMATION: Sequence may possess an intramolecular
     disulphide bridge formed between the cysteine residues present at
     positions 3 and 8, corresponding to the cysteine residues present
     at positions 2 and 7 of human amylin. Feature is present in Compd.
     49.
<220> FEATURE:
<221> NAME/KEY: MOD_RES
<222> LOCATION: (23)..(23)
<223> OTHER INFORMATION: MeGly
<220> FEATURE:
<221> NAME/KEY: MOD_RES
<222> LOCATION: (25)..(25)
<223> OTHER INFORMATION: MeIle
<220> FEATURE:
<221> NAME/KEY: MOD_RES
<222> LOCATION: (36)..(36)
<223> OTHER INFORMATION: 4Hyp

<400> SEQUENCE: 150

Xaa Arg Cys Asn Thr Ala Thr Cys Ala Thr Gln Arg Leu Ala Asp Phe
 1               5                  10                  15

Leu Gln Arg Ser Ser Phe Gly Ala Ile Leu Ser Ser Thr Glu Val Gly
            20                  25                  30

Ser Asn Thr Pro
        35

<210> SEQ ID NO 151
<211> LENGTH: 36
<212> TYPE: PRT
<213> ORGANISM: Artificial sequence
<220> FEATURE:
<223> OTHER INFORMATION: Synthetic amylin analogue
<220> FEATURE:
<221> NAME/KEY: SITE
<222> LOCATION: (1)..(1)
<223> OTHER INFORMATION: Xaa is isoGlu
<220> FEATURE:
<221> NAME/KEY: SITE
<222> LOCATION: (1)..(1)
```

```
<223> OTHER INFORMATION: Linked to [19-carboxynonadecanoyl]
<220> FEATURE:
<221> NAME/KEY: DISULFID
<222> LOCATION: (3)..(8)
<223> OTHER INFORMATION: Sequence may possess an intramolecular
      disulphide bridge formed between the cysteine residues present at
      positions 3 and 8, corresponding to the cysteine residues present
      at positions 2 and 7 of human amylin. Feature is present in Compd.
      50.
<220> FEATURE:
<221> NAME/KEY: MOD_RES
<222> LOCATION: (18)..(18)
<223> OTHER INFORMATION: Aad
<220> FEATURE:
<221> NAME/KEY: MOD_RES
<222> LOCATION: (23)..(23)
<223> OTHER INFORMATION: MeGly
<220> FEATURE:
<221> NAME/KEY: MOD_RES
<222> LOCATION: (25)..(25)
<223> OTHER INFORMATION: MeIle
<220> FEATURE:
<221> NAME/KEY: MOD_RES
<222> LOCATION: (36)..(36)
<223> OTHER INFORMATION: 4Hyp

<400> SEQUENCE: 151

Xaa Arg Cys Asn Thr Ala Thr Cys Ala Thr Gln Arg Leu Ala His Phe
1               5                   10                  15

Leu Glu Arg Ser Ser Phe Gly Ala Ile Leu Ser Ser Thr Glu Val Gly
            20                  25                  30

Ser Asn Thr Pro
            35

<210> SEQ ID NO 152
<211> LENGTH: 36
<212> TYPE: PRT
<213> ORGANISM: Artificial sequence
<220> FEATURE:
<223> OTHER INFORMATION: Synthetic amylin analogue
<220> FEATURE:
<221> NAME/KEY: SITE
<222> LOCATION: (1)..(1)
<223> OTHER INFORMATION: Xaa is isoGlu
<220> FEATURE:
<221> NAME/KEY: SITE
<222> LOCATION: (1)..(1)
<223> OTHER INFORMATION: Linked to [19-carboxynonadecanoyl]
<220> FEATURE:
<221> NAME/KEY: DISULFID
<222> LOCATION: (3)..(8)
<223> OTHER INFORMATION: Sequence may possess an intramolecular
      disulphide bridge formed between the cysteine residues present at
      positions 3 and 8, corresponding to the cysteine residues present
      at positions 2 and 7 of human amylin. Feature is present in Compd.
      51.
<220> FEATURE:
<221> NAME/KEY: MOD_RES
<222> LOCATION: (23)..(23)
<223> OTHER INFORMATION: MeGly
<220> FEATURE:
<221> NAME/KEY: MOD_RES
<222> LOCATION: (25)..(25)
<223> OTHER INFORMATION: MeIle
<220> FEATURE:
<221> NAME/KEY: MOD_RES
<222> LOCATION: (34)..(34)
<223> OTHER INFORMATION: Orn
<220> FEATURE:
<221> NAME/KEY: MOD_RES
<222> LOCATION: (36)..(36)
<223> OTHER INFORMATION: 4Hyp

<400> SEQUENCE: 152
```

```
Xaa Arg Cys Gly Thr Ala Thr Cys Ala Thr Glu Arg Leu Ala His Phe
1               5                   10                  15

Leu Gln Arg Ser Ser Phe Gly Ala Ile Leu Ser Ser Thr Glu Val Gly
            20                  25                  30

Ser Arg Thr Pro
        35

<210> SEQ ID NO 153
<211> LENGTH: 36
<212> TYPE: PRT
<213> ORGANISM: Artificial sequence
<220> FEATURE:
<223> OTHER INFORMATION: Synthetic amylin analogue
<220> FEATURE:
<221> NAME/KEY: SITE
<222> LOCATION: (1)..(1)
<223> OTHER INFORMATION: Xaa is isoGlu
<220> FEATURE:
<221> NAME/KEY: SITE
<222> LOCATION: (1)..(1)
<223> OTHER INFORMATION: Linked to [19-carboxynonadecanoyl]
<220> FEATURE:
<221> NAME/KEY: DISULFID
<222> LOCATION: (3)..(8)
<223> OTHER INFORMATION: Sequence may possess an intramolecular
      disulphide bridge formed between the cysteine residues present at
      positions 3 and 8, corresponding to the cysteine residues present
      at positions 2 and 7 of human amylin. Feature is present in Compd.
      52.
<220> FEATURE:
<221> NAME/KEY: MOD_RES
<222> LOCATION: (23)..(23)
<223> OTHER INFORMATION: MeGly
<220> FEATURE:
<221> NAME/KEY: MOD_RES
<222> LOCATION: (25)..(25)
<223> OTHER INFORMATION: MeIle
<220> FEATURE:
<221> NAME/KEY: MOD_RES
<222> LOCATION: (36)..(36)
<223> OTHER INFORMATION: 4Hyp

<400> SEQUENCE: 153

Xaa Arg Cys Gly Thr Ala Thr Cys Ala Thr Glu Arg Leu Ala His Phe
1               5                   10                  15

Leu Gln Arg Ser Ser Phe Gly Ala Ile Leu Ser Ser Thr Glu Val Gly
            20                  25                  30

Ser Gly Thr Pro
        35

<210> SEQ ID NO 154
<211> LENGTH: 36
<212> TYPE: PRT
<213> ORGANISM: Artificial sequence
<220> FEATURE:
<223> OTHER INFORMATION: Synthetic amylin analogue
<220> FEATURE:
<221> NAME/KEY: SITE
<222> LOCATION: (1)..(1)
<223> OTHER INFORMATION: Xaa is isoGlu
<220> FEATURE:
<221> NAME/KEY: SITE
<222> LOCATION: (1)..(1)
<223> OTHER INFORMATION: Linked to [19-carboxynonadecanoyl]
<220> FEATURE:
<221> NAME/KEY: DISULFID
<222> LOCATION: (3)..(8)
<223> OTHER INFORMATION: Sequence may possess an intramolecular
      disulphide bridge formed between the cysteine residues present at
      positions 3 and 8, corresponding to the cysteine residues present
      at positions 2 and 7 of human amylin. Feature is present in Compd.
      53.
```

```
<220> FEATURE:
<221> NAME/KEY: MOD_RES
<222> LOCATION: (23)..(23)
<223> OTHER INFORMATION: MeGly
<220> FEATURE:
<221> NAME/KEY: MOD_RES
<222> LOCATION: (25)..(25)
<223> OTHER INFORMATION: MeIle
<220> FEATURE:
<221> NAME/KEY: MOD_RES
<222> LOCATION: (34)..(34)
<223> OTHER INFORMATION: Aad
<220> FEATURE:
<221> NAME/KEY: MOD_RES
<222> LOCATION: (36)..(36)
<223> OTHER INFORMATION: 4Hyp

<400> SEQUENCE: 154

Xaa Arg Cys Gly Thr Ala Thr Cys Ala Thr Glu Arg Leu Ala His Phe
1               5                   10                  15

Leu Gln Arg Ser Ser Phe Gly Ala Ile Leu Ser Ser Thr Glu Val Gly
            20                  25                  30

Ser Glu Thr Pro
            35

<210> SEQ ID NO 155
<211> LENGTH: 36
<212> TYPE: PRT
<213> ORGANISM: Artificial sequence
<220> FEATURE:
<223> OTHER INFORMATION: Synthetic amylin analogue
<220> FEATURE:
<221> NAME/KEY: SITE
<222> LOCATION: (1)..(1)
<223> OTHER INFORMATION: Xaa is isoGlu
<220> FEATURE:
<221> NAME/KEY: SITE
<222> LOCATION: (1)..(1)
<223> OTHER INFORMATION: Linked to [19-carboxynonadecanoyl]
<220> FEATURE:
<221> NAME/KEY: DISULFID
<222> LOCATION: (3)..(8)
<223> OTHER INFORMATION: Sequence may possess an intramolecular
      disulphide bridge formed between the cysteine residues present at
      positions 3 and 8, corresponding to the cysteine residues present
      at positions 2 and 7 of human amylin. Feature is present in Compd.
      54.
<220> FEATURE:
<221> NAME/KEY: MOD_RES
<222> LOCATION: (23)..(23)
<223> OTHER INFORMATION: MeGly
<220> FEATURE:
<221> NAME/KEY: MOD_RES
<222> LOCATION: (25)..(25)
<223> OTHER INFORMATION: MeIle
<220> FEATURE:
<221> NAME/KEY: MOD_RES
<222> LOCATION: (36)..(36)
<223> OTHER INFORMATION: 4Hyp

<400> SEQUENCE: 155

Xaa Arg Cys Gly Thr Ala Thr Cys Ala Thr Glu Arg Leu Ala Asp Phe
1               5                   10                  15

Leu Gln Arg Ser Ser Phe Gly Ala Ile Leu Ser Ser Thr Glu Val Gly
            20                  25                  30

Ser Asn Thr Pro
            35

<210> SEQ ID NO 156
<211> LENGTH: 36
<212> TYPE: PRT
```

```
<213> ORGANISM: Artificial sequence
<220> FEATURE:
<223> OTHER INFORMATION: Synthetic amylin analogue
<220> FEATURE:
<221> NAME/KEY: SITE
<222> LOCATION: (1)..(1)
<223> OTHER INFORMATION: Xaa is isoGlu
<220> FEATURE:
<221> NAME/KEY: SITE
<222> LOCATION: (1)..(1)
<223> OTHER INFORMATION: Linked to [19-carboxynonadecanoyl]
<220> FEATURE:
<221> NAME/KEY: DISULFID
<222> LOCATION: (3)..(8)
<223> OTHER INFORMATION: Sequence may possess an intramolecular
      disulphide bridge formed between the cysteine residues present at
      positions 3 and 8, corresponding to the cysteine residues present
      at positions 2 and 7 of human amylin. Feature is present in Compd.
      55.
<220> FEATURE:
<221> NAME/KEY: MOD_RES
<222> LOCATION: (15)..(15)
<223> OTHER INFORMATION: Aad
<220> FEATURE:
<221> NAME/KEY: MOD_RES
<222> LOCATION: (23)..(23)
<223> OTHER INFORMATION: MeGly
<220> FEATURE:
<221> NAME/KEY: MOD_RES
<222> LOCATION: (25)..(25)
<223> OTHER INFORMATION: MeIle
<220> FEATURE:
<221> NAME/KEY: MOD_RES
<222> LOCATION: (36)..(36)
<223> OTHER INFORMATION: 4Hyp

<400> SEQUENCE: 156

Xaa Arg Cys Gly Thr Ala Thr Cys Ala Thr Glu Arg Leu Ala Glu Phe
1               5                   10                  15

Leu Gln Arg Ser Ser Phe Gly Ala Ile Leu Ser Ser Thr Glu Val Gly
            20                  25                  30

Ser Asn Thr Pro
        35

<210> SEQ ID NO 157
<211> LENGTH: 36
<212> TYPE: PRT
<213> ORGANISM: Artificial sequence
<220> FEATURE:
<223> OTHER INFORMATION: Synthetic amylin analogue
<220> FEATURE:
<221> NAME/KEY: SITE
<222> LOCATION: (1)..(1)
<223> OTHER INFORMATION: Xaa is isoGlu
<220> FEATURE:
<221> NAME/KEY: SITE
<222> LOCATION: (1)..(1)
<223> OTHER INFORMATION: Linked to [19-carboxynonadecanoyl]
<220> FEATURE:
<221> NAME/KEY: DISULFID
<222> LOCATION: (3)..(8)
<223> OTHER INFORMATION: Sequence may possess an intramolecular
      disulphide bridge formed between the cysteine residues present at
      positions 3 and 8, corresponding to the cysteine residues present
      at positions 2 and 7 of human amylin. Feature is present in Compd.
      56.
<220> FEATURE:
<221> NAME/KEY: MOD_RES
<222> LOCATION: (23)..(23)
<223> OTHER INFORMATION: MeGly
<220> FEATURE:
<221> NAME/KEY: MOD_RES
<222> LOCATION: (25)..(25)
<223> OTHER INFORMATION: MeIle
<220> FEATURE:
```

```
<221> NAME/KEY: MOD_RES
<222> LOCATION: (36)..(36)
<223> OTHER INFORMATION: 4Hyp

<400> SEQUENCE: 157

Xaa Arg Cys Asn Thr Ala Thr Cys Ala Thr Glu Arg Leu Ala His Phe
1               5                   10                  15

Leu Gln Arg Ser Ser Phe Gly Ala Ile Leu Ser Ser Thr Glu Val Gly
            20                  25                  30

Ser Asn Thr Pro
        35

<210> SEQ ID NO 158
<211> LENGTH: 36
<212> TYPE: PRT
<213> ORGANISM: Artificial sequence
<220> FEATURE:
<223> OTHER INFORMATION: Synthetic amylin analogue
<220> FEATURE:
<221> NAME/KEY: SITE
<222> LOCATION: (1)..(1)
<223> OTHER INFORMATION: Xaa is isoGlu
<220> FEATURE:
<221> NAME/KEY: SITE
<222> LOCATION: (1)..(1)
<223> OTHER INFORMATION: Linked to [19-carboxynonadecanoyl]
<220> FEATURE:
<221> NAME/KEY: DISULFID
<222> LOCATION: (3)..(8)
<223> OTHER INFORMATION: Sequence may possess an intramolecular
      disulphide bridge formed between the cysteine residues present at
      positions 3 and 8, corresponding to the cysteine residues present
      at positions 2 and 7 of human amylin. Feature is present in Compd.
      57.
<220> FEATURE:
<221> NAME/KEY: MOD_RES
<222> LOCATION: (23)..(23)
<223> OTHER INFORMATION: MeGly
<220> FEATURE:
<221> NAME/KEY: MOD_RES
<222> LOCATION: (25)..(25)
<223> OTHER INFORMATION: MeIle
<220> FEATURE:
<221> NAME/KEY: MOD_RES
<222> LOCATION: (36)..(36)
<223> OTHER INFORMATION: 4Hyp

<400> SEQUENCE: 158

Xaa Arg Cys Gln Thr Ala Thr Cys Ala Thr Glu Arg Leu Ala His Phe
1               5                   10                  15

Leu Gln Arg Ser Ser Phe Gly Ala Ile Leu Ser Ser Thr Glu Val Gly
            20                  25                  30

Ser Asn Thr Pro
        35

<210> SEQ ID NO 159
<211> LENGTH: 36
<212> TYPE: PRT
<213> ORGANISM: Artificial sequence
<220> FEATURE:
<223> OTHER INFORMATION: Synthetic amylin analogue
<220> FEATURE:
<221> NAME/KEY: SITE
<222> LOCATION: (1)..(1)
<223> OTHER INFORMATION: Xaa is isoGlu
<220> FEATURE:
<221> NAME/KEY: SITE
<222> LOCATION: (1)..(1)
<223> OTHER INFORMATION: Linked to [19-carboxynonadecanoyl]
<220> FEATURE:
<221> NAME/KEY: DISULFID
```

```
<222> LOCATION: (3)..(8)
<223> OTHER INFORMATION: Sequence may possess an intramolecular
      disulphide bridge formed between the cysteine residues present at
      positions 3 and 8, corresponding to the cysteine residues present
      at positions 2 and 7 of human amylin. Feature is present in Compd.
      58.
<220> FEATURE:
<221> NAME/KEY: MOD_RES
<222> LOCATION: (23)..(23)
<223> OTHER INFORMATION: MeGly
<220> FEATURE:
<221> NAME/KEY: MOD_RES
<222> LOCATION: (25)..(25)
<223> OTHER INFORMATION: MeIle
<220> FEATURE:
<221> NAME/KEY: MOD_RES
<222> LOCATION: (36)..(36)
<223> OTHER INFORMATION: 4Hyp

<400> SEQUENCE: 159

Xaa Arg Cys Asn Thr Ala Thr Cys Ala Thr Gln Arg Leu Ala His Phe
1               5                   10                  15

Leu Gln Arg Ser Ser Phe Gly Ala Ile Leu Ser Ser Thr Glu Val Gly
            20                  25                  30

Ser Asn Thr Pro
        35

<210> SEQ ID NO 160
<211> LENGTH: 36
<212> TYPE: PRT
<213> ORGANISM: Artificial sequence
<220> FEATURE:
<223> OTHER INFORMATION: Synthetic amylin analogue
<220> FEATURE:
<221> NAME/KEY: SITE
<222> LOCATION: (1)..(1)
<223> OTHER INFORMATION: Xaa is isoGlu
<220> FEATURE:
<221> NAME/KEY: SITE
<222> LOCATION: (1)..(1)
<223> OTHER INFORMATION: Linked to [19-carboxynonadecanoyl]
<220> FEATURE:
<221> NAME/KEY: DISULFID
<222> LOCATION: (3)..(8)
<223> OTHER INFORMATION: Sequence may possess an intramolecular
      disulphide bridge formed between the cysteine residues present at
      positions 3 and 8, corresponding to the cysteine residues present
      at positions 2 and 7 of human amylin. Feature is present in Compd.
      59.
<220> FEATURE:
<221> NAME/KEY: MOD_RES
<222> LOCATION: (23)..(23)
<223> OTHER INFORMATION: MeGly
<220> FEATURE:
<221> NAME/KEY: MOD_RES
<222> LOCATION: (25)..(25)
<223> OTHER INFORMATION: MeIle
<220> FEATURE:
<221> NAME/KEY: MOD_RES
<222> LOCATION: (36)..(36)
<223> OTHER INFORMATION: 4Hyp

<400> SEQUENCE: 160

Xaa Arg Cys Pro Thr Ala Thr Cys Ala Thr Asp Arg Leu Ala His Phe
1               5                   10                  15

Leu Gln Arg Ser Ser Phe Gly Ala Ile Leu Ser Ser Thr Asp Val Gly
            20                  25                  30

Ser Asn Thr Pro
        35

<210> SEQ ID NO 161
```

```
<211> LENGTH: 36
<212> TYPE: PRT
<213> ORGANISM: Artificial sequence
<220> FEATURE:
<223> OTHER INFORMATION: Synthetic amylin analogue
<220> FEATURE:
<221> NAME/KEY: SITE
<222> LOCATION: (1)..(1)
<223> OTHER INFORMATION: Xaa is isoGlu
<220> FEATURE:
<221> NAME/KEY: SITE
<222> LOCATION: (1)..(1)
<223> OTHER INFORMATION: Linked to [19-carboxynonadecanoyl]
<220> FEATURE:
<221> NAME/KEY: DISULFID
<222> LOCATION: (3)..(8)
<223> OTHER INFORMATION: Sequence may possess an intramolecular
      disulphide bridge formed between the cysteine residues present at
      positions 3 and 8, corresponding to the cysteine residues present
      at positions 2 and 7 of human amylin. Feature is present in Compd.
      60.
<220> FEATURE:
<221> NAME/KEY: MOD_RES
<222> LOCATION: (23)..(23)
<223> OTHER INFORMATION: MeGly
<220> FEATURE:
<221> NAME/KEY: MOD_RES
<222> LOCATION: (25)..(25)
<223> OTHER INFORMATION: MeIle
<220> FEATURE:
<221> NAME/KEY: MOD_RES
<222> LOCATION: (36)..(36)
<223> OTHER INFORMATION: 4Hyp

<400> SEQUENCE: 161

Xaa Arg Cys Asn Thr Ala Thr Cys Ala Thr Glu Arg Leu Ala His Phe
 1               5                  10                  15

Leu Gln Arg Ser Ser Phe Gly Ala Ile Leu Ser Ser Thr Glu Val Gly
            20                  25                  30

Ser Asp Thr Pro
        35

<210> SEQ ID NO 162
<211> LENGTH: 36
<212> TYPE: PRT
<213> ORGANISM: Artificial sequence
<220> FEATURE:
<223> OTHER INFORMATION: Synthetic amylin analogue
<220> FEATURE:
<221> NAME/KEY: SITE
<222> LOCATION: (1)..(1)
<223> OTHER INFORMATION: Xaa is isoGlu
<220> FEATURE:
<221> NAME/KEY: SITE
<222> LOCATION: (1)..(1)
<223> OTHER INFORMATION: Linked to [19-carboxynonadecanoyl]
<220> FEATURE:
<221> NAME/KEY: DISULFID
<222> LOCATION: (3)..(8)
<223> OTHER INFORMATION: Sequence may possess an intramolecular
      disulphide bridge formed between the cysteine residues present at
      positions 3 and 8, corresponding to the cysteine residues present
      at positions 2 and 7 of human amylin. Feature is present in Compd.
      61.
<220> FEATURE:
<221> NAME/KEY: MOD_RES
<222> LOCATION: (23)..(23)
<223> OTHER INFORMATION: MeGly
<220> FEATURE:
<221> NAME/KEY: MOD_RES
<222> LOCATION: (25)..(25)
<223> OTHER INFORMATION: MeIle

<400> SEQUENCE: 162
```

Xaa Arg Cys Asn Thr Ala Thr Cys Ala Thr Gln Arg Leu Ala His Phe
1               5                   10                  15

Leu Gln Arg Ser Ser Phe Gly Ala Ile Leu Ser Ser Thr Glu Val Gly
            20                  25                  30

Ser Asn Thr Pro
        35

<210> SEQ ID NO 163
<211> LENGTH: 36
<212> TYPE: PRT
<213> ORGANISM: Artificial sequence
<220> FEATURE:
<223> OTHER INFORMATION: Synthetic amylin analogue
<220> FEATURE:
<221> NAME/KEY: SITE
<222> LOCATION: (1)..(1)
<223> OTHER INFORMATION: Xaa is isoGlu
<220> FEATURE:
<221> NAME/KEY: SITE
<222> LOCATION: (1)..(1)
<223> OTHER INFORMATION: Linked to [19-carboxynonadecanoyl]
<220> FEATURE:
<221> NAME/KEY: DISULFID
<222> LOCATION: (3)..(8)
<223> OTHER INFORMATION: Sequence may possess an intramolecular
      disulphide bridge formed between the cysteine residues present at
      positions 3 and 8, corresponding to the cysteine residues present
      at positions 2 and 7 of human amylin. Feature is present in Compd.
      62.
<220> FEATURE:
<221> NAME/KEY: MOD_RES
<222> LOCATION: (23)..(23)
<223> OTHER INFORMATION: MeGly
<220> FEATURE:
<221> NAME/KEY: MOD_RES
<222> LOCATION: (25)..(25)
<223> OTHER INFORMATION: MeIle

<400> SEQUENCE: 163

Xaa Arg Cys Asn Thr Ala Thr Cys Ala Thr Glu Arg Leu Ala His Phe
1               5                   10                  15

Leu Gln Arg Ser Ser Phe Gly Ala Ile Leu Ser Ser Thr Glu Val Gly
            20                  25                  30

Ser Asn Thr Pro
        35

<210> SEQ ID NO 164
<211> LENGTH: 36
<212> TYPE: PRT
<213> ORGANISM: Artificial sequence
<220> FEATURE:
<223> OTHER INFORMATION: Synthetic amylin analogue
<220> FEATURE:
<221> NAME/KEY: SITE
<222> LOCATION: (1)..(1)
<223> OTHER INFORMATION: Xaa is isoGlu
<220> FEATURE:
<221> NAME/KEY: SITE
<222> LOCATION: (1)..(1)
<223> OTHER INFORMATION: Linked to [19-carboxynonadecanoyl]
<220> FEATURE:
<221> NAME/KEY: DISULFID
<222> LOCATION: (3)..(8)
<223> OTHER INFORMATION: Sequence may possess an intramolecular
      disulphide bridge formed between the cysteine residues present at
      positions 3 and 8, corresponding to the cysteine residues present
      at positions 2 and 7 of human amylin. Feature is present in Compd.
      63.
<220> FEATURE:
<221> NAME/KEY: MOD_RES
<222> LOCATION: (23)..(23)
<223> OTHER INFORMATION: MeGly

```
<220> FEATURE:
<221> NAME/KEY: MOD_RES
<222> LOCATION: (25)..(25)
<223> OTHER INFORMATION: MeIle
<220> FEATURE:
<221> NAME/KEY: MOD_RES
<222> LOCATION: (36)..(36)
<223> OTHER INFORMATION: 4Hyp

<400> SEQUENCE: 164

Xaa Arg Cys Pro Thr Ala Thr Cys Ala Thr Glu Arg Leu Ala His Phe
1               5                   10                  15

Leu Gln Arg Ser Ser Phe Gly Ala Ile Leu Ser Ser Thr Glu Val Gly
            20                  25                  30

Ser Asn Thr Pro
        35

<210> SEQ ID NO 165
<211> LENGTH: 36
<212> TYPE: PRT
<213> ORGANISM: Artificial sequence
<220> FEATURE:
<223> OTHER INFORMATION: Synthetic amylin analogue
<220> FEATURE:
<221> NAME/KEY: SITE
<222> LOCATION: (1)..(1)
<223> OTHER INFORMATION: Xaa is isoGlu
<220> FEATURE:
<221> NAME/KEY: SITE
<222> LOCATION: (1)..(1)
<223> OTHER INFORMATION: Linked to [19-carboxynonadecanoyl]
<220> FEATURE:
<221> NAME/KEY: DISULFID
<222> LOCATION: (3)..(8)
<223> OTHER INFORMATION: Sequence may possess an intramolecular
      disulphide bridge formed between the cysteine residues present at
      positions 3 and 8, corresponding to the cysteine residues present
      at positions 2 and 7 of human amylin. Feature is present in Compd.
      64.
<220> FEATURE:
<221> NAME/KEY: MOD_RES
<222> LOCATION: (23)..(23)
<223> OTHER INFORMATION: MeGly
<220> FEATURE:
<221> NAME/KEY: MOD_RES
<222> LOCATION: (25)..(25)
<223> OTHER INFORMATION: MeIle
<220> FEATURE:
<221> NAME/KEY: MOD_RES
<222> LOCATION: (36)..(36)
<223> OTHER INFORMATION: 4Hyp

<400> SEQUENCE: 165

Xaa Arg Cys Pro Thr Ala Thr Cys Ala Thr Gln Arg Leu Ala His Phe
1               5                   10                  15

Leu Gln Arg Ser Ser Phe Gly Ala Ile Leu Ser Ser Thr Glu Val Gly
            20                  25                  30

Ser Asn Thr Pro
        35

<210> SEQ ID NO 166
<211> LENGTH: 36
<212> TYPE: PRT
<213> ORGANISM: Artificial sequence
<220> FEATURE:
<223> OTHER INFORMATION: Synthetic amylin analogue
<220> FEATURE:
<221> NAME/KEY: SITE
<222> LOCATION: (1)..(1)
<223> OTHER INFORMATION: Xaa is isoGlu
<220> FEATURE:
```

```
<221> NAME/KEY: SITE
<222> LOCATION: (1)..(1)
<223> OTHER INFORMATION: Linked to [19-carboxynonadecanoyl]
<220> FEATURE:
<221> NAME/KEY: DISULFID
<222> LOCATION: (3)..(8)
<223> OTHER INFORMATION: Sequence may possess an intramolecular
      disulphide bridge formed between the cysteine residues present at
      positions 3 and 8, corresponding to the cysteine residues present
      at positions 2 and 7 of human amylin. Feature is present in Compd.
      65.
<220> FEATURE:
<221> NAME/KEY: MOD_RES
<222> LOCATION: (23)..(23)
<223> OTHER INFORMATION: MeGly
<220> FEATURE:
<221> NAME/KEY: MOD_RES
<222> LOCATION: (25)..(25)
<223> OTHER INFORMATION: MeIle

<400> SEQUENCE: 166

Xaa Arg Cys Asn Thr Ala Thr Cys Ala Thr Gln Arg Leu Ala Asp Phe
1               5                   10                  15

Leu Gln Arg Ser Ser Phe Gly Ala Ile Leu Ser Ser Thr Glu Val Gly
            20                  25                  30

Ser Asn Thr Pro
        35

<210> SEQ ID NO 167
<211> LENGTH: 36
<212> TYPE: PRT
<213> ORGANISM: Artificial sequence
<220> FEATURE:
<223> OTHER INFORMATION: Synthetic amylin analogue
<220> FEATURE:
<221> NAME/KEY: SITE
<222> LOCATION: (1)..(1)
<223> OTHER INFORMATION: Xaa is isoGlu
<220> FEATURE:
<221> NAME/KEY: SITE
<222> LOCATION: (1)..(1)
<223> OTHER INFORMATION: Linked to [19-carboxynonadecanoyl]
<220> FEATURE:
<221> NAME/KEY: DISULFID
<222> LOCATION: (3)..(8)
<223> OTHER INFORMATION: Sequence may possess an intramolecular
      disulphide bridge formed between the cysteine residues present at
      positions 3 and 8, corresponding to the cysteine residues present
      at positions 2 and 7 of human amylin. Feature is present in Compd.
      66.
<220> FEATURE:
<221> NAME/KEY: MOD_RES
<222> LOCATION: (23)..(23)
<223> OTHER INFORMATION: MeGly
<220> FEATURE:
<221> NAME/KEY: MOD_RES
<222> LOCATION: (25)..(25)
<223> OTHER INFORMATION: MeIle

<400> SEQUENCE: 167

Xaa Arg Cys Asn Thr Ala Thr Cys Ala Thr Glu Arg Leu Ala Asp Phe
1               5                   10                  15

Leu Gln Arg Ser Ser Phe Gly Ala Ile Leu Ser Ser Thr Glu Val Gly
            20                  25                  30

Ser Asn Thr Pro
        35

<210> SEQ ID NO 168
<211> LENGTH: 36
<212> TYPE: PRT
<213> ORGANISM: Artificial sequence
```

```
<220> FEATURE:
<223> OTHER INFORMATION: Synthetic amylin analogue
<220> FEATURE:
<221> NAME/KEY: SITE
<222> LOCATION: (1)..(1)
<223> OTHER INFORMATION: Xaa is isoGlu
<220> FEATURE:
<221> NAME/KEY: SITE
<222> LOCATION: (1)..(1)
<223> OTHER INFORMATION: Linked to [19-carboxynonadecanoyl]
<220> FEATURE:
<221> NAME/KEY: DISULFID
<222> LOCATION: (3)..(8)
<223> OTHER INFORMATION: Sequence may possess an intramolecular
      disulphide bridge formed between the cysteine residues present at
      positions 3 and 8, corresponding to the cysteine residues present
      at positions 2 and 7 of human amylin. Feature is present in Compd.
      67.
<220> FEATURE:
<221> NAME/KEY: MOD_RES
<222> LOCATION: (23)..(23)
<223> OTHER INFORMATION: MeGly
<220> FEATURE:
<221> NAME/KEY: MOD_RES
<222> LOCATION: (25)..(25)
<223> OTHER INFORMATION: MeIle

<400> SEQUENCE: 168

Xaa Arg Cys Pro Thr Ala Thr Cys Ala Thr Glu Arg Leu Ala Asp Phe
1               5                   10                  15

Leu Gln Arg Ser Ser Phe Gly Ala Ile Leu Ser Ser Thr Glu Val Gly
            20                  25                  30

Ser Asn Thr Pro
            35

<210> SEQ ID NO 169
<211> LENGTH: 36
<212> TYPE: PRT
<213> ORGANISM: Artificial sequence
<220> FEATURE:
<223> OTHER INFORMATION: Synthetic amylin analogue
<220> FEATURE:
<221> NAME/KEY: SITE
<222> LOCATION: (1)..(1)
<223> OTHER INFORMATION: Xaa is isoGlu
<220> FEATURE:
<221> NAME/KEY: SITE
<222> LOCATION: (1)..(1)
<223> OTHER INFORMATION: Linked to [19-carboxynonadecanoyl]
<220> FEATURE:
<221> NAME/KEY: DISULFID
<222> LOCATION: (3)..(8)
<223> OTHER INFORMATION: Sequence may possess an intramolecular
      disulphide bridge formed between the cysteine residues present at
      positions 3 and 8, corresponding to the cysteine residues present
      at positions 2 and 7 of human amylin. Feature is present in Compd.
      68.
<220> FEATURE:
<221> NAME/KEY: MOD_RES
<222> LOCATION: (23)..(23)
<223> OTHER INFORMATION: MeGly
<220> FEATURE:
<221> NAME/KEY: MOD_RES
<222> LOCATION: (25)..(25)
<223> OTHER INFORMATION: MeIle
<220> FEATURE:
<221> NAME/KEY: MOD_RES
<222> LOCATION: (36)..(36)
<223> OTHER INFORMATION: 4Hyp

<400> SEQUENCE: 169

Xaa Arg Cys Asn Thr Ala Thr Cys Ala Thr Glu Arg Leu Ala Asp Phe
1               5                   10                  15
```

```
Leu Gln Arg Ser Ser Phe Gly Ala Ile Leu Ser Ser Thr Glu Val Gly
            20                  25                  30

Ser Asn Thr Pro
        35

<210> SEQ ID NO 170
<211> LENGTH: 36
<212> TYPE: PRT
<213> ORGANISM: Artificial sequence
<220> FEATURE:
<223> OTHER INFORMATION: Synthetic amylin analogue
<220> FEATURE:
<221> NAME/KEY: SITE
<222> LOCATION: (1)..(1)
<223> OTHER INFORMATION: Xaa is isoGlu
<220> FEATURE:
<221> NAME/KEY: SITE
<222> LOCATION: (1)..(1)
<223> OTHER INFORMATION: Linked to [19-carboxynonadecanoyl]
<220> FEATURE:
<221> NAME/KEY: DISULFID
<222> LOCATION: (3)..(8)
<223> OTHER INFORMATION: Sequence may possess an intramolecular
      disulphide bridge formed between the cysteine residues present at
      positions 3 and 8, corresponding to the cysteine residues present
      at positions 2 and 7 of human amylin. Feature is present in Compd.
      69.
<220> FEATURE:
<221> NAME/KEY: MOD_RES
<222> LOCATION: (23)..(23)
<223> OTHER INFORMATION: MeGly
<220> FEATURE:
<221> NAME/KEY: MOD_RES
<222> LOCATION: (25)..(25)
<223> OTHER INFORMATION: MeIle
<220> FEATURE:
<221> NAME/KEY: MOD_RES
<222> LOCATION: (36)..(36)
<223> OTHER INFORMATION: 4Hyp

<400> SEQUENCE: 170

Xaa Arg Cys Asn Thr Ala Thr Cys Ala Thr Gln Arg Leu Ala His Phe
1               5                   10                  15

Leu Gln Arg Ser Ser Phe Gly Ala Ile Leu Ser Ser Thr Glu Val Gly
            20                  25                  30

Ser Ser Thr Pro
        35

<210> SEQ ID NO 171
<211> LENGTH: 36
<212> TYPE: PRT
<213> ORGANISM: Artificial sequence
<220> FEATURE:
<223> OTHER INFORMATION: Synthetic amylin analogue
<220> FEATURE:
<221> NAME/KEY: SITE
<222> LOCATION: (1)..(1)
<223> OTHER INFORMATION: Xaa is isoGlu
<220> FEATURE:
<221> NAME/KEY: SITE
<222> LOCATION: (1)..(1)
<223> OTHER INFORMATION: Linked to [19-carboxynonadecanoyl]
<220> FEATURE:
<221> NAME/KEY: DISULFID
<222> LOCATION: (3)..(8)
<223> OTHER INFORMATION: Sequence may possess an intramolecular
      disulphide bridge formed between the cysteine residues present at
      positions 3 and 8, corresponding to the cysteine residues present
      at positions 2 and 7 of human amylin. Feature is present in Compd.
      70.
<220> FEATURE:
<221> NAME/KEY: MOD_RES
<222> LOCATION: (23)..(23)
```

```
<223> OTHER INFORMATION: MeGly
<220> FEATURE:
<221> NAME/KEY: MOD_RES
<222> LOCATION: (25)..(25)
<223> OTHER INFORMATION: MeIle
<220> FEATURE:
<221> NAME/KEY: MOD_RES
<222> LOCATION: (36)..(36)
<223> OTHER INFORMATION: 4Hyp

<400> SEQUENCE: 171

Xaa Arg Cys Pro Thr Ala Thr Cys Ala Thr Glu Arg Leu Ala His Phe
 1               5                  10                  15

Leu Gln Arg Ser Ser Phe Gly Ala Ile Leu Ser Ser Thr Glu Val Gly
             20                  25                  30

Ser Ser Thr Pro
         35

<210> SEQ ID NO 172
<211> LENGTH: 36
<212> TYPE: PRT
<213> ORGANISM: Artificial sequence
<220> FEATURE:
<223> OTHER INFORMATION: Synthetic amylin analogue
<220> FEATURE:
<221> NAME/KEY: SITE
<222> LOCATION: (1)..(1)
<223> OTHER INFORMATION: Xaa is isoGlu
<220> FEATURE:
<221> NAME/KEY: SITE
<222> LOCATION: (1)..(1)
<223> OTHER INFORMATION: Linked to [19-carboxynonadecanoyl]
<220> FEATURE:
<221> NAME/KEY: DISULFID
<222> LOCATION: (3)..(8)
<223> OTHER INFORMATION: Sequence may possess an intramolecular
      disulphide bridge formed between the cysteine residues present at
      positions 3 and 8, corresponding to the cysteine residues present
      at positions 2 and 7 of human amylin. Feature is present in Compd.
      71.
<220> FEATURE:
<221> NAME/KEY: MOD_RES
<222> LOCATION: (23)..(23)
<223> OTHER INFORMATION: MeGly
<220> FEATURE:
<221> NAME/KEY: MOD_RES
<222> LOCATION: (25)..(25)
<223> OTHER INFORMATION: MeIle
<220> FEATURE:
<221> NAME/KEY: MOD_RES
<222> LOCATION: (36)..(36)
<223> OTHER INFORMATION: 4Hyp

<400> SEQUENCE: 172

Xaa Arg Cys Asn Thr Ala Thr Cys Ala Thr Gln Arg Leu Ala His Phe
 1               5                  10                  15

Leu Gln Arg Ser Ser Phe Gly Ala Ile Leu Ser Ser Thr Glu Val Gly
             20                  25                  30

Ser Gly Thr Pro
         35

<210> SEQ ID NO 173
<211> LENGTH: 36
<212> TYPE: PRT
<213> ORGANISM: Artificial sequence
<220> FEATURE:
<223> OTHER INFORMATION: Synthetic amylin analogue
<220> FEATURE:
<221> NAME/KEY: SITE
<222> LOCATION: (1)..(1)
<223> OTHER INFORMATION: Xaa is isoGlu
```

```
<220> FEATURE:
<221> NAME/KEY: SITE
<222> LOCATION: (1)..(1)
<223> OTHER INFORMATION: Linked to [19-carboxynonadecanoyl]
<220> FEATURE:
<221> NAME/KEY: DISULFID
<222> LOCATION: (3)..(8)
<223> OTHER INFORMATION: Sequence may possess an intramolecular
      disulphide bridge formed between the cysteine residues present at
      positions 3 and 8, corresponding to the cysteine residues present
      at positions 2 and 7 of human amylin. Feature is present in Compd.
      72.
<220> FEATURE:
<221> NAME/KEY: MOD_RES
<222> LOCATION: (23)..(23)
<223> OTHER INFORMATION: MeGly
<220> FEATURE:
<221> NAME/KEY: MOD_RES
<222> LOCATION: (25)..(25)
<223> OTHER INFORMATION: MeIle
<220> FEATURE:
<221> NAME/KEY: MOD_RES
<222> LOCATION: (36)..(36)
<223> OTHER INFORMATION: 4Hyp

<400> SEQUENCE: 173

Xaa Arg Cys Pro Thr Ala Thr Cys Ala Thr Glu Arg Leu Ala His Phe
1               5                   10                  15

Leu Gln Arg Ser Ser Phe Gly Ala Ile Leu Ser Ser Thr Glu Val Gly
            20                  25                  30

Ser Gly Thr Pro
        35

<210> SEQ ID NO 174
<211> LENGTH: 36
<212> TYPE: PRT
<213> ORGANISM: Artificial sequence
<220> FEATURE:
<223> OTHER INFORMATION: Synthetic amylin analogue
<220> FEATURE:
<221> NAME/KEY: SITE
<222> LOCATION: (1)..(1)
<223> OTHER INFORMATION: Xaa is isoGlu
<220> FEATURE:
<221> NAME/KEY: SITE
<222> LOCATION: (1)..(1)
<223> OTHER INFORMATION: Linked to [19-carboxynonadecanoyl]
<220> FEATURE:
<221> NAME/KEY: DISULFID
<222> LOCATION: (3)..(8)
<223> OTHER INFORMATION: Sequence may possess an intramolecular
      disulphide bridge formed between the cysteine residues present at
      positions 3 and 8, corresponding to the cysteine residues present
      at positions 2 and 7 of human amylin. Feature is present in Compd.
      73.
<220> FEATURE:
<221> NAME/KEY: MOD_RES
<222> LOCATION: (23)..(23)
<223> OTHER INFORMATION: MeGly
<220> FEATURE:
<221> NAME/KEY: MOD_RES
<222> LOCATION: (25)..(25)
<223> OTHER INFORMATION: MeIle
<220> FEATURE:
<221> NAME/KEY: MOD_RES
<222> LOCATION: (36)..(36)
<223> OTHER INFORMATION: 4Hyp

<400> SEQUENCE: 174

Xaa Arg Cys Asn Thr Ala Thr Cys Ala Thr Gln Arg Leu Ala His Phe
1               5                   10                  15

Leu Gln Arg Ser Ser Phe Gly Ala Ile Leu Ser Ser Thr Glu Val Gly
            20                  25                  30
```

Ser Thr Thr Pro
        35

<210> SEQ ID NO 175
<211> LENGTH: 36
<212> TYPE: PRT
<213> ORGANISM: Artificial sequence
<220> FEATURE:
<223> OTHER INFORMATION: Synthetic amylin analogue
<220> FEATURE:
<221> NAME/KEY: SITE
<222> LOCATION: (1)..(1)
<223> OTHER INFORMATION: Xaa is isoGlu
<220> FEATURE:
<221> NAME/KEY: SITE
<222> LOCATION: (1)..(1)
<223> OTHER INFORMATION: Linked to [19-carboxynonadecanoyl]
<220> FEATURE:
<221> NAME/KEY: DISULFID
<222> LOCATION: (3)..(8)
<223> OTHER INFORMATION: Sequence may possess an intramolecular
      disulphide bridge formed between the cysteine residues present at
      positions 3 and 8, corresponding to the cysteine residues present
      at positions 2 and 7 of human amylin. Feature is present in Compd.
      74.
<220> FEATURE:
<221> NAME/KEY: MOD_RES
<222> LOCATION: (23)..(23)
<223> OTHER INFORMATION: MeGly
<220> FEATURE:
<221> NAME/KEY: MOD_RES
<222> LOCATION: (25)..(25)
<223> OTHER INFORMATION: MeIle
<220> FEATURE:
<221> NAME/KEY: MOD_RES
<222> LOCATION: (36)..(36)
<223> OTHER INFORMATION: 4Hyp

<400> SEQUENCE: 175

Xaa Arg Cys Pro Thr Ala Thr Cys Ala Thr Glu Arg Leu Ala His Phe
1               5                   10                  15

Leu Gln Arg Ser Ser Phe Gly Ala Ile Leu Ser Ser Thr Glu Val Gly
            20                  25                  30

Ser Thr Thr Pro
        35

<210> SEQ ID NO 176
<211> LENGTH: 36
<212> TYPE: PRT
<213> ORGANISM: Artificial sequence
<220> FEATURE:
<223> OTHER INFORMATION: Synthetic amylin analogue
<220> FEATURE:
<221> NAME/KEY: SITE
<222> LOCATION: (1)..(1)
<223> OTHER INFORMATION: Xaa is isoGlu
<220> FEATURE:
<221> NAME/KEY: SITE
<222> LOCATION: (1)..(1)
<223> OTHER INFORMATION: Linked to [19-carboxynonadecanoyl]
<220> FEATURE:
<221> NAME/KEY: DISULFID
<222> LOCATION: (3)..(8)
<223> OTHER INFORMATION: Sequence may possess an intramolecular
      disulphide bridge formed between the cysteine residues present at
      positions 3 and 8, corresponding to the cysteine residues present
      at positions 2 and 7 of human amylin. Feature is present in Compd.
      75.
<220> FEATURE:
<221> NAME/KEY: MOD_RES
<222> LOCATION: (23)..(23)
<223> OTHER INFORMATION: MeGly
<220> FEATURE:

```
<221> NAME/KEY: MOD_RES
<222> LOCATION: (25)..(25)
<223> OTHER INFORMATION: MeIle
<220> FEATURE:
<221> NAME/KEY: MOD_RES
<222> LOCATION: (34)..(34)
<223> OTHER INFORMATION: Aad
<220> FEATURE:
<221> NAME/KEY: MOD_RES
<222> LOCATION: (36)..(36)
<223> OTHER INFORMATION: Hyp

<400> SEQUENCE: 176

Xaa Arg Cys Asn Thr Ala Thr Cys Ala Thr Gln Arg Leu Ala His Phe
1               5                   10                  15

Leu Gln Arg Ser Ser Phe Gly Ala Ile Leu Ser Ser Thr Glu Val Gly
            20                  25                  30

Ser Glu Thr Pro
        35

<210> SEQ ID NO 177
<211> LENGTH: 36
<212> TYPE: PRT
<213> ORGANISM: Artificial sequence
<220> FEATURE:
<223> OTHER INFORMATION: Synthetic amylin analogue
<220> FEATURE:
<221> NAME/KEY: SITE
<222> LOCATION: (1)..(1)
<223> OTHER INFORMATION: Xaa is isoGlu
<220> FEATURE:
<221> NAME/KEY: SITE
<222> LOCATION: (1)..(1)
<223> OTHER INFORMATION: Linked to [19-carboxynonadecanoyl]
<220> FEATURE:
<221> NAME/KEY: DISULFID
<222> LOCATION: (3)..(8)
<223> OTHER INFORMATION: Sequence may possess an intramolecular
      disulphide bridge formed between the cysteine residues present
      at positions 3 and 8, corresponding to the cysteine residues present
      at positions 2 and 7 of human amylin. Feature is present in Compd.
      76.
<220> FEATURE:
<221> NAME/KEY: MOD_RES
<222> LOCATION: (23)..(23)
<223> OTHER INFORMATION: MeGly
<220> FEATURE:
<221> NAME/KEY: MOD_RES
<222> LOCATION: (25)..(25)
<223> OTHER INFORMATION: MeIle
<220> FEATURE:
<221> NAME/KEY: MOD_RES
<222> LOCATION: (34)..(34)
<223> OTHER INFORMATION: Aad
<220> FEATURE:
<221> NAME/KEY: MOD_RES
<222> LOCATION: (36)..(36)
<223> OTHER INFORMATION: Hyp

<400> SEQUENCE: 177

Xaa Arg Cys Pro Thr Ala Thr Cys Ala Thr Glu Arg Leu Ala His Phe
1               5                   10                  15

Leu Gln Arg Ser Ser Phe Gly Ala Ile Leu Ser Ser Thr Glu Val Gly
            20                  25                  30

Ser Glu Thr Pro
        35

<210> SEQ ID NO 178
<211> LENGTH: 34
<212> TYPE: PRT
<213> ORGANISM: Artificial sequence
```

```
<220> FEATURE:
<223> OTHER INFORMATION: Synthetic amylin analogue
<220> FEATURE:
<221> NAME/KEY: SITE
<222> LOCATION: (1)..(1)
<223> OTHER INFORMATION: Xaa is isoGlu
<220> FEATURE:
<221> NAME/KEY: SITE
<222> LOCATION: (1)..(1)
<223> OTHER INFORMATION: Linked to [19-carboxynonadecanoyl]
<220> FEATURE:
<221> NAME/KEY: DISULFID
<222> LOCATION: (3)..(8)
<223> OTHER INFORMATION: Sequence may possess an intramolecular
      disulphide bridge formed between the cysteine residues present at
      positions 3 and 8, corresponding to the cysteine residues present
      at positions 2 and 7 of human amylin. Feature is present in Compd.
      77.
<220> FEATURE:
<221> NAME/KEY: MOD_RES
<222> LOCATION: (21)..(21)
<223> OTHER INFORMATION: MeGly
<220> FEATURE:
<221> NAME/KEY: MOD_RES
<222> LOCATION: (23)..(23)
<223> OTHER INFORMATION: MeIle
<220> FEATURE:
<221> NAME/KEY: MOD_RES
<222> LOCATION: (34)..(34)
<223> OTHER INFORMATION: 4Hyp

<400> SEQUENCE: 178

Xaa Arg Cys Gly Thr Ala Thr Cys Ala Thr Glu Arg Leu Ala His Phe
1               5                   10                  15

Leu Gln Arg Phe Gly Ala Ile Leu Ser Ser Thr Glu Val Gly Ser Asn
            20                  25                  30

Thr Pro

<210> SEQ ID NO 179
<211> LENGTH: 36
<212> TYPE: PRT
<213> ORGANISM: Artificial sequence
<220> FEATURE:
<223> OTHER INFORMATION: Synthetic amylin analogue
<220> FEATURE:
<221> NAME/KEY: SITE
<222> LOCATION: (1)..(1)
<223> OTHER INFORMATION: Xaa is isoGlu
<220> FEATURE:
<221> NAME/KEY: SITE
<222> LOCATION: (1)..(1)
<223> OTHER INFORMATION: Linked to [19-carboxynonadecanoyl]
<220> FEATURE:
<221> NAME/KEY: DISULFID
<222> LOCATION: (3)..(8)
<223> OTHER INFORMATION: Sequence may possess an intramolecular
      disulphide bridge formed between the cysteine residues present at
      positions 3 and 8, corresponding to the cysteine residues present
      at positions 2 and 7 of human amylin. Feature is present in Compd.
      78.
<220> FEATURE:
<221> NAME/KEY: MOD_RES
<222> LOCATION: (23)..(23)
<223> OTHER INFORMATION: MeGly
<220> FEATURE:
<221> NAME/KEY: MOD_RES
<222> LOCATION: (25)..(25)
<223> OTHER INFORMATION: MeIle

<400> SEQUENCE: 179

Xaa Arg Cys Gly Thr Ala Thr Cys Ala Thr Glu Arg Leu Ala His Phe
1               5                   10                  15

Leu Gln Arg Ser Ser Phe Gly Ala Ile Leu Ser Ser Thr Glu Val Gly
```

```
                    20                  25                  30

Ser Asn Thr Pro
        35

<210> SEQ ID NO 180
<211> LENGTH: 34
<212> TYPE: PRT
<213> ORGANISM: Artificial sequence
<220> FEATURE:
<223> OTHER INFORMATION: Synthetic amylin analogue
<220> FEATURE:
<221> NAME/KEY: SITE
<222> LOCATION: (1)..(1)
<223> OTHER INFORMATION: Xaa is isoGlu
<220> FEATURE:
<221> NAME/KEY: SITE
<222> LOCATION: (1)..(1)
<223> OTHER INFORMATION: Linked to [19-carboxynonadecanoyl]
<220> FEATURE:
<221> NAME/KEY: DISULFID
<222> LOCATION: (3)..(8)
<223> OTHER INFORMATION: Sequence may possess an intramolecular
      disulphide bridge formed between the cysteine residues present at
      positions 3 and 8, corresponding to the cysteine residues present
      at positions 2 and 7 of human amylin. Feature is present in Compd.
      79.
<220> FEATURE:
<221> NAME/KEY: MOD_RES
<222> LOCATION: (21)..(21)
<223> OTHER INFORMATION: MeGly
<220> FEATURE:
<221> NAME/KEY: MOD_RES
<222> LOCATION: (23)..(23)
<223> OTHER INFORMATION: MeIle
<220> FEATURE:
<221> NAME/KEY: MOD_RES
<222> LOCATION: (34)..(34)
<223> OTHER INFORMATION: 4Hyp

<400> SEQUENCE: 180

Xaa Arg Cys Asn Thr Ala Thr Cys Ala Thr Gln Arg Leu Ala His Phe
1               5                   10                  15

Leu Gln Arg Phe Gly Ala Ile Leu Ser Ser Thr Glu Val Gly Ser Gly
            20                  25                  30

Thr Pro

<210> SEQ ID NO 181
<211> LENGTH: 36
<212> TYPE: PRT
<213> ORGANISM: Artificial sequence
<220> FEATURE:
<223> OTHER INFORMATION: Synthetic amylin analogue
<220> FEATURE:
<221> NAME/KEY: SITE
<222> LOCATION: (1)..(1)
<223> OTHER INFORMATION: Xaa is isoGlu
<220> FEATURE:
<221> NAME/KEY: SITE
<222> LOCATION: (1)..(1)
<223> OTHER INFORMATION: Linked to [19-carboxynonadecanoyl]
<220> FEATURE:
<221> NAME/KEY: DISULFID
<222> LOCATION: (3)..(8)
<223> OTHER INFORMATION: Sequence may possess an intramolecular
      disulphide bridge formed between the cysteine residues present at
      positions 3 and 8, corresponding to the cysteine residues present
      at positions 2 and 7 of human amylin. Feature is present in Compd.
      80.
<220> FEATURE:
<221> NAME/KEY: MOD_RES
<222> LOCATION: (23)..(23)
<223> OTHER INFORMATION: MeGly
<220> FEATURE:
```

```
<221> NAME/KEY: MOD_RES
<222> LOCATION: (25)..(25)
<223> OTHER INFORMATION: MeIle

<400> SEQUENCE: 181

Xaa Arg Cys Asn Thr Ala Thr Cys Ala Thr Gln Arg Leu Ala Asp Phe
1               5                   10                  15

Leu Gln Arg Ser Ser Phe Gly Ala Ile Leu Ser Ser Thr Glu Val Gly
            20                  25                  30

Ser Gly Thr Pro
        35

<210> SEQ ID NO 182
<211> LENGTH: 36
<212> TYPE: PRT
<213> ORGANISM: Artificial sequence
<220> FEATURE:
<223> OTHER INFORMATION: Synthetic amylin analogue
<220> FEATURE:
<221> NAME/KEY: SITE
<222> LOCATION: (1)..(1)
<223> OTHER INFORMATION: Xaa is isoGlu
<220> FEATURE:
<221> NAME/KEY: SITE
<222> LOCATION: (1)..(1)
<223> OTHER INFORMATION: Linked to [19-carboxynonadecanoyl]
<220> FEATURE:
<221> NAME/KEY: DISULFID
<222> LOCATION: (3)..(8)
<223> OTHER INFORMATION: Sequence may possess an intramolecular
      disulphide bridge formed between the cysteine residues present at
      positions 3 and 8, corresponding to the cysteine residues present
      at positions 2 and 7 of human amylin. Feature is present in Compd.
      81.
<220> FEATURE:
<221> NAME/KEY: MOD_RES
<222> LOCATION: (23)..(23)
<223> OTHER INFORMATION: MeGly
<220> FEATURE:
<221> NAME/KEY: MOD_RES
<222> LOCATION: (25)..(25)
<223> OTHER INFORMATION: MeIle
<220> FEATURE:
<221> NAME/KEY: MOD_RES
<222> LOCATION: (36)..(36)
<223> OTHER INFORMATION: 4Hyp

<400> SEQUENCE: 182

Xaa Arg Cys Asn Thr Ala Thr Cys Ala Thr Gln Arg Leu Ala Asp Phe
1               5                   10                  15

Leu Gln Arg Ser Ser Phe Gly Ala Ile Leu Ser Ser Thr Glu Val Gly
            20                  25                  30

Ser Gly Thr Pro
        35

<210> SEQ ID NO 183
<211> LENGTH: 36
<212> TYPE: PRT
<213> ORGANISM: Artificial sequence
<220> FEATURE:
<223> OTHER INFORMATION: Synthetic amylin analogue
<220> FEATURE:
<221> NAME/KEY: SITE
<222> LOCATION: (1)..(1)
<223> OTHER INFORMATION: Xaa is isoGlu
<220> FEATURE:
<221> NAME/KEY: SITE
<222> LOCATION: (1)..(1)
<223> OTHER INFORMATION: Linked to [19-carboxynonadecanoyl]
<220> FEATURE:
<221> NAME/KEY: DISULFID
```

```
<222> LOCATION: (3)..(8)
<223> OTHER INFORMATION: Sequence may possess an intramolecular
      disulphide bridge formed between the cysteine residues present at
      positions 3 and 8, corresponding to the cysteine residues present
      at positions 2 and 7 of human amylin. Feature is present in Compd.
      82.
<220> FEATURE:
<221> NAME/KEY: MOD_RES
<222> LOCATION: (23)..(23)
<223> OTHER INFORMATION: MeGly
<220> FEATURE:
<221> NAME/KEY: MOD_RES
<222> LOCATION: (25)..(25)
<223> OTHER INFORMATION: MeIle

<400> SEQUENCE: 183

Xaa Arg Cys Asn Thr Ala Thr Cys Ala Thr Gln Arg Leu Ala Asp Phe
1               5                   10                  15

Leu Gln Arg Ser Ser Phe Gly Ala Ile Leu Ser Ser Thr Glu Val Gly
            20                  25                  30

Ser Thr Thr Pro
            35

<210> SEQ ID NO 184
<211> LENGTH: 36
<212> TYPE: PRT
<213> ORGANISM: Artificial sequence
<220> FEATURE:
<223> OTHER INFORMATION: Synthetic amylin analogue
<220> FEATURE:
<221> NAME/KEY: SITE
<222> LOCATION: (1)..(1)
<223> OTHER INFORMATION: Xaa is isoGlu
<220> FEATURE:
<221> NAME/KEY: SITE
<222> LOCATION: (1)..(1)
<223> OTHER INFORMATION: Linked to [19-carboxynonadecanoyl]
<220> FEATURE:
<221> NAME/KEY: DISULFID
<222> LOCATION: (3)..(8)
<223> OTHER INFORMATION: Sequence may possess an intramolecular
      disulphide bridge formed between the cysteine residues present at
      positions 3 and 8, corresponding to the cysteine residues present
      at positions 2 and 7 of human amylin. Feature is present in Compd.
      83.
<220> FEATURE:
<221> NAME/KEY: MOD_RES
<222> LOCATION: (23)..(23)
<223> OTHER INFORMATION: MeGly
<220> FEATURE:
<221> NAME/KEY: MOD_RES
<222> LOCATION: (25)..(25)
<223> OTHER INFORMATION: MeIle
<220> FEATURE:
<221> NAME/KEY: MOD_RES
<222> LOCATION: (36)..(36)
<223> OTHER INFORMATION: 4Hyp

<400> SEQUENCE: 184

Xaa Arg Cys Asn Thr Ala Thr Cys Ala Thr Gln Arg Leu Ala Asp Phe
1               5                   10                  15

Leu Gln Arg Ser Ser Phe Gly Ala Ile Leu Ser Ser Thr Glu Val Gly
            20                  25                  30

Ser Thr Thr Pro
            35

<210> SEQ ID NO 185
<211> LENGTH: 36
<212> TYPE: PRT
<213> ORGANISM: Artificial sequence
<220> FEATURE:
```

```
<223> OTHER INFORMATION: Synthetic amylin analogue
<220> FEATURE:
<221> NAME/KEY: SITE
<222> LOCATION: (1)..(1)
<223> OTHER INFORMATION: Xaa is isoGlu
<220> FEATURE:
<221> NAME/KEY: SITE
<222> LOCATION: (1)..(1)
<223> OTHER INFORMATION: Linked to [19-carboxynonadecanoyl]
<220> FEATURE:
<221> NAME/KEY: DISULFID
<222> LOCATION: (3)..(8)
<223> OTHER INFORMATION: Sequence may possess an intramolecular
      disulphide bridge formed between the cysteine residues present at
      positions 3 and 8, corresponding to the cysteine residues present
      at positions 2 and 7 of human amylin. Feature is present in Compd.
      84.
<220> FEATURE:
<221> NAME/KEY: MOD_RES
<222> LOCATION: (23)..(23)
<223> OTHER INFORMATION: MeGly
<220> FEATURE:
<221> NAME/KEY: MOD_RES
<222> LOCATION: (25)..(25)
<223> OTHER INFORMATION: MeIle

<400> SEQUENCE: 185

Xaa Arg Cys Asn Thr Ala Thr Cys Ala Thr Gln Arg Leu Ala His Phe
1               5                   10                  15

Leu Glu Arg Ser Ser Phe Gly Ala Ile Leu Ser Ser Thr Glu Val Gly
                20                  25                  30

Ser Ser Thr Pro
        35

<210> SEQ ID NO 186
<211> LENGTH: 36
<212> TYPE: PRT
<213> ORGANISM: Artificial sequence
<220> FEATURE:
<223> OTHER INFORMATION: Synthetic amylin analogue
<220> FEATURE:
<221> NAME/KEY: SITE
<222> LOCATION: (1)..(1)
<223> OTHER INFORMATION: Xaa is isoGlu
<220> FEATURE:
<221> NAME/KEY: SITE
<222> LOCATION: (1)..(1)
<223> OTHER INFORMATION: Linked to [19-carboxynonadecanoyl]
<220> FEATURE:
<221> NAME/KEY: DISULFID
<222> LOCATION: (3)..(8)
<223> OTHER INFORMATION: Sequence may possess an intramolecular
      disulphide bridge formed between the cysteine residues present at
      positions 3 and 8, corresponding to the cysteine residues present
      at positions 2 and 7 of human amylin. Feature is present in Compd.
      85.
<220> FEATURE:
<221> NAME/KEY: MOD_RES
<222> LOCATION: (23)..(23)
<223> OTHER INFORMATION: MeGly
<220> FEATURE:
<221> NAME/KEY: MOD_RES
<222> LOCATION: (25)..(25)
<223> OTHER INFORMATION: MeIle

<400> SEQUENCE: 186

Xaa Arg Cys Asn Thr Ala Thr Cys Ala Thr Gln Arg Leu Ala His Phe
1               5                   10                  15

Leu Gln Arg Ser Ser Phe Gly Ala Ile Leu Ser Ser Thr Glu Val Gly
                20                  25                  30

Ser Ser Thr Pro
        35
```

```
<210> SEQ ID NO 187
<211> LENGTH: 36
<212> TYPE: PRT
<213> ORGANISM: Artificial sequence
<220> FEATURE:
<223> OTHER INFORMATION: Synthetic amylin analogue
<220> FEATURE:
<221> NAME/KEY: SITE
<222> LOCATION: (1)..(1)
<223> OTHER INFORMATION: Xaa is isoGlu
<220> FEATURE:
<221> NAME/KEY: SITE
<222> LOCATION: (1)..(1)
<223> OTHER INFORMATION: Linked to [19-carboxynonadecanoyl]
<220> FEATURE:
<221> NAME/KEY: DISULFID
<222> LOCATION: (3)..(8)
<223> OTHER INFORMATION: Sequence may possess an intramolecular
      disulphide bridge formed between the cysteine residues present at
      positions 3 and 8, corresponding to the cysteine residues present
      at positions 2 and 7 of human amylin. Feature is present in Compd.
      86.
<220> FEATURE:
<221> NAME/KEY: MOD_RES
<222> LOCATION: (15)..(15)
<223> OTHER INFORMATION: Aad
<220> FEATURE:
<221> NAME/KEY: MOD_RES
<222> LOCATION: (23)..(23)
<223> OTHER INFORMATION: MeGly
<220> FEATURE:
<221> NAME/KEY: MOD_RES
<222> LOCATION: (25)..(25)
<223> OTHER INFORMATION: MeIle
<220> FEATURE:
<221> NAME/KEY: MOD_RES
<222> LOCATION: (36)..(36)
<223> OTHER INFORMATION: 4Hyp

<400> SEQUENCE: 187

Xaa Arg Cys Asn Thr Ala Thr Cys Ala Thr Gln Arg Leu Ala Glu Phe
1               5                   10                  15

Leu Gln Arg Ser Ser Phe Gly Ala Ile Leu Ser Ser Thr Glu Val Gly
            20                  25                  30

Ser Asn Thr Pro
            35

<210> SEQ ID NO 188
<211> LENGTH: 36
<212> TYPE: PRT
<213> ORGANISM: Artificial sequence
<220> FEATURE:
<223> OTHER INFORMATION: Synthetic amylin analogue
<220> FEATURE:
<221> NAME/KEY: SITE
<222> LOCATION: (1)..(1)
<223> OTHER INFORMATION: Xaa is isoGlu
<220> FEATURE:
<221> NAME/KEY: SITE
<222> LOCATION: (1)..(1)
<223> OTHER INFORMATION: Linked to [19-carboxynonadecanoyl]
<220> FEATURE:
<221> NAME/KEY: DISULFID
<222> LOCATION: (3)..(8)
<223> OTHER INFORMATION: Sequence may possess an intramolecular
      disulphide bridge formed between the cysteine residues present at
      positions 3 and 8, corresponding to the cysteine residues present
      at positions 2 and 7 of human amylin. Feature is present in Compd.
      87.
<220> FEATURE:
<221> NAME/KEY: MOD_RES
<222> LOCATION: (15)..(15)
<223> OTHER INFORMATION: Aad
```

```
<220> FEATURE:
<221> NAME/KEY: MOD_RES
<222> LOCATION: (23)..(23)
<223> OTHER INFORMATION: MeGly
<220> FEATURE:
<221> NAME/KEY: MOD_RES
<222> LOCATION: (25)..(25)
<223> OTHER INFORMATION: MeIle
<220> FEATURE:
<221> NAME/KEY: MOD_RES
<222> LOCATION: (36)..(36)
<223> OTHER INFORMATION: Hyp

<400> SEQUENCE: 188

Xaa Arg Cys Asn Thr Ala Thr Cys Ala Thr Gln Arg Leu Ala Glu Phe
 1               5                  10                  15

Leu Gln Arg Ser Ser Phe Gly Ala Ile Leu Ser Ser Thr Glu Val Gly
             20                  25                  30

Ser Ser Thr Pro
         35

<210> SEQ ID NO 189
<211> LENGTH: 36
<212> TYPE: PRT
<213> ORGANISM: Artificial sequence
<220> FEATURE:
<223> OTHER INFORMATION: Synthetic amylin analogue
<220> FEATURE:
<221> NAME/KEY: SITE
<222> LOCATION: (1)..(1)
<223> OTHER INFORMATION: Xaa is isoGlu
<220> FEATURE:
<221> NAME/KEY: SITE
<222> LOCATION: (1)..(1)
<223> OTHER INFORMATION: Linked to [19-carboxynonadecanoyl]
<220> FEATURE:
<221> NAME/KEY: DISULFID
<222> LOCATION: (3)..(8)
<223> OTHER INFORMATION: Sequence may possess an intramolecular
      disulphide bridge formed between the cysteine residues present at
      positions 3 and 8, corresponding to the cysteine residues present
      at positions 2 and 7 of human amylin. Feature is present in Compd.
      88.
<220> FEATURE:
<221> NAME/KEY: MOD_RES
<222> LOCATION: (23)..(23)
<223> OTHER INFORMATION: MeGly
<220> FEATURE:
<221> NAME/KEY: MOD_RES
<222> LOCATION: (25)..(25)
<223> OTHER INFORMATION: MeIle
<220> FEATURE:
<221> NAME/KEY: MOD_RES
<222> LOCATION: (36)..(36)
<223> OTHER INFORMATION: Hyp

<400> SEQUENCE: 189

Xaa Arg Cys Gln Thr Ala Thr Cys Ala Thr Asp Arg Leu Ala His Phe
 1               5                  10                  15

Leu Gln Arg Ser Ser Phe Gly Ala Ile Leu Ser Ser Thr Glu Val Gly
             20                  25                  30

Ser Asn Thr Pro
         35

<210> SEQ ID NO 190
<211> LENGTH: 36
<212> TYPE: PRT
<213> ORGANISM: Artificial sequence
<220> FEATURE:
<223> OTHER INFORMATION: Synthetic amylin analogue
<220> FEATURE:
```

```
<221> NAME/KEY: SITE
<222> LOCATION: (1)..(1)
<223> OTHER INFORMATION: Xaa is isoGlu
<220> FEATURE:
<221> NAME/KEY: SITE
<222> LOCATION: (1)..(1)
<223> OTHER INFORMATION: Linked to [19-carboxynonadecanoyl]
<220> FEATURE:
<221> NAME/KEY: DISULFID
<222> LOCATION: (3)..(8)
<223> OTHER INFORMATION: Sequence may possess an intramolecular
      disulphide bridge formed between the cysteine residues present at
      positions 3 and 8, corresponding to the cysteine residues present
      at positions 2 and 7 of human amylin. Feature is present in Compd.
      89.
<220> FEATURE:
<221> NAME/KEY: MOD_RES
<222> LOCATION: (15)..(15)
<223> OTHER INFORMATION: Aad
<220> FEATURE:
<221> NAME/KEY: MOD_RES
<222> LOCATION: (23)..(23)
<223> OTHER INFORMATION: MeGly
<220> FEATURE:
<221> NAME/KEY: MOD_RES
<222> LOCATION: (25)..(25)
<223> OTHER INFORMATION: MeIle
<220> FEATURE:
<221> NAME/KEY: MOD_RES
<222> LOCATION: (36)..(36)
<223> OTHER INFORMATION: Hyp

<400> SEQUENCE: 190

Xaa Arg Cys Gln Thr Ala Thr Cys Ala Thr Asp Arg Leu Ala Glu Phe
1               5                   10                  15

Leu Gln Arg Ser Ser Phe Gly Ala Ile Leu Ser Ser Thr Glu Val Gly
            20                  25                  30

Ser Asn Thr Pro
        35

<210> SEQ ID NO 191
<211> LENGTH: 36
<212> TYPE: PRT
<213> ORGANISM: Artificial sequence
<220> FEATURE:
<223> OTHER INFORMATION: Synthetic amylin analogue
<220> FEATURE:
<221> NAME/KEY: SITE
<222> LOCATION: (1)..(1)
<223> OTHER INFORMATION: Xaa is isoGlu
<220> FEATURE:
<221> NAME/KEY: SITE
<222> LOCATION: (1)..(1)
<223> OTHER INFORMATION: Linked to [19-carboxynonadecanoyl]
<220> FEATURE:
<221> NAME/KEY: DISULFID
<222> LOCATION: (3)..(8)
<223> OTHER INFORMATION: Sequence may possess an intramolecular
      disulphide bridge formed between the cysteine residues present at
      positions 3 and 8, corresponding to the cysteine residues present
      at positions 2 and 7 of human amylin. Feature is present in Compd.
      90.
<220> FEATURE:
<221> NAME/KEY: MOD_RES
<222> LOCATION: (23)..(23)
<223> OTHER INFORMATION: MeGly
<220> FEATURE:
<221> NAME/KEY: MOD_RES
<222> LOCATION: (25)..(25)
<223> OTHER INFORMATION: MeIle
<220> FEATURE:
<221> NAME/KEY: MOD_RES
<222> LOCATION: (36)..(36)
<223> OTHER INFORMATION: 4Hyp
```

-continued

```
<400> SEQUENCE: 191

Xaa Arg Cys Gln Thr Ala Thr Cys Ala Thr Glu Arg Leu Ala His Phe
1               5                   10                  15

Leu Gln Arg Ser Ser Phe Gly Ala Ile Leu Ser Ser Thr Glu Val Gly
            20                  25                  30

Ser Gly Thr Pro
        35

<210> SEQ ID NO 192
<211> LENGTH: 36
<212> TYPE: PRT
<213> ORGANISM: Artificial sequence
<220> FEATURE:
<223> OTHER INFORMATION: Synthetic amylin analogue
<220> FEATURE:
<221> NAME/KEY: SITE
<222> LOCATION: (1)..(1)
<223> OTHER INFORMATION: Xaa is isoGlu
<220> FEATURE:
<221> NAME/KEY: SITE
<222> LOCATION: (1)..(1)
<223> OTHER INFORMATION: Linked to [19-carboxynonadecanoyl]
<220> FEATURE:
<221> NAME/KEY: DISULFID
<222> LOCATION: (3)..(8)
<223> OTHER INFORMATION: Sequence may possess an intramolecular
      disulphide bridge formed between the cysteine residues present at
      positions 3 and 8, corresponding to the cysteine residues present
      at positions 2 and 7 of human amylin. Feature is present in Compd.
      91.
<220> FEATURE:
<221> NAME/KEY: MOD_RES
<222> LOCATION: (23)..(23)
<223> OTHER INFORMATION: MeGly
<220> FEATURE:
<221> NAME/KEY: MOD_RES
<222> LOCATION: (25)..(25)
<223> OTHER INFORMATION: MeIle
<220> FEATURE:
<221> NAME/KEY: MOD_RES
<222> LOCATION: (36)..(36)
<223> OTHER INFORMATION: 4Hyp

<400> SEQUENCE: 192

Xaa Arg Cys Gln Thr Ala Thr Cys Ala Thr Asp Arg Leu Ala His Phe
1               5                   10                  15

Leu Gln Arg Ser Ser Phe Gly Ala Ile Leu Ser Ser Thr Glu Val Gly
            20                  25                  30

Ser Gly Thr Pro
        35

<210> SEQ ID NO 193
<211> LENGTH: 36
<212> TYPE: PRT
<213> ORGANISM: Artificial sequence
<220> FEATURE:
<223> OTHER INFORMATION: Synthetic amylin analogue
<220> FEATURE:
<221> NAME/KEY: SITE
<222> LOCATION: (1)..(1)
<223> OTHER INFORMATION: Xaa is isoGlu
<220> FEATURE:
<221> NAME/KEY: SITE
<222> LOCATION: (1)..(1)
<223> OTHER INFORMATION: Linked to [19-carboxynonadecanoyl]
<220> FEATURE:
<221> NAME/KEY: DISULFID
<222> LOCATION: (3)..(8)
<223> OTHER INFORMATION: Sequence may possess an intramolecular
      disulphide bridge formed between the cysteine residues present at
      positions 3 and 8, corresponding to the cysteine residues present
```

```
      at positions 2 and 7 of human amylin. Feature is present in Compd.
      92.
<220> FEATURE:
<221> NAME/KEY: MOD_RES
<222> LOCATION: (23)..(23)
<223> OTHER INFORMATION: MeGly
<220> FEATURE:
<221> NAME/KEY: MOD_RES
<222> LOCATION: (25)..(25)
<223> OTHER INFORMATION: MeIle

<400> SEQUENCE: 193

Xaa Arg Cys Gln Thr Ala Thr Cys Ala Thr Asp Arg Leu Ala His Phe
1               5                   10                  15

Leu Gln Arg Ser Ser Phe Gly Ala Ile Leu Ser Ser Thr Glu Val Gly
            20                  25                  30

Ser Asn Thr Pro
        35

<210> SEQ ID NO 194
<211> LENGTH: 36
<212> TYPE: PRT
<213> ORGANISM: Artificial sequence
<220> FEATURE:
<223> OTHER INFORMATION: Synthetic amylin analogue
<220> FEATURE:
<221> NAME/KEY: SITE
<222> LOCATION: (1)..(1)
<223> OTHER INFORMATION: Xaa is isoGlu
<220> FEATURE:
<221> NAME/KEY: SITE
<222> LOCATION: (1)..(1)
<223> OTHER INFORMATION: Linked to [19-carboxynonadecanoyl]
<220> FEATURE:
<221> NAME/KEY: DISULFID
<222> LOCATION: (3)..(8)
<223> OTHER INFORMATION: Sequence may possess an intramolecular
      disulphide bridge formed between the cysteine residues present at
      positions 3 and 8, corresponding to the cysteine residues present
      at positions 2 and 7 of human amylin. Feature is present in Compd.
      93.
<220> FEATURE:
<221> NAME/KEY: MOD_RES
<222> LOCATION: (15)..(15)
<223> OTHER INFORMATION: Aad
<220> FEATURE:
<221> NAME/KEY: MOD_RES
<222> LOCATION: (23)..(23)
<223> OTHER INFORMATION: MeGly
<220> FEATURE:
<221> NAME/KEY: MOD_RES
<222> LOCATION: (25)..(25)
<223> OTHER INFORMATION: MeIle

<400> SEQUENCE: 194

Xaa Arg Cys Gln Thr Ala Thr Cys Ala Thr Glu Arg Leu Ala Glu Phe
1               5                   10                  15

Leu Gln Arg Ser Ser Phe Gly Ala Ile Leu Ser Ser Thr Glu Val Gly
            20                  25                  30

Ser Asn Thr Pro
        35

<210> SEQ ID NO 195
<211> LENGTH: 36
<212> TYPE: PRT
<213> ORGANISM: Artificial sequence
<220> FEATURE:
<223> OTHER INFORMATION: Synthetic amylin analogue
<220> FEATURE:
<221> NAME/KEY: SITE
<222> LOCATION: (1)..(1)
```

```
<223> OTHER INFORMATION: Xaa is isoGlu
<220> FEATURE:
<221> NAME/KEY: SITE
<222> LOCATION: (1)..(1)
<223> OTHER INFORMATION: Linked to [19-carboxynonadecanoyl]
<220> FEATURE:
<221> NAME/KEY: DISULFID
<222> LOCATION: (3)..(8)
<223> OTHER INFORMATION: Sequence may possess an intramolecular
      disulphide bridge formed between the cysteine residues present
      at positions 3 and 8, corresponding to the cysteine residues present
      at positions 2 and 7 of human amylin. Feature is present in Compd.
      94.
<220> FEATURE:
<221> NAME/KEY: MOD_RES
<222> LOCATION: (15)..(15)
<223> OTHER INFORMATION: Aad
<220> FEATURE:
<221> NAME/KEY: MOD_RES
<222> LOCATION: (23)..(23)
<223> OTHER INFORMATION: MeGly
<220> FEATURE:
<221> NAME/KEY: MOD_RES
<222> LOCATION: (25)..(25)
<223> OTHER INFORMATION: MeIle

<400> SEQUENCE: 195

Xaa Arg Cys Gln Thr Ala Thr Cys Ala Thr Glu Arg Leu Ala Glu Phe
1               5                   10                  15

Leu Gln Arg Ser Ser Phe Gly Ala Ile Leu Ser Ser Thr Glu Val Gly
            20                  25                  30

Ser Gly Thr Pro
        35

<210> SEQ ID NO 196
<211> LENGTH: 34
<212> TYPE: PRT
<213> ORGANISM: Artificial sequence
<220> FEATURE:
<223> OTHER INFORMATION: Synthetic amylin analogue
<220> FEATURE:
<221> NAME/KEY: SITE
<222> LOCATION: (1)..(1)
<223> OTHER INFORMATION: Xaa is isoGlu
<220> FEATURE:
<221> NAME/KEY: SITE
<222> LOCATION: (1)..(1)
<223> OTHER INFORMATION: Linked to [19-carboxynonadecanoyl]
<220> FEATURE:
<221> NAME/KEY: DISULFID
<222> LOCATION: (3)..(8)
<223> OTHER INFORMATION: Sequence may possess an intramolecular
      disulphide bridge formed between the cysteine residues present
      at positions 3 and 8, corresponding to the cysteine residues present
      at positions 2 and 7 of human amylin. Feature is present in Compd.
      95.
<220> FEATURE:
<221> NAME/KEY: MOD_RES
<222> LOCATION: (15)..(15)
<223> OTHER INFORMATION: Aad
<220> FEATURE:
<221> NAME/KEY: MOD_RES
<222> LOCATION: (21)..(21)
<223> OTHER INFORMATION: MeGly
<220> FEATURE:
<221> NAME/KEY: MOD_RES
<222> LOCATION: (23)..(23)
<223> OTHER INFORMATION: MeIle
<220> FEATURE:
<221> NAME/KEY: MOD_RES
<222> LOCATION: (34)..(34)
<223> OTHER INFORMATION: Hyp

<400> SEQUENCE: 196
```

```
Xaa Arg Cys Gln Thr Ala Thr Cys Ala Thr Asp Arg Leu Ala Glu Phe
1               5                   10                  15

Leu Gln Arg Phe Gly Ala Ile Leu Ser Ser Thr Glu Val Gly Ser Asn
            20                  25                  30

Thr Pro

<210> SEQ ID NO 197
<211> LENGTH: 34
<212> TYPE: PRT
<213> ORGANISM: Artificial sequence
<220> FEATURE:
<223> OTHER INFORMATION: Synthetic amylin analogue
<220> FEATURE:
<221> NAME/KEY: SITE
<222> LOCATION: (1)..(1)
<223> OTHER INFORMATION: Xaa is isoGlu
<220> FEATURE:
<221> NAME/KEY: SITE
<222> LOCATION: (1)..(1)
<223> OTHER INFORMATION: Linked to [19-carboxynonadecanoyl]
<220> FEATURE:
<221> NAME/KEY: DISULFID
<222> LOCATION: (3)..(8)
<223> OTHER INFORMATION: Sequence may possess an intramolecular
      disulphide bridge formed between the cysteine residues present at
      positions 3 and 8, corresponding to the cysteine residues present
      at positions 2 and 7 of human amylin. Feature is present in Compd.
      96.
<220> FEATURE:
<221> NAME/KEY: MOD_RES
<222> LOCATION: (21)..(21)
<223> OTHER INFORMATION: MeGly
<220> FEATURE:
<221> NAME/KEY: MOD_RES
<222> LOCATION: (23)..(23)
<223> OTHER INFORMATION: MeIle

<400> SEQUENCE: 197

Xaa Arg Cys Gln Thr Ala Thr Cys Ala Thr Glu Arg Leu Ala His Phe
1               5                   10                  15

Leu Gln Arg Phe Gly Ala Ile Leu Ser Ser Thr Glu Val Gly Ser Asn
            20                  25                  30

Thr Pro

<210> SEQ ID NO 198
<211> LENGTH: 37
<212> TYPE: PRT
<213> ORGANISM: Artificial sequence
<220> FEATURE:
<223> OTHER INFORMATION: Synthetic control sequence Pramlintide
<220> FEATURE:
<221> NAME/KEY: DISULFID
<222> LOCATION: (2)..(7)
<223> OTHER INFORMATION: Intramolecular disulphide bridge between the
      side chains of cysteine residues at positions 2 and 7

<400> SEQUENCE: 198

Lys Cys Asn Thr Ala Thr Cys Ala Thr Gln Arg Leu Ala Asn Phe Leu
1               5                   10                  15

Val His Ser Ser Asn Asn Phe Gly Pro Ile Leu Pro Pro Thr Asn Val
            20                  25                  30

Gly Ser Asn Thr Tyr
        35

<210> SEQ ID NO 199
<211> LENGTH: 37
<212> TYPE: PRT
<213> ORGANISM: Artificial sequence
```

```
<220> FEATURE:
<223> OTHER INFORMATION: Synthetic control sequence NN96, disclosed in
      WO2012/168430
<220> FEATURE:
<221> NAME/KEY: DISULFID
<222> LOCATION: (2)..(7)
<223> OTHER INFORMATION: Intramolecular disulphide bridge between the
      side chains of cysteine residues at positions 2 and 7

<400> SEQUENCE: 199

Arg Cys Asn Thr Ala Thr Cys Ala Thr Gln Arg Leu Ala Glu Phe Leu
1               5                   10                  15

His His Ser Ser Asn Asn Phe Gly Pro Ile Leu Pro Pro Thr Asn Val
            20                  25                  30

Gly Ser Asn Thr Pro
        35

<210> SEQ ID NO 200
<211> LENGTH: 36
<212> TYPE: PRT
<213> ORGANISM: Artificial sequence
<220> FEATURE:
<223> OTHER INFORMATION: Synthetic control sequence Compd. 97
<220> FEATURE:
<221> NAME/KEY: SITE
<222> LOCATION: (1)..(1)
<223> OTHER INFORMATION: Xaa is isoGlu
<220> FEATURE:
<221> NAME/KEY: SITE
<222> LOCATION: (1)..(1)
<223> OTHER INFORMATION: Linked to [19-carboxynonadecanoyl]
<220> FEATURE:
<221> NAME/KEY: DISULFID
<222> LOCATION: (3)..(8)
<223> OTHER INFORMATION: Intramolecular disulphide bridge between the
      side chains of cysteine residues at positions 3 and 8

<400> SEQUENCE: 200

Xaa Arg Cys Asn Thr Ala Thr Cys Ala Thr Gln Arg Leu Ala Glu Phe
1               5                   10                  15

Leu His His Ser Ser Phe Gly Pro Ile Leu Pro Pro Thr Asn Val Gly
            20                  25                  30

Ser Asn Thr Pro
        35

<210> SEQ ID NO 201
<211> LENGTH: 38
<212> TYPE: PRT
<213> ORGANISM: Artificial sequence
<220> FEATURE:
<223> OTHER INFORMATION: Synthetic control sequence Compd. 98
<220> FEATURE:
<221> NAME/KEY: SITE
<222> LOCATION: (1)..(1)
<223> OTHER INFORMATION: Xaa is isoGlu
<220> FEATURE:
<221> NAME/KEY: SITE
<222> LOCATION: (1)..(1)
<223> OTHER INFORMATION: Linked to [19-carboxynonadecanoyl]
<220> FEATURE:
<221> NAME/KEY: DISULFID
<222> LOCATION: (3)..(8)
<223> OTHER INFORMATION: Intramolecular disulphide bridge between the
      side chains of cysteine residues at positions 3 and 8
<220> FEATURE:
<221> NAME/KEY: MOD_RES
<222> LOCATION: (15)..(15)
<223> OTHER INFORMATION: Aad
<220> FEATURE:
<221> NAME/KEY: MOD_RES
<222> LOCATION: (25)..(25)
```

<223> OTHER INFORMATION: MeGly
<220> FEATURE:
<221> NAME/KEY: MOD_RES
<222> LOCATION: (27)..(27)
<223> OTHER INFORMATION: MeIle
<220> FEATURE:
<221> NAME/KEY: MOD_RES
<222> LOCATION: (38)..(38)
<223> OTHER INFORMATION: 4Hyp

<400> SEQUENCE: 201

Xaa Arg Cys Gly Thr Ala Thr Cys Ala Thr Glu Arg Leu Ala Glu Phe
1               5                   10                  15

Leu Gln Arg Ser Ser Asn Asn Phe Gly Ala Ile Leu Ser Ser Thr Glu
            20                  25                  30

Val Gly Ser Asn Thr Pro
        35

<210> SEQ ID NO 202
<211> LENGTH: 38
<212> TYPE: PRT
<213> ORGANISM: Artificial sequence
<220> FEATURE:
<223> OTHER INFORMATION: Synthetic control sequence Compd. 99
<220> FEATURE:
<221> NAME/KEY: SITE
<222> LOCATION: (1)..(1)
<223> OTHER INFORMATION: Xaa is isoGlu
<220> FEATURE:
<221> NAME/KEY: SITE
<222> LOCATION: (1)..(1)
<223> OTHER INFORMATION: Linked to [19-carboxynonadecanoyl]
<220> FEATURE:
<221> NAME/KEY: DISULFID
<222> LOCATION: (3)..(8)
<223> OTHER INFORMATION: Intramolecular disulphide bridge between the
      side chains of cysteine residues at positions 3 and 8
<220> FEATURE:
<221> NAME/KEY: MOD_RES
<222> LOCATION: (25)..(25)
<223> OTHER INFORMATION: MeGly
<220> FEATURE:
<221> NAME/KEY: MOD_RES
<222> LOCATION: (27)..(27)
<223> OTHER INFORMATION: MeIle
<220> FEATURE:
<221> NAME/KEY: MOD_RES
<222> LOCATION: (38)..(38)
<223> OTHER INFORMATION: 4Hyp

<400> SEQUENCE: 202

Xaa Arg Cys Gln Thr Ala Thr Cys Ala Thr Glu Arg Leu Ala His Phe
1               5                   10                  15

Leu Gln Arg Ser Ser Asn Asn Phe Gly Ala Ile Leu Ser Ser Thr Glu
            20                  25                  30

Val Gly Ser Asn Thr Pro
        35

<210> SEQ ID NO 203
<211> LENGTH: 38
<212> TYPE: PRT
<213> ORGANISM: Artificial sequence
<220> FEATURE:
<223> OTHER INFORMATION: Synthetic control sequence Compd. 100
<220> FEATURE:
<221> NAME/KEY: SITE
<222> LOCATION: (1)..(1)
<223> OTHER INFORMATION: Xaa is isoGlu
<220> FEATURE:
<221> NAME/KEY: SITE
<222> LOCATION: (1)..(1)

```
<223> OTHER INFORMATION: Linked to [19-carboxynonadecanoyl]
<220> FEATURE:
<221> NAME/KEY: DISULFID
<222> LOCATION: (3)..(8)
<223> OTHER INFORMATION: Intramolecular disulphide bridge between the
      side chains of cysteine residues at positions 3 and 8
<220> FEATURE:
<221> NAME/KEY: MOD_RES
<222> LOCATION: (15)..(15)
<223> OTHER INFORMATION: Aad
<220> FEATURE:
<221> NAME/KEY: MOD_RES
<222> LOCATION: (25)..(25)
<223> OTHER INFORMATION: MeGly
<220> FEATURE:
<221> NAME/KEY: MOD_RES
<222> LOCATION: (27)..(27)
<223> OTHER INFORMATION: MeIle
<220> FEATURE:
<221> NAME/KEY: MOD_RES
<222> LOCATION: (38)..(38)
<223> OTHER INFORMATION: 4Hyp

<400> SEQUENCE: 203

Xaa Arg Cys Gln Thr Ala Thr Cys Ala Thr Asp Arg Leu Ala Glu Phe
 1               5                  10                  15

Leu Gln Arg Ser Ser Asn Asn Phe Gly Ala Ile Leu Ser Ser Thr Glu
             20                  25                  30

Val Gly Ser Asn Thr Pro
             35
```

The invention claimed is:

1. An amylin analogue which is a compound having the formula:

$$R^1—Z—R^2$$

wherein $R^1$ is hydrogen, $C_{1-4}$ acyl, benzoyl or $C_{1-4}$ alkyl, or a half-life extending moiety M, wherein M is optionally linked to Z via a linker moiety L;

$R^2$ is OH or $NHR^3$, wherein $R^3$ is hydrogen or $C_{1-3}$-alkyl; and

Z is an amino acid sequence of formula I:

(I)
(SEQ ID NO: 3)
Arg-Cys-X3-Thr-Ala-Thr-Cys-Ala-Thr-X10-Arg-Leu-

Ala-X14-Phe-Leu-X17-Arg-X19-X20-Phe-Gly(Me)-Ala-

Ile(Me)-Leu-Ser-Ser-Thr-X31-Val-Gly-Ser-X35-Thr-

X37;

wherein

X3 is selected from the group consisting of Asn, Gly, Pro and Gln;

X10 is selected from the group consisting of Gln, Asp and Glu;

X14 is selected from the group consisting of Asp, His, Asn and Aad;

X17 is selected from the group consisting of His, Asn, Gln, Glu, Thr, Val, Lys and Aad;

X19-X20 is selected from the group consisting of Ser-Ser, Val-Val, Ser-Val and Val-Ser, or is absent;

X31 is selected from the group consisting of Asp, Glu and Asn;

X35 is selected from the group consisting of Asp, Glu, Asn, Ser, Phe, Orn, Aad, Gly and Thr; and X37 is selected from the group consisting of Pro, Apr and Hyp;

and wherein the compound has at least one residue selected from:

X3 is Gln;

X14 is His, Asn or Aad;

X17 is Asn, Gln, Glu, Thr or Aad;

X19-X20 is Val-Ser or Ser-Val; and

X35 is Ser, Phe, Orn, Aad, Gly or Thr;

or a pharmaceutically acceptable salt thereof.

2. An amylin analogue according to claim 1 wherein Z is an amino acid sequence of formula II:

(II)
(SEQ ID NO: 4)
Arg-Cys-X3-Thr-Ala-Thr-Cys-Ala-Thr-X10-Arg-Leu-

Ala-X14-Phe-Leu-X17-Arg-X19-X20-Phe-Gly(Me)-Ala-

Ile(Me)-Leu-Ser-Ser-Thr-Glu-Val-Gly-Ser-X35-Thr-

X37;

wherein

X3 is selected from the group consisting of Asn, Gly and Gln;

X10 is selected from the group consisting of Gln, Asp and Glu;

X14 is selected from the group consisting of Asp, His and Aad;

X17 is selected from the group consisting of His, Asn, Gln, Glu, Lys and Aad;

X19-X20 is Ser-Ser or is absent;

X35 is selected from the group consisting of Asp, Glu, Asn, Ser, Orn, Aad, Gly and Thr; and X37 is selected from the group consisting of Pro and Hyp; and wherein the compound has at least one residue selected from:
X3 is Gln;
X14 is His or Aad;
X17 is Asn, Gln, Glu or Aad; and
X35 is Ser, Phe, Orn, Aad, Gly or Thr.

3. An amylin analogue according to claim 1 wherein Z is an amino acid sequence of formula III:

(III)
(SEQ ID NO: 5)
Arg-Cys-X3-Thr-Ala-Thr-Cys-Ala-Thr-X10-Arg-Leu-Ala-X14-Phe-Leu-X17-Arg-X19-X20-Phe-Gly(Me)-Ala-Ile(Me)-Leu-Ser-Ser-Thr-Glu-Val-Gly-Ser-X35-Thr-X37;

wherein
X3 is selected from the group consisting of Asn, Gly and Gln;
X10 is selected from the group consisting of Gln, Asp and Glu;
X14 is selected from the group consisting of Asp, His and Aad;
X17 is selected from the group consisting of His and Gln;
X19-X20 is Ser-Ser or is absent;
X35 is selected from the group consisting of Asp, Glu, Asn, Aad and Gly; and
X37 is selected from the group consisting of Pro and Hyp; and wherein the compound has at least one residue selected from:
X3 is Gln;
X14 is His or Aad;
X17 is Gln; and
X35 is Aad.

4. An amylin analogue according to claim 1, comprising the residues:
X3 is Gly;
X10 is selected from Glu and Asp;
X14 is selected from His and Aad;
X35 is selected from Gly and Asn; and
X37 is selected from Pro and Hyp.

5. An amylin analogue according to claim 1, comprising the residues:
Gly3+Glu10;
Asn3+Glu10;
Gln3+Glu10;
Asn3+Gln10; or
Gln3+Asp10.

6. An amylin analogue according to claim 1, wherein X14 is selected from His and Aad, and/or X17 is Gln.

7. An amylin analogue according to claim 1, comprising the residues:
Gln17+Glu31+Hyp37
Gly3+Glu10+His14
Asn3+Glu10+His14;
Gln3+Glu10+His14;
Gly3+Glu10+Aad14;
Gly3+Glu10+Asp14;
Asp10+Aad14;
His14+Glu31+Pro37
His14+Glu31+Hyp37
Aad14+Glu31+Pro37;
Aad14+Glu31+Hyp37;
Gly3+Glu31; or
Gly3+Glu10+Glu31+Asn35+Hyp37.

8. An amylin analogue according to claim 1, wherein X19-X20 is Ser-Ser.

9. An amylin analogue according to claim 8, comprising the residues:
Gly3+Ser19+Ser20+Glu31 or
Gly3+Glu10+Ser19+Ser20+Glu31+Asn35+Hyp37.

10. An amylin analogue according to claim 1, wherein Z is:

(SEQ ID NO: 6)
RCNTATCATQRLAHFLHRSSF-Gly(Me)-A-Ile(Me)-LSSTEVGSETP, (SEQ ID NO: 7)
RCNTATCATQRLANFLHRSSF-Gly(Me)-A-Ile(Me)-LSSTEVGSETP, (SEQ ID NO: 8)
RCGTATCATERLAHFLNRSSF-Gly(Me)-A-Ile(Me)-LSSTEVGSNT-Hyp, (SEQ ID NO: 9)
RCGTATCATERLAHFLQRSSF-Gly(Me)-A-Ile(Me)-LSSTEVGSNT-Hyp, (SEQ ID NO: 10)
RCGTATCATERLAHFLERSSF-Gly(Me)-A-Ile(Me)-LSSTEVGSNT-Hyp, (SEQ ID NO: 11)
RCGTATCATERLAHFLTRSSF-Gly(Me)-A-Ile(Me)-LSSTEVGSST-Hyp, (SEQ ID NO: 12)
RCGTATCATERLAHFLTRSSF-Gly(Me)-A-Ile(Me)-LSSTEVGSFT-Hyp, (SEQ ID NO: 13)
RCGTATCATERLAHFLTRSSF-Gly(Me)-A-Ile(Me)-LSSTEVGS-Orn-T-Hyp, (SEQ ID NO: 14)
RCGTATCATERLAHFLTRSSF-Gly(Me)-A-Ile(Me)-LSSTEVGS-Aad-T-Hyp, (SEQ ID NO: 15)
RCGTATCATERLAHFLTRSSF-Gly(Me)-A-Ile(Me)-LSSTEVGSGT-Hyp, (SEQ ID NO: 16)
RCNTATCATQRLAHFLHRF-Gly(Me)-A-Ile(Me)-LSSTEVGSETP,

```
                                                   (SEQ ID NO: 17)
RCGTATCATERLAHFLHRSSF-Gly(Me)-A-Ile(Me)-LSSTEVGSNTP, (SEQ ID NO: 18)
RCNTATCATQRLAHFLHRSSF-Gly(Me)-A-Ile(Me)-LSSTEVGSNTP, (SEQ ID NO: 19)
RCGTATCATERLANFLVRSSF-Gly(Me)-A-Ile(Me)-LSSTEVGSNT-Hyp, (SEQ ID NO: 20)
RCGTATCATERLAHFLTRSSF-Gly(Me)-A-Ile(Me)-LSSTEVGSNT-Hyp, (SEQ ID NO: 21)
RCGTATCATERLAHFLKRSSF-Gly(Me)-A-Ile(Me)-LSSTEVGSNT-Hyp, (SEQ ID NO: 22)
RCNTATCATQRLAHFLHRSVF-Gly(Me)-A-Ile(Me)-LSSTEVGSETP, (SEQ ID NO: 23)
RCNTATCATQRLAHFLHRVSF-Gly(Me)-A-Ile(Me)-LSSTEVGSETP, (SEQ ID NO: 24)
RCGTATCATERLAHFLVRSSF-Gly(Me)-A-Ile(Me)-LSSTEVGSETP, (SEQ ID NO: 25)
RCPTATCATDRLAHFLVRSSF-Gly(Me)-A-Ile(Me)-LSSTDVGSDTP, (SEQ ID NO: 26)
RCNTATCATQRLAHFLVRSSF-Gly(Me)-A-Ile(Me)-LSSTEVGSETP, (SEQ ID NO: 27)
RCPTATCATDRLAHFLHRSSF-Gly(Me)-A-Ile(Me)-LSSTDVGSNTP, (SEQ ID NO: 28)
RCGTATCATERLAHFLHRSSF-Gly(Me)-A-Ile(Me)-LSSTEVGSETP, (SEQ ID NO: 29)
RCPTATCATDRLAHFLHRSSF-Gly(Me)-A-Ile(Me)-LSSTDVGSDTP, (SEQ ID NO: 30)
RCGTATCATERLAHFLQRSSF-Gly(Me)-A-Ile(Me)-LSSTEVGSST-Hyp, (SEQ ID NO: 31)
RCGTATCATERLAHFLNRSSF-Gly(Me)-A-Ile(Me)-LSSTEVGSST-Hyp, (SEQ ID NO: 32)
RCGTATCATERLAHFLHRSSF-Gly(Me)-A-Ile(Me)-LSSTEVGSST-Hyp, (SEQ ID NO: 33)
RCGTATCATERLAHFLVRSSF-Gly(Me)-A-Ile(Me)-LSSTEVGSSI-Hyp, (SEQ ID NO: 34)
RCGTATCATERLAHFLQRSSF-Gly(Me)-A-Ile(Me)-LSSTEVGSFT-Hyp, (SEQ ID NO: 35)
RCGTATCATERLAHFLNRSSF-Gly(Me)-A-Ile(Me)-LSSTEVGSFT-Hyp, (SEQ ID NO: 36)
RCGTATCATERLAHFLQRSSF-Gly(Me)-A-Ile(Me)-LSSTEVGSSTP, (SEQ ID NO: 37)
RCGTATCATERLAHFLNRSSF-Gly(Me)-A-Ile(Me)-LSSTEVGSSTP, (SEQ ID NO: 38)
RCGTATCATERLAHFLERSSF-Gly(Me)-A-Ile(Me)-LSSTEVGSSTP, (SEQ ID NO: 39)
RCGTATCATERLAHFLHRSSF-Gly(Me)-A-Ile(Me)-LSSTEVGSSTP, (SEQ ID NO: 40)
RCGTATCATERLAHFLVRSSF-Gly(Me)-A-Ile(Me)-LSSTEVGSSTP, (SEQ ID NO: 41)
RCGTATCATERLAHFLQRSSF-Gly(Me)-A-Ile(Me)-LSSTEVGSFTP, (SEQ ID NO: 42)
RCGTATCATERLAHFLNRSSF-Gly(Me)-A-Ile(Me)-LSSTEVGSFTP, (SEQ ID NO: 43)
RCGTATCATERLADFLTRSSF-Gly(Me)-A-Ile(Me)-LSSTEVGSST-Hyp,
```

-continued

```
                                                      (SEQ ID NO: 44)
RCGTATCATERLADFLTRSSF-Gly(Me)-A-Ile(Me)-LSSTEVGSFT-Hyp, (SEQ ID NO: 45)
RCGTATCATERLA-Aad-FLTRSSF-Gly(Me)-A-Ile(Me)-LSSTEVGSST-Hyp, (SEQ ID NO: 46)
RCGTATCATERLA-Aad-FLTRSSF-Gly(Me)-A-Ile(Me)-LSSTEVGS-Orn-T-Hyp, (SEQ ID NO: 47)
RCGTATCATERLAHFLTRSSF-Gly(Me)-A-Ile(Me)-LSSTEVGSST-Apr, (SEQ ID NO: 48)
RCGTATCATERLAHFLTRSSF-Gly(Me)-A-Ile(Me)-LSSTEVGSSTP, (SEQ ID NO: 49)
RCGTATCATERLAHFLTRSSF-Gly(Me)-A-Ile(Me)-LSSTEVGS-Orn-TP, (SEQ ID NO: 50)
RCGTATCATERLAHFLTRSSF-Gly(Me)-A-Ile(Me)-LSSTEVGSTT-Hyp, (SEQ ID NO: 51)
RCNTATCATQRLADFLQRSSF-Gly(Me)-A-Ile(Me)-LSSTEVGSNT-Hyp, (SEQ ID NO: 52)
RCNTATCATQRLAHFL-Aad-RSSF-Gly(Me)-A-Ile(Me)-LSSTEVGSNT-Hyp, (SEQ ID NO: 53)
RCGTATCATERLAHFLQRSSF-Gly(Me)-A-Ile(Me)-LSSTEVGS-Orn-T-Hyp, (SEQ ID NO: 54)
RCGTATCATERLAHFLQRSSF-Gly(Me)-A-Ile(Me)-LSSTEVGSGT-Hyp, (SEQ ID NO: 55)
RCGTATCATERLAHFLQRSSF-Gly(Me)-A-Ile(Me)-LSSTEVGS-Aad-T-Hyp, (SEQ ID NO: 56)
RCGTATCATERLADFLQRSSF-Gly(Me)-A-Ile(Me)-LSSTEVGSNT-Hyp, (SEQ ID NO: 57)
RCGTATCATERLA-Aad-FLQRSSF-Gly(Me)-A-Ile(Me)-LSSTEVGSNT-Hyp, (SEQ ID NO: 58)
RCNTATCATERLAHFLQRSSF-GIy(Me)-A-Ile(Me)-LSSTEVGSNT-Hyp, (SEQ ID NO: 59)
RCQTATCATERLAHFLQRSSF-Gly(Me)-A-Ile(Me)-LSSTEVGSNT-Hyp, (SEQ ID NO: 60)
RCNTATCATQRLAHFLQRSSF-Gly(Me)-A-Ile(Me)-LSSTEVGSNT-Hyp, (SEQ ID NO: 61)
RCPTATCATDRLAHFLQRSSF-Gly(Me)-A-Ile(Me)-LSSTDVGSNT-Hyp, (SEQ ID NO: 62)
RCNTATCATERLAHFLQRSSF-Gly(Me)-A-Ile(Me)-LSSTEVGSDT-Hyp, (SEQ ID NO: 63)
RCNTATCATQRLAHFLQRSSF-Gly(Me)-A-Ile(Me)-LSSTEVGSNTP, (SEQ ID NO: 64)
RCNTATCATERLAHFLQRSSF-Gly(Me)-A-Ile(Me)-LSSTEVGSNTP, (SEQ ID NO: 65)
RCPTATCATERLAHFLQRSSF-Gly(Me)-A-Ile(Me)-LSSTEVGSNT-Hyp, (SEQ ID NO: 66)
RCPTATCATQRLAHFLQRSSF-Gly(Me)-A-Ile(Me)-LSSTEVGSNT-Hyp, (SEQ ID NO: 67)
RCNTATCATQRLADFLQRSSF-GIy(Me)-A-Ile(Me)-LSSTEVGSNTP, (SEQ ID NO: 68)
RCNTATCATERLADFLQRSSF-Gly(Me)-A-Ile(Me)-LSSTEVGSNTP, (SEQ ID NO: 69)
RCPTATCATERLADFLQRSSF-Gly(Me)-A-Ile(Me)-LSSTEVGSNTP, (SEQ ID NO: 70)
RCNTATCATERLADFLQRSSF-Gly(Me)-A-Ile(Me)-LSSTEVGSNT-Hyp,
```

-continued

```
                                                  (SEQ ID NO: 71)
RCNTATCATQRLAHFLQRSSF-Gly(Me)-A-Ile(Me)-LSSTEVGSST-Hyp, (SEQ ID NO: 72)
RCPTATCATERLAHFLQRSSF-Gly(Me)-A-Ile(Me)-LSSTEVGSST-Hyp, (SEQ ID NO: 73)
RCNTATCATQRLAHFLQRSSF-Gly(Me)-A-Ile(Me)-LSSTEVGSGT-Hyp, (SEQ ID NO: 74)
RCPTATCATERLAHFLQRSSF-Gly(Me)-A-Ile(Me)-LSSTEVGSGT-Hyp, (SEQ ID NO: 75)
RCNTATCATQRLAHFLQRSSF-Gly(Me)-A-Ile(Me)-LSSTEVGSTT-Hyp, (SEQ ID NO: 76)
RCPTATCATERLAHFLQRSSF-Gly(Me)-A-Ile(Me)-LSSTEVGSTT-Hyp, (SEQ ID NO: 77)
RCNTATCATQRLAHFLQRSSF-Gly(Me)-A-Ile(Me)-LSSTEVGS-Aad-T-Hyp, (SEQ ID NO: 78)
RCPTATCATERLAHFLQRSSF-Gly(Me)-A-Ile(Me)-LSSTEVGS-Aad-T-Hyp, (SEQ ID NO: 79)
RCGTATCATERLAHFLQRF-Gly(Me)-A-Ile(Me)-LSSTEVGSNT-Hyp, (SEQ ID NO: 80)
RCGTATCATERLAHFLQRSSF-Gly(Me)-A-Ile(Me)-LSSTEVGSNTP, (SEQ ID NO: 81)
RCNTATCATQRLAHFLQRF-Gly(Me)-A-Ile(Me)-LSSTEVGSGT-Hyp, (SEQ ID NO: 82)
RCNTATCATQRLADFLQRSSF-Gly(Me)-A-Ile(Me)-LSSTEVGSGTP, (SEQ ID NO: 83)
RCNTATCATQRLADFLQRSSF-Gly(Me)-A-Ile(Me)-LSSTEVGSGT-Hyp, (SEQ ID NO: 84)
RCNTATCATQRLADFLQRSSF-Gly(Me)-A-Ile(Me)-LSSTEVGSTTP, (SEQ ID NO: 85)
RCNTATCATQRLADFLQRSSF-Gly(Me)-A-Ile(Me)-LSSTEVGSTT-Hyp, (SEQ ID NO: 86)
RCNTATCATQRLAHFLERSSF-Gly(Me)-A-Ile(Me)-LSSTEVGSSTP, (SEQ ID NO: 87)
RCNTATCATQRLAHFLQRSSF-Gly(Me)-A-Ile(Me)-LSSTEVGSSTP, (SEQ ID NO: 88)
RCNTATCATQRLA-Aad-FLQRSSF-Gly(Me)-A-Ile(Me)-LSSTEVGSNT-Hyp, (SEQ ID NO: 89)
RCNTATCATQRLA-Aad-FLQRSSF-Gly(Me)-A-Ile(Me)-LSSTEVGSST-Hyp, (SEQ ID NO: 90)
RCQTATCATDRLAHFLQRSSF-Gly(Me)-A-Ile(Me)-LSSTEVGSNT-Hyp, (SEQ ID NO: 91)
RCQTATCATDRLA-Aad-FLQRSSF-Gly(Me)-A-Ile(Me)-LSSTEVGSNT-Hyp, (SEQ ID NO: 92)
RCQTATCATERLAHFLQRSSF-Gly(Me)-A-Ile(Me)-LSSTEVGSGT-Hyp, (SEQ ID NO: 93)
RCQTATCATDRLAHFLQRSSF-Gly(Me)-A-Ile(Me)-LSSTEVGSGT-Hyp, (SEQ ID NO: 94)
RCQTATCATDRLAHFLQRSSF-Gly(Me)-A-Ile(Me)-LSSTEVGSNTP, (SEQ ID NO: 95)
RCQTATCATERLA-Aad-FLQRSSF-Gly(Me)-A-Ile(Me)-LSSTEVGSNTP, (SEQ ID NO: 96)
RCQTATCATERLA-Aad-FLQRSSF-Gly(Me)-A-Ile(Me)-LSSTEVGSGTP, (SEQ ID NO: 97)
RCQTATCATDRLA-Aad-FLQRF-Gly(Me)-A-Ile(Me)-LSSTEVGSNT-Hyp,
```

-continued or

```
                                                             (SEQ ID NO: 98)
RCQTATCATERLAHFLQRF-Gly(Me)-A-Ile(Me)-LSSTEVGSNTP.
```

11. An amylin analogue according to claim 1, wherein R¹ is M- or M-L-.

12. An amylin analogue according to claim 11, wherein M is an alkanoyl group.

13. An amylin analogue according to claim 12, wherein M is selected from 15-carboxy-pentadecanoyl, 17-carboxy-heptadecanoyl and 19-carboxy-nonadecanoyl.

14. An amylin analogue according to claim 1, wherein R¹ is M-L- and L is a residue of an amino acid selected from the group consisting of Gly, Pro, Ala, Val, Leu, Ile, Met, Cys, Phe, Tyr, Trp, His, Lys, Arg, Gln, Asn, α-Glu, γ-Glu, ε-Lys, Asp, β-Asp, Ser, Thr, Gaba, Aib, β-Ala, 4-aminobutanoyl, 5-aminopentanoyl, 6-aminohexanoyl, 7-aminoheptanoyl, 8-aminooctanoyl, 9-aminononanoyl, 10-aminodecanoyl and 8Ado.

15. An amylin analogue according to claim 14, wherein L is a γ-Glu residue.

16. An amylin analogue according to claim 1, wherein R² is NH₂.

17. An amylin analogue according to claim 1, wherein the amylin analogue is is selected from the group consisting of:

```
                                                            (SEQ ID NO: 103)
[19CD]-isoGlu-RCNTATCATQRLAHFLHRSSF-Gly(Me)-A-Ile(Me)-LSSTEVGSETP-NH₂, (SEQ ID NO: 104)
[19CD]-isoGlu-RCNTATCATQRLANFLHRSSF-Gly(Me)-A-Ile(Me)-LSSTEVGSETP-NH₂, (SEQ ID NO: 107)
[19CD]-isoGlu-RCGTATCATERLAHFLNRSSF-Gly(Me)-A-Ile(Me)-LSSTEVGSNT-Hyp-NH₂, (SEQ ID NO: 108)
[19CD]-isoGlu-RCGTATCATERLAHFLQRSSF-Gly(Me)-A-Ile(Me)-LSSTEVGSNT-Hyp-NH₂, (SEQ ID NO: 109)
[19CD]-isoGlu-RCGTATCATERLAHFLERSSF-Gly(Me)-A-Ile(Me)-LSSTEVGSNT-Hyp-NH₂, (SEQ ID NO: 110)
[19CD]-isoGlu-RCGTATCATERLAHFLTRSSF-Gly(Me)-A-Ile(Me)-LSSTEVGSST-Hyp-NH₂, (SEQ ID NO: 111)
[19CD]-isoGlu-RCGTATCATERLAHFLTRSSF-Gly(Me)-A-Ile(Me)-LSSTEVGSFT-Hyp-NH₂, (SEQ ID NO: 112)
[19CD]-isoGlu-RCGTATCATERLAHFLTRSSF-Gly(Me)-A-Ile(Me)-LSSTEVGS-Orn-T-Hyp-NH₂, (SEQ ID NO: 113)
[19CD]-isoGlu-RCGTATCATERLAHFLTRSSF-Gly(Me)-A-Ile(Me)-LSSTEVGS-Aad-T-Hyp-NH₂, (SEQ ID NO: 114)
[19CD]-isoGlu-RCGTATCATERLAHFLTRSSF-Gly(Me)-A-Ile(Me)-LSSTEVGSGT-Hyp-NH₂, (SEQ ID NO: 115)
[19CD]-isoGlu-RCNTATCATQRLAHFLHRFGly(Me)-A-Ile(Me)-LSSTEVGSETP-NH₂, (SEQ ID NO: 116)
[19CD]-isoGlu-RCGTATCATERLAHFLHRSSF-Gly(Me)-A-Ile(Me)-LSSTEVGSNTP-NH₂, (SEQ ID NO: 117)
[19CD]-isoGlu-RCNTATCATQRLAHFLHRSSF-Gly(Me)-A-Ile(Me)-LSSTEVGSNTP-NH₂, (SEQ ID NO: 118)
[19CD]-isoGlu-RCGTATCATERLANFLVRSSF-Gly(Me)-A-Ile(Me)-LSSTEVGSNT-Hyp-NH₂, (SEQ ID NO: 119)
[19CD]-isoGlu-RCGTATCATERLAHFLTRSSF-Gly(Me)-A-Ile(Me)-LSSTEVGSNT-Hyp-NH₂, (SEQ ID NO: 120)
[19CD]-isoGlu-RCGTATCATERLAHFLKRSSF-Gly(Me)-A-Ile(Me)-LSSTEVGSNT-Hyp-NH₂, (SEQ ID NO: 121)
[19CD]-isoGlu-RCNTATCATQRLAHFLHRSVF-Gly(Me)-A-Ile(Me)-LSSTEVGSETP-NH₂, (SEQ ID NO: 122)
[19CD]-isoGlu-RCNTATCATQRLAHFLHRVSF-Gly(Me)-A-Ile(Me)-LSSTEVGSETP-NH₂, (SEQ ID NO: 123)
[19CD]-isoGlu-RCGTATCATERLAHFLVRSSF-Gly(Me)-A-Ile(Me)-LSSTEVGSETP-NH₂, (SEQ ID NO: 124)
[19CD]-isoGlu-RCPTATCATDRLAHFLVRSSF-Gly(Me)-A-Ile(Me)-LSSTDVGSDTP-NH₂,
```

```
                                                                    (SEQ ID NO: 125)
[19CD]-isoGlu-RCNTATCATQRLAHFLVRSSF-Gly(Me)-A-Ile(Me)-LSSTEVGSETP-NH2, (SEQ ID NO: 126)
[19CD]-isoGlu-RCPTATCATDRLAHFLHRSSF-Gly(Me)-A-Ile(Me)-LSSTDVGSNTP-NH2, (SEQ ID NO: 127)
[19CD]-isoGlu-RCGTATCATERLAHFLHRSSF-Gly(Me)-A-Ile(Me)-LSSTEVGSETP-NH2, (SEQ ID NO: 128)
[19CD]-isoGlu-RCPTATCATDRLAHFLHRSSF-Gly(Me)-A-Ile(Me)-LSSTDVGSDTP-NH2, (SEQ ID NO: 129)
[19CD]-isoGlu-RCGTATCATERLAHFLQRSSF-Gly(Me)-A-Ile(Me)-LSSTEVGSST-Hyp-NH2, (SEQ ID NO: 130)
[19CD]-isoGlu-RCGTATCATERLAHFLNRSSF-Gly(Me)-A-Ile(Me)-LSSTEVGSST-Hyp-NH2, (SEQ ID NO: 131)
[19CD]-isoGlu-RCGTATCATERLAHFLHRSSF-Gly(Me)-A-Ile(Me)-LSSTEVGSST-Hyp-NH2, (SEQ ID NO: 132)
[19CD]-isoGlu-RCGTATCATERLAHFLVRSSF-Gly(Me)-A-Ile(Me)-LSSTEVGSST-Hyp-NH2, (SEQ ID NO: 133)
[19CD]-isoGlu-RCGTATCATERLAHFLQRSSF-Gly(Me)-A-Ile(Me)-LSSTEVGSFT-Hyp-NH2, (SEQ ID NO: 134)
[19CD]-isoGlu-RCGTATCATERLAHFLNRSSF-Gly(Me)-A-Ile(Me)-LSSTEVGSFT-Hyp-NH2, (SEQ ID NO: 135)
[19CD]-isoGlu-RCGTATCATERLAHFLQRSSF-Gly(Me)-A-Ile(Me)-LSSTEVGSSTP-NH2, (SEQ ID NO: 136)
[19CD]-isoGlu-RCGTATCATERLAHFLNRSSF-Gly(Me)-A-Ile(Me)-LSSTEVGSSTP-NH2, (SEQ ID NO: 137)
[19CD]-isoGlu-RCGTATCATERLAHFLERSSF-Gly(Me)-A-Ile(Me)-LSSTEVGSSTP-NH2, (SEQ ID NO: 138)
[19CD]-isoGlu-RCGTATCATERLAHFLHRSSF-Gly(Me)-A-Ile(Me)-LSSTEVGSSTP-NH2, (SEQ ID NO: 139)
[19CD]-isoGlu-RCGTATCATERLAHFLVRSSF-Gly(Me)-A-Ile(Me)-LSSTEVGSSTP-NH2, (SEQ ID NO: 140)
[19CD]-isoGlu-RCGTATCATERLAHFLQRSSF-Gly(Me)-A-Ile(Me)-LSSTEVGSFTP-NH2, (SEQ ID NO: 141)
[19CD]-isoGlu-RCGTATCATERLAHFLNRSSF-Gly(Me)-A-Ile(Me)-LSSTEVGSFTP-NH2, (SEQ ID NO: 142)
[19CD]-isoGlu-RCGTATCATERLADFLTRSSF-Gly(Me)-A-Ile(Me)-LSSTEVGSST-Hyp-NH2, (SEQ ID NO: 143)
[19CD]-isoGlu-RCGTATCATERLADFLTRSSF-Gly(Me)-A-Ile(Me)-LSSTEVGSFT-Hyp-NH2, (SEQ ID NO: 144)
[19CD]-isoGlu-RCGTATCATERLA-Aad-FLTRSSF-Gly(Me)-A-Ile(Me)-LSSTEVGSST-Hyp-NH2, (SEQ ID NO: 145)
[19CD]-isoGlu-RCGTATCATERLA-Aad-FLTRSSF-Gly(Me)-A-Ile(Me)-LSSTEVGS-Orn-T-Hyp-NH2, (SEQ ID NO: 146)
[19CD]-isoGlu-RCGTATCATERLAHFLTRSSF-Gly(Me)-A-Ile(Me)-LSSTEVGSST-Apr-NH2, (SEQ ID NO: 147)
[19CD]-isoGlu-RCGTATCATERLAHFLTRSSF-Gly(Me)-A-Ile(Me)-LSSTEVGSSTP-NH2, (SEQ ID NO: 148)
[19CD]-isoGlu-RCGTATCATERLAHFLTRSSF-Gly(Me)-A-Ile(Me)-LSSTEVGS-Orn-TP-NH2, (SEQ ID NO: 149)
[19CD]-isoGlu-RCGTATCATERLAHFLTRSSF-Gly(Me)-A-Ile(Me)-LSSTEVGSTT-Hyp-NH2, (SEQ ID NO: 150)
[19CD]-isoGlu-RCNTATCATQRLADFLQRSSF-Gly(Me)-A-Ile(Me)-LSSTEVGSNT-Hyp-NH2, (SEQ ID NO: 151)
[19CD]-isoGlu-RCNTATCATQRLAHFL-Aad-RSSF-Gly(Me)-A-Ile(Me)-LSSTEVGSNT-Hyp-NH2,
```

-continued (SEQ ID NO: 152)
[19CD]-isoGlu-RCGTATCATERLAHFLQRSSF-Gly(Me)-A-Ile(Me)-LSSTEVGS-Orn-T-Hyp-NH$_2$, (SEQ ID NO: 153)
[19CD]-isoGlu-RCGTATCATERLAHFLQRSSF-Gly(Me)-A-Ile(Me)-LSSTEVGSGT-Hyp-NH$_2$, (SEQ ID NO: 154)
[19CD]-isoGlu-RCGTATCATERLAHFLQRSSF-Gly(Me)-A-Ile(Me)-LSSTEVGS-Aad-T-Hyp-NH$_2$, (SEQ ID NO: 155)
[19CD]-isoGlu-RCGTATCATERLADFLQRSSF-Gly(Me)-A-Ile(Me)-LSSTEVGSNT-Hyp-NH$_2$, (SEQ ID NO: 156)
[19CD]-isoGlu-RCGTATCATERLA-Aad-FLQRSSF-Gly(Me)-A-Ile(Me)-LSSTEVGSNT-Hyp-NH$_2$, (SEQ ID NO: 157)
[19CD]-isoGlu-RCNTATCATERLAHFLQRSSF-Gly(Me)-A-Ile(Me)-LSSTEVGSNT-Hyp-NH$_2$, (SEQ ID NO: 158)
[19CD]-isoGlu-RCQTATCATERLAHFLQRSSF-Gly(Me)-A-Ile(Me)-LSSTEVGSNT-Hyp-NH$_2$, (SEQ ID NO: 159)
[19CD]-isoGlu-RCNTATCATQRLAHFLQRSSF-Gly(Me)-A-Ile(Me)-LSSTEVGSNT-Hyp-NH$_2$, (SEQ ID NO: 160)
[19CD]-isoGlu-RCPTATCATDRLAHFLQRSSF-Gly(Me)-A-Ile(Me)-LSSTDVGSNT-Hyp-NH$_2$, (SEQ ID NO: 161)
[19CD]-isoGlu-RCNTATCATERLAHFLQRSSF-Gly(Me)-A-Ile(Me)-LSSTEVGSDT-Hyp-NH$_2$, (SEQ ID NO: 162)
[19CD]-isoGlu-RCNTATCATQRLAHFLQRSSF-Gly(Me)-A-Ile(Me)-LSSTEVGSNTP-NH$_2$, (SEQ ID NO: 163)
[19CD]-isoGlu-RCNTATCATERLAHFLQRSSF-Gly(Me)-A-Ile(Me)-LSSTEVGSNTP-NH$_2$, (SEQ ID NO: 164)
[19CD]-isoGlu-RCPTATCATERLAHFLQRSSF-Gly(Me)-A-Ile(Me)-LSSTEVGSNT-Hyp-NH$_2$, (SEQ ID NO: 165)
[19CD]-isoGlu-RCPTATCATQRLAHFLQRSSF-Gly(Me)-A-Ile(Me)-LSSTEVGSNT-Hyp-NH$_2$, (SEQ ID NO: 166)
[19CD]-isoGlu-RCNTATCATQRLADFLQRSSF-Gly(Me)-A-Ile(Me)-LSSTEVGSNTP-NH$_2$, (SEQ ID NO: 167)
[19CD]-isoGlu-RCNTATCATERLADFLQRSSF-Gly(Me)-A-Ile(Me)-LSSTEVGSNTP-NH$_2$, (SEQ ID NO: 168)
[19CD]-isoGlu-RCPTATCATERLADFLQRSSF-Gly(Me)-A-Ile(Me)-LSSTEVGSNTP-NH$_2$, (SEQ ID NO: 169)
[19CD]-isoGlu-RCNTATCATERLADFLQRSSF-Gly(Me)-A-Ile(Me)-LSSTEVGSNT-Hyp-NH$_2$, (SEQ ID NO: 170)
[19CD]-isoGlu-RCNTATCATQRLAHFLQRSSF-Gly(Me)-A-Ile(Me)-LSSTEVGSST-Hyp-NH$_2$, (SEQ ID NO: 171)
[19CD]-isoGlu-RCPTATCATERLAHFLQRSSF-Gly(Me)-A-Ile(Me)-LSSTEVGSST-Hyp-NH$_2$, (SEQ ID NO: 172)
[19CD]-isoGlu-RCNTATCATQRLAHFLQRSSF-Gly(Me)-A-Ile(Me)-LSSTEVGSGT-Hyp-NH$_2$, (SEQ ID NO: 173)
[19CD]-isoGlu-RCPTATCATERLAHFLQRSSF-Gly(Me)-A-Ile(Me)-LSSTEVGSGT-Hyp-NH$_2$, (SEQ ID NO: 174)
[19CD]-isoGlu-RCNTATCATQRLAHFLQRSSF-Gly(Me)-A-Ile(Me)-LSSTEVGSTT-Hyp-NH$_2$, (SEQ ID NO: 175)
[19CD]-isoGlu-RCPTATCATERLAHFLQRSSF-GIy(Me)-A-Ile(Me)-LSSTEVGSTT-Hyp-NH$_2$, (SEQ ID NO: 176)
[19CD]-isoGlu-RCNTATCATQRLAHFLQRSSF-Gly(Me)-A-Ile(Me)-LSSTEVGS-Aad-T-Hyp-NH$_2$, (SEQ ID NO: 177)
[19CD]-isoGlu-RCPTATCATERLAHFLQRSSF-Gly(Me)-A-Ile(Me)-LSSTEVGS-Aad-T-Hyp-NH$_2$, (SEQ ID NO: 178)
[19CD]-isoGlu-RCGTATCATERLAHFLQRF-Gly(Me)-A-Ile(Me)-LSSTEVGSNT-Hyp-NH$_2$,

```
                                                                    (SEQ ID NO: 179)
[19CD]-isoGlu-RCGTATCATERLAHFLQRSSF-Gly(Me)-A-Ile(Me)-LSSTEVGSNTP-NH₂, (SEQ ID NO: 180)
[19CD]-isoGlu-RCNTATCATQRLAHFLQRF-Gly(Me)-A-Ile(Me)-LSSTEVGSGT-Hyp-NH₂, (SEQ ID NO: 181)
[19CD]-isoGlu-RCNTATCATQRLADFLQRSSF-Gly(Me)-A-Ile(Me)-LSSTEVGSGTP-NH₂, (SEQ ID NO: 182)
[19CD]-isoGlu-RCNTATCATQRLADFLQRSSF-Gly(Me)-A-Ile(Me)-LSSTEVGSGT-Hyp-NH₂, (SEQ ID NO: 183)
[19CD]-isoGlu-RCNTATCATQRLADFLQRSSF-Gly(Me)-A-Ile(Me)-LSSTEVGSTTP-NH₂, (SEQ ID NO: 184)
[19CD]-isoGlu-RCNTATCATQRLADFLQRSSF-Gly(Me)-A-Ile(Me)-LSSTEVGSTT-Hyp-NH₂, (SEQ ID NO: 185)
[19CD]-isoGlu-RCNTATCATQRLAHFLERSSF-Gly(Me)-A-Ile(Me)-LSSTEVGSSTP-NH₂, (SEQ ID NO: 186)
[19CD]-isoGlu-RCNTATCATQRLAHFLQRSSF-Gly(Me)-A-Ile(Me)-LSSTEVGSSTP-NH₂, (SEQ ID NO: 187)
[19CD]-isoGlu-RCNTATCATQRLA-Aad-FLQRSSF-Gly(Me)-A-Ile(Me)-LSSTEVGSNT-Hyp-NH₂, (SEQ ID NO: 188)
[19CD]-isoGlu-RCNTATCATQRLA-Aad-FLQRSSF-Gly(Me)-A-Ile(Me)-LSSTEVGSST-Hyp-NH₂, (SEQ ID NO: 189)
[19CD]-isoGlu-RCQTATCATDRLAHFLQRSSF-Gly(Me)-A-Ile(Me)-LSSTEVGSNT-Hyp-NH₂, (SEQ ID NO: 190)
[19CD]-isoGlu-RCQTATCATDRLA-Aad-FLQRSSF-Gly(Me)-A-Ile(Me)-LSSTEVGSNT-Hyp-NH₂, (SEQ ID NO: 191)
[19CD]-isoGlu-RCQTATCATERLAHFLQRSSF-Gly(Me)-A-Ile(Me)-LSSTEVGSGT-Hyp-NH₂, (SEQ ID NO: 192)
[19CD]-isoGlu-RCQTATCATDRLAHFLQRSSF-Gly(Me)-A-Ile(Me)-LSSTEVGSGT-Hyp-NH₂, (SEQ ID NO: 193)
[19CD]-isoGlu-RCQTATCATDRLAHFLQRSSF-Gly(Me)-A-Ile(Me)-LSSTEVGSNTP-NH₂, (SEQ ID NO: 194)
[19CD]-isoGlu-RCQTATCATERLA-Aad-FLQRSSF-Gly(Me)-A-Ile(Me)-LSSTEVGSNTP-NH₂, (SEQ ID NO: 195)
[19CD]-isoGlu-RCQTATCATERLA-Aad-FLQRSSF-Gly(Me)-A-Ile(Me)-LSSTEVGSGTP-NH₂, (SEQ ID NO: 196)
[19CD]-isoGlu-RCQTATCATDRLA-Aad-FLQRF-Gly(Me)-A-Ile(Me)-LSSTEVGSNT-Hyp-NH₂, (SEQ ID NO: 197)
[19CD]-isoGlu-RCQTATCATERLAHFLQRF-Gly(Me)-A-Ile(Me)-LSSTEVGSNTP-NH₂,
``` wherein [19CD] represents [19-carboxynonadecanoyl]; and pharmaceutically acceptable salts thereof.

18. An amylin analogue according to claim 1, comprising an intramolecular disulphide bridge formed between the cysteine residues present at positions 2 and 7 of the amino acid sequence.

19. A pharmaceutical composition comprising an amylin analogue according to claim 1, in combination with a pharmaceutically acceptable carrier, excipient or vehicle.

20. A device comprising an amylin analogue according to claim 1, for delivery of the amylin analogue to a subject.

21. A kit comprising an amylin analogue according to claim 1, and optionally further comprising packaging and instructions for use.

22. An amylin analogue according to claim 1, wherein the amylin analogue is selected from the group consisting of:

```
[19CD]-isoGlu-R-C( )-NTAT-C( )-ATQRLADFLHRSSF-Gly(Me)-A-Ile(Me)-LSSTEVGSETP-NH₂
(Compd. 1) (SEQ ID NO: 102);

[19CD]-isoGlu-R-C( )-NTAT-C( )-ATQRLAHFLHRSSF-Gly(Me)-A-Ile(Me)-LSSTEVGSETP-NH₂
(Compd. 2) (SEQ ID NO: 103);

[19CD]-isoGlu-R-C( )-NTAT-C( )-ATQRLANFLHRSSF-Gly(Me)-A-Ile(Me)-LSSTEVGSETP-NH₂
(Compd. 3) (SEQ ID NO: 104);
```

-continued

[19CD]-isoGlu-R-C( )-GTAT-C( )-ATERLAHFLNRSSF-Gly(Me)-A-Ile(Me)-LSSTEVGSNT-Hyp-NH$_2$
(Compd. 6) (SEQ ID NO: 107);

[19CD]-isoGlu-R-C( )-GTAT-C( )-ATERLAHFLQRSSF-Gly(Me)-A-Ile(Me)-LSSTEVGSNT-Hyp-NH$_2$
(Compd. 7) (SEQ ID NO: 108);

[19CD]-isoGlu-R-C( )-GTAT-C( )-ATERLAHFLERSSF-Gly(Me)-A-Ile(Me)-LSSTEVGSNT-Hyp-NH$_2$
(Compd. 8) (SEQ ID NO: 109);

[19CD]-isoGlu-R-C( )-GTAT-C( )-ATERLAHFLTRSSF-Gly(Me)-A-Ile(Me)-LSSTEVGSST-Hyp-NH$_2$
(Compd. 9) (SEQ ID NO: 110);

[19CD]-isoGlu-R-C( )-GTAT-C( )-ATERLAHFLTRSSF-Gly(Me)-A-Ile(Me)-LSSTEVGSFT-Hyp-NH$_2$
(Compd. 10) (SEQ ID NO: 111);

[19CD]-isoGlu-R-C( )-GTAT-C( )-ATERLAHFLTRSSF-Gly(Me)-A-Ile(Me)-LSSTEVGS-Orn-T-Hyp-NH$_2$
(Compd. 11) (SEQ ID NO: 112);

[19CD]-isoGlu-R-C( )-GTAT-C( )-ATERLAHFLTRSSF-Gly(Me)-A-Ile(Me)-LSSTEVGS-Aad-T-Hyp-NH$_2$
(Compd. 12) (SEQ ID NO: 113);

[19CD]-isoGlu-R-C( )-GTAT-C( )-ATERLAHFLTRSSF-Gly(Me)-A-Ile(Me)-LSSTEVGSGT-Hyp-NH$_2$
(Compd. 13) (SEQ ID NO: 114);

[19CD]-isoGlu-R-C( )-NTAT-C( )-ATQRLAHFLHRF-Gly(Me)-A-Ile(Me)-LSSTEVGSETP-NH$_2$
(Compd. 14) (SEQ ID NO: 115);

[19CD]-isoGlu-R-C( )-GTAT-C( )-ATERLAHFLHRSSF-Gly(Me)-A-Ile(Me)-LSSTEVGSNTP-NH$_2$
(Compd. 15) (SEQ ID NO: 116);

[19CD]-isoGlu-R-C( )-NTAT-C( )-ATQRLAHFLHRSSF-Gly(Me)-A-Ile(Me)-LSSTEVGSNTP-NH$_2$
(Compd. 16) (SEQ ID NO: 117);

[19CD]-isoGlu-R-C( )-GTAT-C( )-ATERLANFLVRSSF-Gly(Me)-A-Ile(Me)-LSSTEVGSNT-Hyp-NH$_2$
(Compd. 17) (SEQ ID NO: 118);

[19CD]-isoGlu-R-C( )-GTAT-C( )-ATERLAHFLTRSSF-Gly(Me)-A-Ile(Me)-LSSTEVGSNT-Hyp-NH$_2$
(Compd. 18) (SEQ ID NO: 119);

[19CD]-isoGlu-R-C( )-GTAT-C( )-ATERLAHFLKRSSF-Gly(Me)-A-Ile(Me)-LSSTEVGSNT-Hyp-NH$_2$
(Compd. 19) (SEQ ID NO: 120);

[19CD]-isoGlu-R-C( )-NTAT-C( )-ATQRLAHFLHRSVF-Gly(Me)-A-Ile(Me)-LSSTEVGSETP-NH$_2$
(Compd. 20) (SEQ ID NO: 121);

[19CD]-isoGlu-R-C( )-NTAT-C( )-ATQRLAHFLHRVSF-Gly(Me)-A-Ile(Me)-LSSTEVGSETP-NH$_2$
(Compd. 21) (SEQ ID NO: 122);

[19CD]-isoGlu-R-C( )-GTAT-C( )-ATERLAHFLVRSSF-Gly(Me)-A-Ile(Me)-LSSTEVGSETP-NH$_2$
(Compd. 22) (SEQ ID NO: 123);

[19CD]-isoGlu-R-C( )-PTAT-C( )-ATDRLAHFLVRSSF-Gly(Me)-A-Ile(Me)-LSSTDVGSDTP-NH$_2$
(Compd. 23) (SEQ ID NO: 124);

[19CD]-isoGlu-R-C( )-NTAT-C( )-ATQRLAHFLVRSSF-Gly(Me)-A-Ile(Me)-LSSTEVGSETP-NH$_2$
(Compd. 24) (SEQ ID NO: 125);

[19CD]-isoGlu-R-C( )-PTAT-C( )-ATDRLAHFLHRSSF-Gly(Me)-A-Ile(Me)-LSSTDVGSNTP-NH$_2$
(Compd. 25) (SEQ ID NO: 126);

[19CD]-isoGlu-R-C( )-GTAT-C( )-ATERLAHFLHRSSF-Gly(Me)-A-Ile(Me)-LSSTEVGSETP-NH$_2$
(Compd. 26) (SEQ ID NO: 127);

[19CD]-isoGlu-R-C( )-PTAT-C( )-ATDRLAHFLHRSSF-Gly(Me)-A-Ile(Me)-LSSTDVGSDTP-NH$_2$
(Compd. 27) (SEQ ID NO: 128);

[19CD]-isoGlu-R-C( )-GTAT-C( )-ATERLAHFLQRSSF-Gly(Me)-A-Ile(Me)-LSSTEVGSST-Hyp-NH$_2$
(Compd. 28) (SEQ ID NO: 129);

[19CD]-isoGlu-R-C( )-GTAT-C( )-ATERLAHFLNRSSF-Gly(Me)-A-Ile(Me)-LSSTEVGSST-Hyp-NH$_2$
(Compd. 29) (SEQ ID NO: 130);

[19CD]-isoGlu-R-C( )-GTAT-C( )-ATERLAHFLHRSSF-Gly(Me)-A-Ile(Me)-LSSTEVGSST-Hyp-NH$_2$
(Compd. 30) (SEQ ID NO: 131);

[19CD]-isoGlu-R-C( )-GTAT-C( )-ATERLAHFLVRSSF-Gly(Me)-A-Ile(Me)-LSSTEVGSST-Hyp-NH$_2$
(Compd. 31) (SEQ ID NO: 132);

[19CD]-isoGlu-R-C( )-GTAT-C( )-ATERLAHFLQRSSF-Gly(Me)-A-Ile(Me)-LSSTEVGSFT-Hyp-NH$_2$
(Compd. 32) (SEQ ID NO: 133);

-continued

[19CD]-isoGlu-R-C( )-GTAT-C( )-ATERLAHFLNRSSF-Gly(Me)-A-Ile(Me)-LSSTEVGSFT-Hyp-NH$_2$
(Compd. 33) (SEQ ID NO: 134);

[19CD]-isoGlu-R-C( )-GTAT-C( )-ATERLAHFLQRSSF-Gly(Me)-A-Ile(Me)-LSSTEVGSSTP-NH$_2$
(Compd. 34) (SEQ ID NO: 135);

[19CD]-isoGlu-R-C( )-GTAT-C( )-ATERLAHFLNRSSF-Gly(Me)-A-Ile(Me)-LSSTEVGSSTP-NH$_2$
(Compd. 35) (SEQ ID NO: 136);

[19CD]-isoGlu-R-C( )-GTAT-C( )-ATERLAHFLERSSF-Gly(Me)-A-Ile(Me)-LSSTEVGSSTP-NH$_2$
(Compd. 36) (SEQ ID NO: 137);

[19CD]-isoGlu-R-C( )-GTAT-C( )-ATERLAHFLHRSSF-Gly(Me)-A-Ile(Me)-LSSTEVGSSTP-NH$_2$
(Compd. 37) (SEQ ID NO: 138);

[19CD]-isoGlu-R-C( )-GTAT-C( )-ATERLAHFLVRSSF-Gly(Me)-A-Ile(Me)-LSSTEVGSSTP-NH$_2$
(Compd. 38) (SEQ ID NO: 139);

[19CD]-isoGlu-R-C( )-GTAT-C( )-ATERLAHFLQRSSF-Gly(Me)-A-Ile(Me)-LSSTEVGSFTP-NH$_2$
(Compd. 39) (SEQ ID NO: 140);

[19CD]-isoGlu-R-C( )-GTAT-C( )-ATERLAHFLNRSSF-Gly(Me)-A-Ile(Me)-LSSTEVGSFTP-NH$_2$
(Compd. 40) (SEQ ID NO: 141);

[19CD]-isoGlu-R-C( )-GTAT-C( )-ATERLADFLTRSSF-Gly(Me)-A-Ile(Me)-LSSTEVGSST-Hyp-NH$_2$
(Compd. 41) (SEQ ID NO: 142);

[19CD]-isoGlu-R-C( )-GTAT-C( )-ATERLADFLTRSSF-Gly(Me)-A-Ile(Me)-LSSTEVGSFT-Hyp-NH$_2$
(Compd. 42) (SEQ ID NO: 143);

[19CD]-isoGlu-R-C( )-GTAT-C( )-ATERLA-Aad-FLTRSSF-Gly(Me)-A-Ile(Me)-LSSTEVGSST-Hyp-NH$_2$
(Compd. 43) (SEQ ID NO: 144);

[19CD]-isoGlu-R-C( )-GTAT-C( )-ATERLA-Aad-FLTRSSF-Gly(Me)-A-Ile(Me)-LSSTEVGS-Orn-T-Hyp-NH$_2$
(Compd. 44) (SEQ ID NO: 145);

[19CD]-isoGlu-R-C( )-GTAT-C( )-ATERLAHFLTRSSF-Gly(Me)-A-Ile(Me)-LSSTEVGSST-Apr-NH$_2$
(Compd. 45) (SEQ ID NO: 146);

[19CD]-isoGlu-R-C( )-GTAT-C( )-ATERLAHFLTRSSF-Gly(Me)-A-Ile(Me)-LSSTEVGSSTP-NH$_2$
(Compd. 46) (SEQ ID NO: 147);

[19CD]-isoGlu-R-C( )-GTAT-C( )-ATERLAHFLTRSSF-Gly(Me)-A-Ile(Me)-LSSTEVGS-Orn-TP-NH$_2$
(Compd. 47) (SEQ ID NO: 148);

[19CD]-isoGlu-R-C( )-GTAT-C( )-ATERLAHFLTRSSF-Gly(Me)-A-Ile(Me)-LSSTEVGSTT-Hyp-NH$_2$
(Compd. 48) (SEQ ID NO: 149);

[19CD]-isoGlu-R-C( )-NTAT-C( )-ATQRLADFLQRSSF-Gly(Me)-A-Ile(Me)-LSSTEVGSNT-Hyp-NH$_2$
(Compd. 49) (SEQ ID NO: 150);

[19CD]-isoGlu-R-C( )-NTAT-C( )-ATQRLAH FL-Aad-RSSF-Gly(Me)-A-Ile(Me)-LSSTEVGSNT-Hyp-NH$_2$
(Compd. 50) (SEQ ID NO: 151);

[19CD]-isoGlu-R-C( )-GTAT-C( )-ATERLAHFLQRSSF-Gly(Me)-A-Ile(Me)-LSSTEVGS-Orn-T-Hyp-NH$_2$
(Compd. 51) (SEQ ID NO: 152);

[19CD]-isoGlu-R-C( )-GTAT-C( )-ATERLAHFLQRSSF-Gly(Me)-A-Ile(Me)-LSSTEVGSGT-Hyp-NH$_2$
(Compd. 52) (SEQ ID NO: 153);

[19CD]-isoGlu-R-C( )-GTAT-C( )-ATERLAHFLQRSSF-Gly(Me)-A-Ile(Me)-LSSTEVGS-Aad-T-Hyp-NH$_2$
(Compd. 53) (SEQ ID NO: 154);

[19CD]-isoGlu-R-C( )-GTAT-C( )-ATERLADFLQRSSF-Gly(Me)-A-Ile(Me)-LSSTEVGSNT-Hyp-NH$_2$
(Compd. 54) (SEQ ID NO: 155);

[19CD]-isoGlu-R-C( )-GTAT-C( )-ATERLA-Aad-FLQRSSF-Gly(Me)-A-Ile(Me)-LSSTEVGSNT-Hyp-NH$_2$
(Compd. 55) (SEQ ID NO: 156);

[19CD]-isoGlu-R-C( )-NTAT-C( )-ATERLAHFLQRSSF-Gly(Me)-A-Ile(Me)-LSSTEVGSNT-Hyp-NH$_2$
(Compd. 56) (SEQ ID NO: 157);

[19CD]-isoGlu-R-C( )-QTAT-C( )-ATERLAHFLQRSSF-Gly(Me)-A-Ile(Me)-LSSTEVGSNT-Hyp-NH$_2$
(Compd. 57) (SEQ ID NO: 158);

[19CD]-isoGlu-R-C( )-NTAT-C( )-ATQRLAHFLQRSSF-Gly(Me)-A-Ile(Me)-LSSTEVGSNT-Hyp-NH$_2$
(Compd. 58) (SEQ ID NO: 159);

[19CD]-isoGlu-R-C( )-PTAT-C( )-ATDRLAHFLQRSSF-Gly(Me)-A-Ile(Me)-LSSTDVGSNT-Hyp-NH$_2$
(Compd. 59) (SEQ ID NO: 160);

-continued

[19CD]-isoGlu-R-C( )-NTAT-C( )-ATERLAHFLQRSSF-Gly(Me)-A-Ile(Me)-LSSTEVGSDT-Hyp-NH$_2$
(Compd. 60) (SEQ ID NO: 161);

[19CD]-isoGlu-R-C( )-NTAT-C( )-ATQRLAHFLQRSSF-Gly(Me)-A-Ile(Me)-LSSTEVGSNTP-NH$_2$
(Compd. 61) (SEQ ID NO: 162);

[19CD]-isoGlu-R-C( )-NTAT-C( )-ATERLAHFLQRSSF-Gly(Me)-A-Ile(Me)-LSSTEVGSNTP-NH$_2$
(Compd. 62) (SEQ ID NO: 163);

[19CD]-isoGlu-R-C( )-PTAT-C( )-ATERLAHFLQRSSF-Gly(Me)-A-Ile(Me)-LSSTEVGSNT-Hyp-NH$_2$
(Compd. 63) (SEQ ID NO: 164);

[19CD]-isoGlu-R-C( )-PTAT-C( )-ATQRLAHFLQRSSF-Gly(Me)-A-Ile(Me)-LSSTEVGSNT-Hyp-NH$_2$
(Compd. 64) (SEQ ID NO: 165);

[19CD]-isoGlu-R-C( )-NTAT-C( )-ATQRLADFLQRSSF-Gly(Me)-A-Ile(Me)-LSSTEVGSNTP-NH$_2$
(Compd. 65) (SEQ ID NO: 166);

[19CD]-isoGlu-R-C( )-NTAT-C( )-ATERLADFLQRSSF-Gly(Me)-A-Ile(Me)-LSSTEVGSNTP-NH$_2$
(Compd. 66) (SEQ ID NO: 167);

[19CD]-isoGlu-R-C( )-PTAT-C( )-ATERLADFLQRSSF-Gly(Me)-A-Ile(Me)-LSSTEVGSNTP-NH$_2$
(Compd. 67) (SEQ ID NO: 168);

[19CD]-isoGlu-R-C( )-NTAT-C( )-ATERLADFLQRSSF-Gly(Me)-A-Ile(Me)-LSSTEVGSNT-Hyp-NH$_2$
(Compd. 68) (SEQ ID NO: 169);

[19CD]-isoGlu-R-C( )-NTAT-C( )-ATQRLAHFLQRSSF-Gly(Me)-A-Ile(Me)-LSSTEVGSST-Hyp-NH$_2$
(Compd. 69) (SEQ ID NO: 170);

[19CD]-isoGlu-R-C( )-PTAT-C( )-ATERLAHFLQRSSF-Gly(Me)-A-Ile(Me)-LSSTEVGSST-Hyp-NH$_2$
(Compd. 70) (SEQ ID NO: 171);

[19CD]-isoGlu-R-C( )-NTAT-C( )-ATQRLAHFLQRSSF-Gly(Me)-A-Ile(Me)-LSSTEVGSGT-Hyp-NH$_2$
(Compd. 71) (SEQ ID NO: 172);

[19CD]-isoGlu-R-C( )-PTAT-C( )-ATERLAHFLQRSSF-Gly(Me)-A-Ile(Me)-LSSTEVGSGT-Hyp-NH$_2$
(Compd. 72) (SEQ ID NO: 173);

[19CD]-isoGlu-R-C( )-NTAT-C( )-ATQRLAHFLQRSSF-Gly(Me)-A-Ile(Me)-LSSTEVGSTT-Hyp-NH$_2$
(Compd. 73) (SEQ ID NO: 174);

[19CD]-isoGlu-R-C( )-PTAT-C( )-ATERLAHFLQRSSF-Gly(Me)-A-Ile(Me)-LSSTEVGSTT-Hyp-NH$_2$
(Compd. 74) (SEQ ID NO: 175);

[19CD]-isoGlu-R-C( )-NTAT-C( )-ATQRLAHFLQRSSF-Gly(Me)-A-Ile(Me)-LSSTEVGS-Aad-T-Hyp-NH$_2$
(Compd. 75) (SEQ ID NO: 176);

[19CD]-isoGlu-R-C( )-PTAT-C( )-ATERLAHFLQRSSF-Gly(Me)-A-Ile(Me)-LSSTEVGS-Aad-T-Hyp-NH$_2$
(Compd. 76) (SEQ ID NO: 177);

[19CD]-isoGlu-R-C( )-GTAT-C( )-ATERLAHFLQRF-Gly(Me)-A-Ile(Me)-LSSTEVGSNT-Hyp-NH$_2$
(Compd. 77) (SEQ ID NO: 178);

[19CD]-isoGlu-R-C( )-GTAT-C( )-ATERLAHFLQRSSF-Gly(Me)-A-Ile(Me)-LSSTEVGSNTP-NH$_2$
(Compd. 78) (SEQ ID NO: 179);

[19CD]-isoGlu-R-C( )-NTAT-C( )-ATQRLAHFLQRF-Gly(Me)-A-Ile(Me)-LSSTEVGSGT-Hyp-NH$_2$
(Compd. 79) (SEQ ID NO: 180);

[19CD]-isoGlu-R-C( )-NTAT-C( )-ATQRLADFLQRSSF-Gly(Me)-A-Ile(Me)-LSSTEVGSGTP-NH$_2$
(Compd. 80) (SEQ ID NO: 181);

[19CD]-isoGlu-R-C( )-NTAT-C( )-ATQRLADFLQRSSF-Gly(Me)-A-Ile(Me)-LSSTEVGSGT-Hyp-NH$_2$
(Compd. 81) (SEQ ID NO: 182);

[19CD]-isoGlu-R-C( )-NTAT-C( )-ATQRLADFLQRSSF-Gly(Me)-A-Ile(Me)-LSSTEVGSTTP-NH$_2$
(Compd. 82) (SEQ ID NO: 183);

[19CD]-isoGlu-R-C( )-NTAT-C( )-ATQRLADFLQRSSF-Gly(Me)-A-Ile(Me)-LSSTEVGSTT-Hyp-NH$_2$
(Compd. 83) (SEQ ID NO: 184);

[19CD]-isoGlu-R-C( )-NTAT-C( )-ATQRLAHFLERSSF-Gly(Me)-A-Ile(Me)-LSSTEVGSSTP-NH$_2$
(Compd. 84) (SEQ ID NO: 185);

[19CD]-isoGlu-R-C( )-NTAT-C( )-ATQRLAHFLQRSSF-Gly(Me)-A-Ile(Me)-LSSTEVGSSTP-NH$_2$
(Compd. 85) (SEQ ID NO: 186);

[19CD]-isoGlu-R-C( )-NTAT-C( )-ATQRLA-Aad-FLQRSSF-Gly(Me)-A-Ile(Me)-LSSTEVGSNT-Hyp-NH$_2$
(Compd. 86) (SEQ ID NO: 187);

```
[19CD]-isoGlu-R-C( )-NTAT-C( )-ATQRLA-Aad-FLQRSSF-Gly(Me)-A-Ile(Me)-LSSTEVGSST-Hyp-NH₂
(Compd. 87) (SEQ ID NO: 188);

[19CD]-isoGlu-R-C( )-QTAT-C( )-ATDRLAHFLQRSSF-Gly(Me)-A-Ile(Me)-LSSTEVGSNT-Hyp-NH₂
(Compd. 88) (SEQ ID NO: 189);

[19CD]-isoGlu-R-C( )-QTAT-C( )-ATDRLA-Aad-FLQRSSF-Gly(Me)-A-Ile(Me)-LSSTEVGSNT-Hyp-NH₂
(Compd. 89) (SEQ ID NO: 190);

[19CD]-isoGlu-R-C( )-QTAT-C( )-ATERLAHFLQRSSF-Gly(Me)-A-Ile(Me)-LSSTEVGSGT-Hyp-NH₂
(Compd. 90) (SEQ ID NO: 191);

[19CD]-isoGlu-R-C( )-QTAT-C( )-ATDRLAHFLQRSSF-Gly(Me)-A-Ile(Me)-LSSTEVGSGT-Hyp-NH₂
(Compd. 91) (SEQ ID NO: 192);

[19CD]-isoGlu-R-C( )-QTAT-C( )-ATDRLAHFLQRSSF-Gly(Me)-A-Ile(Me)-LSSTEVGSNTP-NH₂
(Compd. 92) (SEQ ID NO: 193);

[19CD]-isoGlu-R-C( )-QTAT-C( )-ATERLA-Aad-FLQRSSF-Gly(Me)-A-Ile(Me)-LSSTEVGSNTP-NH₂
(Compd. 93) (SEQ ID NO: 194);

[19CD]-isoGlu-R-C( )-QTAT-C( )-ATERLA-Aad-FLQRSSF-Gly(Me)-A-Ile(Me)-LSSTEVGSGTP-NH₂
(Compd. 94); (SEQ ID NO: 195)

[19CD]-isoGlu-R-C( )-QTAT-C( )-ATDRLA-Aad-FLQRF-Gly(Me)-A-Ile(Me)-LSSTEVGSNT-Hyp-NH₂
(Compd. 95) (SEQ ID NO: 196); and

[19CD]-isoGlu-R-C( )-QTAT-C( )-ATERLAHFLQRF-Gly(Me)-A-Ile(Me)-LSSTEVGSNTP-NH₂
(Compd. 96) (SEQ ID NO: 197);
``` or a pharmaceutically acceptable salt thereof;
wherein parentheses "0" indicate an intramolecular disulfide bridge between the side chains of cysteine residues at positions 2 and 7.

23. An amylin analogue which is:
[19CD]-isoGlu-R-C( )-GTAT-C( )-ATERLAHFLQRSSF-Gly(Me)-A-Ile(Me)-LSSTEVGSNT-Hyp-NH₂
(Compd. 7) (SEQ ID NO: 108), or a pharmaceutically acceptable salt thereof.

24. An amylin analogue which is:
[19CD]-isoGlu-R—C( )-NTAT-C( )-ATQRLAD-FLQRSSF-Gly(Me)-A-Ile(Me)-LSSTEVGSNT-Hyp-NH₂ (Compd. 49) (SEQ ID NO: 150), or a pharmaceutically acceptable salt thereof.

25. An amylin analogue which is:
[19CD]-isoGlu-R-C( )-GTAT-C( )-ATERLA-Aad-FLQRSSF-Gly(Me)-A-Ile(Me)-LSSTEVGSNT-Hyp-NH₂ (Compd. 55) (SEQ ID NO: 156), or a pharmaceutically acceptable salt thereof.

26. An amylin analogue which is:
[19CD]-isoGlu-R—C( )-NTAT-C( )-ATERLAH-FLQRSSF-Gly(Me)-A-Ile(Me)-LSSTEVGSNT-Hyp-NH₂ (Compd. 56) (SEQ ID NO: 157), or a pharmaceutically acceptable salt thereof.

27. An amylin analogue which is:
[19CD]-isoGlu-R-C( )-QTAT-C( )-ATERLAHFLQRSSF-Gly(Me)-A-Ile(Me)-LSSTEVGSNT-Hyp-NH₂
(Compd. 57) (SEQ ID NO: 158), or a pharmaceutically acceptable salt thereof.

28. A method for the synthesis of an amylin analogue according to claim 1, comprising synthesizing the amylin analogue by solid-phase or liquid-phase methodology, optionally isolating and purifying the final product, and further optionally comprising the step of forming a disulfide bond between the thiol groups of the cysteine side chains at positions 2 and 7.

29. A method of treating, inhibiting or reducing weight gain, promoting weight loss, reducing food intake, and/or reducing excess body weight in a subject in need, said method comprises administering to said subject a therapeutically effective amount of an amylin analogue according to claim 1.

30. A method of treating obesity, morbid obesity, obesity prior to surgery, obesity-linked inflammation, obesity-linked gallbladder disease, obesity-induced sleep apnea and respiratory problems, degeneration of cartilage, osteoarthritis, or reproductive health complications of obesity or overweight such as infertility in a subject in need, said method comprises administering to said subject a therapeutically effective amount of an amylin analogue according to claim 1.

31. A method of prevention or treatment of Alzheimer's disease, diabetes, type 1 diabetes, type 2 diabetes, pre-diabetes, insulin resistance syndrome, impaired glucose tolerance (IGT), disease states associated with elevated blood glucose levels, metabolic disease including metabolic syndrome, hyperglycemia, hypertension, atherogenic dyslipidemia, hepatic steatosis ("fatty liver"), kidney failure, arteriosclerosis (e.g. atherosclerosis), macrovascular disease, microvascular disease, diabetic heart (including diabetic cardiomyopathy and heart failure as a diabetic complication), coronary heart disease, peripheral artery disease or stroke, and/or combinations thereof in a subject in need, said method comprises administering to said subject a therapeutically effective amount of an amylin analogue according to claim 1.

32. A method of lowering circulating LDL levels and/or increasing HDL/LDL ratio in a subject, said method comprises administering to said subject an amylin analogue according to claim 1.

\* \* \* \* \*